US010016159B2

(12) United States Patent
Van Ooijen et al.

(10) Patent No.: US 10,016,159 B2
(45) Date of Patent: Jul. 10, 2018

(54) DETERMINATION OF TGF-β PATHWAY ACTIVITY USING UNIQUE COMBINATION OF TARGET GENES

(71) Applicant: KONINKLIJKE PHILIPS N.V., Eindhoven (NL)

(72) Inventors: Hendrik Jan Van Ooijen, Eindhoven (NL); Anja Van De Stolpe, Eindhoven (NL); Dianne Arnoldina Margaretha Wilhelmina Van Strijp, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 14/922,561

(22) Filed: Oct. 26, 2015

(65) Prior Publication Data
US 2016/0113572 A1 Apr. 28, 2016

(30) Foreign Application Priority Data
Oct. 24, 2014 (EP) .................................... 14190270

(51) Int. Cl.
G01N 33/48 (2006.01)
A61B 5/00 (2006.01)
C12Q 1/6886 (2018.01)
G06F 19/22 (2011.01)
G06F 19/18 (2011.01)
G06G 7/58 (2006.01)
G06F 19/12 (2011.01)
G06F 19/20 (2011.01)
G06F 19/24 (2011.01)

(52) U.S. Cl.
CPC .......... A61B 5/4839 (2013.01); C12Q 1/6886 (2013.01); G06F 19/18 (2013.01); G06F 19/22 (2013.01); C12Q 2600/158 (2013.01); C12Q 2600/16 (2013.01); G06F 19/12 (2013.01); G06F 19/20 (2013.01); G06F 19/24 (2013.01)

(58) Field of Classification Search
CPC ...... G01N 33/66; G01N 33/582; G06F 19/18; G06F 19/22; G06F 19/24
See application file for complete search history.

(56) References Cited

U.S. PATENT DOCUMENTS

| | | |
|---|---|---|
| 5,436,134 A | 7/1995 | Haugland |
| 5,658,751 A | 8/1997 | Yue |
| 5,874,219 A | 2/1999 | Rava |
| 6,004,761 A | 12/1999 | Linsley |
| 6,146,897 A | 11/2000 | Cohenford |
| 6,171,798 B1 | 1/2001 | Levine |
| 6,225,047 B1 | 5/2001 | Hutchens |
| 6,308,170 B1 | 10/2001 | Balaban |
| 6,391,550 B1 | 5/2002 | Lockhart |
| 6,675,104 B2 | 1/2004 | Paulse |
| 6,720,149 B1 | 4/2004 | Rava |
| 6,844,165 B2 | 1/2005 | Hutchens |
| 6,884,578 B2 | 4/2005 | Warrington |
| 7,056,674 B2 | 6/2006 | Baker |
| 7,081,340 B2 | 7/2006 | Baker |
| 7,160,734 B2 | 1/2007 | Hutchens |
| 7,208,470 B2 | 4/2007 | Duan |
| 7,299,134 B2 | 11/2007 | Rich |
| 7,526,637 B2 | 4/2009 | Jung |
| 7,569,345 B2 | 8/2009 | Cobleigh |
| 7,695,913 B2 | 4/2010 | Cowens |
| 7,723,033 B2 | 5/2010 | Baker |
| 7,754,431 B2 | 7/2010 | Ring |
| 7,754,861 B2 | 7/2010 | Boschetti |
| 7,816,084 B2 | 10/2010 | Ring |
| 7,838,224 B2 | 11/2010 | Baker |
| 7,858,304 B2 | 12/2010 | Baker |
| 7,888,019 B2 | 2/2011 | Kiefer |
| 7,930,104 B2 | 4/2011 | Baker |
| 7,939,261 B2 | 5/2011 | Baker |
| 8,008,003 B2 | 8/2011 | Baker |
| 8,021,894 B2 | 9/2011 | Hutchens |
| 8,026,060 B2 | 9/2011 | Watson |
| 8,029,995 B2 | 10/2011 | Watson |
| 8,029,997 B2 | 10/2011 | Kennedy |
| 8,034,565 B2 | 10/2011 | Cobleigh |

(Continued)

FOREIGN PATENT DOCUMENTS

| | | |
|---|---|---|
| WO | 2012154567 A2 | 11/2012 |
| WO | 2013003384 A1 | 1/2013 |

(Continued)

OTHER PUBLICATIONS

Shen, Haige "Bayesian Analysis in Cancer Pathway Studies and Probabilistic Pathway Annotation", Duke University 2008.
Chen, Min et al "A Powerful Bayesian Meta Anaylsis Method to Integrate Multiple Gene Set Enrichment Studies", Bioinformatic, vol. 29, No. 7, 2013, pp. 862-869.
Fanelli, Laise P. et al "Modeling TGF-Beta Signaling Pathway in Epithelial-Mesenchymal Transistion", AIP Advances, 2012, vol. 2, No. 1. Abstract only.
Zhang, Ping et al "Joint Loading-Driven Bone Formation and Signaling Pathways Predicted from Genome-Wide Expression Profiles", Sciencedirect—Bone, vol. 44, 2009, pp. 989-998.
Derynck, Rik et al Smad-Dependent and Smad-Independent Pathways in TGF-Beta Family Signalling:, Nature, vol. 425, 2003, pp. 577-584.

(Continued)

Primary Examiner — Eric S Dejong

(57) ABSTRACT

A bioinformatics process which provides an improved means to detect TGF-β cellular signaling pathway in a subject, such as a human, based on the expression levels of one or more unique target gene(s) of the TGF-β cellular signaling pathway measured in a sample. The invention includes an apparatus comprising a digital processor configured to perform such a method, a non-transitory storage medium storing instructions that are executable by a digital processing device to perform such a method, and a computer program comprising program code means for causing a digital processing device to perform such a method. Kits are also provided for measuring expression levels of unique sets of TGF-β cellular signaling pathway target genes.

33 Claims, 24 Drawing Sheets

(56) References Cited

U.S. PATENT DOCUMENTS

| | | |
|---|---|---|
| 8,067,178 B2 | 11/2011 | Baker |
| 8,071,286 B2 | 12/2011 | Baker |
| 8,148,076 B2 | 4/2012 | Baker |
| 8,153,378 B2 | 4/2012 | Cowens |
| 8,153,379 B2 | 4/2012 | Watson |
| 8,153,380 B2 | 4/2012 | Watson |
| 8,198,024 B2 | 6/2012 | Watson |
| 8,206,919 B2 | 6/2012 | Cobleigh |
| 8,273,537 B2 | 9/2012 | Watson |
| 8,367,345 B2 | 2/2013 | Cowens |
| 8,451,450 B2 | 5/2013 | Heng |
| 8,518,639 B2 | 8/2013 | Rihet |
| 8,632,980 B2 | 1/2014 | Baker |
| 8,703,736 B2 | 4/2014 | Whatcott |
| 8,725,426 B2 | 5/2014 | Shak |
| 8,741,605 B2 | 6/2014 | Cobleigh |
| 8,765,383 B2 | 7/2014 | Cowens |
| 8,808,994 B2 | 8/2014 | Kiefer |
| 8,868,352 B2 | 10/2014 | Baker |
| 8,906,625 B2 | 12/2014 | Kiefer |
| 8,911,940 B2 | 12/2014 | Weiss |
| 2006/0234911 A1 | 10/2006 | Hoffmann |
| 2010/0131432 A1 | 5/2010 | Kennedy |
| 2011/0053804 A1 | 3/2011 | Massague |
| 2012/0009581 A1 | 1/2012 | Bankaitis-Davis |

FOREIGN PATENT DOCUMENTS

| | | |
|---|---|---|
| WO | 2013011479 A2 | 1/2013 |
| WO | 2013075059 A1 | 5/2013 |
| WO | 2014102668 A2 | 7/2014 |
| WO | 2014174003 A1 | 10/2014 |
| WO | 2015101635 A1 | 7/2015 |

OTHER PUBLICATIONS

Wahdan-Alaswad, Reema S. et al "Inhibition of mTORCI Kinase Activates Smads 1 and 5 but Not SmadS in Human Prostate Cancer Cells, Mediating Cytostatic Response to Rapamycin", Molecular Cancer Research, Signaling and Regulation, 2012, pp. 821-834.

Nacif, Michael et al "Targeting Transforming Growth Factor BETA(TGF-BETA) in Cancer and Non-Neoplastic Diseases", Journal of Cancer Therapy, vol. 5, 2014, pp. 735-747.

Padua, David et al "Roles of TGFβ in Metastasis", Cell Research vol. 19, 2009, pp. 89-102.

Verhaegh, Wim et al "Selection of Personalized Patient Therapy through the Use of Knowledge-Based Computational Models That Identify Tumor-Driving Signal Transduction Pathways", Cancer Research, vol. 74, No. 11, 2014, pp. 2936-2945.

Sheen, Yhun Y. et al "Targeting the Transforming Growth Factor-b Signaling in Cancer Therapy", Biomolecules & Therapeutics, vol. 21, No. 5, 2013, pp. 323-331.

Sharkey, David J. et al "TGF-b Mediates Proinflammatory Seminal Fluid Signaling in Human Cervical Epithelial Cells", The Journal of Immunology, vol. 189, 2012, pp. 1024-1035.

DETERMINATION OF TGF-β PATHWAY ACTIVITY USING UNIQUE COMBINATION OF TARGET GENES

RELATED APPLICATIONS

This application claims the benefit of European Patent Application No. EP14190270.0, filed Oct. 24, 2014, the entirety of the specification and claims thereof is hereby incorporated by reference for all purposes.

INCORPORATION-BY-REFERENCE OF MATERIAL SUBMITTED ON AS A TEXT FILE VIA THE OFFICE ELECTRONIC FILING SYSTEM (EFS-WEB)

A Sequence Listing associated with this application is provided in text format in lieu of a paper copy, and is hereby incorporated by reference into the specification. The name of the text file containing the Sequence Listing is 2014PF00582_2015-10-26_sequencelisting_ST25.txt. The text file is 295 KB, was created on Oct. 26, 2015, and is being submitted electronically via EFS-Web.

FIELD OF THE INVENTION

The present invention is in the field of systems biology, bioinformatics, genomic mathematical processing and proteomic mathematical processing. In particular, the invention includes a systems-based mathematical process for determining the activity of a TGF-β cellular signaling pathway in a subject based on expression levels of a unique set of selected target gene(s) in a subject. The invention further provides an apparatus that includes a digital processor configured to perform such a method, a non-transitory storage medium storing instructions that are executable by a digital processing device to perform such a method, and a computer program comprising a program code means for causing a digital processing device to perform such a method. The present invention also includes kits for the determination of expression levels of the unique combinations of target genes.

BACKGROUND OF THE INVENTION

As knowledge of tumors including cancers evolve, it becomes more clear that they are extraordinarily heterogeneous and multifactorial. Tumors and cancers have a wide range of genotypes and phenotypes, they are influenced by their individualized cell receptors (or lack thereof), microenvironment, extracellular matrix, tumor vascularization, neighboring immune cells, and accumulations of mutations, with differing capacities for proliferation, migration, stem cell properties and invasion. This scope of heterogeneity exists even among same classes of tumors. See generally: *Nature* Insight: Tumor Heterogeneity (entire issue of articles), 19 Sep. 2013 (Vol. 501, Issue 7467); Zellmer and Zhang, "Evolving concepts of tumor heterogeneity", *Cell and Bioscience* 2014, 4:69.

Traditionally, physicians have treated tumors, including cancers, as the same within class type (including within receptor type) without taking into account the enormous fundamental individualized nature of the diseased tissue. Patients have been treated with available chemotherapeutic agents based on class and receptor type, and if they do not respond, they are treated with an alternative therapeutic, if it exists. This is an empirical approach to medicine.

There has been a growing trend toward taking into account the heterogeneity of tumors at a more fundamental level as a means to create individualized therapies, however, this trend is still in its formative stages. What is desperately needed are approaches to obtain more metadata about the tumor to inform therapeutic treatment in a manner that allows the prescription of approaches more closely tailored to the individual tumor, and perhaps more importantly, avoiding therapies destined to fail and waste valuable time, which can be life-determinative.

A number of companies and institutions are active in the area of classical, and some more advanced, genetic testing, diagnostics, and predictions for the development of human diseases, including, for example: Affymetrix, Inc.; Bio-Rad, Inc; Roche Diagnostics; Genomic Health, Inc.; Regents of the University of California; Illumina; Fluidigm Corporation; Sequenom, Inc.; High Throughput Genomics; NanoString Technologies; Thermo Fisher; Danaher; Becton, Dickinson and Company; bioMerieux; Johnson & Johnson, Myriad Genetics, and Hologic.

Several companies have developed technology or products directed to gene expression profiling and disease classification. For example, Genomic Health, Inc. is the assignee of numerous patents pertaining to gene expression profiling, for example: U.S. Pat. Nos. 7,081,340; 8,808,994; 8,034, 565; 8,206,919; 7,858,304; 8,741,605; 8,765,383; 7,838, 224; 8,071,286; 8,148,076; 8,008,003; 8,725,426; 7,888, 019; 8,906,625; 8,703,736; 7,695,913; 7,569,345; 8,067, 178; 7,056,674; 8,153,379; 8,153,380; 8,153,378; 8,026, 060; 8,029,995; 8,198,024; 8,273,537; 8,632,980; 7,723, 033; 8,367,345; 8,911,940; 7,939,261; 7,526,637; 8,868, 352; 7,930,104; 7,816,084; 7,754,431 and 7,208,470, and their foreign counterparts.

U.S. Pat. No. 9,076,104 to the Regents of the University of California titled "Systems and Methods for Identifying Drug Targets using Biological Networks" claims a method with computer executable instructions by a processor for predicting gene expression profile changes on inhibition of proteins or genes of drug targets on treating a disease, that includes constructing a genetic network using a dynamic Bayesian network based at least in part on knowledge of drug inhibiting effects on a disease, associating a set of parameters with the constructed dynamic Bayesian network, determining the values of a joint probability distribution via an automatic procedure, deriving a mean dynamic Bayesian network with averaged parameters and calculating a quantitative prediction based at least in part on the mean dynamic Bayesian network, wherein the method searches for an optimal combination of drug targets whose perturbed gene expression profiles are most similar to healthy cells.

Affymetrix has developed a number of products related to gene expression profiling. Non-limiting examples of U.S. patents to Affymetrix include: U.S. Pat. Nos. 6,884,578; 8,029,997; 6,308,170; 6,720,149; 5,874,219; 6,171,798; and 6,391,550.

Likewise, Bio-Rad has a number of products directed to gene expression profiling. Illustrative examples of U.S. patents to Bio-Rad include: U.S. Pat. Nos. 8,021,894; 8,451, 450; 8,518,639; 6,004,761; 6,146,897; 7,299,134; 7,160, 734; 6,675,104; 6,844,165; 6,225,047; 7,754,861 and 6,004, 761.

Koninklijke Philips N.V. (NL) has filed a number of patent applications in the general area of assessment of cellular signaling pathway activity using various mathematical models, including U.S. Ser. No. 14/233,546 (WO 2013/ 011479), titled "Assessment of Cellular Signaling Pathway Using Probabilistic Modeling of Target Gene Expression";

U.S. Ser. No. 14/652,805 (WO 2014/102668) titled "Assessment of Cellular Signaling Pathway Activity Using Linear Combinations of Target Gene Expressions; WO 2014/174003 titled "Medical Prognosis and Prediction of Treatment Response Using Multiple Cellular Signaling Pathway Activities; and WO 2015/101635 titled "Assessment of the PI3K Cellular Signaling Pathway Activity Using Mathematical Modeling of Target Gene Expression.

Despite this progress, more work is needed to definitively characterize tumor cellular behavior. In particular, there is a critical need to determine which pathways have become pathogenic to the cell. However, it is difficult to identify and separate abnormal cellular signaling from normal cellular pathway activity.

Transforming growth factor-β (TGF-β) is a cytokine that controls various functions in many cell types in humans, such as proliferation, differentiation, and wound healing. In pathological disorders, such as cancer (e.g., colon, breast, prostate), the TGF-β cellular signaling pathway can play two opposing roles, either as a tumor suppressor or as a tumor promoter. TGF-β may act as a tumor suppressor in the early phases of cancer development, however in more progressed cancerous tissue TGF-β can act as a tumor promoter by acting as a regulator of invasion and metastasis (see Padua D. and Massague J., "Roles of TGF-β in metastasis", Cell Research, Vol. 19, No. 1, 2009, pages 89 to 102).

TGF-β exists in three isoforms (gene names: TGF-β1, TGF-β2, TGF-β3). It is secreted as an inactive precursor homodimeric protein, which is known to be increased in cancer cells compared to their normal counterparts (see Massague J., "How cells read TGF-β signals", Nature Reviews Molecular Cell Biology, Vol. 1, No. 3, 2000, pages 169 to 178).

The TGF-β precursor can be proteolytically activated, after which it binds to an extracellular TGF-β receptor that initiates an intracellular "SMAD" signaling pathway. Various SMAD proteins (receptor-regulated or R-SMADs (SMAD 1, 2, 3, 5 and 8) and SMAD4) form a heterocomplex that enters the nucleus where it acts as a transcription factor, inducing the expression of a range of proteins which affect tumor growth (see FIG. 1; L. TGF-β=Latent TGF-β; PR=Proteasome; PH=Phosphatase; Co—R=Co-repressors; Co-A=Co-activators). The term "TGF-β cellular signaling pathway" herein refers to a signaling process triggered by TGF-β binding to the extracellular TGF receptor causing the intracellular SMAD cascade, which ultimately leads to the formation of a SMAD complex that acts as a transcription factor.

A number of anti-TGF-β therapies are in preclinical or clinical development (see Yingling J. M. et al., "Development of TGF-β signaling inhibitors for cancer therapy", *Nature Reviews Drug Discovery*, Vol. 3, No. 12, 2004, pages 1011 to 1022; Nacif and Shaker, "Targeting Transforming Growth Factor-B (TGF-β) in Cancer and Non-Neoplastic Diseases"; Journal of Cancer Therapy, 2014, 5, 735-747).

However, physicians must use caution in administering an anti-TGF-β drug to a patient with a tumor, including cancer, because in some tumors, TGF-β is playing a tumor suppressing role. It is therefore important to be able to more accurately assess the functional state of the TGF-β cellular signaling pathway at specific points in disease progression. For example, the TGF-β cellular signaling pathway, with respect to cancer, is more likely to be tumor-promoting in its active state and tumor-suppressing in its passive state. Notwithstanding, it can be difficult to discern the difference in a diseased cell.

It is therefore an object of the invention to provide a more accurate process to determine the tumorigenic propensity of the TGF-β cellular signaling pathway in a cell, as well as associated methods of therapeutic treatment, kits, systems, etc.

SUMMARY OF THE INVENTION

The present invention includes methods and apparatuses for determining the activity level of a TGF-β cellular signaling pathway in a subject, typically a human with diseased tissue such as a tumor or cancer, wherein the activity level of the TGF-β cellular signaling pathway is determined by calculating a level of TGF-β transcription factor element in a sample of the involved tissue isolated from the subject, wherein the level of the TGF-β transcription factor element in the sample are determined by measuring the expression levels of a unique set of target genes controlled by the TGF-β transcription factor element using a calibrated pathway model that compares the expression levels of the target genes in the sample with expression levels of the target genes in the calibrated pathway model.

In particular, the unique set of target genes whose expression level is analyzed in the model includes at least three target genes, at least four target genes, at least five target genes, at least six target genes, at least seven target genes, at least eight target genes, at least nine target genes, at least ten target genes or more selected from ANGPTL4, CDC42EP3, CDKN1A, CDKN2B, CTGF, GADD45A, GADD45B, HMGA2, ID1, IL11, SERPINE1, INPP5D, JUNB, MMP2, MMP9, NKX2-5, OVOL1, PDGFB, PTHLH, SGK1, SKIL, SMAD4, SMAD5, SMAD6, SMAD7, SNAIL SNAI2, TIMP1, and VEGFA. In one embodiment, the unique set of target genes whose expression level is analyzed in the model includes ANGPTL4 and CDC42EP3, and at least one or more, for example, two, three, four, five, six, seven or more of CDKN1A, CTGF, GADD45A, GADD45B, HMGA2, ID1, IL11, SERPINE1, JUNB, PDGFB, PTHLH, SGK1, SKIL, SMAD4, SMAD5, SMAD6, SMAD7, SNAI2, and VEGFA. In one embodiment, the unique set of target genes is ANGPTL4 and CDC42EP3, and at least one or more, for example, two, three, four, five, six, seven, eight, nine, or ten target genes selected from CDKN1A, CTGF, GADD45B, ID1, IL11, JUNB, PDGFB, SKIL, SMAD7, and SNAI2. In one embodiment, the unique set of target genes is ANGPTL4 and CDC42EP3, and at least one or more, for example, two, three, four, five, six, seven, eight, nine, or ten of target genes selected from CDKN1A, CTGF, GADD45B, ID1, SERPINE1, JUNB, VEGFA, SKIL, SMAD7, and SNAI2. In one embodiment, the target genes analyzed include at least ANGPTL4, CDC42EP3, ID1, SERPINE1, JUNB, SKIL, and SMAD7.

Using this invention, health care providers will be able to more accurately assess the functional state of the TGF-β cellular signaling pathway at specific points in disease progression. Without being bound by any particular theory, it is believed that the identified target genes of the present invention in combination with the analytical methods described herein reduces the noise associated with the use of large subsets of target genes as previously described in the literature. Furthermore, as described and exemplified below, the use of specific combinations of select target genes allows for the precise determination of cellular signaling activity, and allows for an increased accuracy in the determination of disease state and prognosis. Accordingly, such cellular signaling pathway status can be used to, for example but not limited to, identify the presence or absence of disease and/or particular disease state or advancement, identify the presence or absence of a disorder or disease state, identify a particular subtype within a disease or disorder based one the activity level of the TGF-β cellular signaling pathway, derive a course of treatment based on the presence or absence of TGF-β signaling activity for example by administering a TGF-β inhibitor, and/or monitor disease progression in order to, for example, adjust therapeutic protocols based on a predicted drug efficacy in light of the determined activity of the TGF-β cellular signaling pathway in the sample.

The term "TGF-β transcriptional factor element" or "TGF-β TF element" or "TF element" refers to either a protein or protein complex transcriptional factor triggered by the binding of TGF-β to its receptor or an intermediate downstrean signaling agent between the binding of TGF-β to its receptor and the final transcriptional factor protein or protein complex. It is known that TGF-β binds to an extracellular TGF-β receptor that initiates an intracellular "SMAD" signaling pathway and that various SMAD proteins (receptor-regulated or R-SMADs (SMAD 1, 2, 3, 5 and 8) and SMAD4) can form a heterocomplex.

The present invention is based on the realization of the inventors that a suitable way of identifying effects occurring in the TGF-β cellular signaling pathway can be based on a measurement of the signaling output of the TGF-β cellular signaling pathway, which is—amongst others—the transcription of the unique target genes described herein by a TGF-β transcription factor (TF) element controlled by the TGF-β cellular signaling pathway. This realization by the inventors assumes that the TF level is at a quasi-steady state in the sample which can be detected by means of—amongst others—the expression values of the target genes. The TGF-β cellular signaling pathway targeted herein is known to control many functions in many cell types in humans, such as proliferation, differentiation and wound healing. Regarding pathological disorders, such as cancer (e.g., colon, pancreatic, lung, brain or breast cancer), the TGF-β cellular signaling pathway plays two opposite roles, either as a tumor suppressor or as a tumor promoter, which is detectable in the expression profiles of the target genes and thus exploited by means of a mathematical model.

The present invention makes it possible to determine the activity level of the TGF-β cellular signaling pathway in a subject by (i) determining a level of a TGF-β TF element in a sample from the subject, wherein the determining is based at least in part on evaluating a mathematical model relating expression levels of one or more target gene(s) of the TGF-β cellular signaling pathway, the transcription of which is controlled by the TGF-β TF element, to the level of the TGF-β TF element, and by (ii) calculating the activity of the TGF-β cellular signaling pathway in the subject based on the determined level of the TGF-β TF element in the sample of the subject. In certain embodiments, the calculated activity level of the TGF-β cellular signaling pathway is indicative of an active TGF-β cellular signaling pathway. This, for example, allows improving the possibilities of characterizing subjects that have a particular disease or disease subtype, for example a cancer, e.g., a colon, pancreatic, lung, brain, or breast cancer, which is at least partially driven by a tumor-promoting activity of the TGF-β cellular signaling pathway, and that are therefore likely to respond to inhibitors of the TGF-β cellular signaling pathway or other appropriate treatments for the classified disorder. In particular embodiments, treatment determination can be based on specific TGF-β activity. In a particular embodiment the TGF-β cellular signaling status can be set at a cutoff value of odds of the TGF-β cellular signaling pathway being activate of, for example, 10:1, 5:1, 4:1, 2:1, 1:1, 1:2, 1:4, 1:5, or 1:10.

In one aspect of the invention, provided herein is a method of determining a TGF-β cellular signaling pathway activity in a subject, for example a human, comprising the steps of:

a. calculating a level of TGF-β transcription factor element in a sample isolated from the subject, wherein the level of the TGF-β transcription factor element in the sample is associated with TGF-β cellular signaling, and wherein the activity level of the TGF-β transcription factor element in the sample are calculated by:
  i. receiving data on the expression levels of at least three or more, for example, at least four, at least five, at least six, at least seven or more target genes isolated from the sample, wherein the TGF-β transcription factor element controls transcription of the at least three or more target genes,
  ii. calculating the levels of a TGF-β transcription factor element in the sample using a calibrated pathway model, wherein the calibrated pathway model compares the expression levels of the at least three or more target genes in the sample with expression levels of the at least three or more target genes in the calibrated pathway model which defines an activity level of a TGF-β transcription factor element; and,
b. calculating the activity level of the TGF-β cellular signaling pathway in the sample based on the calculated level of TGF-β transcription factor element in the sample.

In one embodiment, the method further comprises assigning a TGF-β cellular signaling pathway activity status to the calculated activity level of the TGF-β cellular signaling pathway in the sample wherein the activity status is indicative of either an active TGF-β cellular signaling pathway or a passive TGF-β cellular signaling pathway. In one embodiment, the status of the TGF-β cellular signaling pathway is established by establishing a specific threshold for activity as described further below. In one embodiment, the threshold is set as a probability that the cellular signaling pathway is active, for example, a 10:1, 5:1, 4:1, 3:1, 2:1, 1:1, 1:2, 1:4, 1:5, or 1:10. In one embodiment, the activity status is based, for example, on a minimum calculated activity. In one embodiment, the method further comprises assigning to the calculated TGF-β cellular signaling in the sample a probability that the TGF-β cellular signaling pathway is active.

As contemplated herein, the level of the TGF-β transcription factor element is determined using a calibrated pathway model executed by one or more computer processors, as further described below. The calibrated pathway model compares the expression levels of the at least three target genes in the sample with expression levels of the at least three target genes in the calibrated pathway model which define a level of a TGF-β transcription factor element. In one embodiment, the calibrated pathway model is a probabilistic model incorporating conditional probabilistic relationships that compare the expression levels of the at least three target genes in the sample with expression levels of the at least three target genes in the model which define a level of a TGF-β transcription factor element to determine the level of the TGF-β transcription factor element in the sample. In one embodiment, the probabilistic model is a Bayesian network model. In an alternative embodiment, the calibrated pathway model can be a linear or pseudo-linear model. In an embodiment, the linear or pseudo-linear model is a linear or pseudo-linear combination model.

As contemplated herein, the expression levels of the unique set of target genes can be determined using standard methods known in the art. For example, the expression levels of the target genes can be determined by measuring the level of mRNA of the target genes, through quantitative reverse transcriptase-polymerase chain reaction techniques, using probes associated with a mRNA sequence of the target genes, using a DNA or RNA microarray, and/or by measuring the protein level of the protein encoded by the target genes. Once the expression level of the target genes is determined, the expression levels of the target genes within the sample can be utilized in the model in a raw state or, alternatively, following normalization of the expression level data. For example, expression level data can be normalized by transforming it into continuous data, z-score data, discrete data, or fuzzy data.

As contemplated herein, the calculation of TGF-β signaling in the sample is performed on a computerized device having a processor capable of executing a readable program code for calculating the TGF-β signaling in the sample according to the methods described above. Accordingly, the computerized device can include means for receiving expression level data, wherein the data is expression levels of at least three target genes derived from the sample, a means for calculating the level of a TGF-β transcription factor element in the sample using a calibrated pathway model, wherein the calibrated pathway model compares the expression levels of the at least three target genes in the sample with expression levels of the at least three target genes in the model which define a level a TGF-β transcription factor element; a means for calculating the TGF-β cellular signaling in the sample based on the calculated levels of a TGF-β transcription factor element in the sample; and a means for assigning a TGF-β cellular signaling pathway activity probability or status to the calculated TGF-β cellular signaling in the sample, and, optionally, a means for displaying the TGF-β signaling pathway activity probability or status.

In accordance with another disclosed aspect, further provided herein is a non-transitory storage medium capable of storing instructions that are executable by a digital processing device to perform the method according to the present invention as described herein. The non-transitory storage medium may be a computer-readable storage medium, such as a hard drive or other magnetic storage medium, an optical disk or other optical storage medium, a random access memory (RAM), read only memory (ROM), flash memory, or other electronic storage medium, a network server, or so forth. The digital processing device may be a handheld device (e.g., a personal data assistant or smartphone), a notebook computer, a desktop computer, a tablet computer or device, a remote network server, or so forth.

Further contemplated herein are methods of treating a subject having a disease or disorder associated with an activated TGF-β cellular signaling pathway, or a disorder whose advancement or progression is exacerbated or caused by, wether partially or wholly, an activated TGF-β cellular signaling pathway, wherein the determination of the TGF-β cellular signaling pathway activity is based on the methods described above, and administering to the subject a TGF-β inhibitor if the information regarding the activity level of TGF-β cellular signaling pathway is indicative of an active TGF-β cellullar signaling pathway. In one embodiment, the disorder is one of an auto-immune and other immune disorders, cancer, bronchial asthma, heart disease, diabetes, hereditary hemorrhagic telangiectasia, Marfan syndrome, Vascular Ehlers-Danlos syndrome, Loeys-Dietz syndrome, Parkinson's disease, Chronic kidney disease, Multiple Sclerosis, fibrotic diseases such as liver, lng, or kidney fibrosis, Dupuytren's disease, or Alzheimer's disease. In a particular embodiment, the subject is suffering from a cancer, for example, a breast cancer, lung cancer, a colon cancer, pancreatic cancer, brain cancer, or breast cancer. In a more particular embodiment, the cancer is a breast cancer.

Also contemplated herein is a kit for measuring the expression levels of at least three or more TGF-β cellular signaling pathway target genes, for example, four, five, six, seven, eight, nine, ten, eleven, twelve, or more target genes as described herein. In one embodiment, the kit includes one or more components, for example probes, for example labeled probes, and/or PCR primers, for measuring the expression levels of at least three target genes, at least four target genes, at least five target genes, or at least six or more target genes selected from ANGPTL4, CDC42EP3, CDKN1A, CDKN2B, CTGF, GADD45A, GADD45B, HMGA2, ID1, IL11, SERPINE1, INPP5D, JUNB, MMP2, MMP9, NKX2-5, OVOL1, PDGFB, PTHLH, SGK1, SKIL, SMAD4, SMAD5, SMAD6, SMAD7, SNAIL SNAI2, TIMP1, and VEGFA. In one embodiment, the kit includes one or more components for measuring the expression levels of the target genes ANGPTL4 and CDC42EP3, and at least one or more, for example, two, three, four, five, six, seven, or more of CDKN1A, CTGF, GADD45A, GADD45B, HMGA2, ID1, IL11, SERPINE1, JUNB, PDGFB, PTHLH, SGK1, SKIL, SMAD4, SMAD5, SMAD6, SMAD7, SNAI2, and VEGFA. In one embodiment, the kit includes one or more components for measuring the expression levels of the target genes ANGPTL4 and CDC42EP3, and at least one or more, for example, two, three, four, five, six, seven, eight, nine, or ten target genes selected from CDKN1A, CTGF, GADD45B, ID1, IL11, JUNB, PDGFB, SKIL, SMAD7, and SNAI2.

In one embodiment, the kit includes one or more components for measuring the expression levels of the target genes ANGPTL4 and CDC42EP3, and at least one or more, for example, two, three, four, five, six, seven, eight, nine, or ten of target genes selected from CDKN1A, CTGF, GADD45B, ID1, SERPINE1, JUNB, VEGFA, SKIL, SMAD7, and SNAI2. In one embodiment, the kit includes one or more components for measuring the expression levels of at least the target genes ANGPTL4, CDC42EP3, ID1, SERPINE1, JUNB, SKIL, and SMAD7.

As contemplated herein, the one or more components or means for measuring the expression levels of the particular target genes can be selected from the group consisting of: an DNA array chip, an oligonucleotide array chip, a protein array chip, an antibody, a plurality of probes, for example, labeled probes, a set of RNA reverser-transcriptase sequencing components, and/or RNA or DNA, including cDNA, amplification primers. In one embodiment, the kit includes a set of labeled probes directed to a portion of an mRNA or cDNA sequence of the targeted genes as described herein. In one embodiment, the kit includes a set of primers and probes directed to a portion of an mRNA or cDNA sequence of the targeted genes as described further below, for example, a set of specific primers or probes selected from the sequences of Table 1 or Table 2. In one embodiment, the labeled probes are contained in a standardized 96-well plate. In one embodiment, the kit further includes primers or probes directed to a set of reference genes, for example, as represented in Table 3. Such reference genes can be, for example, constitutively expressed genes useful in normalizing or standardizing expression levels of the target gene expression levels described herein.

In one embodiment, the kit further includes a non-transitory storage medium containing instructions that are executable by a digital processing device to perform a method according to the present invention as described herein. In one embodiment, the kit includes an identification code that provides access to a server or computer network for analyzing the activity level of the TGF-β cellular signaling pathway based on the expression levels of the target genes and the methods described herein.

In one aspect of the invention, provided herein is a method for calculating activity of a TGF-β cellular signaling pathway using mathematical modelling of target gene expressions, namely a method comprising:

inferring activity of a TGF-β cellular signaling pathway in a subject based at least on expression levels of one or more target gene(s) of the TGF-β cellular signaling pathway measured in a sample of the subject, wherein the calculating comprises:

inferring a level of a TGF-β transcription factor (TF) element in the sample of the subject, the TGF-β TF element controlling transcription of the one or more target gene(s) of the TGF-β cellular signaling pathway, the determining being based at least in part on evaluating a mathematical model relating expression levels of the one or more target gene(s) of the TGF-β cellular signaling pathway to the level of the TGF-β TF element;

inferring the activity of the TGF-β cellular signaling pathway in the subject based on the determined level of the TGF-β TF element in the sample of the subject, wherein the calculating is performed by a digital processing device using the mathematical model.

DETAILED DESCRIPTION OF THE INVENTION

Figure 1:
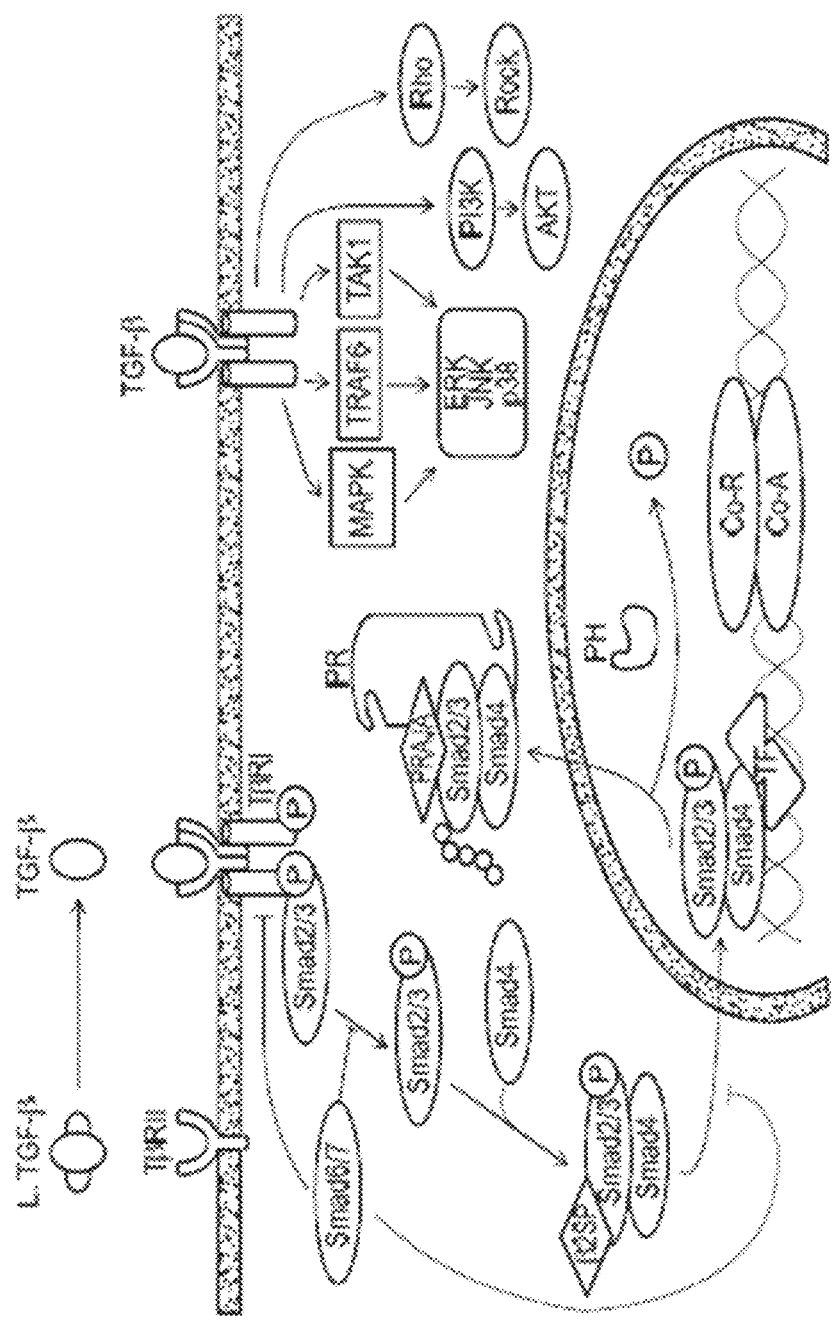
FIG. 1 shows schematically and exemplarily TGF-β signaling through the canonical cellular signaling pathway (left part) which is initiated upon binding of the TGF-β protein to the receptor. The initiated cellular signaling pathway ultimately results in the translocation of SMAD2/3 and SMAD4 to the nucleus and binding to the DNA thereby starting target gene transcription (see Sheen Y. Y. et al., "Targeting the transforming growth factor-β signaling in cancer therapy", Biomolecules and Therapeutics, Vol. 21, No. 5, 2013, pages 323 to 331).

Provided herein are methods and apparatuses, and in particular computer implemented methods and apparatuses, for determining the activity levels of a TGF-β cellular signaling pathway in a subject, wherein the TGF-β cellular signaling is calculated by a) calculating an activity level of TGF-β transcription factor element in a sample isolated from a subject, and wherein the activity levels of the TGF-β transcription factor element in the sample is calculated by measuring the expression levels of a unique set of target genes, wherein the TGF-β transcription factor element controls transcription of the target genes, calculating the levels of the TGF-β transcription factor element in the sample using a calibrated pathway model, wherein the calibrated pathway model compares the expression levels of the target genes in the sample with expression levels of the target genes in the calibrated pathway model which define a level of a TGF-β transcription factor element; and calculating the TGF-β cellular signaling in the sample based on the calculated levels of TGF-β transcription factor element in the sample.

In particular, the unique set of target genes whose expression levels is analyzed in the model includes at least three or more genes, for example, three, four, five, six, or seven target genes selected from ANGPTL4, CDC42EP3, ID1, IL11, SERPINE1, JUNB, SKIL, or SMAD7. It has been discovered that analyzing a specific set of target genes as described herein in the disclosed pathway model provides for an advantageously accurate TGF-β cellular signaling pathway activity determination. Accordingly, such status can be used to, for example but not limited to, identify the presence or absence of disease and/or particular disease state or advancement, diagnose a specific disease or disease state, or diagnose the presence or absence of a particular disease, derive a course of treatment based on the presence or absence of TGF-β signaling activity, monitor disease progression in order to, for example, adjust therapeutic protocols based on a predicted drug efficacy in light of the determined activity of the TGF-β signaling pathway in the sample, or develop TGF-β targeted therapeutics.

Definitions

All terms used herein are intended to have their plain and ordinary meaning as normally ascribed in the art unless otherwise specifically indicated herein.

Herein, the "level" of a TF element denotes the level of activity of the TF element regarding transcription of its target genes.

The term "subject" or "host", as used herein, refers to any living being. In some embodiments, the subject is an animal, for example a mammal, including a human. In a particular embodiment, the subject is a human. In one embodiment, the human is suspected of having a disorder mediated or exacerbated by an active TGF-β cellular signaling pathway, for example, a cancer. In one embodiment, the human has or is suspected of having a breast cancer.

The term "sample", as used herein, means any biological specimen isolated from a subject. Accordingly, "sample" as used herein is contemplated to encompasses the case where e.g. a tissue and/or cells and/or a body fluid of the subject have been isolated from the subject. Performing the claimed method may include where a portion of this sample is extracted, e.g., by means of Laser Capture Microdissection (LCM), or by scraping off the cells of interest from the slide, or by fluorescence-activated cell sorting techniques. In addition, the term "sample", as used herein, also encompasses the case where e.g. a tissue and/or cells and/or a body fluid of the subject has been taken from the subject and has been put on a microscope slide, and the claimed method is performed on the slide. In addition, the term "samples," as used herein, may also encompass circulating tumor cells or CTCs.

The term "TGF-β transcription factor element" or "TGF-β TF element" or "TF element" refers to a signaling agent downstream of the binding of TGF-β to its receptor which controls target gene expression, which may be a transcription factor protein or protein complex or a precursor of an active transcription protein complex. It can be, in embodiments, a signaling agent triggered by the binding of TGF-β to its receptor downstream of TGF-β extracellular receptor binding and upstream of the formation of the active transcription factor protein complex. For example, it is known that when TGF-β binds to an extracellular TGF-β receptor, it initiates an intracellular "SMAD" signaling pathway and that one or more SMAD proteins (for example receptor-regulated or R-SMADs (SMAD 1, 2, 3, 5 and 8) and SMAD4) participate in, and may form a heterocomplex which participates in, the TGF-β transcription signaling cascade which controls expression.

The term "target gene" as used herein, means a gene whose transcription is directly or indirectly controlled by a TGF-β transcription factor element. The "target gene" may be a "direct target gene" and/or an "indirect target gene" (as described herein).

As contemplated herein, target genes include at least ANGPTL4, CDC42EP3, CDKN1A, CDKN2B, CTGF, GADD45A, GADD45B, HMGA2, ID1, IL11, SERPINE1, INPP5D, JUNB, MMP2, MMP9, NKX2-5, OVOL1, PDGFB, PTHLH, SGK1, SKIL, SMAD4, SMAD5, SMAD6, SMAD7, SNAI1, SNAI2, TIMP1, and VEGFA.

As contemplated herein, the present invention includes:
A) A computer implemented method for determining the activity level of a TGF-β cellular signaling pathway in a subject performed by a computerized device having a processor comprising:
   a. calculating an activity level a TGF-β transcription factor element in a sample isolated from the subject, wherein the activity level of the TGF-β transcription factor element in the sample is calculated by:
      i. receiving data on the expression levels of at least three target genes derived from the sample, wherein the TGF-β transcription factor element controls transcription of the at least three target genes, and wherein the at least three target genes are selected from CDC42EP3, ANGPTL4, ID1, IL11, SERPINE1, JUNB, SKIL, and SMAD7;
      ii. calculating the activity level of the TGF-β transcription factor element in the sample using a calibrated pathway model, wherein the calibrated pathway model compares the expression levels of the at least three target genes in the sample with expression levels of the at least three target genes in the model which define an activity level of the TGF-β transcription factor element; and,
   b. calculating the activity level of the TGF-β cellular signaling pathway in the sample based on the calculated activity levels of TGF-β transcription factor element in the sample.

In one embodiment, the method further comprises assigning a TGF-β cellular signaling pathway activity status to the calculated activity level of the TGF-β cellular signaling in the sample, wherein the activity status is indicative of either an active TGF-β cellular signaling pathway or a passive TGF-β cellular signaling pathway. In one embodiment, the method further comprises displaying the TGF-β cellular signaling pathway activity status. In one embodiment, the at least three target genes are ANGPTL4, and at least two of CDC42EP3, ID1, IL11, SERPINE1, JUNB, SKIL, or SMAD7. In one embodiment, the at least three target genes are ANGPTL4, CDC42EP3, and at least one of ID1, IL11, SERPINE1, JUNB, SKIL, or SMAD7. In one embodiment, data on the expression levels of the target genes ANGPTL4, CDC42EP3, ID1, IL11, JUNB, SKIL, and SMAD7 is received. In one embodiment, data on the expression levels of the target genes ANGPTL4, CDC42EP3, ID1, SERPINE1, JUNB, SKIL, and SMAD7 is received. In one embodiment, data on at least one additional target gene selected from CDKN1A, CTGF, GADD45B, PDGFB, VEGFA, and SNAI2 is received. In one embodiment, data on the expression levels of the additional target genes CDKN1A, CTGF, GADD45B, PDGFB, and SNAI2 is received. In one embodiment, data on the expression levels of the additional target genes CDKN1A, CTGF, GADD45B, VEGFA, and SNAI2 is received. In one embodiment, data on at least one additional target gene selected from CDKN1A, CTGF, GADD45B, PDGFB, VEGFA, and SNAI2 is received. In one embodiment, data on the expression levels of the additional target genes CDKN1A, CTGF, GADD45B, PDGFB, and SNAI2 is received. In one embodiment, data on the expression levels of the additional target genes CDKN1A, CTGF, GADD45B, VEGFA, and SNAI2 is received. In one embodiment, data on the expression levels of the additional target genes CDKN2B, GADD45A, HMGA2, INPP5D, MMP2, MMP9, NKX2-5, OVOL1, PTHLH, SGK1, SMAD4, SMAD5, SMAD6, SNAI1, and TIMP1 is received. In one embodiment, data on the expression levels of the additional target genes CDKN2B, GADD45A, HMGA2, INPP5D, MMP2, MMP9, NKX2-5, OVOL1, PTHLH, SGK1, SMAD4, SMAD5, SMAD6, SNAIL and TIMP1 is received. In one embodiment, data on the expression levels of the additional target genes CDKN2B, GADD45A, HMGA2, INPP5D, MMP2, MMP9, NKX2-5, OVOL1, PTHLH, SGK1, SMAD4, SMAD5, SMAD6, SNAI1, and TIMP1 is received. In one embodiment, data on the expression levels of the additional target genes CDKN2B, GADD45A, HMGA2, INPP5D, MMP2, MMP9, NKX2-5, OVOL1, PTHLH, SGK1, SMAD4, SMAD5, SMAD6, SNAIL and TIMP1 is received. In one embodiment, the calibrated pathway model is a probabilistic model incorporating conditional probabilistic relationships that compare the expression levels of the at least three target genes in the sample with expression levels of the at least three target genes in the model which define a level of TGF-β transcription factor element to determine the activity level of the TGF-β transcription factor element in the sample. In one embodiment, the probabilistic model is a Bayesian network model. In one embodiment, the calibrated pathway model is a linear model incorporating relationships that compare the expression levels of the at least three target genes in the sample with expression levels of the at least three target genes in the model which define a level of TGF-β transcription factor element to determine the activity level of the TGF-β transcription factor element in the sample.

B) A computer program product for determining the activity level of a TGF-β cellular signaling pathway in a subject comprising
   a. a non-transitory computer readable storage medium having computer readable program code embodied therewith, the computer readable program code executable by at least one processor to:

i. calculate a level of TGF-β transcription factor element in a sample isolated from a subject, wherein the level of the TGF-β transcription factor element in the sample is calculated by:
  1. receiving data on the expression levels of at least three target genes derived from the sample, wherein the at least three target genes are selected from CDC42EP3, ANGPTL4, ID1, IL11, SERPINE1, JUNB, SKIL, and SMAD7;
  2. calculating the level of the TGF-β transcription factor element in the sample using a calibrated pathway model, wherein the calibrated pathway model compares the expression levels of the at least three target genes in the sample with expression levels of the at least three target genes in the model which define an activity level of TGF-β transcription factor element; and,
ii. calculate the activity level of the TGF-β cellular signaling pathway in the sample based on the calculated TGF-β transcription factor element level in the sample.

In one embodiment, the computer readable program code is executable by at least one processor to assign a TGF-β cellular signaling pathway activity status to the calculated activity level of the TGF-β cellular signaling in the sample, wherein the activity status is indicative of either an active TGF-β cellular signaling pathway or a passive TGF-β cellular signaling pathway. In one embodiment, the computer readable program code is executable by at least one processor to display the TGF-β signaling pathway activity status. In one embodiment, the at least three target genes are ANGPTL4, and at least two of CDC42EP3, ID1, IL11, SERPINE1, JUNB, SKIL, or SMAD7. In one embodiment, the at least three target genes are ANGPTL4, CDC42EP3, and at least one of ID1, IL11, SERPINE1, JUNB, SKIL, or SMAD7. In one embodiment, the data on the expression levels of the target genes ANGPTL4, CDC42EP3, ID1, IL11, JUNB, SKIL, and SMAD7 is received. In one embodiment, the data on the expression levels of the target genes ANGPTL4, CDC42EP3, ID1, SERPINE1, JUNB, SKIL, and SMAD7 is received. In one embodiment, data on at least one additional target gene selected from CDKN1A, CTGF, GADD45B, PDGFB, VEGFA, and SNAI2 is received. In one embodiment, data on the expression levels of the additional target genes CDKN1A, CTGF, GADD45B, PDGFB, and SNAI2 is received. In one embodiment, data on the expression levels of the additional target genes CDKN1A, CTGF, GADD45B, VEGFA, and SNAI2 is received. In one embodiment, data on at least one additional target gene selected from CDKN1A, CTGF, GADD45B, PDGFB, VEGFA, and SNAI2 is received. In one embodiment, data on the expression levels of the additional target genes CDKN1A, CTGF, GADD45B, PDGFB, and SNAI2 is received. In one embodiment, data on the expression levels of the additional target genes CDKN1A, CTGF, GADD45B, VEGFA, and SNAI2 is received. In one embodiment, data on the expression levels of at least one additional target gene selected from CDKN2B, GADD45A, HMGA2, INPP5D, MMP2, MMP9, NKX2-5, OVOL1, PTHLH, SGK1, SMAD4, SMAD5, SMAD6, SNAI1, and TIMP1 is received. In one embodiment, data on the expression levels of at least one additional target gene selected from CDKN2B, GADD45A, HMGA2, INPP5D, MMP2, MMP9, NKX2-5, OVOL1, PTHLH, SGK1, SMAD4, SMAD5, SMAD6, SNAI1, and TIMP1 is received. In one embodiment, data on the expression levels of at least one additional target gene selected from CDKN2B, GADD45A, HMGA2, INPP5D, MMP2, MMP9, NKX2-5, OVOL1, PTHLH, SGK1, SMAD4, SMAD5, SMAD6, SNAIL and TIMP1 is received. In one embodiment, data on the expression levels of at least one additional target gene selected from CDKN2B, GADD45A, HMGA2, INPP5D, MMP2, MMP9, NKX2-5, OVOL1, PTHLH, SGK1, SMAD4, SMAD5, SMAD6, SNAIL and TIMP1 is received. In one embodiment, the calibrated pathway model is a probabilistic model incorporating conditional probabilistic relationships that compare the expression levels of the at least three target genes in the sample with expression levels of the at least three target genes in the model which define a level of TGF-β transcription factor element to determine the activity level of TGF-β transcription factor element in the sample. In one embodiment, the probabilistic model is a Bayesian network model. In one embodiment, the calibrated pathway model is a linear model incorporating relationships that compare the expression levels of the at least three target genes in the sample with expression levels of the at least three target genes in the model which define a level of TGF-β transcription factor element to determine the activity level of aTGF-β transcription factor element in the sample.

C) A method of treating a subject suffering from a disease associated with an activated TGF-β cellular signaling pathway comprising:
  a. receiving information regarding the activity level of a TGF-β cellular signaling pathway derived from a sample isolated from the subject, wherein the activity level of the TGF-β cellular signaling pathway is determined by:
    i. calculating an activity level of TGF-β transcription factor element in a sample isolated from the subject, wherein the level of the TGF-β transcription factor element in the sample is calculated by:
      1. receiving data on the expression levels of at least three target genes derived from the sample, wherein the TGF-β transcription factor element controls transcription of the at least three target genes, and wherein the at least three target genes are selected from CDC42EP3, ANGPTL4, ID1, IL11, SERPINE1, JUNB, SKIL, and SMAD7;
      2. calculating the level of the TGF-β transcription factor element in the sample using a calibrated pathway model, wherein the calibrated pathway model compares the expression levels of the at least three target genes in the sample with expression levels of the at least three target genes in the model which define an activity level of the TGF-β transcription factor element; and,
    ii. calculating the activity level of the TGF-β cellular signaling pathway in the sample based on the calculated TGF-β transcription factor element level in the sample; and,
  b. administering to the subject a TGF-β inhibitor if the information regarding the activity level of the TGF-β cellular signaling pathway is indicative of an pathogenically active TGF-β cellular signaling pathway.

In one embodiment, the at least three target genes are ANGPTL4, and at least two of CDC42EP3, ID1, IL11, SERPINE1, JUNB, SKIL, or SMAD7. In one embodiment, the at least three target genes are ANGPTL4, CDC42EP3, and at least one of ID1, IL11, SERPINE1, JUNB, SKIL, or SMAD7. In one embodiment, data on the expression levels of the target genes ANGPTL4, CDC42EP3, ID1, IL11, JUNB, SKIL, and SMAD7 is received. In one embodiment, data on the expression levels of the target genes ANGPTL4, CDC42EP3, ID1, SERPINE1, JUNB, SKIL, and SMAD7 is received. In one embodiment, data on at least one additional target gene selected from CDKN1A, CTGF, GADD45B, PDGFB, VEGFA, and SNAI2 is received. In one embodiment, data on the expression levels of the additional target genes CDKN1A, CTGF, GADD45B, PDGFB, and SNAI2 is received. In one embodiment, data on the expression levels of the additional target genes CDKN1A, CTGF, GADD45B, VEGFA, and SNAI2 is received. In one embodiment, data on at least one additional target gene selected from CDKN1A, CTGF, GADD45B, PDGFB, VEGFA, and SNAI2 is received. In one embodiment, data on the expression levels of the additional target genes CDKN1A, CTGF, GADD45B, PDGFB, and SNAI2 is received. In one embodiment, data on the expression levels of the additional target genes CDKN1A, CTGF, GADD45B, VEGFA, and SNAI2 is received. In one embodiment, data on the expression levels of the additional target genes CDKN2B, GADD45A, HMGA2, INPP5D, MMP2, MMP9, NKX2-5, OVOL1, PTHLH, SGK1, SMAD4, SMAD5, SMAD6, SNAI1, and TIMP1 is received. In one embodiment, data on the expression levels of the additional target genes CDKN2B, GADD45A, HMGA2, INPP5D, MMP2, MMP9, NKX2-5, OVOL1, PTHLH, SGK1, SMAD4, SMAD5, SMAD6, SNAIL and TIMP1 is received. In one embodiment, data on the expression levels of the additional target genes CDKN2B, GADD45A, HMGA2, INPP5D, MMP2, MMP9, NKX2-5, OVOL1, PTHLH, SGK1, SMAD4, SMAD5, SMAD6, SNAI1, and TIMP1 is received. In one embodiment, data on the expression levels of the additional target genes CDKN2B, GADD45A, HMGA2, INPP5D, MMP2, MMP9, NKX2-5, OVOL1, PTHLH, SGK1, SMAD4, SMAD5, SMAD6, SNAIL and TIMP1 is received. In one embodiment, the calibrated pathway model is a probabilistic model incorporating conditional probabilistic relationships that compare the expression levels of the at least three target genes in the sample with expression levels of the at least three target genes in the model which define a level of TGF-β transcription factor element to determine the activity level of the TGF-β transcription factor element in the sample. In one embodiment, the probabilistic model is a Bayesian network model. In one embodiment, the calibrated pathway model is a linear model incorporating relationships that compare the expression levels of the at least three target genes in the sample with expression levels of the at least three target genes in the model which define a level of TGF-β transcription factor element to determine the activity level of the TGF-β transcription factor element in the human cancer sample. In illustrative embodiment, the TGF-β inhibitor is Terameprocol, Fresolimumab, Sotatercept, Galunisertib, SB431542, LY2109761, LDN-193189, SB525334, SB505124, GW788388, LY364947, RepSox, LDN-193189 HCl, K02288, LDN-214117, SD-208, EW-7197, ML347, LDN-212854, DMH1, Pirfenidone, Hesperetin, Trabedersen, Lerdelimumab, Metelimumab, trx-SARA, ID11, Ki26894, or SB-431542. In one embodiment, the disease is a cancer. In one embodiment, the cancer is colon, breast, prostate, pancreatic, lung, brain, leukemia, lymphoma, or glioma. In one embodiment, the cancer is breast cancer.

D) A kit for measuring expression levels of TGF-β cellular signaling pathway target genes comprising:
  a. a set of polymerase chain reaction primers directed to at least six TGF-β cellular signaling pathway target genes from a sample isolated from a subject; and
  b. a set of probes directed to the at least six TGF-β cellular signaling pathway target genes;

wherein the at least six TGF-β cellular signaling pathway target genes are selected from CDC42EP3, ANGPTL4, ID1, SERPINE1, JUNB, SKIL, and SMAD7.

In one embodiment, the at least six target genes are ANGPTL4, and at least five of CDC42EP3, ID1, IL11, SERPINE1, JUNB, SKIL, or SMAD7. In one embodiment, the at least six target genes are ANGPTL4, CDC42EP3, and at least four of ID1, IL11, SERPINE1, JUNB, SKIL, or SMAD7. In one embodiment, the target genes are ANGPTL4, CDC42EP3, ID1, IL11, JUNB, SKIL, and SMAD7. In one embodiment, the target genes are ANGPTL4, CDC42EP3, ID1, SERPINE1, JUNB, SKIL, and SMAD7. In one embodiment, the kit includes at least one additional set of primers and probes directed to a target gene selected from CDKN1A, CTGF, GADD45B, PDGFB, VEGFA, and SNAI2. In one embodiment, the kit includes additional sets of primers and probes directed to target genes CDKN1A, CTGF, GADD45B, PDGFB, and SNAI2. In one embodiment, the kit includes additional sets of primers and probes directed to target genes CDKN1A, CTGF, GADD45B, VEGFA, and SNAI2. In one embodiment, the kit includes at least one additional set of primers and probes directed to a target gene selected from CDKN1A, CTGF, GADD45B, PDGFB, VEGFA, and SNAI2. In one embodiment, the kit includes additional sets of primers and probes directed to target genes CDKN1A, CTGF, GADD45B, PDGFB, and SNAI2. In one embodiment, the kit includes additional sets of primers and probes directed to target genes CDKN1A, CTGF, GADD45B, VEGFA, and SNAI2. In one embodiment, the kit includes additional sets of primers and probes directed to target genes CDKN2B, GADD45A, HMGA2, INPP5D, MMP2, MMP9, NKX2-5, OVOL1, PTHLH, SGK1, SMAD4, SMAD5, SMAD6, SNAIL and TIMP1. In one embodiment, the kit includes additional sets of primers and probes directed to target genes CDKN2B, GADD45A, HMGA2, INPP5D, MMP2, MMP9, NKX2-5, OVOL1, PTHLH, SGK1, SMAD4, SMAD5, SMAD6, SNAIL and TIMP1. In one embodiment, the kit includes additional sets of primers and probes directed to target genes CDKN2B, GADD45A, HMGA2, INPP5D, MMP2, MMP9, NKX2-5, OVOL1, PTHLH, SGK1, SMAD4, SMAD5, SMAD6, SNAIL and TIMP1. In one embodiment, the kit includes additional sets of primers and probes directed to target genes CDKN2B, GADD45A, HMGA2, INPP5D, MMP2, MMP9, NKX2-5, OVOL1, PTHLH, SGK1, SMAD4, SMAD5, SMAD6, SNAIL and TIMP1. In one embodiment, the probes are labeled. In one embodiment, the set of probes are SEQ. ID. NOS. 74, 77, 80, 83, 86, 89, 92, 95, 98, 101, 104, and 107. In one embodiment, the set of primers are SEQ. ID. NOS. 72 and 73, 75 and 76, 78 and 79, 81 and 82, 84 and 85, 87 and 88, 90 and 91, 93 and 94, 96 and 97, 99 and 100, 102 and 103, and 105 and 106. In one embodiment, a computer program product for determining the activity level of a TGF-β cellular signaling pathway in the subject comprising a non-transitory computer readable storage medium having computer readable program code embodied therewith, the computer readable program code executable by at least one processor to: (i) calculate a level of TGF-β transcription factor element in the sample, wherein the level of the TGF-β transcription factor element in the sample is associated with TGF-β cellular signaling, and wherein the level of the TGF-β transcription factor element in the sample is calculated by: (1) receiving data on the expression levels of the at least six target genes derived from the sample; (2) calculating the level of the TGF-β transcription factor element in the sample using a calibrated pathway model, wherein the calibrated pathway model compares the expression levels of the at least six target genes in the sample with expression levels of the at least six target genes in the model which define an activity level of TGF-β transcription factor element; and, (ii) calculate the activity level of the TGF-β cellular signaling pathway in the sample based on the calculated TGF-β transcription factor element level in the sample.

E) A kit for determining the activity level of a TGF-β cellular signaling pathway in a subject comprising:
   a. one or more components capable of identifying expression levels of at least three TGF-β cellular signaling pathway target genes from a sample of the subject, wherein the at least three TGF-β cellular signaling pathway target genes are selected from CDC42EP3, ANGPTL4, ID1, SERPINE1, JUNB, SKIL, or SMAD7; and,
   b. a non-transitory computer readable storage medium having computer readable program code embodied therewith, the computer readable program code executable by at least one processor to:
      i. calculate a level of TGF-β transcription factor element in the sample, wherein the level of TGF-β transcription factor element in the sample is associated with TGF-β cellular signaling, and wherein the level of the TGF-β transcription factor element in the sample is calculated by:
         1. receiving data on the expression levels of the at least three target genes derived from the sample;
         2. calculating the level of the TGF-β transcription factor element in the sample using a calibrated pathway model, wherein the calibrated pathway model compares the expression levels of the at least three target genes in the sample with expression levels of the at least three target genes in the model which define an activity level of the TGF-β transcription factor element; and,
      ii. calculate the activity level of the TGF-β cellular signaling pathway in the sample based on the calculated TGF-β transcription factor element level in the sample.

Determining the Activity Level of the TGF-β Cellular Signaling Pathway

The present invention provides new and improved methods and apparatuses, and in particular computer implemented methods and apparatuses, as disclosed herein, to assess the functional state or activity of the TGF-β cellular signaling pathway.

In one aspect of the invention, provided herein is a method of determining TGF-β cellular signaling in a subject comprising the steps of:
   a. calculating a level of TGF-β transcription factor element in a sample isolated from a subject, wherein the level of TGF-β transcription factor element in the sample is associated with an activity level of the TGF-β cellular signaling pathway, and wherein the activity level of the TGF-β transcription factor element in the sample is calculated by:
      i. receiving data on the expression levels of at least three or more target genes derived from the sample, wherein the TGF-β transcription factor element controls transcription of the at least three or more target genes,
      ii. calculating the level of TGF-β transcription factor element in the sample using a calibrated pathway model, wherein the calibrated pathway model compares the expression levels of the at least three or more target genes in the sample with expression levels of the at least three or more target genes in the calibrated pathway model which define an activity level of the TGF-β transcription factor element; and,
   b. calculating the activity level of the TGF-β cellular signaling pathway in the sample based on the calculated levels of TGF-β transcription factor element in the sample. As contemplated herein, the method of calculating the activity level of the TGF-β cellular signaling pathway is performed by a computer processor.

Figure 2:
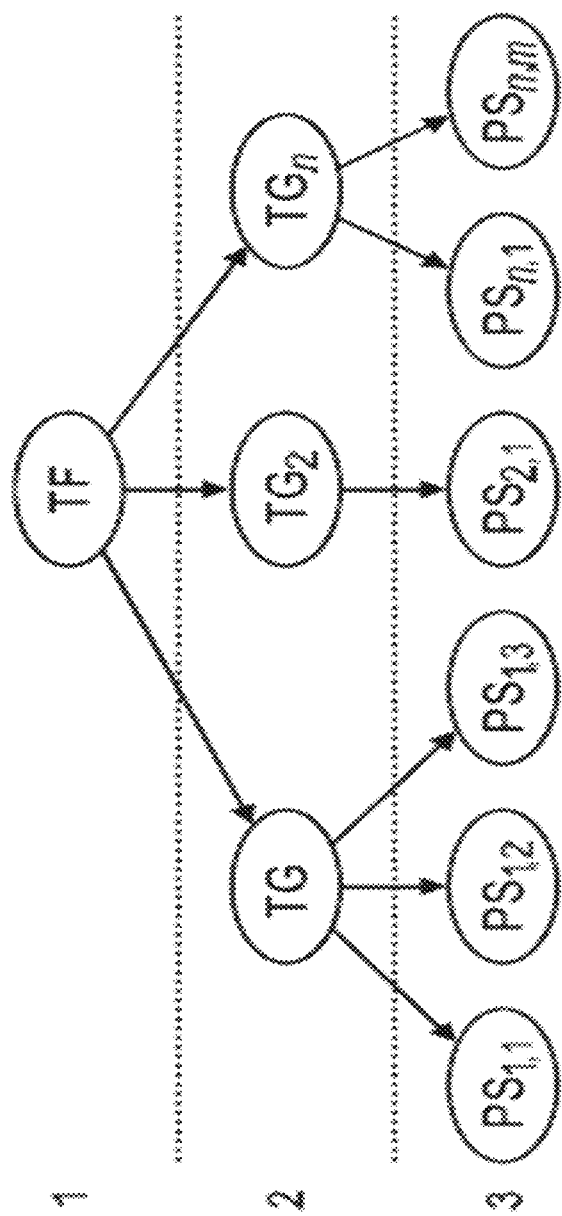
FIG. 2 shows schematically and exemplarily a mathematical model, herein, a Bayesian network model, useful in modelling the transcriptional program of the TGF-β cellular signaling pathway.

As a non-limiting generalized example, FIG. 2 provides an exemplary flow diagram used to determine the activity level of the TGF-β cellular signaling pathway based on a computer implemented mathematical model constructed of three nodes: (a) a transcription factor (TF) element (for example, but not limited to being, discretized into the states "absent" and "present" or as a continuous observable) in a first layer 1; (b) target gene(s) $TG_1$, $TG_2$, $TG_n$ (for example, but not limited to being, discretized into the states "down" and "up" or as a continuous observable) in a second layer 2, and; (c) measurement nodes linked to the expression levels of the target gene(s) in a third layer 3. The expression levels of the target genes can be determined by, for example, but not limited to, microarray probesets $PS_{1,1}$, $PS_{1,2}$, $PS_{1,3}$, $PS_{2,1}$, $PS_{n,1}$, $PS_{n,m}$ (for example, but limited to being, discretized into the states "low" and "high" or as a continuous observable), but could also be any other gene expression measurements such as, for example, RNAseq or RT-qPCR. The expression of the target genes depends on the activation of the respective transcription factor element, and the measured intensities of the selected probesets depend in turn on the expression of the respective target genes. The model is used to calculate TGF-B pathway activity by first determining probeset intensities, i.e., the expression level of the target genes, and calculating backwards in the model what the probability is that the transcription factor element must be present.

The present invention makes it possible to determine the activity of the TGF-β cellular signaling pathway in a subject by (i) determining a level of a TGF-β TF element in the sample of the subject, wherein the determining is based at least in part on evaluating a mathematical model relating expression levels of one or more target gene(s) of the TGF-β cellular signaling pathway, the transcription of which is controlled by the TGF-β TF element, to the level of the TGF-β TF element, and by (ii) calculating the activity of the TGF-β cellular signaling pathway in the subject based on the determined level of the TGF-β TF element in the sample of the subject. This, for example, allows improving the possibilities of characterizing patients that have a disease, for example, cancer, e.g., a colon, pancreatic, lung, brain or breast cancer, which is at least partially driven by a tumor-promoting activity of the TGF-β cellular signaling pathway, and that are therefore likely to respond to inhibitors of the TGF-β cellular signaling pathway.

Figure 3:
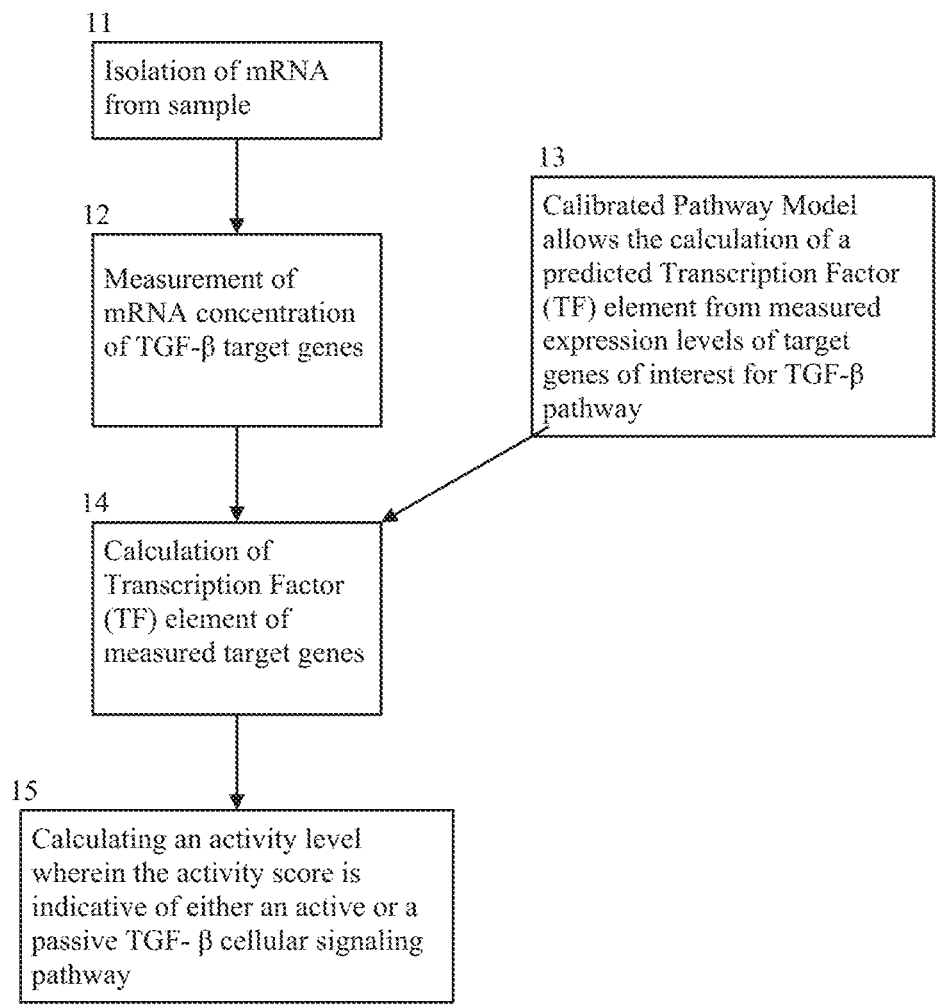
FIG. 3 shows an exemplary flow chart for calculating the activity level of the TGF-β cellular signaling pathway based on expression levels of target genes derived from a sample.

Generalized Workflow for Determining the Activity Level of TGF-β Cellular Signaling An example flow chart illustrating an exemplary calculation of the activity level of TGF-β cellular signaling from a sample isolated from a subject is provided in FIG. 3. First, the mRNA from a sample is isolated (11). Second, the mRNA expression levels of a unique set of at least three or more TGF-β target genes, as described herein, are measured (12) using methods for measuring gene expression that are known in the art. Next, the calculation of transcription factor element (13) is calculated using a calibrated pathway model (14), wherein the calibrated pathway model compares the expression levels of the at least three or more target genes in the sample with expression levels of the at least three target genes in the calibrated pathway model which have been correlated with a level of a TGF-β transcription factor element. Finally, the activity level of the TGF-β cellular signaling pathway is calculated in the sample based on the calculated levels of TGF-β transcription factor element in the sample (15). For example, the TGF-β signaling pathway is determined to be active if the activity is above a certain threshold, and can be categorized as passive if the activity falls below a certain threshold.

Target Genes

The present invention utilizes the analyses of the expression levels of unique sets of target genes. Particularly suitable target genes are described in the following text passages as well as the examples below (see, e.g., Tables 4-7, 9, and 11-12 below).

Thus, according to an embodiment the target gene(s) is/are selected from the group consisting of the target genes listed in Table 4, Table 5, Table 6, Table 7, Table 9, Table 11, or Table 12, below.

In particular, the unique set of target genes whose expression is analyzed in the model includes at least three or more target genes, for example, three, four, five, six, seven or more, selected from ANGPTL4, CDC42EP3, ID1, IL11, SERPINE1, JUNB, SKIL, or SMAD7.

In one embodiment, the at least three target genes are ANGPTL4, and at least two of CDC42EP3, ID1, IL11, JUNB, SKIL, or SMAD7. In one embodiment, the at least three target genes are CDC42EP3, and at least two of ANGPTL4, ID1, IL11, JUNB, SKIL, or SMAD7.

In one embodiment, the at least three target genes are ANGPTL4, and at least two of CDC42EP3, ID1, SERPINE1, JUNB, SKIL, or SMAD7. In one embodiment, the at least three target genes are CDC42EP3, and at least two of ANGPTL4, ID1, SERPINE1, JUNB, SKIL, or SMAD7.

In one embodiment, the at least three target genes are ANGPTL4, CDC42EP3, and at least one of ID1, IL11, JUNB, SKIL, or SMAD7. In one embodiment, the at least three target genes are ANGPTL4, CDC42EP3, and at least one of ID1, SERPINE1, JUNB, SKIL, or SMAD7.

In one embodiment, the expression levels of the target genes ANGPTL4, CDC42EP3, ID1, IL11, JUNB, SKIL, and SMAD7 are used in calculating the activity level of the TGF-β cellular signaling pathway.

In one embodiment, the expression levels of the target genes ANGPTL4, CDC42EP3, ID1, SERPINE1, JUNB, SKIL, and SMAD7 is used in calculating TGF-β cellular signaling.

In one embodiment, the expression level of at least one additional target gene selected from CDKN1A, CTGF, GADD45B, PDGFB, and SNAI2 is used in calculating TGF-β cellular signaling. In one embodiment, the expression levels of the additional target genes CDKN1A, CTGF, GADD45B, PDGFB, and SNAI2 are used in calculating TGF-β cellular signaling. In one embodiment, the expression levels of target genes ANGPTL4, CDC42EP3, ID1, IL11, JUNB, SKIL, SMAD7, CDKN1A, CTGF, GADD45B, PDGFB, and SNAI2 are used in calculating TGF-β cellular signaling.

In one embodiment, the expression level of at least one additional target gene selected from CDKN1A, CTGF, GADD45B, VEGFA, and SNAI2 is used in calculating TGF-β cellular signaling. In one embodiment, the expression levels of the additional target genes CDKN1A, CTGF, GADD45B, VEGFA, and SNAI2 are used in calculating TGF-β cellular signaling. In one embodiment, the expression levels of target genes ANGPTL4, CDC42EP3, ID1, IL11, JUNB, SKIL, SMAD7, CDKN1A, CTGF, GADD45B, VEGFA, and SNAI2 are used in calculating TGF-β cellular signaling. In one embodiment, the expression levels of target genes ANGPTL4, CDC42EP3, ID1, SERPINE1, JUNB, SKIL, SMAD7, CDKN1A, CTGF, GADD45B, VEGFA, and SNAI2 are used in calculating TGF-β cellular signaling.

As contemplated herein, the expression levels of other target genes, in further addition to those described above, may be included in the pathway modeling to calculate activity levels of pathway the TGF-β cellular signaling pathway, including GADD45A, HMGA2, PTHLH, SGK1, SMAD4, SMAD5, SMAD6, SMAD7, VEGFA, INPP5D, MMP2, MMP9, NKX2-5, OVOL1, and TIMP1.

In one embodiment, the method comprises:

calculating the activity of the TGF-β cellular signaling pathway in the subject based at least on expression levels of one or more, two or more, or at least three, target gene(s) of the TGF-β cellular signaling pathway measured in the sample of the subject selected from the group consisting of: ANGPTL4, CDC42EP3, CDKN1A, CDKN2B, CTGF, GADD45A, GADD45B, HMGA2, ID1, IL11, INPP5D, JUNB, MMP2, MMP9, NKX2-5, OVOL1, PDGFB, PTHLH, SGK1, SKIL, SMAD4, SMAD5, SMAD6, SMAD7, SNAI1, SNAI2, TIMP1, and VEGFA, or from the group consisting of: ANGPTL4, CDC42EP3, CDKN1A, CTGF, GADD45A, GADD45B, HMGA2, ID1, IL11, JUNB, PDGFB, PTHLH, SGK1, SKIL, SMAD4, SMAD5, SMAD6, SMAD7, SNAI2, and VEGFA, or from the group consisting of: ANGPTL4, CDC42EP3, CDKN1A, CTGF, GADD45B, ID1, IL11, JUNB, PDGFB, SKIL, SMAD7, and SNAI2, or from the group consisting of: ANGPTL4, CDC42EP3, ID1, IL11, JUNB, SKIL, and SMAD7.

It has been found by the present inventors that the genes in the successively shorter lists become more and more probative for determining the activity of the TGF-β cellular signaling pathway.

Measuring Levels of Gene Expression

Data derived from the unique set of target genes described herein is further utilized to determine the activity level of the TGF-β cellular signaling pathway using the methods described herein.

Methods for analyzing gene expression levels in isolated samples are generally known. For example, methods such as Northern blotting, the use of PCR, nested PCR, quantitative real-time PCR (qPCR), RNA-seq, or microarrays can all be used to derive gene expression level data. All methods known in the art for analyzing gene expression of the target genes are contemplated herein.

Methods of determining the expression product of a gene using PCR based methods may be of particular use. In order to quantify the level of gene expression using PCR, the amount of each PCR product of interest is typically estimated using conventional quantitative real-time PCR (qPCR) to measure the accumulation of PCR products in real time after each cycle of amplification. This typically utilizes a detectible reporter such as an intercalating dye, minor groove binding dye, or fluorogenic probe whereby the application of light excites the reporter to fluoresce and the resulting fluorescence is typically detected using a CCD camera or photomultiplier detection system, such as that disclosed in U.S. Pat. No. 6,713,297 which is hereby incorporated by reference.

In some embodiments, the probes used in the detection of PCR products in the quantitative real-time PCR (qPCR)

assay can include a fluorescent marker. Numerous fluorescent markers are commercially available. For example, Molecular Probes, Inc. (Eugene, Oreg.) sells a wide variety of fluorescent dyes. Non-limiting examples include Cy5, Cy3, TAMRA, R6G, R110, ROX, JOE, FAM, Texas Red™, and Oregon Green™. Additional fluorescent markers can include IDT ZEN Double-Quenched Probes with traditional 5' hydrolysis probes in qPCR assays. These probes can contain, for example, a 5' FAM dye with either a 3' TAMRA Quencher, a 3' Black Hole Quencher (BHQ, Biosearch Technologies), or an internal ZEN Quencher and 3' Iowa Black Fluorescent Quencher (IBFQ).

Fluorescent dyes useful according to the invention can be attached to oligonucleotide primers using methods well known in the art. For example, one common way to add a fluorescent label to an oligonucleotide is to react an N-Hydroxysuccinimide (NHS) ester of the dye with a reactive amino group on the target. Nucleotides can be modified to carry a reactive amino group by, for example, inclusion of an allyl amine group on the nucleobase. Labeling via allyl amine is described, for example, in U.S. Pat. Nos. 5,476,928 and 5,958,691, which are incorporated herein by reference. Other means of fluorescently labeling nucleotides, oligonucleotides and polynucleotides are well known to those of skill in the art.

Other fluorogenic approaches include the use of generic detection systems such as SYBR-green dye, which fluoresces when intercalated with the amplified DNA from any gene expression product as disclosed in U.S. Pat. Nos. 5,436,134 and 5,658,751 which are hereby incorporated by reference.

Another useful method for determining target gene expression levels includes RNA-seq, a powerful analytical tool used for transcriptome analyses, including gene expression level difference between different physiological conditions, or changes that occur during development or over the course of disease progression.

Another approach to determine gene expression levels includes the use of microarrays for example RNA and DNA microarray, which are well known in the art. Microarrays can be used to quantify the expression of a large number of genes simultaneously.

Calibrated Pathway Model

As contemplated herein, the expression levels of the unique set of target genes described herein are used to calculate the level TGF-β transcription factor element using a calibrated pathway model as further described below. The calibrated pathway model compares the expression levels of the at least three target genes in the sample with expression levels of the at least three target genes in the calibrated pathway model which define a level of TGF-β transcription factor element.

As contemplated herein, the calibrated pathway model is based on the application of a mathematical model. For example, the calibrated model can be based on a probabilistic model, for example a Bayesian network, or a linear or pseudo-linear model.

In one embodiment, the calibrated pathway model is a probabilistic model incorporating conditional probabilistic relationships that compare the expression levels of the at least three target genes in the sample with expression levels of the at least three target genes in the calibrated pathway model which define a level TGF-β transcription factor element to determine the level of the TGF-β transcription factor element in the sample. In one embodiment, the probabilistic model is a Bayesian network model.

In an alternative embodiment, the calibrated pathway model can be a linear or pseudo-linear model. In an embodiment, the linear or pseudo-linear model is a linear or pseudo-linear combination model.

Figure 4:
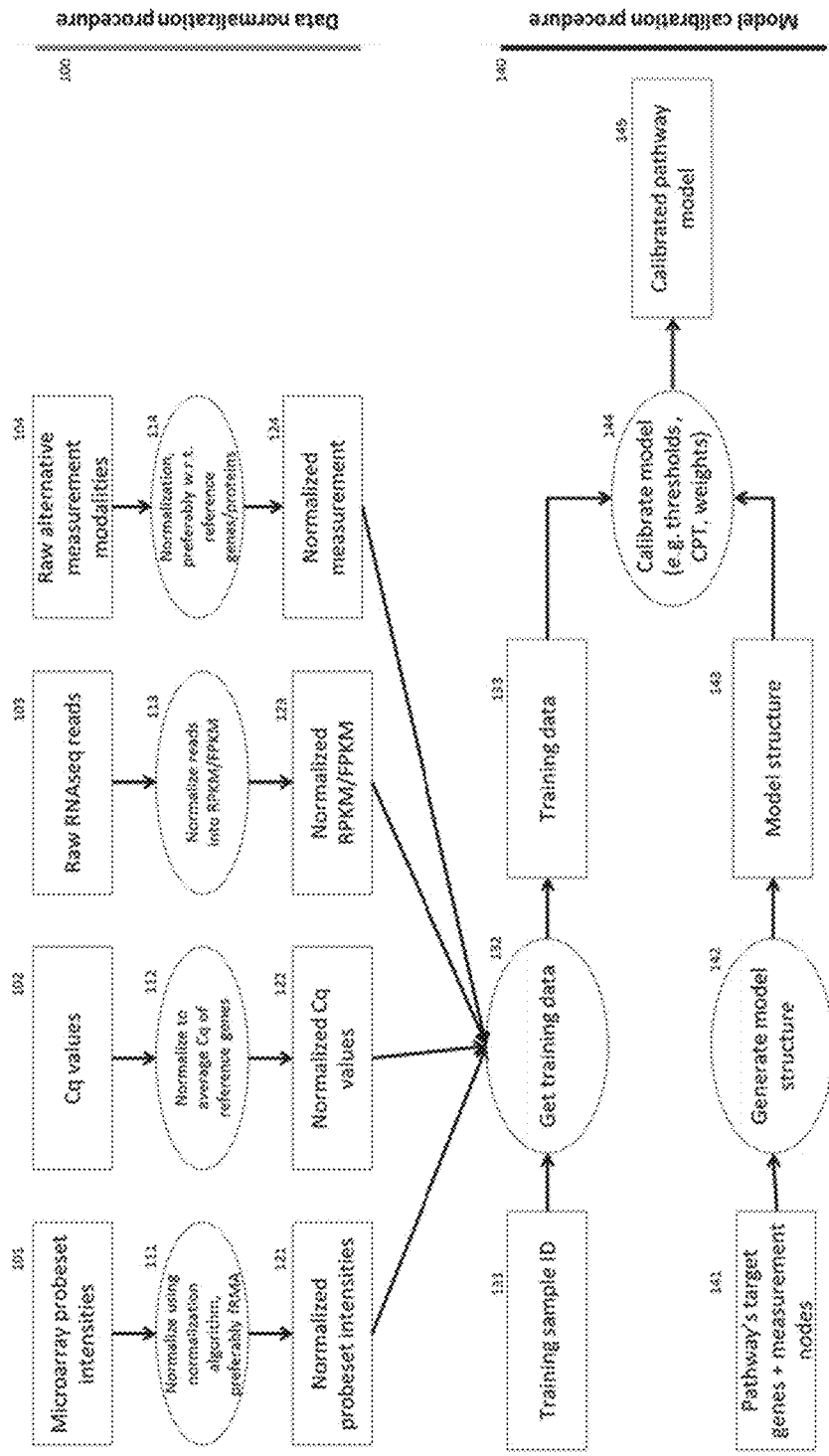
FIG. 4 shows an exemplary flow chart for obtaining a calibrated pathway model as described herein.

A non-limiting exemplary flow chart for a calibrated pathway model is shown in FIG. 4. As an initial step, the training data for the mRNA expression levels is collected and normalized. The data can be collected using, for example microarray probeset intensities (101), real-time PCR Cq values (102), raw RNAseq reads (103), or alternative measurement modalities (104) known in the art. The raw expression level data can then be normalized for each method, respectively, by normalization using a normalization algorithm, for example, frozen robust military analysis (fRMA) or MAS5.0 (111), normalization to average Cq of reference genes (112), normalization of reads into reads/fragments per kilobase of transcript per million mapped reads (RPKM/FPKM) (113), or normalization to w.r.t. reference genes/proteins (114). This normalization procedure leads to a normalized probeset intensity (121), normalized Cq values (122), normalized RPKM/FPKM (123), or normalized measurement (124) for each method, respectively, which indicate target gene expression levels within the training samples.

Once the training data has been normalized, a training sample ID or IDs (131) is obtained and the training data of these specific samples is obtained from one of the methods for determining gene expression (132). The final gene expression results from the training sample are output as training data (133). All of the data from various training samples are incorporated to calibrate the model (including for example, thresholds, CPTs, for example in the case of the probabilistic or Bayesian network, weights, for example, in the case of the linear or pseudo-linear model, etc) (144). In addition, the pathway's target genes and measurement nodes (141) are used to generate the model structure for example, as described in FIG. 2 (142). The resulting model structure (143) of the pathway is then incorporated with the training data (133) to calibrate the model (144), wherein the gene expression levels of the target genes is indicative of the transcription factor element activity. As a result of the transcription factor element calculations in the training samples, a calibrated pathway model (145) is calculated which assigns the TGF-β cellular signaling pathway activity level for a subsequently examined sample of interest, for example from a subject with a cancer, based on the target gene expression levels in the training samples.

Transcription Factor Element Calculation

Figure 5:
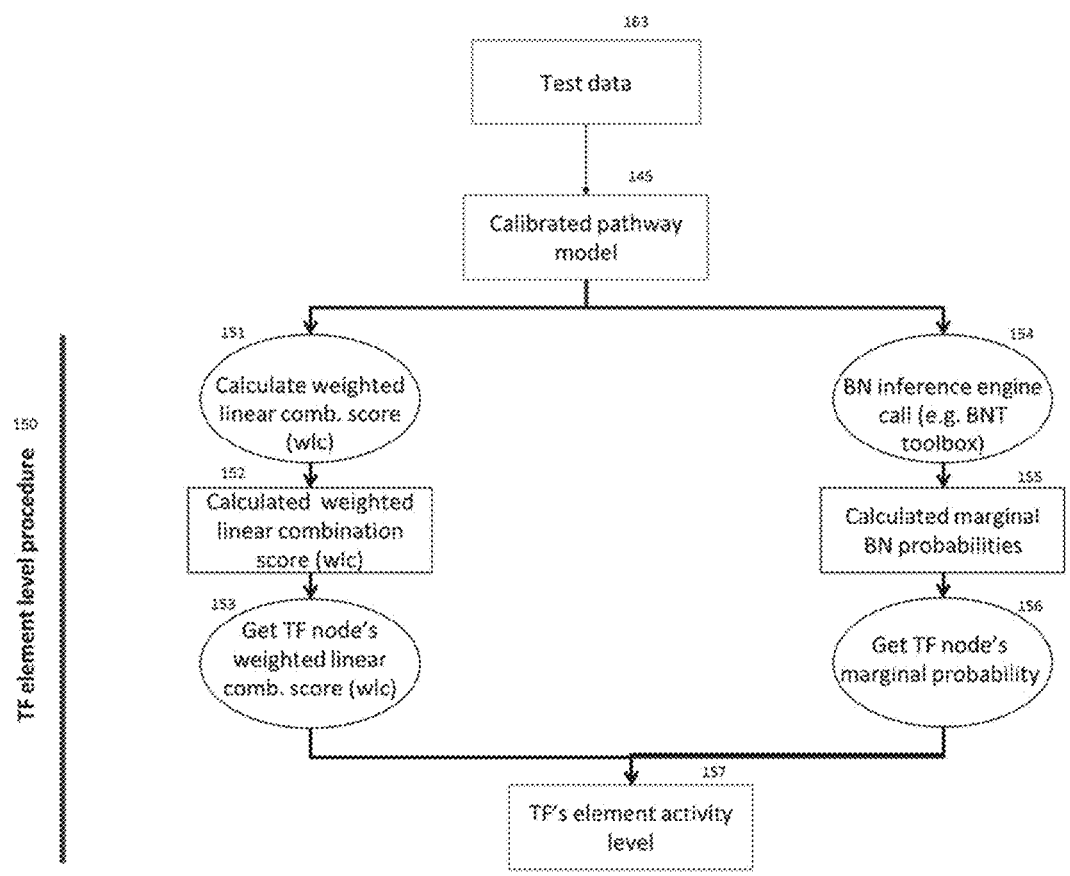
FIG. 5 shows an exemplary flow chart for calculating the Transcription Factor (TF) Element as described herein.

A non-limiting exemplary flow chart for calculating the Transcription Factor Element activity level is provided in FIG. 5. The expression level data (test data) (163) from a sample isolated from a subject is input into the calibrated pathway model (145). The mathematical model may be a probabilistic model, for example a Bayesian network model, a linear model, or pseudo-linear model.

The mathematical model may be a probabilistic model, for example a Bayesian network model, based at least in part on conditional probabilities relating the TGF-β TF element and expression levels of the one or more target gene(s) of the TGF-β cellular signaling pathway measured in the sample of the subject, or the mathematical model may be based at least in part on one or more linear combination(s) of expression levels of the one or more target gene(s) of the TGF-β cellular signaling pathway measured in the sample of the subject. In particular, the determining of the activity of the TGF-β cellular signaling pathway may be performed as disclosed in the published international patent application WO 2013/

011479 A2 ("Assessment of cellular signaling pathway activity using probabilistic modeling of target gene expression"), and incorporated herein by reference. Briefly, the data is entered into a Bayesian network (BN) inference engine call (for example, a BNT toolbox) (154). This leads to a set of values for the calculated marginal BN probabilities of all the nodes in the BN (155). From these probabilities, the transcription factor (TF) node's probability (156) is determined and establishes the TF's element activity level (157).

Alternatively, the mathematical model may be a linear model. For example, a linear model can be used as described in the published international patent application WO 2014/102668 A2 ("Assessment of cellular signaling pathway activity using linear combination(s) of target gene expressions"), the contents of which are herewith incorporated in their entirety. Further details regarding the calculating/determining of cellular signaling pathway activity using mathematical modeling of target gene expression can also be found in Verhaegh W. et al., "Selection of personalized patient therapy through the use of knowledge-based computational models that identify tumor-driving signal transduction pathways", Cancer Research, Vol. 74, No. 11, 2014, pages 2936 to 2945. Briefly, the data is entered into a calculated weighted linear combination score (w/c) (151). This leads to a set of values for the calculated weighted linear combination score (152). From these weighted linear combination scores, the transcription factor (TF) node's weighted linear combination score (153) is determined and establishes the TF's element activity level (157).

Procedure for Discretized Observables

Figure 6:
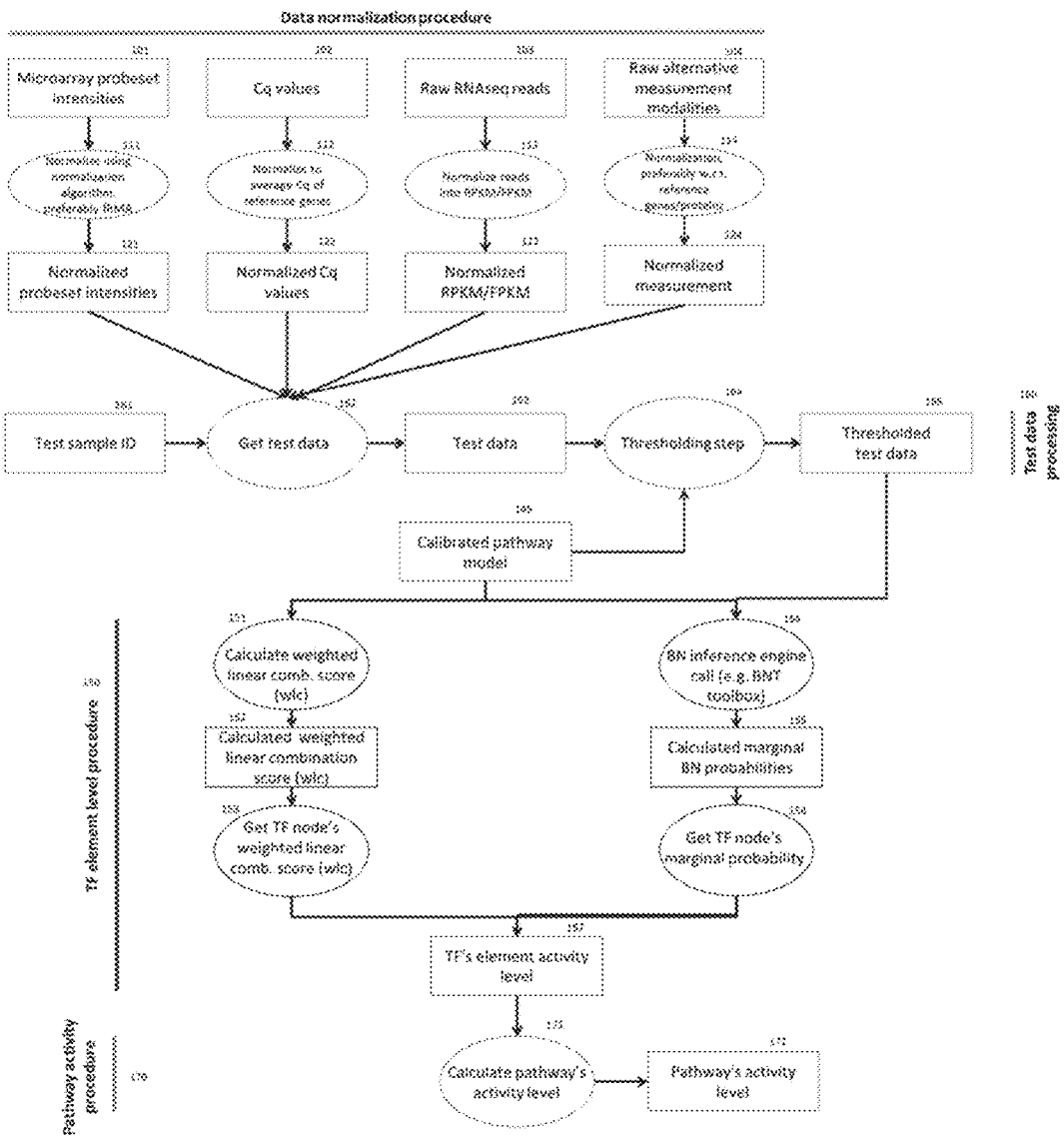
FIG. 6 shows an exemplary flow chart for calculating the TGF-β cellular signaling pathway activity level using discretized observables.

A non-limiting exemplary flow chart for calculating the activity level of a TGF-β cellular signaling pathway as a discretized observable is shown in FIG. 6. First, the test sample is isolated and given a test sample ID (161). Next, the test data for the mRNA expression levels is collected and normalized (162). The test data can be collected using the same methods as discussed for the training samples in FIG. 5, using microarray probeset intensities (101), real-time PCR Cq values (102), raw RNAseq reads (103), or an alternative measurement modalities (104). The raw expression level data can then be normalized for each method, respectively, by normalization using an algorithm, for example fRMA or MAS5.0 (111), normalization to average Cq of reference genes (112), normalization of reads into RPKM/FPKM (113), and normalization to w.r.t. reference genes/proteins (114). This normalization procedure leads to a normalized probeset intensity (121), normalized Cq values (122), normalized RPKM/FPKM (123), or normalized measurement (124) for each method, respectively.

Once the test data has been normalized, the resulting test data (163) is analyzed in a thresholding step (164) based on the calibrated pathway model (145), resulting in the thresholded test data (165). In using discrete observables, in one non-limiting example, every expression above a certain threshold is, for example, given a value of 1 and values below the threshold are given a value of 0, or in an alternative embodiment, the probability mass above the threshold as described herein is used as a thresholded value. Based on the calibrated pathway model, this value represents the TF's element activity level (157), which is then used to calculate the pathway's activity level (171). The final output gives the pathway's activity level (172) in the test sample being examined from the subject.

Procedure for Continuous Observables

Figure 7:
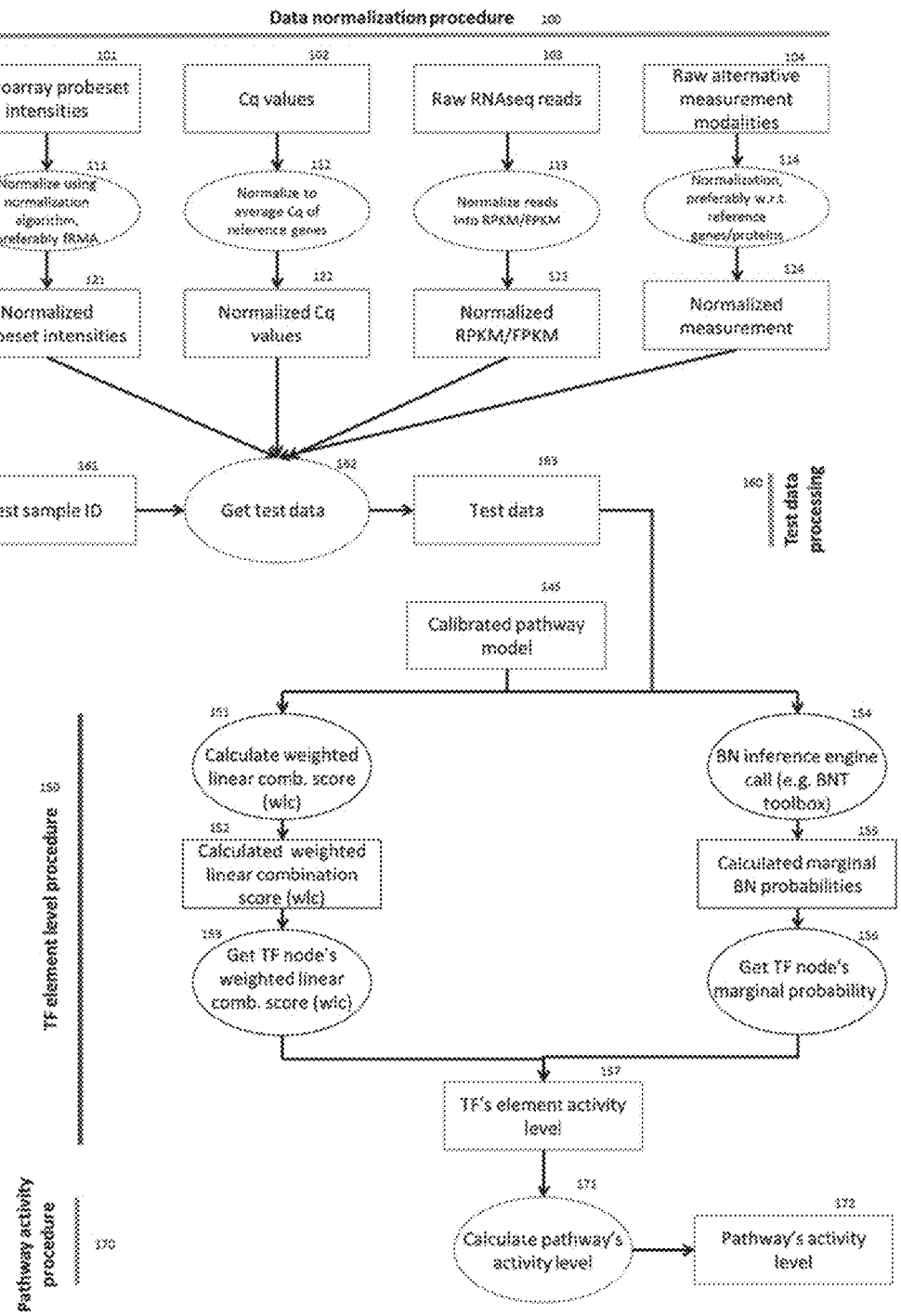
FIG. 7 shows an exemplary flow chart for calculating the TGF-β cellular signaling pathway activity level using continuous observables.

A non-limiting exemplary flow chart for calculating the activity level of a TGF-β cellular signaling pathway as a continuous observable is shown in FIG. 7. First, the test sample is isolated and given a test sample ID (161). Next, the test data for the mRNA expression levels is collected and normalized (162). The test data can be collected using the same methods as discussed for the training samples in FIG. 5, using microarray probeset intensities (101), real-time PCR Cq values (102), raw RNAseq reads (103), or an alternative measurement modalities (104). The raw expression level data can then be normalized for each method, respectively, by normalization using an algorithm, for example fRMA (111), normalization to average Cq of reference genes (112), normalization of reads into RPKM/FPKM (113), and normalization to w.r.t. reference genes/proteins (114). This normalization procedure leads to a a normalized probeset intensity (121), normalized Cq values (122), normalized RPKM/FPKM (123), or normalized measurement (124) for each method, respectively.

Once the test data has been normalized, the resulting test data (163) is analyzed in the calibrated pathway model (145). In using continuous observables, as one non-limiting example, the expression levels are converted to values between 0 and 1 using a sigmoid function as described in further detail below. The transcription factor element calculation as described herein is used to interpret the test data in combination with the calibrated pathway model, the resulting value represents the TF's element activity level (157), which is then used to calculate the pathway's activity level (171). The final output then gives the pathway's activity level (172) in the test sample.

Kits for Calculating TGF-β Signaling Pathway Activity

In some embodiments, the present invention utilizes kits comprising primer and probe sets for the analyses of the expression levels of unique sets of target genes (See Target Gene discussion above). Particularly suitable oligo sequences for use as primers and probes for inclusion in a kit are described in the following text passages (see, e.g., Tables 1, 2, and 3).

Also contemplated herein is a kit comprising one or more components for measuring a set of unique TGF-β target genes as described further below. In one non-limiting embodiment, the kit includes one or more components for measuring the expression levels of at least three target genes selected from ANGPTL4, and at least two of CDC42EP3, ID1, IL11, JUNB, SKIL, or SMAD7. In one embodiment, the at least three target genes are CDC42EP3, and at least two of ANGPTL4, ID1, IL11, JUNB, SKIL, or SMAD7. In one embodiment, the at least three target genes are ANGPTL4, and at least two of CDC42EP3, ID1, SERPINE1, JUNB, SKIL, or SMAD7. In one embodiment, the at least three target genes are CDC42EP3, and at least two of ANGPTL4, ID1, SERPINE1, JUNB, SKIL, or SMAD7. In one embodiment, the at least three target genes are ANGPTL4, CDC42EP3, and at least one of ID1, IL11, JUNB, SKIL, or SMAD7. In one embodiment, the at least three target genes are ANGPTL4, CDC42EP3, and at least one of ID1, SERPINE1, JUNB, SKIL, or SMAD7. In one embodiment, the kit includes one or more components for measuring the expression levels of the target genes ANGPTL4, CDC42EP3, ID1, IL11, JUNB, SKIL, and SMAD7. In one embodiment, the kit includes one or more components for measuring the expression levels of the target genes ANGPTL4, CDC42EP3, ID1, SERPINE1, JUNB, SKIL, and SMAD7.

In one embodiment, the kit includes one or more components for measuring the expression levels of at least three target genes, wherein the target genes are selected from ANGPTL4, CDC42EP3, ID1, SERPINE1, JUNB, SKIL, or SMAD7, and the one or more components is selected from the primers and probes listed in Table 1.

TABLE 1

Non-limiting example of primers and probes for a kit for measuring gene expression of TGF-β target genes.

| Oligo Name | Sequence 5'-3' | SEQ ID No. | Target Gene |
| --- | --- | --- | --- |
| SMAD7_For1 | TGCCTTCCTCCGCTGAAAC | 72 | SMAD7 |
| SMAD7_Rev2 | ACCACGCACCAGTGTGAC | 73 | SMAD7 |
| SMAD7_probe1 | TCCCAACTTCTTCTGGAGCCTGGG | 74 | SMAD7 |
| SKIL_For1 | GAAATGAAGGAGAAGTTTAGCA | 75 | SKIL |
| SKIL_Rev1 | GCTTTATAACAGGATACCATGAC | 76 | SKIL |
| SKIL_Probe1 | ACAGATGCACCATCAGGAATGGAATTACA | 77 | SKIL |
| ID1_For2 | TGAGGGAGAACAAGACCGAT | 84 | ID1 |
| ID1_Rev1 | ACTAGTAGGTGTGCAGAGA | 85 | ID1 |
| ID1_Probe1 | CACTGCGCCCTTAACTGCATCCA | 86 | ID1 |
| ANGPTL4_For3 | GCGAATTCAGCATCTGCAAAG | 87 | ANGPTL4 |
| ANGPTL4_Rev4 | CTTTCTTCGGGCAGGCTT | 88 | ANGPTL4 |
| ANGPTL4_Probe2 | ACCACAAGCACCTAGACCATGAGGT | 89 | ANGPTL4 |
| CDC42EP3_For1 | TGTGGTCAAGACTGGATGATG | 93 | CDCCDC42EP3 |
| CDC42EP3_Rev1 | CAGAAGTGGCTTCGAAATGA | 94 | CDCCDC42EP3 |
| CDC42EP3_Probe1 | TCTCTAGGAAGCCTCACTTGGCCG | 95 | CDCCDC42EP3 |
| JUNB_For2 | AATGGAACAGCCCTTCTACCA | 96 | JUNB |
| JUNB_Rev1 | GCTCGGTTTCAGGAGTTTGTA | 97 | JUNB |
| JUNB_Probe1 | TCATACACAGCTACGGGATACGG | 98 | JUNB |
| SERPINE1_For1 | CCACAAATCAGACGGCAGCA | 105 | SERPINE1 |
| SERPINE1_Rev1 | GTCGTAGTAATGGCCATCGG | 106 | SERPINE1 |
| SERPINE1_Probe1 | CCCATGATGGCTCAGACCAACAAGT | 107 | SERPINE1 |

In one embodiment, the kit includes one or more components for measuring the expression levels of at least three target genes, wherein the target genes are selected from ANGPTL4, and at least two of CDC42EP3, ID1, SERPINE1, JUNB, SKIL, or SMAD7, and the one or more components is selected from the primers and probes listed in Table 1. In one embodiment, the kit includes one or more components for measuring the expression levels of at least three target genes, wherein the target genes are CDC42EP3, and at least two of ANGPTL4, ID1, SERPINE1, JUNB, SKIL, or SMAD7, and the one or more components is selected from the PCR primers and probes listed in Table 1. In another embodiment, the kit includes one or more components for measuring the expression levels of at least three target genes, wherein the target genes are ANGPTL4, CDC42EP3, and at least one of ID1, SERPINE1, JUNB, SKIL, or SMAD7, and the one or more components is selected from the PCR primers and probes listed in Table 1. In one embodiment, the kit includes one or more components for measuring the expression levels of the target genes ANGPTL4, CDC42EP3, ID1, SERPINE1, JUNB, SKIL, and SMAD7, and the one or more components is selected from the PCR primers and probes listed in Table 1.

In one embodiment, the kit includes one or more components for measuring the expression level of at least one additional target gene selected from CDKN1A, CTGF, GADD45B, PDGFB, and SNAI2. In one embodiment, the kit includes one or more components for measuring the expression level of at least one additional target gene selected from CDKN1A, CTGF, GADD45B, VEGFA, and SNAI2. In one embodiment, the kit includes one or more components for measuring the expression levels of target genes ANGPTL4, CDC42EP3, ID1, IL11, JUNB, SKIL, SMAD7, CDKN1A, CTGF, GADD45B, PDGFB, and SNAI2.

In one embodiment, the kit includes one or more components for measuring the expression levels of target genes ANGPTL4, CDC42EP3, ID1, SERPINE1, JUNB, SKIL, SMAD7, CDKN1A, CTGF, GADD45B, VEGFA, and SNAI2. In one non-limiting embodiment, the kit includes one or more components for measuring the expression levels of target genes ANGPTL4, CDC42EP3, ID1, SERPINE1, JUNB, SKIL, SMAD7, CDKN1A, CTGF, GADD45B, VEGFA, and SNAI2, wherein the one or more components includes the PCR primers and probes listed in Table 2. The PCR primers for each gene are designated Forward (For) and Reverse (Rev) and the probes for detection of the PCR products for each gene are labeled Probe. In one non-limiting embodiment, the probes listed in Table 2 are labeled with a 5' FAM dye with an internal ZEN Quencher and 3' Iowa Black Fluorescent Quencher (IBFQ).

TABLE 2

Oligo Sequences for Target Genes

| Oligo Name | Sequence 5'-3' | SEQ ID No. | Target Gene |
|---|---|---|---|
| SMAD7_For1 | TGCCTTCCTCCGCTGAAAC | 72 | SMAD7 |
| SMAD7_Rev2 | ACCACGCACCAGTGTGAC | 73 | SMAD7 |
| SMAD7_probe1 | TCCCAACTTCTTCTGGAGCCTGGG | 74 | SMAD7 |
| SKIL_For1 | GAAATGAAGGAGAAGTTTAGCA | 75 | SKIL |
| SKIL_Rev1 | GCTTTATAACAGGATACCATGAC | 76 | SKIL |
| SKIL_Probe1 | ACAGATGCACCATCAGGAATGGAATTACA | 77 | SKIL |
| CTGF_For1 | GAAGCTGACCTGGAAGAGAA | 78 | CTGF |
| CTGF_Rev1 | CCACAGAATTTAGCTCGGTATG | 79 | CTGF |
| CTGF_Probe2 | CCTATCAAGTTTGAGCTTTCTGGCTG | 80 | CTGF |
| CDKN1A_For1 | GAGACTCTCAGGGTCGAAA | 81 | CDKN1A |
| CDKN1A_Rev2 | CTGTGGGCGGATTAGGGCT | 82 | CDKN1A |
| CDKN1A_Probe1 | ATTTCTACCACTCCAAACGCCGGC | 83 | CDKN1A |
| ID1_For2 | TGAGGGAGAACAAGACCGAT | 84 | ID1 |
| ID1_Rev1 | ACTAGTAGGTGTGCAGAGA | 85 | ID1 |
| ID1_Probe1 | CACTGCGCCCTTAACTGCATCCA | 86 | ID1 |
| ANGPTL4_For3 | GCGAATTCAGCATCTGCAAAG | 87 | ANGPTL4 |
| ANGPTL4_Rev4 | CTTTCTTCGGGCAGGCTT | 88 | ANGPTL4 |
| ANGPTL4_Probe2 | ACCACAAGCACCTAGACCATGAGGT | 89 | ANGPTL4 |
| GADD45B_For1 | GTCGGCCAAGTTGATGAATG | 90 | GADD45B |
| GADD45B_Rev1 | GATGAGCGTGAAGTGGATTTG | 91 | GADD45B |
| GADD45B_probe1 | CCATTGACGAGGAGGAGGAGGAT | 92 | GADD45B |
| CDC42EP3_For1 | TGTGGTCAAGACTGGATGATG | 93 | CDC42EP3 |
| CDC42EP3_Rev1 | CAGAAGTGGCTTCGAAATGA | 94 | CDC42EP3 |
| CDC42EP3_Probe1 | TCTCTAGGAAGCCTCACTTGGCCG | 95 | CDC42EP3 |
| JUNB_For2 | AATGGAACAGCCCTTCTACCA | 96 | JUNB |
| JUNB_Rev1 | GCTCGGTTTCAGGAGTTTGTA | 97 | JUNB |
| JUNB_Probe1 | TCATACACAGCTACGGGATACGG | 98 | JUNB |
| SNAI2_For1 | GTTGCTTCAAGGACACATTAG | 99 | SNAI2 |
| SNAI2_Rev1 | GCAGATGAGCCCTCAGATTT | 100 | SNAI2 |
| SNAI2_Probe1 | TGCCCTCACTGCAACAGAGCATTT | 101 | SNAI2 |
| VEGFA_For1 | GAAGGAGGAGGGCAGAATC | 102 | VEGFA |
| VEGFA_Rev1 | GTCTCGATTGGATGGCAGTA | 103 | VEGFA |
| VEGFA_Probe1 | AGTTCATGGATGTCTATCAGCGCAGC | 104 | VEGFA |
| SERPINE1_For1 | CCACAAATCAGACGGCAGCA | 105 | SERPINE1 |
| SERPINE1_Rev1 | GTCGTAGTAATGGCCATCGG | 106 | SERPINE1 |
| SERPINE1_Probe1 | CCCATGATGGCTCAGACCAACAAGT | 107 | SERPINE1 |

In one non-limiting embodiment, the kit includes one or more components for measuring the expression levels of control genes, wherein the one or more components includes a PCR primer set and probe for at least one of the control genes listed in Table 3. The PCR primers for each gene are designated Forward (F) and Reverse (R) and the probes for detection of the PCR products for each gene are labeled Probe (P or FAM). In one non-limiting embodiment, the probes listed in Table 3 are labeled with a 5' FAM dye with an internal ZEN Quencher and 3' Iowa Black Fluorescent Quencher (IBFQ).

TABLE 3

Oligo Sequences for Controls

| Oligo Name | Sequence 5'-3' | SEQ ID No. | Reference gene |
|---|---|---|---|
| Hum_BACT_F1 | CCAACCGCGAGAAGATGA | 108 | ACTB |
| Hum_BACT_R1 | CCAGAGGCGTACAGGGATAG | 109 | ACTB |
| Hum_BACT_P1 | CCATGTACGTTGCTATCCAGGCT | 110 | ACTB |
| Hum_POLR2A_F1 | AGTCCTGAGTCCGGATGAA | 111 | POLR2A |
| Hum_POLR2A_R1 | CCTCCCTCAGTCGTCTCT | 112 | POLR2A |
| Hum_POLR2A_P1 | TGACGGAGGGTGGCATCAAATACC | 113 | POLR2A |
| Hum_PUM1_F2 | GCCAGCTTGTCTTCAATGAAAT | 114 | PUM1 |
| Hum_PUM1_R2 | CAAAGCCAGCTTCTGTTCAAG | 115 | PUM1 |
| Hum_PUM1_P1 | ATCCACCATGAGTTGGTAGGCAGC | 116 | PUM1 |
| Hum_TBP_F1 | GCCAAGAAGAAAGTGAACATCAT | 117 | TBP |
| Hum_TBP1_R1 | ATAGGGATTCCGGGAGTCAT | 118 | TBP |
| Hum_TBP_P1 | TCAGAACAACAGCCTGCCACCTTA | 119 | TBP |
| K-ALPHA-1_F1 | TGACTCCTTCAACACCTTCTTC | 120 | TUBA1B |
| K-ALPHA-1_R1 | TGCCAGTGCGAACTTCAT | 121 | TUBA1B |
| K-ALPHA-1_FAM1 | CCGGGCTGTGTTTGTAGACTTGGA | 122 | TUBA1B |
| ALAS1_F1 | AGCCACATCATCCCTGT | 123 | ALAS1 |
| ALAS1_R1 | CGTAGATGTTATGTCTGCTCAT | 124 | ALAS1 |
| ALAS1_FAM1 | TTTAGCAGCATCTGCAACCCGC | 125 | ALAS1 |
| Hum_HPRT1_F1 | GAGGATTTGGAAAGGGTGTTTATT | 126 | HPRT1 |
| Hum_HPRT1_R1 | ACAGAGGGCTACAATGTGATG | 127 | HPRT1 |
| Hum_HPRT1_P1 | ACGTCTTGCTCGAGATGTGATGAAGG | 128 | HPRT1 |
| Hum_RPLP0_F2 | TAAACCCTGCGTGGCAAT | 129 | RPLP0 |
| Hum_RPLP0_R2 | ACATTTCGGATAATCATCCAATAGTTG | 130 | RPLP0 |
| Hum_RPLP0_P1 | AAGTAGTTGGACTTCCAGGTCGCC | 131 | RPLP0 |
| Hum_B2M_F1 | CCGTGGCCTTAGCTGTG | 132 | B2M |
| Hum_B2M_R1 | CTGCTGGATGACGTGAGTAAA | 133 | B2M |
| Hum_B2M_P1 | TCTCTCTTTCTGGCCTGGAGGCTA | 134 | B2M |
| TPT1_F_PACE | AAATGTTAACAAATGTGGCAATTAT | 135 | TPT1 |
| TPT1_R_PACE | AACAATGCCTCCACTCCAAA | 136 | TPT1 |
| TPT1_P_PACE | TCCACACAACACCAGGACTT | 137 | TPT1 |
| EEF1A1_F_PACE | TGAAAACTACCCCTAAAAGCCA | 138 | EEF1A1 |
| EEF1A1_R_PACE | TATCCAAGACCCAGGCATACT | 139 | EEF1A1 |
| EEF1A1_P_PACE | TAGATTCGGGCAAGTCCACCA | 140 | EEF1A1 |
| RPL41_F_PACE | AAGATGAGGCAGAGGTCCAA | 141 | RPL41 |

TABLE 3-continued

Oligo Sequences for Controls

| Oligo Name | Sequence 5'-3' | SEQ ID No. | Reference gene |
|---|---|---|---|
| RPL41_R_PACE | TCCAGAATGTCACAGGTCCA | 142 | RPL41 |
| RPL41_P_PACE | TGCTGGTACAAGTTGTGGGA | 143 | RPL41 |

As contemplated herein, the one or more components for measuring the expression levels of the particular target genes can be selected from the group consisting of: an DNA array chip, an oligonucleotide array chip, a protein array chip, an antibody, a plurality of probes, for example, labeled probes, a set of RNA reverser-transcriptase sequencing components, and/or RNA or DNA, including cDNA, amplification primers. In one embodiment, the kit includes a set of labeled probes directed to the cDNA sequence of the targeted genes as described herein contained in a standardized 96-well plate. In one embodiment, the kit further includes a non-transitory storage medium containing instructions that are executable by a digital processing device to perform a method according to the present invention as described herein.

In accordance with another disclosed aspect, a kit for measuring expression levels of one or more, two or more, or at least three, target gene(s) of the TGF-β cellular signaling pathway in a sample of a subject comprises:
one or more components for determining the expression levels of the one or more, two or more, or at least three, target gene(s) of the TGF-β cellular signaling pathway,
wherein the one or more components are, for example, selected from the group consisting of: an DNA array chip, an oligonucleotide array chip, a protein array chip, an antibody, a plurality of probes, RNA sequencing and a set of primers, and
wherein the one or more, two or more, or at least three, target gene(s) of the TGF-β cellular signaling pathway is/are selected from the group consisting of: ANGPTL4, CDC42EP3, CDKN1A, CDKN2B, CTGF, GADD45A, GADD45B, HMGA2, ID1, IL11, INPP5D, JUNB, MMP2, MMP9, NKX2-5, OVOL1, PDGFB, PTHLH, SGK1, SKIL, SMAD4, SMAD5, SMAD6, SMAD7, SNAIL SNAI2, TIMP1, and VEGFA, or ANGPTL4, CDC42EP3, CDKN1A, CDKN2B, CTGF, GADD45A, GADD45B, HMGA2, ID1, IL11, SERPINE1, INPP5D, JUNB, MMP2, MMP9, NKX2-5, OVOL1, PDGFB, PTHLH, SGK1, SKIL, SMAD4, SMAD5, SMAD6, SMAD7, SNAIL SNAI2, TIMP1, and VEGFA, or from the group consisting of: ANGPTL4, CDC42EP3, CDKN1A, CTGF, GADD45A, GADD45B, HMGA2, ID1, IL11, JUNB, PDGFB, PTHLH, SGK1, SKIL, SMAD4, SMAD5, SMAD6, SMAD7, SNAI2, and VEGFA or ANGPTL4, CDC42EP3, CDKN1A, CTGF, GADD45A, GADD45B, HMGA2, ID1, SERPINE1, JUNB, PDGFB, PTHLH, SGK1, SKIL, SMAD4, SMAD5, SMAD6, SMAD7, SNAI2, and VEGFA, or from the group consisting of: ANGPTL4, CDC42EP3, CDKN1A, CTGF, GADD45B, ID1, IL11, JUNB, PDGFB, SKIL, SMAD7, and SNAI2, or ANGPTL4, CDC42EP3, CDKN1A, CTGF, GADD45B, ID1, SERPINE1, JUNB, VEGFA, SKIL, SMAD7, and SNAI2, or from the group consisting of: ANGPTL4, CDC42EP3, ID1, IL11, JUNB, SKIL, and SMAD7, or ANGPTL4, CDC42EP3, ID1, SERPINE1, JUNB, SKIL, and SMAD7.

In accordance with another disclosed aspect, a kit for measuring expression levels of two, three or more target genes of a set of target genes of the TGF-β cellular signaling pathway in a sample of a subject comprises:
one or more components for determining the expression levels of the two, three or more target genes of the set of target genes of the TGF-β cellular signaling pathway,
wherein the one or more components are, for example, selected from the group consisting of: an DNA array chip, an oligonucleotide array chip, a protein array chip, an antibody, a plurality of probes, RNA sequencing and a set of primers.

In one embodiment,
the set of target genes of the TGF-β cellular signaling pathway includes at least seven, or in an alternative, all target genes selected from the group consisting of: ANGPTL4, CDC42EP3, CDKN1A, CDKN2B, CTGF, GADD45A, GADD45B, HMGA2, ID1, IL11, INPP5D, JUNB, MMP2, MMP9, NKX2-5, OVOL1, PDGFB, PTHLH, SGK1, SKIL, SMAD4, SMAD5, SMAD6, SMAD7, SNAIL SNAI2, TIMP1, and VEGFA, or ANGPTL4, CDC42EP3, CDKN1A, CDKN2B, CTGF, GADD45A, GADD45B, HMGA2, ID1, IL11, SERPINE1, INPP5D, JUNB, MMP2, MMP9, NKX2-5, OVOL1, PDGFB, PTHLH, SGK1, SKIL, SMAD4, SMAD5, SMAD6, SMAD7, SNAIL SNAI2, TIMP1, and VEGFA, or from the group consisting of: ANGPTL4, CDC42EP3, CDKN1A, CTGF, GADD45A, GADD45B, HMGA2, ID1, IL11, JUNB, PDGFB, PTHLH, SGK1, SKIL, SMAD4, SMAD5, SMAD6, SMAD7, SNAI2, and VEGFA, or ANGPTL4, CDC42EP3, CDKN1A, CTGF, GADD45A, GADD45B, HMGA2, ID1, SERPINE1, JUNB, PDGFB, PTHLH, SGK1, SKIL, SMAD4, SMAD5, SMAD6, SMAD7, SNAI2, and VEGFA, or from the group consisting of: ANGPTL4, CDC42EP3, CDKN1A, CTGF, GADD45B, ID1, IL11, JUNB, PDGFB, SKIL, SMAD7, and SNAI2, or ANGPTL4, CDC42EP3, CDKN1A, CTGF, GADD45B, ID1, SERPINE1, JUNB, VEGFA, SKIL, SMAD7, and SNAI2, or from the group consisting of: ANGPTL4, CDC42EP3, ID1, IL11, JUNB, SKIL, and SMAD7, or ANGPTL4, CDC42EP3, ID1, SERPINE1, JUNB, SKIL, and SMAD7.

In one embodiment, the PCR cycling is performed in a microtiter or multi-well plate format. This format, which uses plates comprising multiple reaction wells, not only increases the throughput of the assay process, but is also well adapted for automated sampling steps due to the modular nature of the plates and the uniform grid layout of the wells on the plates. Common microtiter plate designs useful according to the invention have, for example 12, 24, 48, 96, 384, or more wells, although any number of wells that physically fit on the plate and accommodate the desired reaction volume (usually 10-100 μl) can be used according to the invention. Generally, the 96 or 384 well plate format can be utilized. In one embodiment, the method is performed in a 96 well plate format. In one embodiment, the method is performed in a 384 well plate format.

The present invention includes kits for measuring gene expression. Provided herein is a kit for measuring expression levels of two, three or more target genes of a set of target genes of the TGF-β cellular signaling pathway in a sample of a subject, comprising: one or more components for determining the expression levels of the two, three or more target genes of the set of target genes of the TGF-β cellular signaling pathway, wherein the set of target genes of the TGF-β cellular signaling pathway includes at least seven, or, in an alternative, all target genes selected from the group consisting of: ANGPTL4, CDC42EP3, CDKN1A, CDKN2B, CTGF, GADD45A, GADD45B, HMGA2, ID1, IL11, INPP5D, JUNB, MMP2, MMP9, NKX2-5, OVOL1, PDGFB, PTHLH, SGK1, SKIL, SMAD4, SMAD5, SMAD6, SMAD7, SNAIL SNAI2, TIMP1, and VEGFA, or ANGPTL4, CDC42EP3, CDKN1A, CDKN2B, CTGF, GADD45A, GADD45B, HMGA2, ID1, IL11, SERPINE1, INPP5D, JUNB, MMP2, MMP9, NKX2-5, OVOL1, PDGFB, PTHLH, SGK1, SKIL, SMAD4, SMAD5, SMAD6, SMAD7, SNAIL SNAI2, TIMP1, and VEGFA, or from the group consisting of: ANGPTL4, CDC42EP3, CDKN1A, CTGF, GADD45A, GADD45B, HMGA2, ID1, IL11, JUNB, PDGFB, PTHLH, SGK1, SKIL, SMAD4, SMAD5, SMAD6, SMAD7, SNAI2, and VEGFA, or ANGPTL4, CDC42EP3, CDKN1A, CTGF, GADD45A, GADD45B, HMGA2, ID1, SERPINE1, JUNB, PDGFB, PTHLH, SGK1, SKIL, SMAD4, SMAD5, SMAD6, SMAD7, SNAI2, and VEGFA, or from the group consisting of: ANGPTL4, CDC42EP3, CDKN1A, CTGF, GADD45B, ID1, IL11, JUNB, PDGFB, SKIL, SMAD7, and SNAI2, or ANGPTL4, CDC42EP3, CDKN1A, CTGF, GADD45B, ID1, SERPINE1, JUNB, VEGFA, SKIL, SMAD7, and SNAI2, or from the group consisting of: ANGPTL4, CDC42EP3, ID1, IL11, JUNB, SKIL, and SMAD7, or ANGPTL4, CDC42EP3, ID1, SERPINE1, JUNB, SKIL, and SMAD7.

In one embodiment, the kit comprises an apparatus comprising a digital processor. In another embodiment, the kit comprises a non-transitory storage medium storing instructions that are executable by a digital processing device. In yet another embodiment, the kit comprises a computer program comprising program code means for causing a digital processing device to perform the methods described herein.

In an additional embodiment, the kit contains one or more components that are for example selected from the group consisting of: a DNA array chip, an oligonucleotide array chip, a protein array chip, an antibody, a plurality of probes, RNA sequencing and a set of primers. In one embodiment, the kit contains a plurality of probes. In one embodiment, the kit contains a set of primers. In one embodiment, the kit contains a 6, 12, 24, 48, 96, or 384-well PCR plate. In one embodiment, the kit includes a 96 well PCR plate. In one embodiment, the kit includes a 384 well PCR plate.

In one embodiment, the kit for measuring the expression levels of TGF-β cellular signaling pathway genes comprises a means for measuring the expression levels of a set of TGF-β cellular signaling pathway genes, wherein the genes consist of ANGPTL4, and at least two of CDC42EP3, ID1, SERPINE1, JUNB, SKIL, or SMAD7. In one embodiment, the kit for measuring the expression levels of TGF-β cellular signaling pathway genes comprises a means for measuring the expression levels of a set of TGF-β cellular signaling pathway genes, wherein the genes consist of ANGPTL4, CDC42EP3, and at least one of ID1, SERPINE1, JUNB, SKIL, or SMAD7. In one embodiment, the kit for measuring the expression levels of TGF-β cellular signaling pathway genes comprises a means for measuring the expression levels of a set of TGF-13 cellular signaling pathway genes, wherein the genes consist of ANGPTL4, CDC42EP3, ID1, SERPINE1, JUNB, SKIL, and SMAD7. In another embodiment, the genes further consist of at least one additional gene selected from CDKN1A, CTGF, GADD45B, PDGFB, and SNAI2. In another embodiment, the genes further consist of CDKN1A, CTGF, GADD45B, PDGFB, and SNAI2. In a further embodiment, the genes further consist of at least one additional gene selected from GADD45A, HMGA2, PTHLH, SGK1, SMAD4, SMAD5, SMAD6, SMAD7, and VEGFA. In a further embodiment, the genes further consist of GADD45A, HMGA2, PTHLH, SGK1, SMAD4, SMAD5, SMAD6, SMAD7, and VEGFA. In a further embodiment, the genes further consist of at least one additional gene selected from INPP5D, MMP2, MMP9, NKX2-5, OVOL1, and TIMP1. In a further embodiment, the genes further consist of INPP5D, MMP2, MMP9, NKX2-5, OVOL1, and TIMP1.

In one embodiment, a kit for measuring the expression levels of TGF-β cellular signaling target genes comprises a 96-well plate and a set of labeled probes for detecting expression of a set of TGF-β cellular signaling pathway genes comprising ANGPTL4, CDC42EP3, ID1, SERPINE1, JUNB, SKIL, or SMAD7. In one embodiment, a kit for measuring the expression levels of TGF-β cellular signaling target genes comprises a 96-well plate and a set of labeled probes for detecting expression of a set of TGF-β cellular signaling pathway genes comprising ANGPTL4, CDC42EP3, and at least one of ID1, SERPINE1, JUNB, SKIL, or SMAD7. In one embodiment, a kit for measuring the expression levels of TGF-β cellular signaling target genes comprises a 96-well plate and a set of labeled probes for detecting expression of a set of TGF-β cellular signaling pathway genes comprising ANGPTL4, CDC42EP3, ID1, SERPINE1, JUNB, SKIL, and SMAD7. In another embodiment, the genes further consist of at least one additional gene selected from CDKN1A, CTGF, GADD45B, PDGFB, and SNAI2. In another embodiment, the genes further consist of CDKN1A, CTGF, GADD45B, PDGFB, and SNAI2. In a further embodiment, the genes further consist of at least one additional gene selected from GADD45A, HMGA2, PTHLH, SGK1, SMAD4, SMAD5, SMAD6, SMAD7, and VEGFA. In a further embodiment, the genes further consist of GADD45A, HMGA2, PTHLH, SGK1, SMAD4, SMAD5, SMAD6, SMAD7, and VEGFA. In a further embodiment, the genes further consist of at least one additional gene selected from INPP5D, MMP2, MMP9, NKX2-5, OVOL1, and TIMP1. In a further embodiment, the genes further consist of INPP5D, MMP2, MMP9, NKX2-5, OVOL1, and TIMP1.

In one embodiment, the kit further comprises an instruction manual measuring the expression levels of TGF-β cellular signaling target genes. In another embodiment, the kit further comprises an access code to access a computer program code for calculating the TGF-β cellular signaling pathway activity in the sample. In a further embodiment, the kit further comprises an access code to access a website for calculating the TGF-β cellular signaling pathway activity in the sample according to the methods described above.

Target Gene Expression Level Determination Procedure

Figure 8:
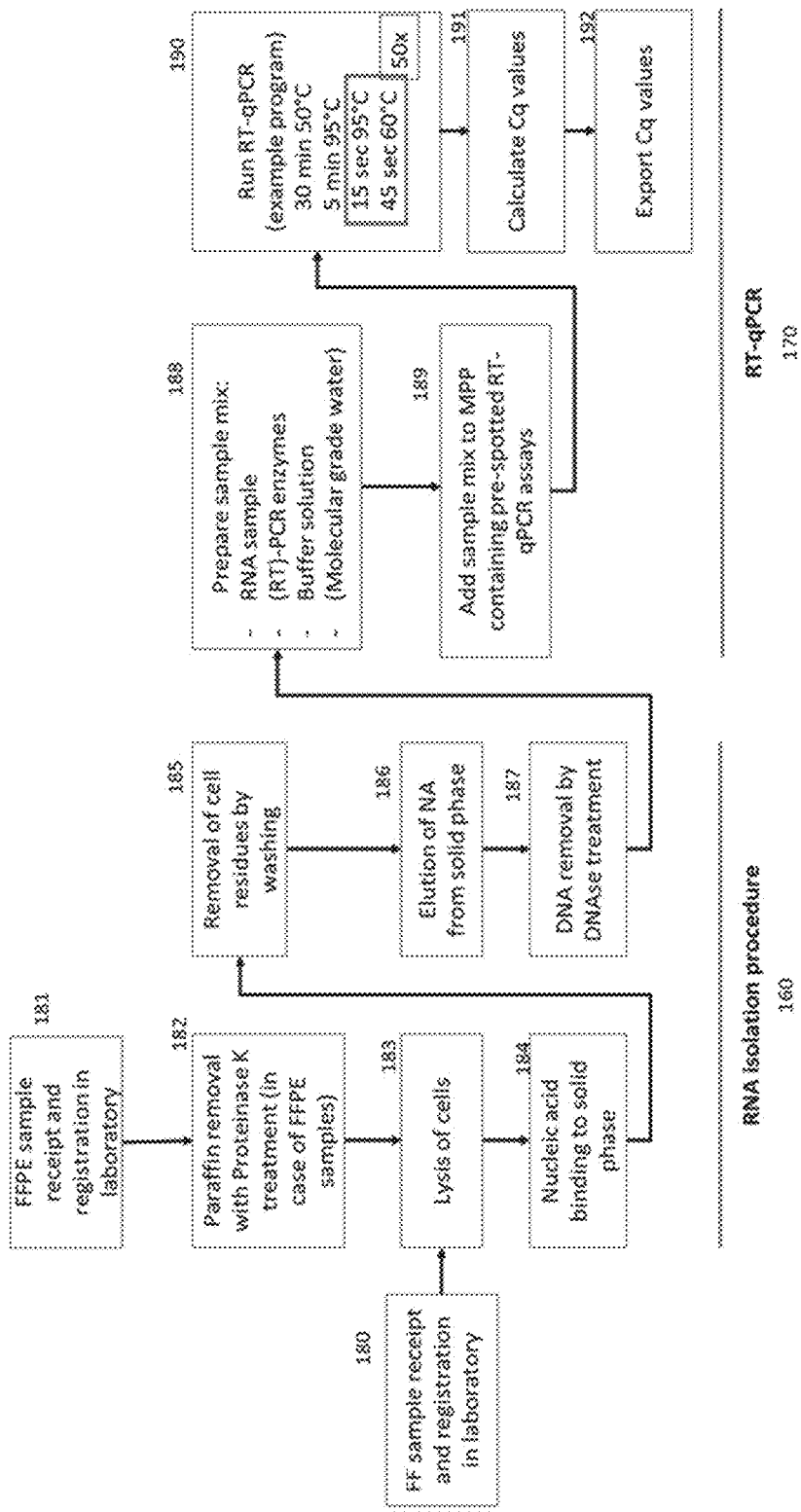
FIG. 8 shows an exemplary flow chart for determining Cq values from RT-qPCR analysis of the target genes of the TGF-β cellular signaling pathway.
Figure 9:
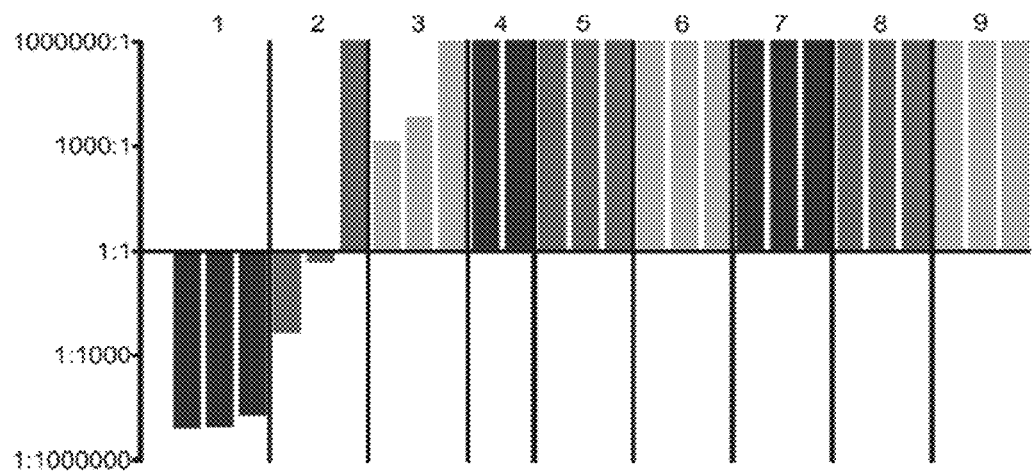
FIGS. 9 to 12 show training results of the exemplary Bayesian network model based on the evidence curated list of target genes (FIG. 9), the 20 target genes shortlist (FIG. 10), the 12 target genes shortlist (FIG. 11), and the 7 target genes shortlist of the TGF-β cellular signaling pathway (FIG. 12) (see Tables 4 to 7), respectively. (Legend: 1—Control; 2—TGF-β stimulation with 5 ng/mL for 0.5 h; 3—TGF-β stimulation with 5 ng/mL for 1 h; 4—TGF-β stimulation with 5 ng/mL for 2 h; 5—TGF-β stimulation with 5 ng/mL for 4 h; 6—TGF-β stimulation with 5 ng/mL for 8 h; 7—TGF-β stimulation with 5 ng/mL for 16 h; 8—TGF-β stimulation with 5 ng/mL for 24 h; 9—TGF-β stimulation with 5 ng/mL for 72 h)
Figure 10:
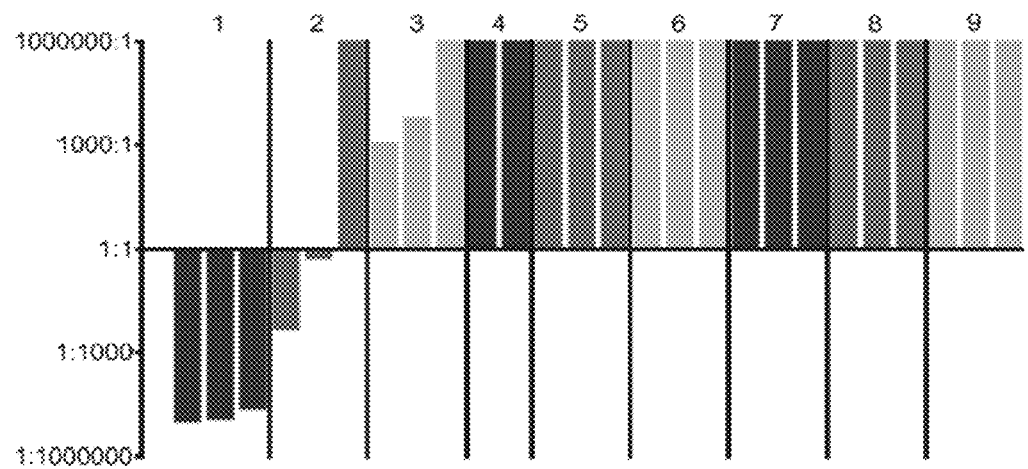
Figure 11:
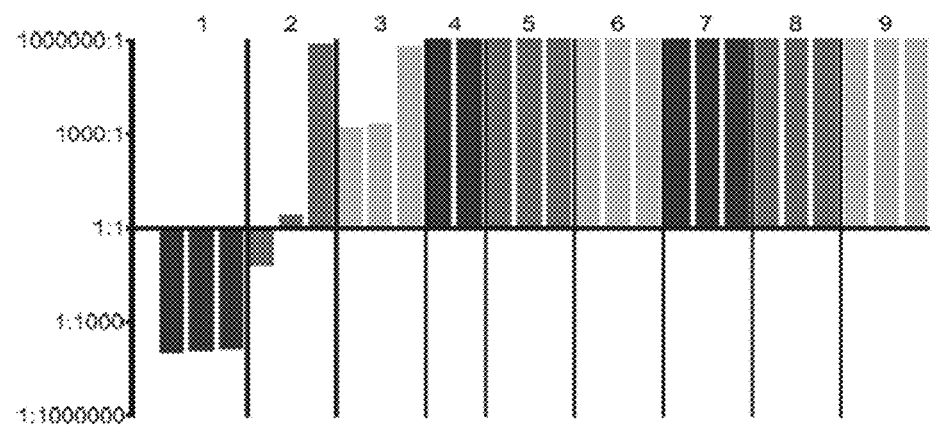
Figure 12:
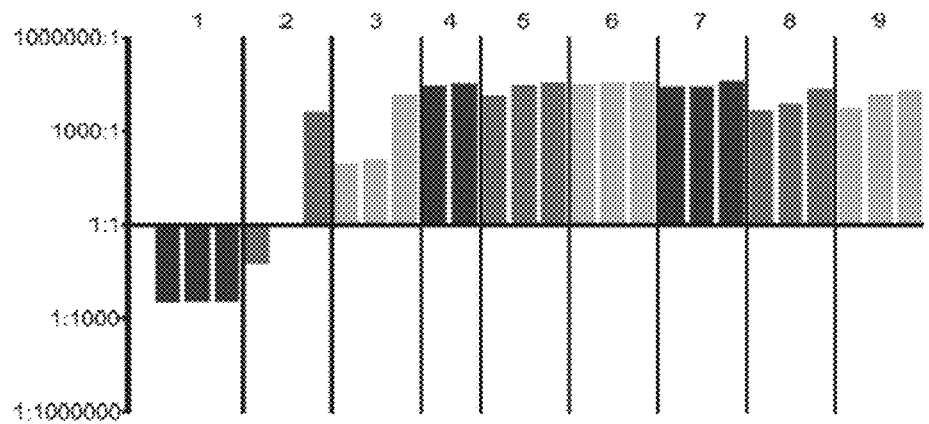

A non-limiting exemplary flow chart for deriving target gene expression levels from a sample isolated from a subject is shown in FIG. 8. In one exemplary embodiment, samples are received and registered in a laboratory. Samples can include, for example, Formalin-Fixed, Paraffin-Embedded (FFPE) samples (181) or fresh frozen (FF) samples (180). FF samples can be directly lysed (183). For FFPE samples, the paraffin can be removed with a heated incubation step upon addition of Proteinase K (182). Cells are then lysed (183), which destroys the cell and nuclear membranes which makes the nucleic acid (NA) available for further processing. The nucleic acid is bound to a solid phase (184) which could for example, be beads or a filter. The nucleic acid is then washed with washing buffers to remove all the cell debris which is present after lysis (185). The clean nucleic acid is then detached from the solid phase with an elution buffer (186). The DNA is removed by DNAse treatment to ensure that only RNA is present in the sample (187). The nucleic acid sample can then be directly used in the RT-qPCR sample mix (188). The RT-qPCR sample mixes contains the RNA sample, the RT enzyme to prepare cDNA from the RNA sample and a PCR enzyme to amplify the cDNA, a buffer solution to ensure functioning of the enzymes and can potentially contain molecular grade water to set a fixed volume of concentration. The sample mix can then be added to a multiwell plate (i.e., 96 well or 384 well plate) which contains dried RT-qPCR assays (189). The RT-qPCR can then be run in a PCR machine according to a specified protocol (190). An example PCR protocol includes i) 30 minutes at 50° C.; ii) 5 minutes at 95° C.; iii) 15 seconds at 95° C.; iv) 45 seconds at 60° C.; v) 50 cycles repeating steps iii and iv. The Cq values are then determined with the raw data by using the second derivative method (191). The Cq values are exported for analysis (192).

Computer Programs and Computer Implemented Methods

As contemplated herein, the calculation of TGF-β signaling in the sample is performed on a computerized device having a processor capable of executing a readable program code for calculating the TGF-β cellular signaling pathway activity in the sample according to the methods described above. Accordingly, the computerized device can include means for receiving expression level data, wherein the data is expression levels of at least three target genes derived from the sample, a means for calculating the level of TGF-β transcription factor element in the sample using a calibrated pathway model, wherein the calibrated pathway model compares the expression levels of the at least three target genes in the sample with expression levels of the at least three target genes in the model which have been correlated with a level TGF-β transcription factor element; a means for calculating the TGF-β cellular signaling in the sample based on the calculated levels of TGF-β transcription factor element in the sample; and a means for assigning a TGF-β cellular signaling pathway activity probability or status to the calculated TGF-β cellular signaling in the sample, and a means for displaying the TGF-β signaling pathway activity probability or status.

In accordance with another disclosed aspect, a non-transitory storage medium stores instructions that are executable by a digital processing device to perform a method according to the present invention as described herein. The non-transitory storage medium may be a computer-readable storage medium, such as a hard drive or other magnetic storage medium, an optical disk or other optical storage medium, a random access memory (RAM), read only memory (ROM), flash memory, or other electronic storage medium, a network server, or so forth. The digital processing device may be a handheld device (e.g., a personal data assistant or smartphone), a notebook computer, a desktop computer, a tablet computer or device, a remote network server, or so forth.

In accordance with another disclosed aspect, an apparatus comprises a digital processor configured to perform a method according to the present invention as described herein.

In accordance with another disclosed aspect, a computer program comprises program code means for causing a digital processing device to perform a method according to the present invention as described herein. The digital processing device may be a handheld device (e.g., a personal data assistant or smartphone), a notebook computer, a desktop computer, a tablet computer or device, a remote network server, or so forth.

In one embodiment, a computer program or system is provided for predicting the activity status of a TGF-β transcription factor element in a human cancer sample that includes a means for receiving data corresponding to the expression level of one or more TGF-β target genes in a sample from a host. In some embodiments, a means for receiving data can include, for example, a processor, a central processing unit, a circuit, a computer, or the data can be received through a website.

In one embodiment, a computer program or system is provided for predicting the activity status of a TGF-β transcription factor element in a human cancer sample that includes a means for displaying the TGF-β pathway signaling status in a sample from a host. In some embodiments, a means for displaying can include a computer monitor, a visual display, a paper print out, a liquid crystal display (LCD), a cathode ray tube (CRT), a graphical keyboard, a character recognizer, a plasma display, an organic light-emitting diode (OLED) display, or a light emitting diode (LED) display, or a physical print out.

In accordance with another disclosed aspect, a signal represents a determined activity of a TGF-β cellular signaling pathway in a subject, wherein the determined activity results from performing a method according to the present invention as described herein. The signal can be a digital signal or it can be an analog signal.

In one aspect of the present invention, a computer implemented method is provided for predicting the activity status of a TGF-β signaling pathway in a human cancer sample performed by a computerized device having a processor comprising: a) calculating an activity level of a TGF-β transcription factor element in a human cancer sample, wherein the level of the TGF-β transcription factor element in the human cancer sample is associated with the activity of a TGF-β cellular signaling pathway, and wherein the level of the TGF-β transcription factor element in the human cancer sample is calculated by i) receiving data on the expression levels of at least three target genes derived from the human cancer sample, wherein the TGF-β transcription factor controls transcription of the at least three target genes, and wherein the at least three target genes are ANGPTL4, and at least two of CDC42EP3, ID1, IL11, JUNB, SKIL, or SMAD7 ii) calculating the activity level of the TGF-β transcription factor element in the human cancer sample using a calibrated pathway model, wherein the calibrated pathway model compares the expression levels of the at least three target genes in the human cancer sample with expression levels of the at least three target genes in the model which have been correlated with an activity level of a TGF-β transcription factor element; b) calculating the TGF-β cellular signaling pathway activity in the human cancer sample based on the calculated TGF-β transcription factor element activity level in the human cancer sample; c) assigning a TGF-β cellular signaling pathway activity status to the TGF-β cellular signaling pathway in the human cancer sample, wherein the activity status is indicative of either an active TGF-β cellular signaling pathway or a passive TGF-β cellular signaling pathway; and d) displaying the TGF-β signaling pathway activity status.

In one aspect of the invention, a system is provided for determining the activity level of a TGF-β cellular signaling pathway in a subject comprising a) a processor capable of calculating an activity level of TGF-β transcription factor element in a sample derived from the subject; b) a means for receiving data, wherein the data is an expression level of at least three target genes derived from the sample; c) a means for calculating the level of the TGF-β transcription factor element in the sample using a calibrated pathway model, wherein the calibrated pathway model compares the expression levels of the at least three target genes in the sample with expression levels of the at least three target genes in the model which define an activity level of TGF-β transcription factor element; d) a means for calculating the activity level of the TGF-β cellular signaling pathway in the sample based on the calculated activity level of TGF-β transcription factor element in the sample; a means for assigning a TGF-β cellular signaling pathway activity status to the calculated activity level of the TGF-β cellular signaling pathway in the sample, wherein the activity status is indicative of either an active TGF-β cellular signaling pathway or a passive TGF-β cellular signaling pathway; and f) a means for displaying the TGF-β signaling pathway activity status.

TGF-β Mediated Diseases and Disorders and Methods of Treatment

As contemplated herein, the methods and apparatuses of the present invention can be utilized to assess TGF-β cellular signaling pathway activity in a subject, for example a subject suspected of having, or having, a disease or disorder wherein the status of the TGF-β signaling pathway is probabtive, either wholly or partially, of disease presence or progression. In one embodiment, provided herein is a method of treating a subject comprising receiving information regarding the activity status of a TGF-β cellular signaling pathway derived from a sample isolated from the subject using the methods described herein and administering to the subject a TGF-β inhibitor if the information regarding the level of TGF-β cellular signaling pathway is indicative of an active TGF-β signaling pathway. In a particular embodiment, the TGF-β cellular signaling pathway activity indication is set at a cutoff value of odds of the TGF-B cellular signaling pathway being active of 10:1, 5:1, 4:1, 2:1, 1:1, 1:2, 1:4, 1:5, 1:10. TGF-β inhibitors are known and include, but are not limtied to, Terameprocol, Fresolimumab, Sotatercept, Galunisertib, SB431542, LY2109761, LDN-193189, SB525334, SB505124, GW788388, LY364947, RepSox, LDN-193189 HCl, K02288, LDN-214117, SD-208, EW-7197, ML347, LDN-212854, DMH1, Pirfenidone, Hesperetin, Trabedersen, Lerdelimumab, Metelimumab, trx-SARA, ID11, Ki26894, or SB-431542.

In one embodiment, the disease or disorder is one of an auto-immune and other immune disorders, cancer, bronchial asthma, heart disease, diabetes, hereditary hemorrhagic telangiectasia, Marfan syndrome, Vascular Ehlers-Danlos syndrome, Loeys-Dietz syndrome, Parkinson's disease, Chronic kidney disease, Multiple Sclerosis, fibrotic diseases such as liver, lng, or kidney fibrosis, Dupuytren's disease, or Alzheimer's disease.

In a particular embodiment, the subject is suffering from, or suspected to have, a cancer, for example, but not limited to, a primary tumor or a metastatic tumor, a solid tumor, for example, melanoma, lung cancer (including lung adenocarcinoma, basal cell carcinoma, squamous cell carcinoma, large cell carcinoma, bronchioloalveolar carcinoma, bronchiogenic carcinoma, non-small-cell carcinoma, small cell carcinoma, mesothelioma); breast cancer (including ductal carcinoma, lobular carcinoma, inflammatory breast cancer, clear cell carcinoma, mucinous carcinoma, serosal cavities breast carcinoma); colorectal cancer (colon cancer, rectal cancer, colorectal adenocarcinoma); anal cancer; pancreatic cancer (including pancreatic adenocarcinoma, islet cell carcinoma, neuroendocrine tumors); prostate cancer; prostate adenocarcinoma; ovarian carcinoma (ovarian epithelial carcinoma or surface epithelial-stromal tumor including serous tumor, endometrioid tumor and mucinous cystadenocarcinoma, sex-cord-stromal tumor); liver and bile duct carcinoma (including hepatocellular carcinoma, cholangiocarcinoma, hemangioma); esophageal carcinoma (including esophageal adenocarcinoma and squamous cell carcinoma); oral and oropharyngeal squamous cell carcinoma; salivary gland adenoid cystic carcinoma; bladder cancer; bladder carcinoma; carcinoma of the uterus (including endometrial adenocarcinoma, ocular, uterine papillary serous carcinoma, uterine clear-cell carcinoma, uterine sarcomas and leiomyosarcomas, mixed mullerian tumors); glioma, glioblastoma, medulloblastoma, and other tumors of the brain; kidney cancers (including renal cell carcinoma, clear cell carcinoma, Wilm's tumor); cancer of the head and neck (including squamous cell carcinomas); cancer of the stomach (gastric cancers, stomach adenocarcinoma, gastrointestinal stromal tumor); testicular cancer; germ cell tumor; neuroendocrine tumor; cervical cancer; carcinoids of the gastrointestinal tract, breast, and other organs; signet ring cell carcinoma; mesenchymal tumors including sarcomas, fibrosarcomas, haemangioma, angiomatosis, haemangiopericytoma, pseudoangiomatous stromal hyperplasia, myofibroblastoma, fibromatosis, inflammatory myofibroblastic tumor, lipoma, angiolipoma, granular cell tumor, neurofibroma, schwannoma, angiosarcoma, liposarcoma, rhabdomyosarcoma, osteosarcoma, leiomyoma, leiomysarcoma, skin, including melanoma, cervical, retinoblastoma, head and neck cancer, pancreatic, brain, thyroid, testicular, renal, bladder, soft tissue, adenal gland, urethra, cancers of the penis, myxosarcoma, chondrosarcoma, osteosarcoma, chordoma, malignant fibrous histiocytoma, lymphangiosarcoma, mesothelioma, squamous cell carcinoma; epidermoid carcinoma, malignant skin adnexal tumors, adenocarcinoma, hepatoma, hepatocellular carcinoma, renal cell carcinoma, hypernephroma, cholangiocarcinoma, transitional cell carcinoma, choriocarcinoma, seminoma, embryonal cell carcinoma, glioma anaplastic; glioblastoma multiforme, neuroblastoma, medulloblastoma, malignant meningioma, malignant schwannoma, neurofibrosarcoma, parathyroid carcinoma, medullary carcinoma of thyroid, bronchial carcinoid, pheochromocytoma, Islet cell carcinoma, malignant carcinoid, malignant paraganglioma, melanoma, Merkel cell neoplasm, cystosarcoma phylloide, salivary cancers, thymic carcinomas, and cancers of the vagina among others.

In one embodiment, the methods described herein are useful for treating a host suffering from a lymphoma or lymphocytic or myelocytic proliferation disorder or abnormality. For example, the subject suffering from a Hodgkin Lymphoma of a Non-Hodgkin Lymphoma. For example, the subject can be suffering from a Non-Hodgkin Lymphoma such as, but not limited to: an AIDS-Related Lymphoma; Anaplastic Large-Cell Lymphoma; Angioimmunoblastic Lymphoma; Blastic NK-Cell Lymphoma; Burkitt's Lymphoma; Burkitt-like Lymphoma (Small Non-Cleaved Cell Lymphoma); Chronic Lymphocytic Leukemia/Small Lymphocytic Lymphoma; Cutaneous T-Cell Lymphoma; Diffuse Large B-Cell Lymphoma; Enteropathy-Type T-Cell Lymphoma; Follicular Lymphoma; Hepatosplenic Gamma-Delta T-Cell Lymphoma; Lymphoblastic Lymphoma; Mantle Cell Lymphoma; Marginal Zone Lymphoma; Nasal T-Cell Lymphoma; Pediatric Lymphoma; Peripheral T-Cell Lymphomas; Primary Central Nervous System Lymphoma; T-Cell Leukemias; Transformed Lymphomas; Treatment-Related T-Cell Lymphomas; or Waldenstrom's Macroglobulinemia.

Alternatively, the subject may be suffering from a Hodgkin Lymphoma, such as, but not limited to: Nodular Sclerosis Classical Hodgkin's Lymphoma (CHL); Mixed Cellularity CHL; Lymphocyte-depletion CHL; Lymphocyte-rich CHL; Lymphocyte Predominant Hodgkin Lymphoma; or Nodular Lymphocyte Predominant HL.

In one embodiment, the subject may be suffering from a specific T-cell, a B-cell, or a NK-cell based lymphoma, proliferative disorder, or abnormality. For example, the subject can be suffering from a specific T-cell or NK-cell lymphoma, for example, but not limited to: Peripheral T-cell lymphoma, for example, peripheral T-cell lymphoma and peripheral T-cell lymphoma not otherwise specified (PTCL-NOS); anaplastic large cell lymphoma, for example anaplastic lymphoma kinase (ALK) positive, ALK negative anaplastic large cell lymphoma, or primary cutaneous anaplastic large cell lymphoma; angioimmunoblastic lymphoma; cutaneous T-cell lymphoma, for example mycosis fungoides, Sézary syndrome, primary cutaneous anaplastic large cell lymphoma, primary cutaneous CD30+ T-cell lymphoproliferative disorder; primary cutaneous aggressive epidermotropic CD8+ cytotoxic T-cell lymphoma; primary cutaneous gamma-delta T-cell lymphoma; primary cutaneous small/medium CD4+ T-cell lymphoma. and lymphomatoid papulosis; Adult T-cell Leukemia/Lymphoma (ATLL); Blastic NK-cell Lymphoma; Enteropathy-type T-cell lymphoma; Hematosplenic gamma-delta T-cell Lymphoma; Lymphoblastic Lymphoma; Nasal NK/T-cell Lymphomas; Treatment-related T-cell lymphomas; for example lymphomas that appear after solid organ or bone marrow transplantation; T-cell prolymphocytic leukemia; T-cell large granular lymphocytic leukemia; Chronic lymphoproliferative disorder of NK-cells; Aggressive NK cell leukemia; Systemic EBV+ T-cell lymphoproliferative disease of childhood (associated with chronic active EBV infection); Hydroa vacciniforme-like lymphoma; Adult T-cell leukemia/lymphoma; Enteropathy-associated T-cell lymphoma; Hepatosplenic T-cell lymphoma; or Subcutaneous panniculitis-like T-cell lymphoma.

Alternatively, the subject may be suffering from a specific B-cell lymphoma or proliferative disorder such as, but not limited to: multiple myeloma; Diffuse large B cell lymphoma; Follicular lymphoma; Mucosa-Associated Lymphatic Tissue lymphoma (MALT); Small cell lymphocytic lymphoma; Mantle cell lymphoma (MCL); Burkitt lymphoma; Mediastinal large B cell lymphoma; Waldenström macroglobulinemia; Nodal marginal zone B cell lymphoma (NMZL); Splenic marginal zone lymphoma (SMZL); Intravascular large B-cell lymphoma; Primary effusion lymphoma; or Lymphomatoid granulomatosis; Chronic lymphocytic leukemia/small lymphocytic lymphoma; B-cell prolymphocytic leukemia; Hairy cell leukemia; Splenic lymphoma/leukemia, unclassifiable; Splenic diffuse red pulp small B-cell lymphoma; Hairy cell leukemia-variant; Lymphoplasmacytic lymphoma; Heavy chain diseases, for example, Alpha heavy chain disease, Gamma heavy chain disease, Mu heavy chain disease; Plasma cell myeloma; Solitary plasmacytoma of bone; Extraosseous plasmacytoma; Primary cutaneous follicle center lymphoma; T cell/histiocyte rich large B-cell lymphoma; DLBCL associated with chronic inflammation; Epstein-Barr virus (EBV)+ DLBCL of the elderly; Primary mediastinal (thymic) large B-cell lymphoma; Primary cutaneous DLBCL, leg type; ALK+ large B-cell lymphoma; Plasmablastic lymphoma; Large B-cell lymphoma arising in HHV8-associated multicentric; Castleman disease; B-cell lymphoma, unclassifiable, with features intermediate between diffuse large B-cell lymphoma and Burkitt lymphoma; B-cell lymphoma, unclassifiable, with features intermediate between diffuse large B-cell lymphoma and classical Hodgkin lymphoma; Nodular sclerosis classical Hodgkin lymphoma; Lymphocyte-rich classical Hodgkin lymphoma; Mixed cellularity classical Hodgkin lymphoma; or Lymphocyte-depleted classical Hodgkin lymphoma.

In one embodiment, the subject is suffering from a leukemia. For example, the subject may be suffering from an acute or chronic leukemia of a lymphocytic or myelogenous origin, such as, but not limited to: Acute lymphoblastic leukemia (ALL); Acute myelogenous leukemia (AML); Chronic lymphocytic leukemia (CLL); Chronic myelogenous leukemia (CML); juvenile myelomonocytic leukemia (JMML); hairy cell leukemia (HCL); acute promyelocytic leukemia (a subtype of AML); T-cell prolymphocytic leukemia (TPLL); large granular lymphocytic leukemia; or Adult T-cell chronic leukemia; large granular lymphocytic leukemia (LGL). In one embodiment, the patient suffers from an acute myelogenous leukemia, for example an undifferentiated AML (M0); myeloblastic leukemia (M1; with/without minimal cell maturation); myeloblastic leukemia (M2; with cell maturation); promyelocytic leukemia (M3 or M3 variant [M3V]); myelomonocytic leukemia (M4 or M4 variant with eosinophilia [M4E]); monocytic leukemia (M5); erythroleukemia (M6); or megakaryoblastic leukemia (M7).

In a particular embodiment, the subject is suffering, or suspected to be suffering from, a breast cancer, lung cancer, a colon cancer, pancreatic cancer, or brain cancer. In a particular embodiment, the subject is suffering from, or suspected to be suffering from, a breast cancer.

The sample(s) to be used in accordance with the present invention can be an extracted sample, that is, a sample that has been extracted from the subject. Examples of the sample include, but are not limited to, a tissue, cells, blood and/or a body fluid of a subject. It can be, e.g., a sample obtained from a cancer lesion, or from a lesion suspected for cancer, or from a metastatic tumor, or from a body cavity in which fluid is present which is contaminated with cancer cells (e.g., pleural or abdominal cavity or bladder cavity), or from other body fluids containing cancer cells, and so forth, for example, via a biopsy procedure or other sample extraction procedure. The cells of which a sample is extracted may also be tumorous cells from hematologic malignancies (such as leukemia or lymphoma). In some cases, the cell sample may also be circulating tumor cells, that is, tumor cells that have entered the bloodstream and may be extracted using suitable isolation techniques, e.g., apheresis or conventional venous blood withdrawal. Aside from blood, a body fluid of which a sample is extracted may be urine, gastrointestinal contents, or anextravasate.

In one aspect of the present invention, the methods and apparatuses described herein are used to identify an active TGF-β cellular signaling pathway in a subject suffering from a cancer, and administering to the subject an anti-cancer agent, for example a TGF-β inhibitor, selected from, but not limited to, Terameprocol, Fresolimumab, Sotatercept, Galunisertib, SB431542, LY2109761, LDN-193189, SB525334, SB505124, GW788388, LY364947, RepSox, LDN-193189 HCl, K02288, LDN-214117, SD-208, EW-7197, ML347, LDN-212854, DMH1, Pirfenidone, Hesperetin, Trabedersen, Lerdelimumab, Metelimumab, trx-SARA, ID11, Ki26894, or SB-431542. Another aspect of the present invention relates to a method (as described herein), further comprising:

determining whether the TGF-β cellular signaling pathway is operating abnormally in the subject based on the calculated activity of the TGF-β cellular signaling pathway in the subject.

Here, the term "abnormally" denotes disease-promoting activity of the TGF-β cellular signaling pathway, for example, a tumor-promoting activity.

The present invention also relates to a method (as described herein) further comprising:

recommending prescribing a drug, for example a TGF-β inhibitor, for the subject that corrects for abnormal operation of the TGF-β cellular signaling pathway, wherein the recommending is performed if the TGF-β cellular signaling pathway is determined to be operating abnormally in the subject based on the calculated/determined activity of the TGF-β cellular signaling pathway.

The present invention also relates to a method (as described herein), wherein the calculating/determining comprises:

calculating the activity of the TGF-β cellular signaling pathway in the subject based at least on expression levels of two, three or more target genes of a set of target genes of the TGF-β cellular signaling pathway measured in the sample of the subject.

In one embodiment, the set of target genes of the TGF-β cellular signaling pathway includes at least seven, or in an alternative, all target genes selected from the group consisting of: ANGPTL4, CDC42EP3, CDKN1A, CDKN2B, CTGF, GADD45A, GADD45B, HMGA2, ID1, IL11, INPP5D, JUNB, MMP2, MMP9, NKX2-5, OVOL1, PDGFB, PTHLH, SGK1, SKIL, SMAD4, SMAD5, SMAD6, SMAD7, SNAIL SNAI2, TIMP1, and VEGFA, or from the group consisting of: ANGPTL4, CDC42EP3, CDKN1A, CTGF, GADD45A, GADD45B, HMGA2, ID1, IL11, JUNB, PDGFB, PTHLH, SGK1, SKIL, SMAD4, SMAD5, SMAD6, SMAD7, SNAI2, and VEGFA, or from the group consisting of: ANGPTL4, CDC42EP3, CDKN1A, CTGF, GADD45B, ID1, IL11, JUNB, PDGFB, SKIL, SMAD7, and SNAI2, or from the group consisting of: ANGPTL4, CDC42EP3, ID1, IL11, JUNB, SKIL, and SMAD7.

The present invention as described herein can, e.g., also advantageously be used in connection with:

diagnosis based on the determined activity of the TGF-β cellular signaling pathway in the subject;

prognosis based on the determined activity of the TGF-β cellular signaling pathway in the subject;

drug prescription based on the determined activity of the TGF-β cellular signaling pathway in the subject;

prediction of drug efficacy based on the determined activity of the TGF-β cellular signaling pathway in the subject;

prediction of adverse effects based on the determined activity of the TGF-β cellular signaling pathway in the subject;

monitoring of drug efficacy;
drug development;
assay development;
pathway research;
cancer staging;

enrollment of the subject in a clinical trial based on the determined activity of the TGF-β cellular signaling pathway in the subject;

selection of subsequent test to be performed; and
selection of companion diagnostics tests.

Further advantages will be apparent to those of ordinary skill in the art upon reading and understanding the attached figures, the following description and, in particular, upon reading the detailed examples provided herein below.

It shall be understood that an embodiment of the present invention can also be any combination of the dependent claims or above embodiments with the respective independent claim.

These and other aspects of the invention will be apparent from and elucidated with reference to the embodiments described hereinafter.

EXAMPLES

The following examples merely illustrate exemplary methods and selected aspects in connection therewith. The teaching provided therein may be used for constructing several tests and/or kits, e.g., to detect, predict and/or diagnose the abnormal activity of the TGF-B cellular signaling pathways. Furthermore, upon using methods as described herein drug prescription can advantageously be guided, drug response prediction and monitoring of drug efficacy (and/or adverse effects) can be made, drug resistance can be predicted and monitored, e.g., to select subsequent test(s) to be performed (like a companion diagnostic test). The following examples are not to be construed as limiting the scope of the present invention.

Example 1

Mathematical Model Construction

As described in detail in the published international patent application WO 2013/011479 A2 ("Assessment of cellular signaling pathway activity using probabilistic modeling of target gene expression"), by constructing a probabilistic model, e.g., a Bayesian network model, and incorporating conditional probabilistic relationships between expression levels of one or more target gene(s) of a cellular signaling pathway, herein, the TGF-β cellular signaling pathway, and the level of a transcription factor (TF) element, herein, the TGF-β TF element, the TF element controlling transcription of the one or more target gene(s) of the cellular signaling pathway, such a model may be used to determine the activity of the cellular signaling pathway with a high degree of accuracy. Moreover, the probabilistic model can be readily updated to incorporate additional knowledge obtained by later clinical studies, by adjusting the conditional probabilities and/or adding new nodes to the model to represent additional information sources. In this way, the probabilistic model can be updated as appropriate to embody the most recent medical knowledge.

In another easy to comprehend and interpret approach described in detail in the published international patent application WO 2014/102668 A2 ("Assessment of cellular signaling pathway activity using linear combination(s) of target gene expressions"), the activity of a cellular signaling pathway, herein, the TGF-β cellular signaling pathway, may be determined by constructing and evaluating a linear or (pseudo-)linear model incorporating relationships between expression levels of one or more target gene(s) of the cellular signaling pathway and the level of a transcription factor (TF) element, herein, the TGF-β TF element, the TF element controlling transcription of the one or more target gene(s) of the cellular signaling pathway, the model being based at least in part on one or more linear combination(s) of expression levels of the one or more target gene(s).

In both approaches, the expression levels of the one or more target gene(s) may, for example, be measurements of the level of mRNA, which can be the result of, e.g., (RT)-PCR and microarray techniques using probes associated with the target gene(s) mRNA sequences, and of RNA-sequencing. In another embodiment, the expression levels of the one or more target gene(s) can be measured by protein levels, e.g., the concentrations and/or activity of the protein(s) encoded by the target gene(s).

The aforementioned expression levels may optionally be converted in many ways that might or might not suit the application better. For example, four different transformations of the expression levels, e.g., microarray-based mRNA levels, may be:

- "continuous data", i.e., expression levels as obtained after preprocessing of microarrays using well known algorithms such as MAS5.0 and fRMA,
- "z-score", i.e., continuous expression levels scaled such that the average across all samples is 0 and the standard deviation is 1,
- "discrete", i.e., every expression above a certain threshold is set to 1 and below it to 0 (e.g., the threshold for a probeset may be chosen as the (weighted) median of its value in a set of a number of positive and the same number of negative clinical samples),
- "fuzzy", i.e., the continuous expression levels are converted to values between 0 and 1 using a sigmoid function of the following format: $1/(1+\exp((thr-expr)/se))$, with expr being the continuous expression levels, thr being the threshold as mentioned before and se being a softening parameter influencing the difference between 0 and 1.

One of the simplest linear models that can be constructed is a model having a node representing the transcription factor (TF) element, herein, the TGF-β TF element, in a first layer and weighted nodes representing direct measurements of the target gene(s) expression levels, e.g., by one probeset that is particularly highly correlated with the particular target gene, e.g., in microarray or (q)PCR experiments, in a second layer. The weights can be based either on calculations from a training data set or based on expert knowledge. This approach of using, in the case where possibly multiple expression levels are measured per target gene (e.g., in the case of microarray experiments, where one target gene can be measured with multiple probesets), only one expression level per target gene is particularly simple. A specific way of selecting the one expression level that is used for a particular target gene is to use the expression level from the probeset that is able to separate active and passive samples of a training data set the best. One method to determine this probeset is to perform a statistical test, e.g., the t-test, and select the probeset with the lowest p-value. The training data set's expression levels of the probeset with the lowest p-value is by definition the probeset with the least likely probability that the expression levels of the (known) active and passive samples overlap. Another selection method is based on odds-ratios. In such a model, one or more expression level(s) are provided for each of the one or more target gene(s) and the one or more linear combination(s) comprise a linear combination including for each of the one or more target gene(s) a weighted term, each weighted term being based on only one expression level of the one or more expression level(s) provided for the respective target gene. If the only one expression level is chosen per target gene as described above, the model may be called a "most discriminant probesets" model.

In an alternative to the "most discriminant probesets" model, it is possible, in the case where possibly multiple expression levels are measured per target gene, to make use of all the expression levels that are provided per target gene. In such a model, one or more expression level(s) are provided for each of the one or more target gene(s) and the one or more linear combination(s) comprise a linear combination of all expression levels of the one or more expression level(s) provided for the one or more target gene(s). In other words, for each of the one or more target gene(s), each of the one or more expression level(s) provided for the respective target gene may be weighted in the linear combination by its own (individual) weight. This variant may be called an "all probesets" model. It has an advantage of being relatively simple while making use of all the provided expression levels.

Both models as described above have in common that they are what may be regarded as "single-layer" models, in which the level of the TF element is calculated based on a linear combination of expression levels of the one or more probeset of the one or more target genes.

After the level of the TF element, herein, the TGF-β TF element, has been determined by evaluating the respective model, the determined TF element level can be thresholded in order to infer the activity of the cellular signaling pathway, herein, the TGF-β cellular signaling pathway. An exemplary method to calculate such an appropriate threshold is by comparing the determined TF element levels wlc of training samples known to have a passive cellular signaling pathway and training samples with an active cellular signaling pathway. A method that does so and also takes into account the variance in these groups is given by using a threshold $$thr = \frac{\sigma_{wlc_{pas}}\mu_{wlc_{act}} + \sigma_{wlc_{act}}\mu_{wlc_{pas}}}{\sigma_{wlc_{pas}} + \sigma_{wlc_{act}}} \quad (1)$$

where σ and μ are the standard deviation and the mean of the determined TF element levels wlc for the training samples. In case only a small number of samples are available in the active and/or passive training samples, a pseudocount may be added to the calculated variances based on the average of the variances of the two groups:

$$\tilde{v} = \frac{v_{wlc_{act}} + v_{wlc_{pas}}}{2} \quad (2)$$

$$\tilde{v}_{wlc_{act}} = \frac{x\tilde{v} + (n_{act} - 1)v_{wlc_{act}}}{x + n_{act} - 1}$$

$$\tilde{v}_{wlc_{pas}} = \frac{x\tilde{v} + (n_{pas} - 1)v_{wlc_{pas}}}{x + n_{pas} - 1}$$

where v is the variance of the determined TF element levels wlc of the groups, x is a positive pseudocount, e.g., 1 or 10, and nact and npas are the number of active and passive samples, respectively. The standard deviation σ can next be obtained by taking the square root of the variance v.

The threshold can be subtracted from the determined TF element levels wlc for ease of interpretation, resulting in a cellular signaling pathway's activity score in which negative values correspond to a passive cellular signaling pathway and positive values correspond to an active cellular signaling pathway.

As an alternative to the above-described "single-layer" models, a "two-layer" may also be used in an example. In such a model, a summary value is calculated for every target gene using a linear combination based on the measured intensities of its associated probesets ("first (bottom) layer"). The calculated summary value is subsequently combined with the summary values of the other target genes of the cellular signaling pathway using a further linear combination ("second (upper) layer"). Again, the weights can be either learned from a training data set or based on expert knowledge or a combination thereof. Phrased differently, in the "two-layer" model, one or more expression level(s) are provided for each of the one or more target gene(s) and the one or more linear combination(s) comprise for each of the one or more target gene(s) a first linear combination of all expression levels of the one or more expression level(s) provided for the respective target gene ("first (bottom) layer"). The model is further based at least in part on a further linear combination including for each of the one or more target gene(s) a weighted term, each weighted term being based on the first linear combination for the respective target gene ("second (upper) layer").

The calculation of the summary values can, in an exemplary version of the "two-layer" model, include defining a threshold for each target gene using the training data and subtracting the threshold from the calculated linear combination, yielding the target gene summary. Here the threshold may be chosen such that a negative target gene summary value corresponds to a down-regulated target gene and that a positive target gene summary value corresponds to an up-regulated target gene. Also, it is possible that the target gene summary values are transformed using, e.g., one of the above-described transformations (fuzzy, discrete, etc.), before they are combined in the "second (upper) layer".

After the level of the TF element has been determined by evaluating the "two-layer" model, the determined TF element level can be thresholded in order to infer the activity of the cellular signaling pathway, as described above.

In the following, the models described above are collectively denoted as "(pseudo-)linear" models. A more detailed description of the training and use of probabilistic models, e.g., a Bayesian network model, is provided in Example 3 below.

Example 2

Selection of Target Genes

A transcription factor (TF) is a protein complex (i.e., a combination of proteins bound together in a specific structure) or a protein that is able to regulate transcription from target genes by binding to specific DNA sequences, thereby controlling the transcription of genetic information from DNA to mRNA. The mRNA directly produced due to this action of the TF complex is herein referred to as a "direct target gene" (of the transcription factor). Cellular signaling pathway activation may also result in more secondary gene transcription, referred to as "indirect target genes". In the following, (pseudo-)linear models or Bayesian network models (as exemplary mathematical models) comprising or consisting of direct target genes as direct links between cellular signaling pathway activity and mRNA level, are exemplified, however the distinction between direct and indirect target genes is not always evident. Herein, a method to select direct target genes using a scoring function based on available scientific literature data is presented. Nonetheless, an accidental selection of indirect target genes cannot be ruled out due to limited information as well as biological variations and uncertainties. In order to select the target genes, the MEDLINE database of the National Institute of Health accessible at "www.ncbi.nlm.nih.gov/pubmed" and herein further referred to as "Pubmed" was employed to generate a lists of target genes. Furthermore, three additional lists of target genes were selected based on the probative nature of their expression.

Publications containing putative TGF-β target genes were searched for by using queries such as ("TGF-β" AND "target gene") in the period of fourth quarter of 2013 and the first quarter of 2014. The resulting publications were further analyzed manually following the methodology described in more detail below.

Specific cellular signaling pathway mRNA target genes were selected from the scientific literature, by using a ranking system in which scientific evidence for a specific target gene was given a rating, depending on the type of scientific experiments in which the evidence was accumulated. While some experimental evidence is merely suggestive of a gene being a direct target gene, like for example an mRNA increasing as detected by means of an increasing intensity of a probeset on a microarray of a cell line in which it is known that the TGF-β cellular signaling pathway is active, other evidence can be very strong, like the combination of an identified TGF-β cellular signaling pathway TF binding site and retrieval of this site in a chromatin immunoprecipitation (ChIP) assay after stimulation of the specific cellular signaling pathway in the cell and increase in mRNA after specific stimulation of the cellular signaling pathway in a cell line.

Several types of experiments to find specific cellular signaling pathway target genes can be identified in the scientific literature:

1. ChIP experiments in which direct binding of a TF of the cellular signaling pathway of interest to its binding site on the genome is shown. Example: By using chromatin immunoprecipitation (ChIP) technology subsequently putative functional TGF-β TF binding sites in the DNA of cell lines with and without active induction of the TGF-β cellular signaling pathway, e.g., by stimulation with TGF-β, were identified, as a subset of the binding sites recognized purely based on nucleotide sequence. Putative functionality was identified as ChIP-derived evidence that the TF was found to bind to the DNA binding site.
2. Electrophoretic Mobility Shift (EMSA) assays which show in vitro binding of a TF to a fragment of DNA containing the binding sequence. Compared to ChIP-based evidence EMSA-based evidence is less strong, since it cannot be translated to the in vivo situation.
3. Stimulation of the cellular signaling pathway and measuring mRNA expression using a microarray, RNA sequencing, quantitative PCR or other techniques, using TGF-β cellular signaling pathway-inducible cell lines and measuring mRNA profiles measured at least one, but may be, in an alternative, several time points after induction—in the presence of cycloheximide, which inhibits translation to protein, thus the induced mRNAs are assumed to be direct target genes.
4. Similar to 3, but alternatively measure the mRNAs expression further downstream with protein abundance measurements, such as western blot.

5. Identification of TF binding sites in the genome using a bioinformatics approach. Example for the TGF-β TF element: Using the SMAD binding motif 5'-AGAC-3', a software program was run on the human genome sequence, and potential binding sites were identified, both in gene promoter regions and in other genomic regions.
6. Similar as 3, only in the absence of cycloheximide.
7. Similar to 4, only in the absence of cycloheximide.

In the simplest form one can give every potential gene 1 point for each of these experimental approaches in which the gene was identified as being a target gene of the TGF-β family of transcription factors. Using this relative ranking strategy, one can make a list of most reliable target genes.

Alternatively, ranking in another way can be used to identify the target genes that are most likely to be direct target genes, by giving a higher number of points to the technology that provides most evidence for an in vivo direct target gene. In the list above, this would mean 8 points for experimental approach 1), 7 for 2), and going down to 1 point for experimental approach 8). Such a list may be called a "general list of target genes".

Despite the biological variations and uncertainties, the inventors assumed that the direct target genes are the most likely to be induced in a tissue-independent manner. A list of these target genes may be called an "evidence curated list of target genes". Such an evidence curated list of target genes has been used to construct computational models of the TGF-β cellular signaling pathway that can be applied to samples coming from different tissue sources.

The following will illustrate exemplary how the selection of an evidence curated target gene list specifically was constructed for the TGF-β cellular signaling pathway.

A scoring function was introduced that gave a point for each type of experimental evidence, such as ChIP, EMSA, differential expression, knock down/out, luciferase gene reporter assay, sequence analysis, that was reported in a publication. The same experimental evidence is sometimes mentioned in multiple publications resulting in a corresponding number of points, e.g., two publications mentioning a ChIP finding results in twice the score that is given for a single ChIP finding. Further analysis was performed to allow only for genes that had diverse types of experimental evidence and not only one type of experimental evidence, e.g., differential expression. Those genes that had more than one type of experimental evidence available were selected (as shown in Table 4).

A further selection of the evidence curated list of target genes (listed in Table 5) was made by the inventors. The target genes of the evidence curated list that were proven to be more probative in determining the activity of the TGF-β signaling pathway from the training samples were selected. Herein, samples from GSE17708 stimulated with 5 ng/mL TGF-β for 4 hours were chosen as active or tumor promoting TGF-β activity whereas the unstimulated samples were chosen as the passive or tumor suppressing TGF-β samples for training, alternatively, one can use patient samples of primary cells or other cell lines stimulated with and deprived of TGF-β, e.g. GSE6653, GSE42373 and GSE18670. All target genes that had a "soft" odds ratio (see below) between active and passive training samples of more than 2 or less than 0.5 for negatively regulated target genes were selected for the "20 target genes shortlist". Target genes that were found to have a "soft" odds ratio of more than 10 or less than 0.1 are selected for the "12 target genes shortlist". The "7 target genes shortlist" consists of target genes that were found to have a "soft" odds ratio of more than 15 or less than 1/15. The 20 target genes shortlist, the 12 target genes shortlist, and the 7 target genes shortlist are shown in Tables 5 to 7, respectively.

TABLE 4

"Evidence curated list of target genes" of the TGF-β cellular signaling pathway used in the TGF-β cellular signaling pathway models and associated probesets used to measure the mRNA expression level of the target genes.

| Target gene | Probeset |
| --- | --- |
| ANGPTL4 | 223333_s_at |
|  | 221009_s_at |
| CDC42EP3 | 209286_a |
|  | 209288_s_at |
|  | 225685_at |
|  | 209287_s_at |
| CDKN1A | 202284_s_at |
|  | 1555186_at |
| CDKN2B | 236313_at |
|  | 207530_s_at |
| CTGF | 209101_at |
| GADD45A | 203725_at |
| GADD45B | 207574_s_at |
|  | 209305_s_at |
|  | 209304_x_at |
| HMGA2 | 208025_s_at |
|  | 1567224_at |
|  | 1568287_at |
|  | 1558683_a_at |
|  | 1561633_at |
|  | 1559891_at |
|  | 1558682_at |
| ID1 | 208937_s_at |
| IL11 | 206924_at |
|  | 206926_s_at |
| INPP5D | 203331_s_at |
|  | 1568943_at |
|  | 203332_s_at |
| JUNB | 201473_at |
| MMP2 | 1566678_at |
|  | 201069_at |
| MMP9 | 203936_s_at |
| NKX2-5 | 206578_at |
| OVOL1 | 206604_at |
|  | 229396_at |
| PDGFB | 204200_s_at |
|  | 216061_x_at |
|  | 217112_at |
|  | 217430_x_at |
| PTHLH | 210355_at |
|  | 206300_s_at |
|  | 1556773_at |
|  | 211756_at |
| SGK1 | 201739_at |
| SKIL | 206675_s_at |
|  | 225227_at |
|  | 215889_at |
| SMAD4 | 202526_at |
|  | 202527_s_at |
|  | 1565703_at |
|  | 235725_at |
| SMAD5 | 225223_at |
|  | 235451_at |
|  | 225219_at |
|  | 205187_at |
|  | 205188_s_at |
| SMAD6 | 207069_s_at |
|  | 209886_s_at |
| SMAD7 | 204790_at |
| SNAI1 | 219480_at |
| SNAI2 | 213139_at |
| TIMP1 | 201666_at |
| VEGFA | 210513_s_at |
|  | 210512_s_at |
|  | 212171_x_at |
|  | 211527_x_at |

TABLE 5

"20 target genes shortlist" of target genes of the TGF-β cellular signaling pathway based on the evidence curated list of target genes.

ANGPTL4
CDC42EP3
CDKN1A
CTGF
GADD45A
GADD45B
HMGA2
ID1
IL11
JUNB
PDGFB
PTHLH
SGK1
SKIL
SMAD4
SMAD5
SMAD6
SMAD7
SNAI2
VEGFA

TABLE 6

"12 target genes shortlist" of target genes of the TGF-β cellular signaling pathway based on the evidence curated list of target genes.

ANGPTL4
CDC42EP3
CDKN1A
CTGF
GADD45B
ID1
IL11
JUNB
PDGFB
SKIL
SMAD7
SNAI2

TABLE 7

"7 target genes shortlist" of target genes of the TGF-β cellular signaling pathway based on the evidence curated list of target genes.

ANGPTL4
CDC42EP3
ID1
IL11
JUNB
SKIL
SMAD7

Example 3

Training and Using the Mathematical Model

Before the mathematical model can be used to infer the activity of the cellular signaling pathway, herein, the TGF-β cellular signaling pathway, in a subject, the model must be appropriately trained.

If the mathematical model is a probabilistic model, e.g., a Bayesian network model, based at least in part on conditional probabilities relating the TGF-β TF element and expression levels of the one or more target gene(s) of the TGF-β cellular signaling pathway measured in the sample of the subject, the training may, for example, be performed as described in detail in the published international patent application WO 2013/011479 A2 ("Assessment of cellular signaling pathway activity using probabilistic modeling of target gene expression").

If the mathematical model is based at least in part on one or more linear combination(s) of expression levels of the one or more target gene(s) of the TGF-β cellular signaling pathway measured in the sample of the subject, the training may, for example, be performed as described in detail in the published international patent application WO 2014/102668 A2 ("Assessment of cellular signaling pathway activity using linear combination(s) of target gene expressions").

Herein, an exemplary Bayesian network model as shown in FIG. 2 was used to model the transcriptional program of the TGF-β cellular signaling pathway in a simple manner. The model consists of three types of nodes: (a) a transcription factor (TF) element (with states "absent" and "present") in a first layer 1; (b) target gene(s) TG1, TG2, TGn (with states "down" and "up") in a second layer 2, and; (c) measurement nodes linked to the expression levels of the target gene(s) in a third layer 3. These can be microarray probesets PS1,1, PS1,2, PS1,3, PS2,1, PSn,1, PS n,m (with states "low" and "high"), as exemplified herein, but could also be other gene expression measurements such as RNAseq or RT-qPCR.

A suitable implementation of the mathematical model, herein, the exemplary Bayesian network model, is based on microarray data. The model describes (i) how the expression levels of the target gene(s) depend on the activation of the TF element, and (ii) how probeset intensities, in turn, depend on the expression levels of the respective target gene(s). For the latter, probeset intensities may be taken from fRMA pre-processed Affymetrix HG-U133Plus2.0 microarrays, which are widely available from the Gene Expression Omnibus (GEO, www.ncbi.nlm.nih.gov/geo) and ArrayExpress (www.ebi.ac.uk/arrayexpress).

As the exemplary Bayesian network model is a simplification of the biology of a cellular signaling pathway, herein, the TGF-β cellular signaling pathway, and as biological measurements are typically noisy, a probabilistic approach was opted for, i.e., the relationships between (i) the TF element and the target gene(s), and (ii) the target gene(s) and their respective probesets, are described in probabilistic terms. Furthermore, it was assumed that the activity of the oncogenic cellular signaling pathway which drives tumor growth is not transiently and dynamically altered, but long term or even irreversibly altered. Therefore the exemplary Bayesian network model was developed for interpretation of a static cellular condition. For this reason complex dynamic cellular signaling pathway features were not incorporated into the model.

Once the exemplary Bayesian network model is built and calibrated (see below), the model can be used on microarray data of a new sample by entering the probeset measurements as observations in the third layer 3, and mathematically inferring backwards in the model what the probability must have been for the TF element to be "present". Here, "present" is considered to be the phenomenon that the TF element is bound to the DNA and is controlling transcription of the cellular signaling pathway's target genes, and "absent" the case that the TF element is not controlling transcription. This probability is hence the primary read-out that may be used to indicate activity of the cellular signaling pathway, herein, the TGF-β cellular signaling pathway, which can next be translated into the odds of the cellular signaling pathway being active by taking the ratio of the probability of it being active vs. it being passive (i.e., the odds are given by p/(1−p), where p is the predicted probability of the cellular signaling pathway being active).

In the exemplary Bayesian network model, the probabilistic relations have been made quantitative to allow for a quantitative probabilistic reasoning. In order to improve the generalization behavior across tissue types, the parameters describing the probabilistic relationships between (i) the TF element and the target gene(s) have been carefully hand-picked. If the TF element is "absent", it is most likely that the target gene is "down", hence a probability of 0.95 is chosen for this, and a probability of 0.05 is chosen for the target gene being "up". The latter (non-zero) probability is to account for the (rare) possibility that the target gene is regulated by other factors or that it is accidentally observed as being "up" (e.g. because of measurement noise). If the TF element is "present", then with a probability of 0.70 the target gene is considered "up", and with a probability of 0.30 the target gene is considered "down". The latter values are chosen this way, because there can be several causes why a target gene is not highly expressed even though the TF element is present, e.g., because the gene's promoter region is methylated. In the case that a target gene is not up-regulated by the TF element, but down-regulated, the probabilities are chosen in a similar way, but reflecting the down-regulation upon presence of the TF element. The parameters describing the relationships between (ii) the target gene(s) and their respective probesets have been calibrated on experimental data. For the latter, in this example, microarray data was used from patients samples which are known to have an active TGF-β cellular signaling pathway whereas normal, healthy samples from the same dataset were used as passive TGF-β cellular signaling pathway samples, but this could also be performed using cell line experiments or other patient samples with known cellular signaling pathway activity status. The resulting conditional probability tables are given by:

A: for upregulated target genes

|   | PSi, j = low | PSi, j = high |
|---|---|---|
| TGi = down | $\dfrac{AL_{i,j} + 1}{AL_{i,j} + AH_{i,j} + 2}$ | $\dfrac{AH_{i,j} + 1}{AL_{i,j} + AH_{i,j} + 2}$ |
| TGi = up | $\dfrac{PL_{i,j} + 1}{PL_{i,j} + PH_{i,j} + 2}$ | $\dfrac{PH_{i,j} + 1}{PL_{i,j} + PH_{i,j} + 2}$ |

B: for downregulated target genes

|   | PSi, j = low | PSi, j = high |
|---|---|---|
| TGi = down | $\dfrac{PL_{i,j} + 1}{PL_{i,j} + PH_{i,j} + 2}$ | $\dfrac{PH_{i,j} + 1}{PL_{i,j} + PH_{i,j} + 2}$ |
| TGi = up | $\dfrac{AL_{i,j} + 1}{AL_{i,j} + AH_{i,j} + 2}$ | $\dfrac{AH_{i,j} + 1}{AL_{i,j} + AH_{i,j} + 2}$ |

In these tables, the variables $AL_{i,j}$, $AH_{i,j}$, $PL_{i,j}$, and $PH_{i,j}$ indicate the number of calibration samples with an "absent" (A) or "present" (P) transcription complex that have a "low" (L) or "high" (H) probeset intensity, respectively. Dummy counts have been added to avoid extreme probabilities of 0 and 1.

To discretize the observed probeset intensities, for each probeset $PS_{i,j}$ a threshold $t_{i,j}$ was used, below which the observation is called "low", and above which it is called "high". This threshold has been chosen to be the (weighted) median intensity of the probeset in the used calibration dataset. Due to the noisiness of microarray data, a fuzzy method was used when comparing an observed probeset intensity to its threshold, by assuming a normal distribution with a standard deviation of 0.25 (on a log 2 scale) around the reported intensity, and determining the probability mass below and above the threshold.

If instead of the exemplary Bayesian network described above, a (pseudo-)linear model as described in Example 1 above was employed, the weights indicating the sign and magnitude of the correlation between the nodes and a threshold to call whether a node is either "absent" or "present" would need to be determined before the model could be used to infer cellular signaling pathway activity in a test sample. One could use expert knowledge to fill in the weights and the threshold a priori, but typically the model would be trained using a representative set of training samples, of which, for example, the ground truth is known, e.g., expression data of probesets in samples with a known "present" transcription factor complex (=active cellular signaling pathway) or "absent" transcription factor complex (=passive cellular signaling pathway).

Known in the field are a multitude of training algorithms (e.g., regression) that take into account the model topology and changes the model parameters, here, the weights and the threshold, such that the model output, here, a weighted linear score, is optimized. Alternatively, it is also possible to calculate the weights directly from the expression observed levels without the need of an optimization algorithm.

A first method, named "black and white"-method herein, boils down to a ternary system, in which each weight is an element of the set {−1, 0, 1}. If this is put in a biological context, the −1 and 1 correspond to target genes or probesets that are down- and up-regulated in case of cellular signaling pathway activity, respectively. In case a probeset or target gene cannot be statistically proven to be either up- or down-regulated, it receives a weight of 0. In one example, a left-sided and right-sided, two sample t-test of the expression levels of the active cellular signaling pathway samples versus the expression levels of the samples with a passive cellular signaling pathway can be used to determine whether a probe or gene is up- or down-regulated given the used training data. In cases where the average of the active samples is statistically larger than the passive samples, i.e., the p-value is below a certain threshold, e.g., 0.3, the target gene or probeset is determined to be up-regulated. Conversely, in cases where the average of the active samples is statistically lower than the passive samples, the target gene or probeset is determined to be down-regulated upon activation of the cellular signaling pathway. In case the lowest p-value (left- or right-sided) exceeds the aforementioned threshold, the weight of the target gene or probeset can be defined to be 0.

A second method, named "log odds"-weights herein, is based on the logarithm (e.g., base e) of the odds ratio. The odds ratio for each target gene or probeset is calculated based on the number of positive and negative training samples for which the probeset/target gene level is above and below a corresponding threshold, e.g., the (weighted) median of all training samples. A pseudo-count can be added to circumvent divisions by zero. A further refinement is to count the samples above/below the threshold in a somewhat more probabilistic manner, by assuming that the probeset/target gene levels are e.g. normally distributed around its observed value with a certain specified standard deviation (e.g., 0.25 on a 2-log scale), and counting the probability mass above and below the threshold. Herein, an odds ratio calculated in combination with a pseudo-count and using probability masses instead of deterministic measurement values is called a "soft" odds ratio.

Further details regarding the determining of cellular signaling pathway activity using mathematical modeling of target gene expression can be found in Verhaegh W. et al., "Selection of personalized patient therapy through the use of knowledge-based computational models that identify tumor-driving signal transduction pathways", Cancer Research, Vol. 74, No. 11, 2014, pages 2936 to 2945.

Herein, expression data of human A549 lung adenocarcinoma cell line samples that were either treated with 5 ng/mL TGF-β, resulting in an tumor promoting activity of the TGF-β cellular signaling pathway (from now on referred to as TGF-β active), and a control experiment without TGF-β stimulation, resulting in a tumor suppressing activity of the TGF-β cellular signaling pathway (from now on referred to as TGF-β passive), was used for calibration. These microarrays are publically available under GSE17708 from the gene expression omnibus (GEO, www.ncbi.nlm.nih.gov/geo/, last accessed Mar. 5, 2014). The samples stimulated with 5 ng/mL TGF-β for 4 hours were chosen as representatives of the active or tumor promoting TGF-β cell lines based on the observed fold change of the selected genes (Table 4) compared to the unstimulated samples that were chosen as the passive or tumor suppressing TGF-β samples for training. Alternatively, one can use patient samples of primary cells or other cell lines stimulated with and deprived of TGF-β, e.g. GSE6653, GSE42373 and GSE18670.

FIGS. 9 to 12 show training results of the exemplary Bayesian network model based on the list of evidence curated target genes, the 20 target genes shortlist, the 12 target genes shortlist and the 7 target genes shortlist of the TGF-β cellular signaling pathway (see Tables 4 to 7), respectively. In the diagrams, the vertical axis indicates the odds that the TF element is "present" resp. "absent", which corresponds to the TGF-β cellular signaling pathway being active resp. passive, wherein values above the horizontal axis correspond to the TF element being more likely "present"/active and values below the horizontal axis indicate that the odds that the TF element is "absent"/passive are larger than the odds that it is "present"/active. The A549 cell line samples that were stimulated with TGF-β for 4 hours (group 5) were used to represent the active or tumor promoting training samples, whereas the unstimulated samples (group 1) were used as a representation of the passive or tumor suppressing TGF-β cellular signaling pathway. The models using the different target gene lists were able to clearly separate the passive from the active training samples. In addition, one can appreciate from the results that all stimulation of 1 hour or longer resulted in the TGF-β cellular signaling pathway having tumor promoting activities for all four target gene lists. Stimulation of 0.5 h with TGF-β resulted in TGF-β activities varying from TGF-β passive to active, which is likely caused by the relatively short TGF-β stimulation. (Legend: 1—Control; 2—TGF-β stimulation with 5 ng/mL for 0.5 h; 3—TGF-β stimulation with 5 ng/mL for 1 h; 4—TGF-β stimulation with 5 ng/mL for 2 h; 5—TGF-β stimulation with 5 ng/mL for 4 h; 6—TGF-β stimulation with 5 ng/mL for 8 h; 7—TGF-β stimulation with 5 ng/mL for 16 h; 8—TGF-β stimulation with 5 ng/mL for 24 h; 9—TGF-β stimulation with 5 ng/mL for 72 h)

In the following, validation results of the trained exemplary Bayesian network model using the evidence curated list of target genes, the 20 target genes shortlist, the 12 target genes shortlist, and the 7 target genes shortlist, respectively, are shown in FIGS. 13 to 23.

FIGS. 13 to 16 show TGF-β cellular signaling pathway activity predictions of the trained exemplary Bayesian network models using the evidence curated list of target genes, the 20 target genes shortlist, the 12 target genes shortlist, and the 7 target genes shortlist (see Tables 4 to 7), respectively, for human mammary epithelial cells (HMEC-TR) from GSE28448. In the diagrams, the vertical axis indicates the odds that the TF element is "present" resp. "absent", which corresponds to the TGF-β cellular signaling pathway being active resp. passive, wherein values above the horizontal axis correspond to the TF element being more likely "present"/active and values below the horizontal axis indicate that the odds that the TF element is "absent"/passive are larger than the odds that it is "present"/active. Each bar represents a sample from the dataset. Some of the samples were transfected with siRNA for TIFγ (groups 5 and 6) or SMAD4 (groups 3 and 4) and another set of samples consisted of controls (no transfection, groups 1 and 2). Samples in groups 2, 4 and 6 were stimulated with 5 ng/mL TGF-β, and those in groups 1, 3 and 5 were not stimulated. The models using the different target gene lists all correctly predicted for all four target gene lists an increased TGF-β activity in the TGF-β-stimulated samples in groups 2 (controls) and 6 (TIFγ-silenced) and no significant increase in the SMAD-silenced samples (group 4) compared to the corresponding unstimulated samples (see Hesling C. et al., "Antagonistic regulation of EMT by TIF1γ and SMAD4 in mammary epithelial cells", EMBO Reports, Vol. 12, No. 7, 2011, pages 665 to 672). (Legend: 1—Control, no TGF-β; 2—Control, TGF-β; 3—siRNA SMAD4, no TGF-β; 4—siRNA SMAD4, TGF-β; 5—siRNA TIFγ, no TGF-β; 6—siRNA TIFγ, TGF-β)

Figure 17:
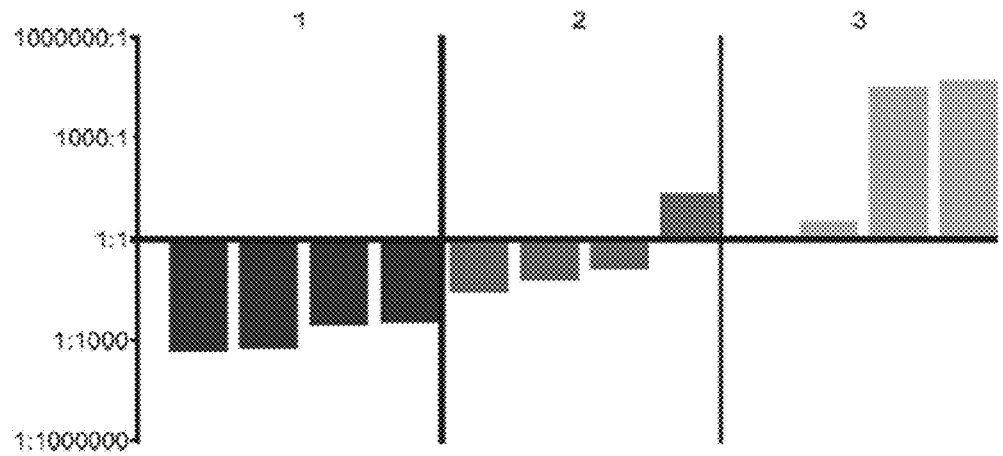
FIG. 17 shows TGF-β cellular signaling pathway activity predictions of the trained exemplary Bayesian network model using the evidence curated list of target genes (see Table 4) for ectocervical epithelial cells (Ect1) from GSE35830, which were stimulated with seminal plasma or 5 ng/mL TGF-β. (Legend: 1—Control, no TGF-β; 2—Stimulated with 10% seminal plasma; 3—stimulated with 5 ng/mL TGF-β3)

FIG. 17 shows TGF-β cellular signaling pathway activity predictions of the trained exemplary Bayesian network model using the evidence curated list of target genes (see Table 4) for ectocervical epithelial cells (Ect1) from GSE35830, which were stimulated with seminal plasma or 5 ng/mL TGF-β3. In the diagram, the vertical axis indicates the odds that the TF element is "present" resp. "absent", which corresponds to the TGF-β cellular signaling pathway being active resp. passive, wherein values above the horizontal axis correspond to the TF element being more likely "present"/active and values below the horizontal axis indicate that the odds that the TF element is "absent"/passive are larger than the odds that it is "present"/active. Each bar represents a sample from the dataset. Seminal plasma also contains high levels of TGF-131, TGF-β2 and TGF-β3. However, they are predominantly (between 95% and 99%) present in the latent variant, as opposed to the active form (see Sharkey D. J. et al., "TGF-βeta mediates proinflammatory seminal fluid signaling in human cervical epithelial cells", Journal of Immunology, Vol. 189, No. 2, 2012, pages 1024 to 1035). The third and the fourth, i.e., two out of the four, TGF-β3 stimulated samples (group 3) show a strong preference for tumor promoting TGF-β activity, the other two samples, i.e., first and second samples, were found to be more similar to the third and fourth sample of the seminal fluid group (group 2) with cluster analysis. The unstimulated samples (group 1) correctly predicts a passive or tumor suppressing TGF-β activity, whereas the samples stimulated with seminal plasma were predicted to have a TGF-β activity in between which can be caused by the high fraction of latent (i.e., passive) TGF-β isoforms and thus lower stimulation of the TGF-β pathway. (Legend: 1—Control, no TGF-β; 2—Stimulated with 10% seminal plasma; 3—stimulated with 5 ng/mL TGF-β3)

Figure 18:
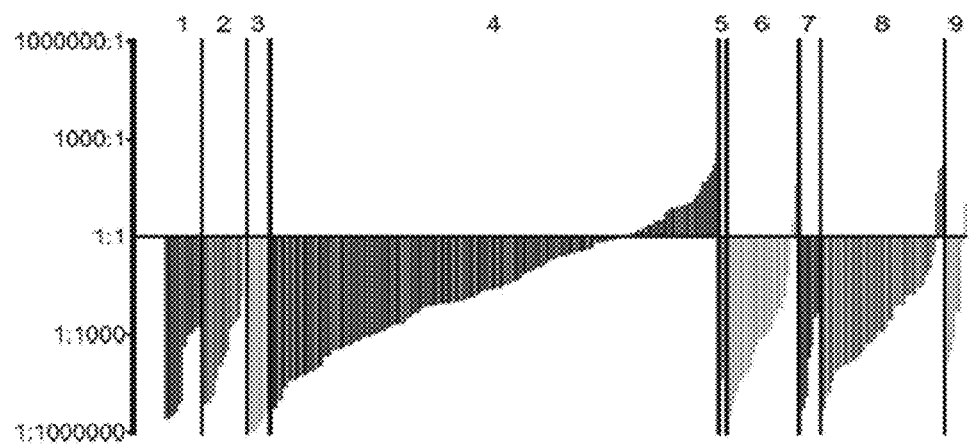
FIG. 18 shows TGF-β cellular signaling pathway activity predictions of the trained exemplary Bayesian network model using the evidence curated list of target genes (see Table 4) for patient gliomas from GSE16011. (Legend: 1—Astrocytoma (grade II); 2—Astrocytoma (grade III); 3—Control; 4—Glioblastoma multiforme (grade IV); 5—Oligoastrocytic (grade II); 6—Oligoastrocytic (grade III); 7—Oligodendroglial (grade II); 8—Oligodendroglial (grade III); 9—Pilocytic astrocytoma (grade I))

FIG. 18 shows TGF-β cellular signaling pathway activity predictions of the trained exemplary Bayesian network model using the evidence curated list of target genes (see Table 4) for patient gliomas from GSE16011. In the diagram, the vertical axis indicates the odds that the TF element is "present" resp. "absent", which corresponds to the TGF-β cellular signaling pathway being active resp. passive, wherein values above the horizontal axis correspond to the TF element being more likely "present"/active and values below the horizontal axis indicate that the odds that the TF element is "absent"/passive are larger than the odds that it is "present"/active. Each bar represents a sample from the dataset. It is known from literature that gliomas produce more TGF-β (all isoforms) than normal cells (see Kaminska B. et al., "TGF beta signaling and its role in glioma pathogenesis", Advances in Experimental Medicine and Biology, Vol. 986, 2013, pages 171 to 187). This is also visible in the predicted TGF-β activities which are negative for all controls (group 3), yet in approximately 15% of the gliomas (groups 1, 2, 4-9) a tumor promoting TGF-β was predicted expectedly due to the increased TGF-β secretion in these tumors. (Legend: 1—Astrocytoma (grade II); 2—Astrocytoma (grade III); 3—Control; 4—Glioblastoma multiforme (grade IV); 5—Oligoastrocytic (grade II); 6—Oligoastrocytic (grade III); 7—Oligodendroglial (grade II); 8—Oligodendroglial (grade III); 9—Pilocytic astrocytoma (grade I))

Figure 19:
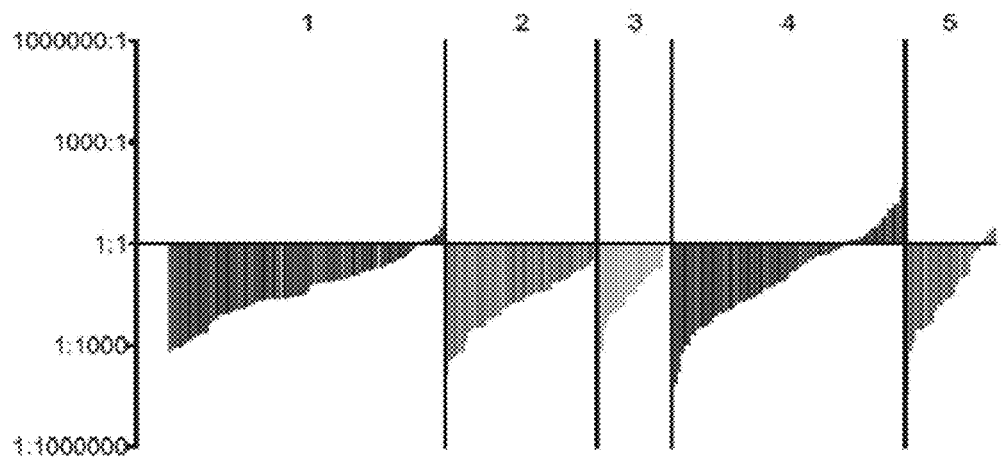
FIG. 19 shows TGF-β cellular signaling pathway activity predictions of the trained exemplary Bayesian network model using the evidence curated list of target genes (see Table 4) for breast cancer samples from GSE21653. (Legend: 1—Luminal A; 2—Luminal B; 3—HER2; 4 Basal; 5—Normal-like)
Figure 20:
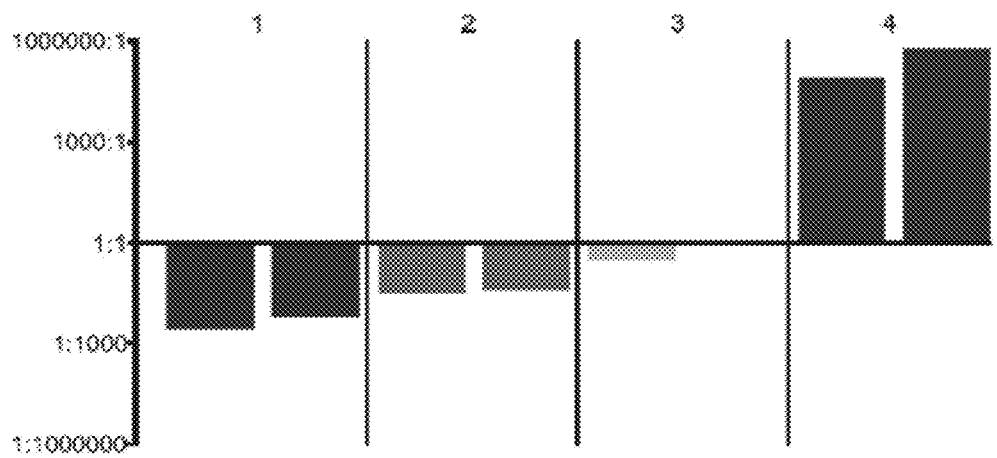
FIGS. 20 to 23 show TGF-β cellular signaling pathway activity predictions of the trained exemplary Bayesian network models using the evidence curated list of target genes, the 20 target genes shortlist, the 12 target genes shortlist, and the 7 target genes shortlist (see Tables 4 to 7), respectively, for 2D and 3D cultures of A549 lung adenocarcinoma cell lines from GSE42373, which were stimulated with or without a 10 ng/mL TNF and 2 ng/mL TGF-β. (Legend: 1—2D control; 2—2D TGF-β and TNFα; 3—3D control; 4—3D TGF-β and TNFα)
Figure 21:
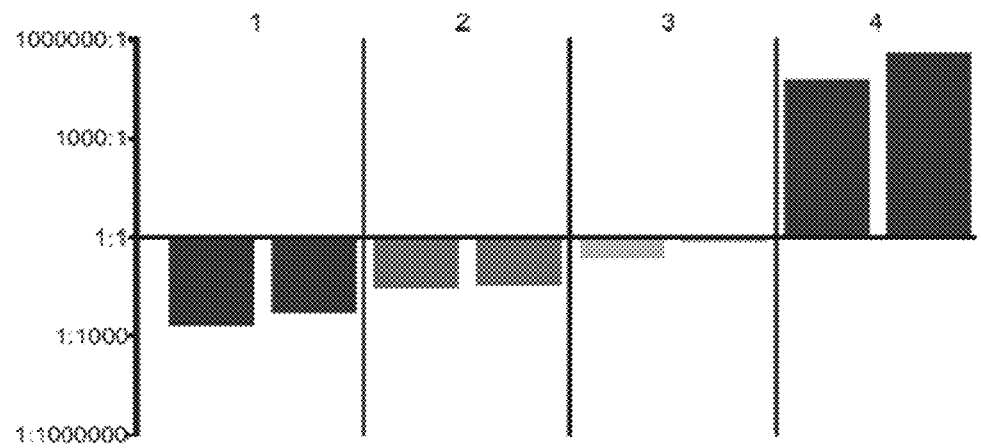
Figure 22:
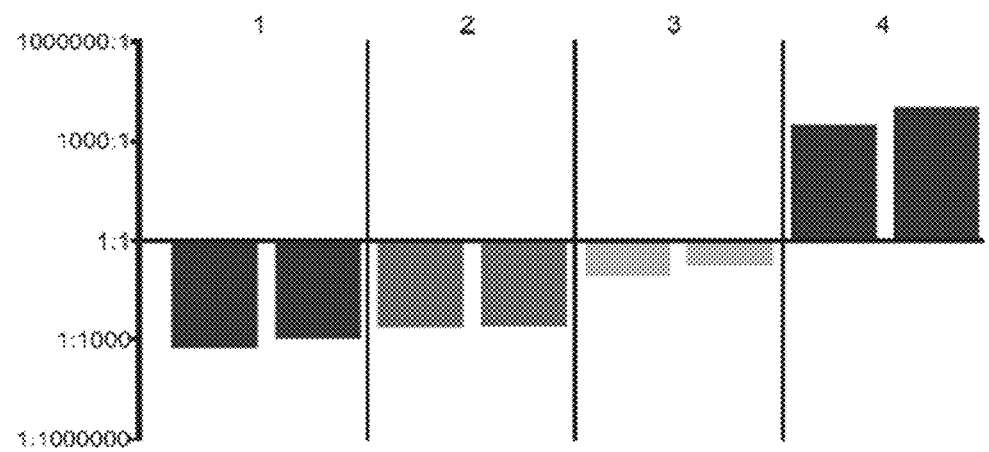
Figure 23:
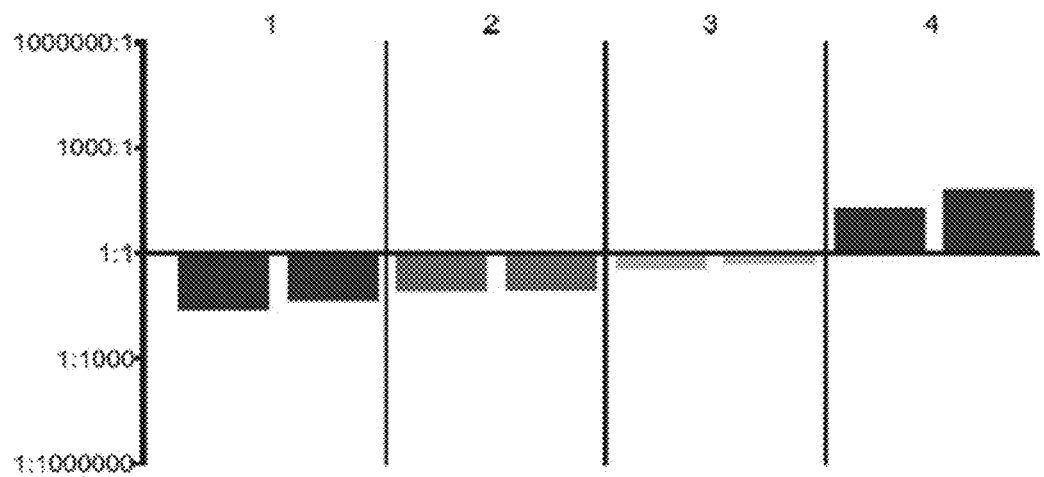

FIG. 19 shows TGF-β cellular signaling pathway activity predictions of the trained exemplary Bayesian network model using the evidence curated list of target genes (see Table 4) for breast cancer samples from GSE21653. In the diagram, the vertical axis indicates the odds that the TF element is "present" resp. "absent", which corresponds to the TGF-β cellular signaling pathway being active resp. passive, wherein values above the horizontal axis correspond to the TF element being more likely "present"/active and values below the horizontal axis indicate that the odds that the TF element is "absent"/passive are larger than the odds that it is "present"/active. Each bar represents a sample from the dataset. As expected, most breast cancers were predicted to have a passive TGF-β cellular signaling pathway. Also in line with expectations, the highest fraction of TGF-β active or tumor promoting TGF-β activity was found in the basal samples. (Legend: 1—Luminal A; 2—Luminal B; 3—HER2; 4—Basal; 5—Normal-like)

FIGS. 20 to 23 show TGF-β cellular signaling pathway activity predictions of the trained exemplary Bayesian network models using the evidence curated list of target genes, the 20 target genes shortlist, the 12 target genes shortlist, and the 7 target genes shortlist (see Tables 4 to 7), respectively, for 2D and 3D cultures of A549 lung adenocarcinoma cell lines from GSE42373, which were stimulated with or without 10 ng/mL TNF and 2 ng/mL TGF-β. In the diagram, the vertical axis indicates the odds that the TF element is "present" resp. "absent", which corresponds to the TGF-β cellular signaling pathway being active resp. passive, wherein values above the horizontal axis correspond to the TF element being more likely "present"/active and values below the horizontal axis indicate that the odds that the TF element is "absent"/passive are larger than the odds that it is "present"/active. Each bar represents a sample from the dataset. Cieślik et al., "Epigenetic coordination of signaling pathways during the epithelial-mesenchymal transition", Epigenetics & Chromatin, Vol. 6, No. 1, 2013, demonstrated that in these experiments epithelial-mesenchymal transition (EMT) is efficiently induced in the 3D culture model. This is also demonstrated in the TGF-β cellular signaling pathway activity predictions as both samples from this group (group 4) are the only samples predicted with a tumor promoting TGF-β activity which is known to cause EMT. The control group of the 2D culture without stimulation (group 1) was correctly predicted to have no TGF-β activity, whereas the stimulated 2D culture (group 2) evidently was not able to initiate the TGF-β tumor promoting activity (no EMT), which was also found by Cieślik et al. The unstimulated 3D culture samples (group 3) are also predicted to have a passive TGF-β activity, albeit the odds are very small. (Legend: 1—2D control; 2—2D TGF-β and TNFα; 3—3D control; 4—3D TGF-β and TNFα)

Figure 24:
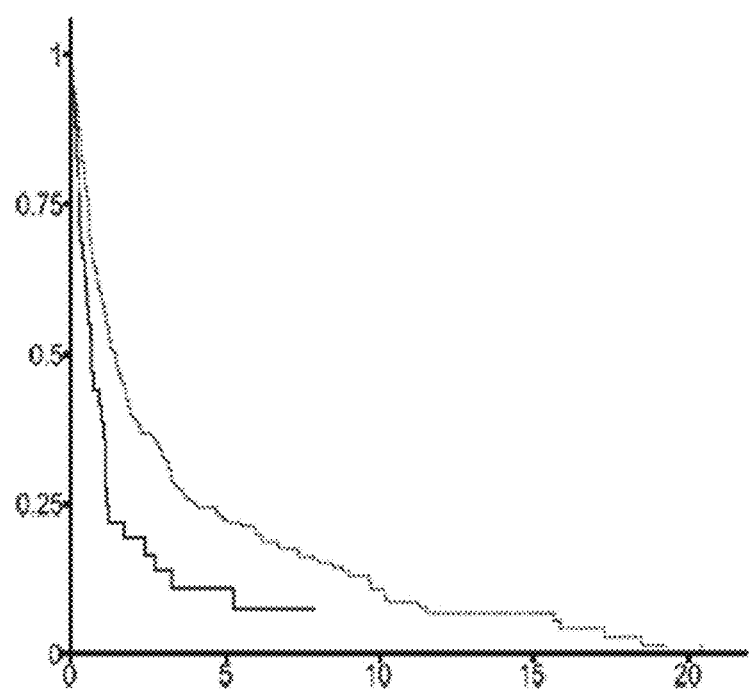
FIG. 24 illustrates a prognosis of glioma patients (GSE16011) depicted in a Kaplan-Meier plot using the trained exemplary Bayesian network model using the evidence curated list of target genes (see Table 4).

FIG. 24 illustrates overall survival of 284 glioma patients (GSE16011; see also FIG. 18) depicted in a Kaplan-Meier plot. In the diagram, the vertical axis indicates the overall survival as a fraction of the patient group and the horizontal axis indicates time in years. The plot indicates that a tumor-suppressing TGF-β cellular signaling pathway (TGF-β passive, dotted line) is protective for overall survival, whereas having a tumor-promoting TGF-β pathway is associated with significantly higher risk of death (indicated by the steeper slope of the curve). (The patient group with a predicted active TGF-β TF element consisted of 37 patients (solid line), whereas the patient group with a predicted passive TGF-β TF element consisted of 235 patients (dotted line)). The prognostic value of the activity level of the TGF-β TF element is also demonstrated in the hazard ratio of the predicted probability of TGF-β activity: 2.17 (95% CI: 1.44-3.28, p=1.22e-4) and the median survival which is 0.7 years for tumor-promoting TGF-β active patients versus 1.34 years for tumor-suppressing TGF-β patients.

Figure 13:
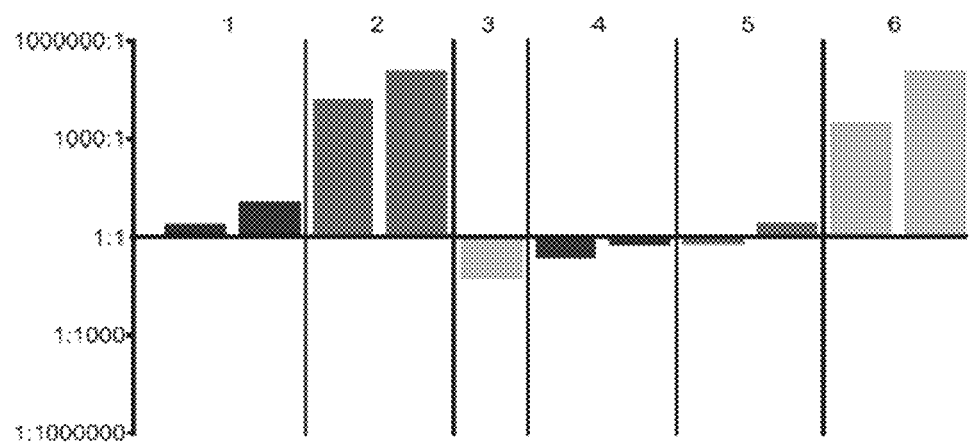
FIGS. 13 to 16 show TGF-β cellular signaling pathway activity predictions of the trained exemplary Bayesian network models using the evidence curated list of target genes (FIG. 13), the 20 target genes shortlist (FIG. 14), the 12 target genes shortlist (FIG. 15), and the 7 target genes shortlist (FIG. 16) (see Tables 4 to 7), respectively, for human mammary epithelial cells (HMEC-TR) from GSE28448. (Legend: 1—Control, no TGF-β; 2—Control, TGF-β; 3—siRNA SMAD4, no TGF-β; 4—siRNA SMAD4, TGF-β; 5—siRNA TIFγ, no TGF-β; 6—siRNA TIFγ, TGF-β)
Figure 14:
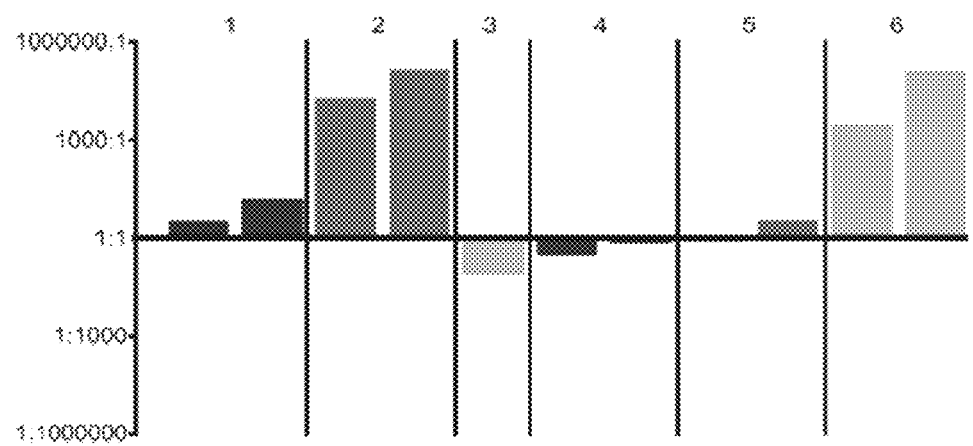
Figure 15:
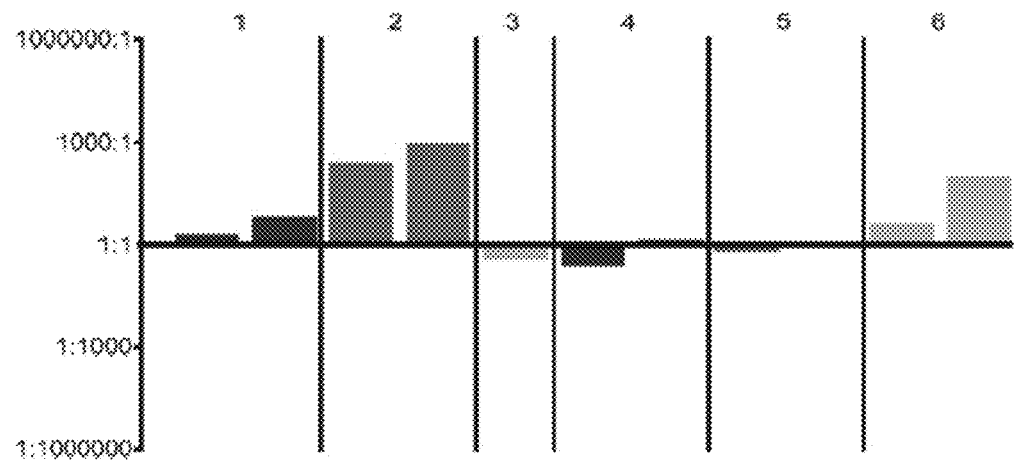
Figure 16:
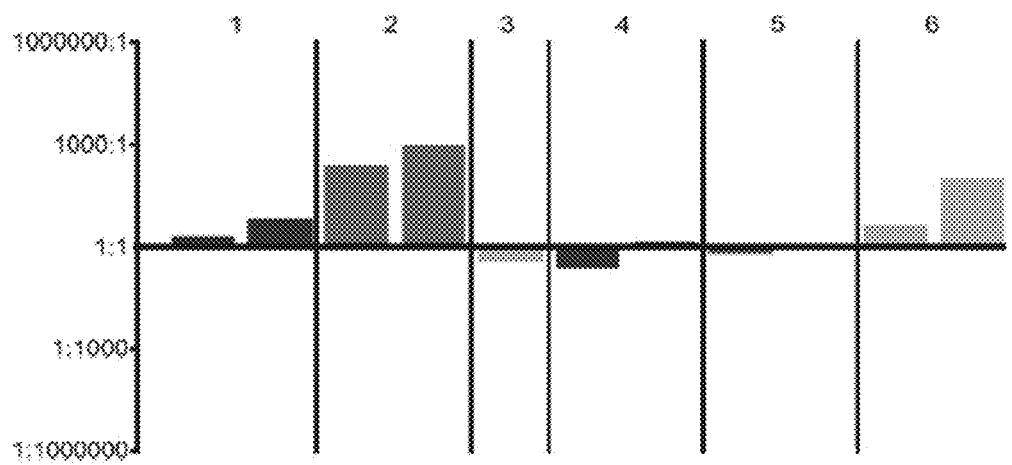
Figure 25:
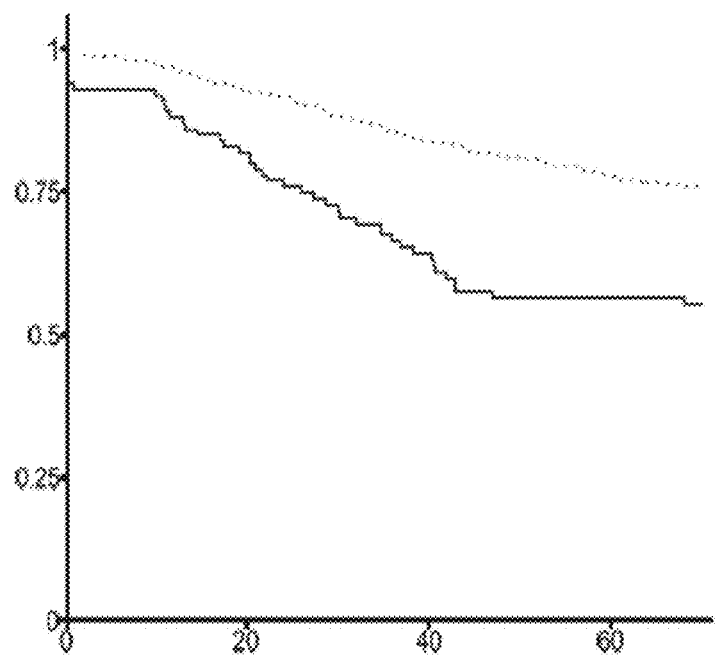
FIG. 25 illustrates a prognosis of breast cancer patients (GSE6532, GSE9195, E-MTAB-365, GSE20685 and GSE21653) depicted in a Kaplan-Meier plot using the trained exemplary Bayesian network model using the evidence curated list of target genes (see Table 4).

FIG. 25 illustrates disease free survival of a cohort of 1169 breast cancer patients (GSE6532, GSE9195, E-MTAB-365, GSE20685 and GSE21653; see also FIG. 13 above) depicted in a Kaplan-Meier plot. In the diagram, the vertical axis indicates the disease free survival as a fraction of the patient group and the horizontal axis indicates time in months. The plot indicates that a tumor-suppressing TGF-β cellular signaling pathway (TGF-β passive, dotted line) is protective for disease free survival, whereas having a tumor-promoting TGF-β pathway is associated with significantly higher risk of disease recurrence (indicated by the steeper slope of the curve). (The patient group with a predicted active TGF-β TF element consisted of 103 patients (solid line), whereas the patient group with a predicted passive TGF-β TF element consisted of 1066 patients (dotted line)). The prognostic value of the activity level of the TGF-β TF element is also demonstrated in the hazard ratio of the predicted probability of TGF-β activity: 3.66 (95% CI: 2.37-5.33, p=4.0e-10) and the 75% survival which is 2.3 years for tumor-promoting TGF-β active patients versus 6.4 years for tumor-suppressing TGF-β patients.

Instead of applying the mathematical model, e.g., the exemplary Bayesian network model, on mRNA input data coming from microarrays or RNA sequencing, it may be beneficial in clinical applications to develop dedicated assays to perform the sample measurements, for instance on an integrated platform using qPCR to determine mRNA levels of target genes. The RNA/DNA sequences of the disclosed target genes can then be used to determine which primers and probes to select on such a platform.

Validation of such a dedicated assay can be done by using the microarray-based mathematical model as a reference model, and verifying whether the developed assay gives similar results on a set of validation samples. Next to a dedicated assay, this can also be done to build and calibrate similar mathematical models using RNA sequencing data as input measurements.

The set of target genes which are found to best indicate specific cellular signaling pathway activity, e.g., Tables 4 to 7, based on microarray/RNA sequencing based investigation using the mathematical model, e.g., the exemplary Bayesian network model, can be translated into a multiplex quantitative PCR assay to be performed on a sample of the subject and/or a computer to interpret the expression measurements and/or to infer the activity of the TGF-β cellular signaling pathway. To develop such a test (e.g., FDA-approved or a CLIA waived test in a central service lab or a laboratory developed test for research use only) for cellular signaling pathway activity, development of a standardized test kit is required, which needs to be clinically validated in clinical trials to obtain regulatory approval.

The present invention relates to a method comprising determining activity of a TGF-β cellular signaling pathway in a subject based at least on expression levels of one or more target gene(s) of the TGF-β cellular signaling pathway measured in a sample of the subject. The present invention further relates to an apparatus comprising a digital processor configured to perform such a method, a non-transitory storage medium storing instructions that are executable by a digital processing device to perform such a method, and a computer program comprising program code means for causing a digital processing device to perform such a method.

The method may be used, for instance, in diagnosing an (abnormal) activity of the TGF-β cellular signaling pathway, in prognosis based on the determined activity of the TGF-β cellular signaling pathway, in the enrollment of a subject in a clinical trial based on the determined activity of the TGF-β cellular signaling pathway, in the selection of subsequent test(s) to be performed, in the selection of companion diagnostics tests, in clinical decision support systems, or the like. In this regard, reference is made to the published international patent application WO 2013/011479 A2 ("Assessment of cellular signaling pathway activity using probabilistic modeling of target gene expression"), to the published international patent application WO 2014/102668 A2 ("Assessment of cellular signaling pathway activity using linear combination(s) of target gene expressions"), and to Verhaegh W. et al., "Selection of personalized patient therapy through the use of knowledge-based computational models that identify tumor-driving signal transduction pathways", Cancer Research, Vol. 74, No. 11, 2014, pages 2936 to 2945, which describe these applications in more detail.

Example 4

Comparison of the Evidence Curated List with a Broad Literature List

The list of target genes of the TGF-β cellular signaling pathway constructed based on literature evidence following the procedure as described herein ("evidence curated list of target genes", see Table 4) is compared here with a "broad literature list" of putative target genes of the TGF-β cellular signaling pathway constructed not following above mentioned procedure. The alternative list is a compilation of genes attributed to responding to activity of the TGF-β cellular signaling pathway provided within Thomson-Reuters's Metacore (last accessed May 14, 2013). This database was queried for genes that are transcriptionally regulated directly downstream of the family of SMAD proteins, i.e. SMAD1, SMAD2, SMAD3, SMAD4, SMAD5 and/or SMAD8. This query resulted in 217 unique genes. A further selection was made based on the number of publication references supporting the attributed transcriptional regulation of the respective gene by the SMAD family. Genes that had three or more references were selected for the broad literature list. In other words, no manual curation of the references and no calculation of an evidence score based on the experimental evidence was performed. This procedure resulted in 61 genes, of which a micro-RNA (MIR29B2) not available on the Affymetrix HG-U133Plus2.0 microarray platform and one gene (BGLAP) was not found to have a probeset available on the Affymetrix HG-U133Plus2.0 microarray platform according to the Bioconductor plugin of R. Eventually, this lead to 59 putative target genes which are shown in Table 8 with the associated probesets on the Affymetrix HG-U133Plus2.0 microarray platform.

TABLE 8

"Broad literature list" of putative target genes of the TGF-β cellular signaling pathway used in the TGF-β cellular signaling pathway models and associated probesets used to measure the mRNA expression level of the genes.

| Gene | Probeset |
| --- | --- |
| ATF3 | 1554420_at |
|  | 1554980_a_at |
|  | 202672_s_at |
| CCL2 | 216598_s_at |
| CDH1 | 201130_s_at |
|  | 201131_s_at |
| CDKN1A | 202284_s_at |
| CDKN2B | 207530_s_at |
|  | 236313_at |
| COL1A2 | 202403_s_at |
|  | 202404_s_at |
|  | 229218_at |
| COL3A1 | 201852_x_at |
|  | 211161_s_at |
|  | 215076_s_at |
|  | 215077_at |
|  | 232458_at |
| COL7A1 | 204136_at |
|  | 217312_s_at |
| CTGF | 209101_at |
| CTNNB1 | 1554411_at |
|  | 201533_at |
|  | 223679_at |
| DLX5 | 213707_s_at |
| EDN1 | 1564630_at |
|  | 218995_s_at |
|  | 222802_at |
| FN1 | 1558199_at |
|  | 210495_x_at |
|  | 211719_x_at |
|  | 212464_s_at |
|  | 214701_s_at |
|  | 214702_at |
|  | 216442_x_at |
| FOXP3 | 221333_at |
|  | 221334_s_at |
|  | 224211_at |
| FSHB | 214489_at |
| FST | 204948_s_at |
|  | 207345_at |
|  | 226847_at |
| FSTL3 | 203592_s_at |
| GNRHR | 211522_s_at |
|  | 211523_at |
|  | 216341_s_at |
| GSC | 1552338_at |
| HAMP | 220491_at |

TABLE 8-continued

"Broad literature list" of putative target genes of the TGF-β cellular signaling pathway used in the TGF-β cellular signaling pathway models and associated probesets used to measure the mRNA expression level of the genes.

| Gene | Probeset |
| --- | --- |
| HEY1 | 218839_at |
|  | 44783_s_at |
| IBSP | 207370_at |
|  | 236028_at |
| ID1 | 208937_s_at |
| ID2 | 201565_s_at |
|  | 201566_x_at |
| ID3 | 207826_s_at |
| IL11 | 206924_at |
|  | 206926_s_at |
| IL6 | 205207_at |
| ITGB1 | 1553530_a_at |
|  | 1553678_a_at |
|  | 211945_s_at |
|  | 215878_at |
|  | 215879_at |
|  | 216178_x_at |
|  | 216190_x_at |
| ITGB5 | 201124_at |
|  | 201125_s_at |
|  | 214020_x_at |
|  | 214021_x_at |
| JUN | 201464_x_at |
|  | 201465_s_at |
|  | 201466_s_at |
|  | 213281_at |
| JUNB | 201473_at |
| LEFTY2 | 206012_at |
| MTXL1 | 231746_at |
| MMP13 | 205959_at |
| MMP9 | 203936_s_at |
| MSX2 | 205555_s_at |
|  | 205556_at |
|  | 210319_x_at |
| MYC | 202431_s_at |
| NKX2-5 | 206578_at |
| NODAL | 220689_at |
|  | 230916_at |
|  | 237896_at |
| PDGFB | 204200_s_at |
|  | 216055_at |
|  | 216061_x_at |
|  | 217112_at |
| PMEPA1 | 217875_s_at |
|  | 222449_at |
|  | 222450_at |
| PPARG | 208510_s_at |
| PTGS2 | 1554997_a_at |
|  | 204748_at |
| PTHLH | 206300_s_at |
|  | 210355_at |
|  | 211756_at |
| SERPINE1 | 1568765_at |
|  | 202627_s_at |
|  | 202628_s_at |
| SKIL | 206675_s_at |
|  | 215889_at |
|  | 217591_at |
|  | 225227_at |
|  | 232379_at |
| SLC25A5 | 200657_at |
| SMAD6 | 207069_s_at |
|  | 209886_s_at |
|  | 209887_at |
|  | 213565_s_at |
| SMAD7 | 204790_at |
| SNAI1 | 219480_at |
| SNAI2 | 213139_at |
| SP7 | 1552340_at |
| SPP1 | 1568574_x_at |
|  | 209875_s_at |

TABLE 8-continued

"Broad literature list" of putative target genes of the TGF-β cellular signaling pathway used in the TGF-β cellular signaling pathway models and associated probesets used to measure the mRNA expression level of the genes.

| Gene | Probeset |
| --- | --- |
| TAGLN | 1555724_s_at |
|  | 205547_s_at |
|  | 226523_at |
| TERT | 1555271_a_at |
|  | 207199_at |
| TGFBR1 | 206943_at |
|  | 224793_s_at |
|  | 236561_at |
| TIMP1 | 201666_at |
| VEGFA | 210512_s_at |
|  | 210513_s_at |
|  | 211527_x_at |
|  | 212171_x_at |
| VIM | 1555938_x_at |
|  | 201426_s_at |

Figure 26:
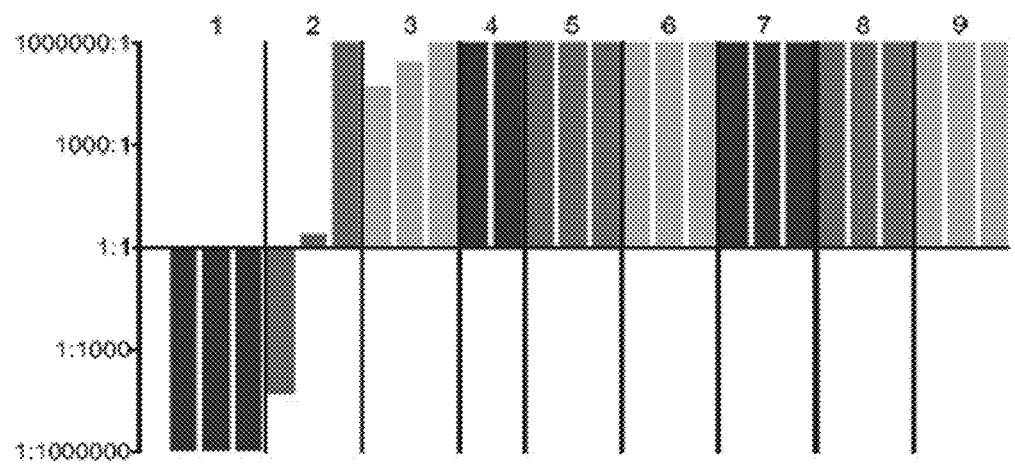
FIG. 26 shows training results of the exemplary Bayesian network model based on the broad literature list of putative target genes of the TGF-β cellular signaling pathway (see Table 8). (Legend: 1—Control; 2—TGF-β stimulation with 5 ng/mL for 0.5 h; 3—TGF-β stimulation with 5 ng/mL for 1 h; 4—TGF-β stimulation with 5 ng/mL for 2 h; 5—TGF-β stimulation with 5 ng/mL for 4 h; 6—TGF-β stimulation with 5 ng/mL for 8 h; 7—TGF-β stimulation with 5 ng/mL for 16 h; 8—TGF-β stimulation with 5 ng/mL for 24 h; 9—TGF-β stimulation with 5 ng/mL for 72 h)

Subsequently an exemplary Bayesian network model was constructed using the procedure as explained herein. Similarly to the description of the TGF-β cellular signaling pathway model based on the evidence curated list, the conditional probability tables of the edges between probesets and their respective putative target genes of this model including the broad literature list were trained using fRMA processed data from GSE17708. The training results depicted in FIG. 26 show a clear separation between passive (group 1) and active (group 5) training samples. More extreme values of pathway activity are found, especially in group 2 and 3, compared to the training results of the Bayesian model based on the evidence curated lists (see FIGS. 9 to 12). In the diagram, the vertical axis indicates the odds that the TF element is "present" resp. "absent", which corresponds to the TGF-β cellular signaling pathway being active resp. passive, wherein values above the horizontal axis correspond to the TF element being more likely "present"/active and values below the horizontal axis indicate that the odds that the TF element is "absent"/passive are larger than the odds that it is "present"/active. Each bar represents a sample from the dataset. (Legend: 1—Control; 2—TGF-β stimulation with 5 ng/mL for 0.5 h; 3—TGF-β stimulation with 5 ng/mL for 1 h; 4—TGF-β stimulation with 5 ng/mL for 2 h; 5—TGF-β stimulation with 5 ng/mL for 4 h; 6—TGF-β stimulation with 5 ng/mL for 8 h; 7—TGF-β stimulation with 5 ng/mL for 16 h; 8—TGF-β stimulation with 5 ng/mL for 24 h; 9—TGF-β stimulation with 5 ng/mL for 72 h).

Next the trained exemplary network Bayesian model based on the broad literature list was tested on a number of datasets.

Figure 27:
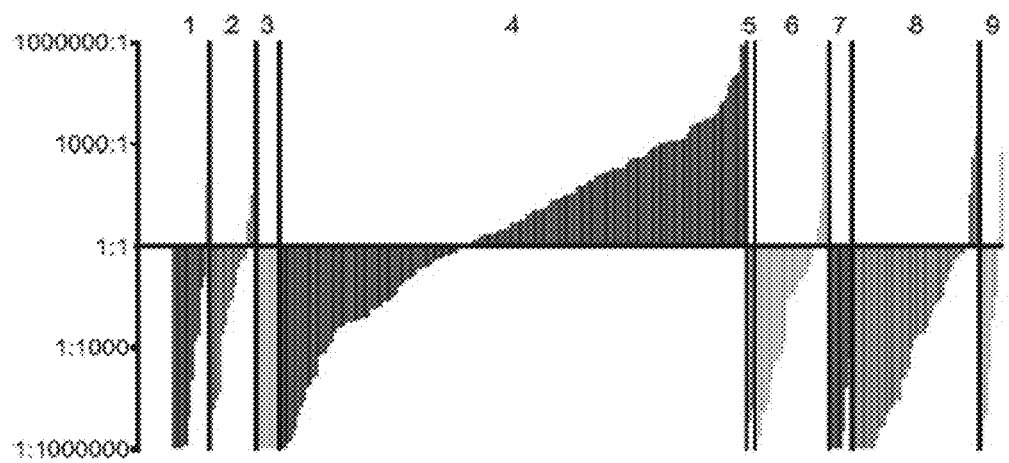
FIG. 27 shows TGF-β cellular signaling pathway activity predictions of the trained Bayesian network model using the broad literature list of putative target genes (see Table 8) for patient gliomas from GSE16011. (Legend: 1—Astrocytoma (grade II); 2—Astrocytoma (grade III); 3—Control; 4—Glioblastoma multiforme (grade IV); 5—Oligoastrocytic (grade II); 6—Oligoastrocytic (grade III); 7—Oligodendroglial (grade II); 8—Oligodendroglial (grade III); 9—Pilocytic astrocytoma (grade I))

FIG. 27 shows TGF-β cellular signaling pathway activity predictions of the trained Bayesian network model based on broad literature list for patient gliomas from GSE16011. In the diagram, the vertical axis indicates the odds that the TF element is "present" resp. "absent", which corresponds to the TGF-β cellular signaling pathway being active resp. passive, wherein values above the horizontal axis correspond to the TF element being more likely "present"/active and values below the horizontal axis indicate that the odds that the TF element is "absent"/passive are larger than the odds that it is "present"/active. Each bar represents a sample from the dataset. Although it is known from the literature that gliomas produce more TGF-β (all isoforms) than normal cells (see Kaminska B. et al., "TGF beta signaling and its role in glioma pathogenesis", Advances in Experimental Medicine and Biology, Vol. 986, 2013, pages 171 to 187), the large fraction (>50%) of glioblastoma multiforme (grade IV) patients (group 4) is apparently an overestimation of the number of tumors with an active TGF-β cellular signaling pathway. On the other hand, the TGF-β tumor-promoting activity of all controls (group 3) are correctly predicted to be negative. (Legend: 1—Astrocytoma (grade II); 2—Astrocytoma (grade III); 3—Control; 4—Glioblastoma multiforme (grade IV); 5—Oligoastrocytic (grade II); 6—Oligoastrocytic (grade III); 7—Oligodendroglial (grade II); 8—Oligodendroglial (grade III); 9 Pilocytic astrocytoma (grade I))

Figure 28:
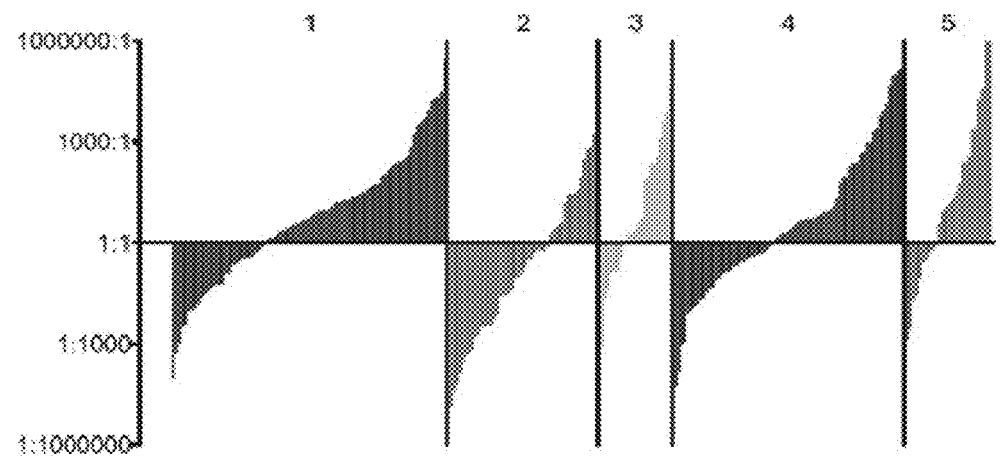
FIG. 28 shows TGF-β cellular signaling pathway activity predictions of the trained Bayesian network model using the broad literature list of putative target genes (see Table 8) for breast cancer samples from GSE21653. (Legend: 1—Luminal A; 2—Luminal B; 3—HER2; 4—Basal; 5—Normal-like)

FIG. 28 shows TGF-β cellular signaling pathway activity predictions of the trained Bayesian network model based on broad literature list for breast cancer samples from GSE21653. In the diagram, the vertical axis indicates the odds that the TF element is "present" resp. "absent", which corresponds to the TGF-β cellular signaling pathway being active resp. passive, wherein values above the horizontal axis correspond to the TF element being more likely "present"/active and values below the horizontal axis indicate that the odds that the TF element is "absent"/passive are larger than the odds that it is "present"/active. Each bar represented a sample from the dataset. Unexpectedly, most breast cancer samples were predicted to have a tumor-promoting TGF-β cellular signaling pathway. In addition, the highest fraction of patient samples with tumor-promoting TGF-β activity is found in the luminal A subtype. Luminal A is known to have the best prognosis among the different breast cancer subtypes which does not correspond with the aggressiveness of the TGF-β tumor-promoting activity. (Legend: 1—Luminal A; 2—Luminal B; 3—HER2; 4—Basal; 5—Normal-like)

As evidenced by the above example, the selection of unique TGF-β target gene sets in combination with the mathematical models described herein for determining the activity level of TGF-β cellular signaling pathway in a sample produces a more robust, precise, and accurate activity status determination than the use of a broader literature list, despite the fact that the number of target genes is larger. By focusing on the specific target genes identified herein, a useful determination of TGF-β cellular signaling pathway activity is provided that can be further used in treatment or prognostic modalities as described herein.

Example 5

Selection of SERPINE1 as Bona Fide TGF-β Target Gene

A revision of the available literature evidence of TGF-β was performed in January 2015, also including all new scientific papers up to 19 Jan. 2015. Similarly, publications were found using the MEDLINE database of the National Institute of Health accessible at "www.ncbi.nlm.nih.gov/pubmed" using queries such as ("TGF-β" AND "target gene"). After manually evaluating the scientific papers for experimental evidence of a number of target genes being a putative target gene of TGF-β using the methodology as described in Example 2 above, a number of putative TGF-β target genes, unexploited in the initial evaluation during the fourth quarter of 2013 and first quarter of 2014, were found. All available experimental evidence was reevaluated and a new ranking of putative target genes was prepared based on the strength of the available experimental evidence for the putative target gene using the methodology as described in Example 2. This resulted in one additional putative TGF-β target gene, SERPINE1, achieving an experimental evidence score above the set threshold. Consequently, SERPINE1 was considered to be a bona fide direct target gene of the TGF-β pathway and tested for improved TGF-β pathway activity level calculations.

Using two Bayesian networks based on the 11 highest ranked target genes: ANGPTL4, CDC42EP3, CDKN1A, CTGF, GADD45B, ID1, JUNB, SKIL, SMAD7, SNAI2 and VEGFA plus or minus the newly selected SERPINE1 trained using the same data and methodology as described in Example 3 above, resulting in a '11-gene list+SERPINE1' and a '11-gene list' model, respectively.

TABLE 9

"11-gene list + SERPINE1" (or "revised 12 target genes shortlist" list of target genes of the TGF-β cellular signaling pathway includes:

ANGPTL4
CDC42EP3
CDKN1A
CTGF
GADD45B
ID1
JUNB
SERPINE1
SKIL
SMAD7
SNAI2
VEGFA

TABLE 10

"11-gene list" of target genes of the TGF-β cellular signaling pathway includes:

ANGPTL4
CDC42EP3
CDKN1A
CTGF
GADD45B
ID1
JUNB
SKIL
SMAD7
SNAI2
VEGFA

Based on the additional inclusion of the SERPINE1 gene, the target gene lists (See Tables 5 and 7) can be revised into additional non-limiting embodiments, as described in Tables 11 and 12.

TABLE 11

The "revised 20 target genes shortlist" of target genes of the TGF-β cellular signaling pathway includes:

ANGPTL4
CDC42EP3
CDKN1A
CTGF
GADD45A
GADD45B
HMGA2
ID1
JUNB
PDGFB
PTHLH
SERPINE1
SGK1
SKIL
SMAD4
SMAD5

TABLE 11-continued

The "revised 20 target genes shortlist" of target genes
of the TGF-β cellular signaling pathway includes:

SMAD6
SMAD7
SNAI2
VEGFA

TABLE 12

The "revised 7 target genes shortlist" of target genes
of the TGF-β cellular signaling pathway includes:

ANGPTL4
CDC42EP3
ID1
JUNB
SERPINE1
SKIL
SMAD7

Including one more target gene in the mathematical calculation of the pathway activity is expected to have a small effect on the predictions of the pathway activity, which is anticipated to scale the pathway activity level minutely. In the examples below, it is shown that in addition to this anticipated effect there are also markedly different pathway activity levels in several examples which can only be explained by SERPINE1 having an unexpected, advantageous effect on the pathway activity calculations.

Figure 29:
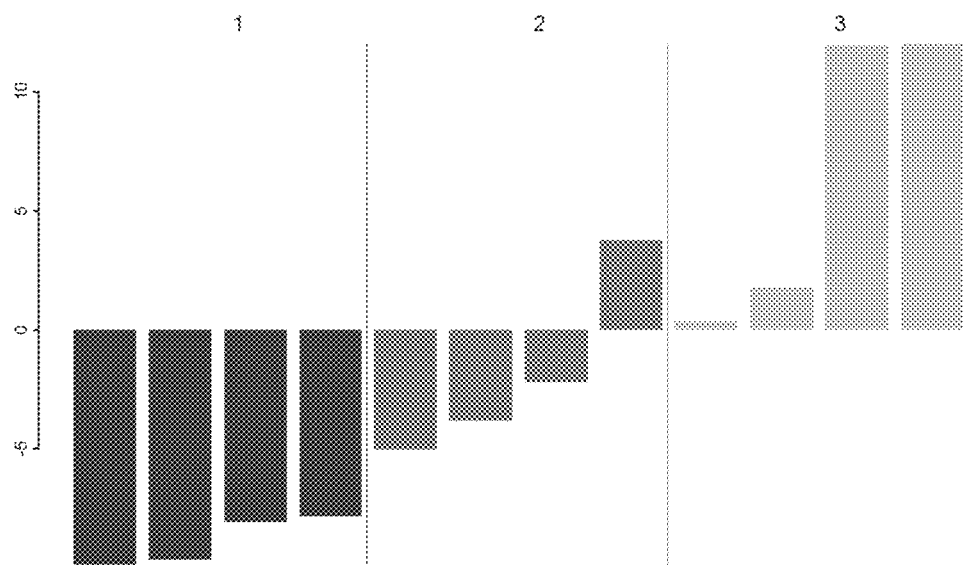
FIG. 29 shows TGF-β pathway activity predictions calculated by the '11-gene list'-Bayesian network on ectocervical epithelial cells (Ect1) stimulated with seminal plasma or 5 ng/mL TGF-β3 (GSE35830). (Legend: 1—Control, no TGF-β; 2—Stimulated with 10% seminal plasma; 3—stimulated with 5 ng/mL TGF-β3)
Figure 30:
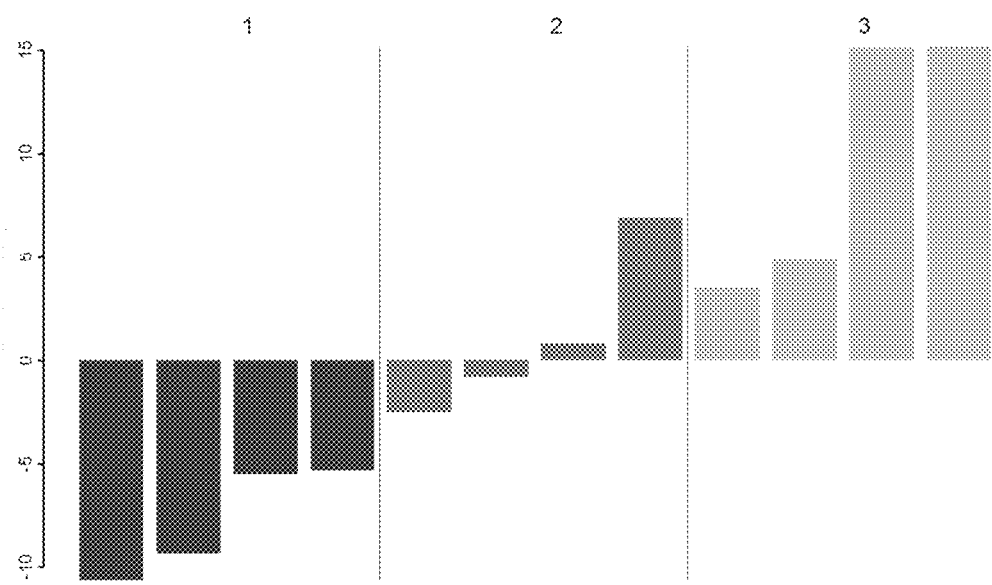
FIG. 30 shows TGF-β pathway activity predictions calculated by the '11-gene list+SERPINE1'-Bayesian network on ectocervical epithelial cells (Ect1) stimulated with seminal plasma or 5 ng/mL TGF-β3 (GSE35830). (Legend: 1—Control, no TGF-β; 2—Stimulated with 10% seminal plasma; 3—stimulated with 5 ng/mL TGF-β3)

FIGS. 29 and 30 show the predictions of TGF-β activity using both models in Ect1 cell lines stimulated with seminal plasma or 5 ng/mL TGF-β3 or without stimulation from GSE35830. It is clearly visible that including SERPINE1 as an additional target gene improves the capability of the model to detect passive samples with higher accuracy. Furthermore, the model predictions of the second group stimulated with seminal plasma and the third group stimulated with TGF-β3 are more accurate as they predict a higher activity of the TGF-β pathway.

Figure 31:
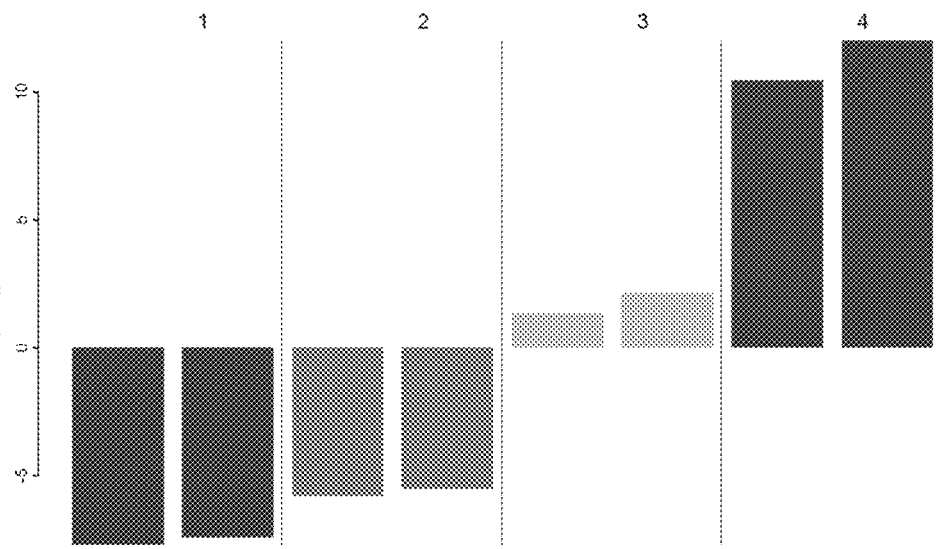
FIG. 31 shows TGF-β pathway activity predictions calculated by the '11-gene list'-Bayesian network in 2D and 3D cultures of A549 lung adenocarcinoma cell lines stimulated with or without a 10 ng/mL TNF and 2 ng/mL TGF-β (GSE42373). (Legend: 1—2D control, 2—2D TGF-β and TNFα, 3—3D control, 4—3D TGF-β and TNFα)
Figure 32:
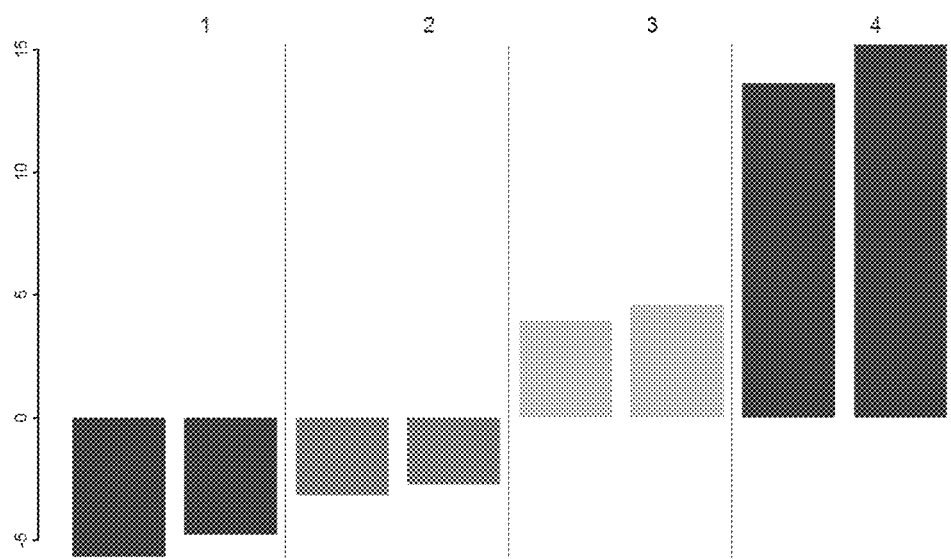
FIG. 32 shows TGF-β pathway activity predictions calculated by the '11-gene list+SERPINE1'-Bayesian network in 2D and 3D cultures of A549 lung adenocarcinoma cell lines stimulated with or without a 10 ng/mL TNF and 2 ng/mL TGF-β (GSE42373). (Legend: 1—2D control, 2—2D TGF-β and TNFα, 3—3D control, 4—3D TGF-β and TNFα)

A second example of improved TGF-β pathway activity predictions is found in A549 lung adenocarcinoma cell line samples grown in 2D and 3D cultures stimulated with or without TNF and TGF-β. The model predictions using both the '11-gene' Bayesian network model and the 11-gene list+SERPINE1' are shown in FIGS. 31 and 32. EMT was only efficiently induced in the 3D culture model with stimulation (group 4). This induction of EMT is diagnosed with a higher accuracy in the '11-gene list+SERPINE1' model compared to the '11-gene list' model, also in case the relative difference between groups 3 and 4 is considered.

A third example is the TGF-β pathway activity predictions using both models in glioma patients and some control samples from GSE16011. It is known from literature that TGF-β signaling plays a significant role in gliomas (see Kaminska B. et al., "TGF beta signaling and its role in glioma pathogenesis", Advances in Experimental Medicine and Biology, Vol. 986, 2013, pages 171 to 187). The Bayesian network based on '11-gene list+SERPINE1' improves the separation of passive from active samples compared to the '11-gene list' Bayesian network. In addition, a higher fraction of patients is predicted to have an active TGF-β pathway which is more in line with scientific consensus (see e.g. Kaminska et al.). Moreover, the normal brain samples are predicted to have a passive TGF-β with higher probabilities, which is in agreement with the fact that the TGF-β signaling pathway is expected to be in its tumor-suppressive role or passive role.

Figure 33:
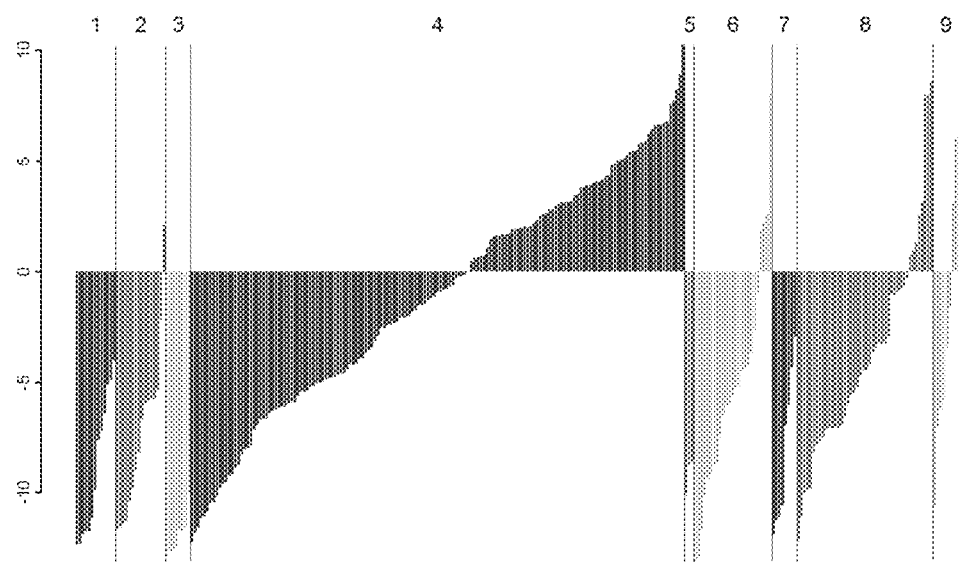
FIG. 33 shows TGF-β pathway activity predictions calculated by the '11-gene list'-Bayesian on glioma patients and some control samples from GSE16011. (Legend: 1—Astrocytoma (grade II); 2—Astrocytoma (grade III); 3—Control; 4—Glioblastoma multiforme (grade IV); 5—Oligoastrocytic (grade II); 6—Oligoastrocytic (grade III); 7—Oligodendroglial (grade II); 8—Oligodendroglial (grade III); 9—Pilocytic astrocytoma (grade I))
Figure 34:
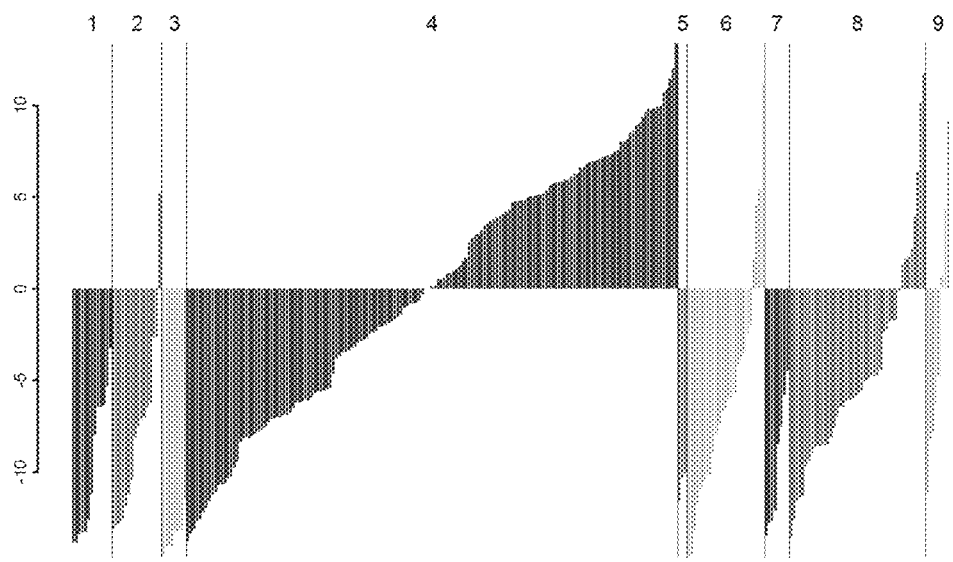
FIG. 34 shows TGF-β pathway activity predictions calculated by the '11-gene list+SERPINE1'-Bayesian on glioma patients and some control samples from GSE16011. (Legend: 1—Astrocytoma (grade II); 2—Astrocytoma (grade III); 3—Control; 4—Glioblastoma multiforme (grade IV); 5—Oligoastrocytic (grade II); 6—Oligoastrocytic (grade III); 7—Oligodendroglial (grade II); 8—Oligodendroglial (grade III); 9—Pilocytic astrocytoma (grade I))

The last example demonstrating the improved TGF-β pathway activity predictions by including SERPINE1 in the pathway model is shown by comparing the results of Cox's regression analysis of the 284 glioma patients from GSE16011 using the Bayesian network model based on the '11-gene list+SERPINE1' and '11-gene list'. As shown in FIGS. 33 and 34, the hazard ratio of the probability of TGF-β activity is significantly higher in case the '11-gene list+SERPINE1' is used: 2.57, p=7.87e-10 vs 2.33, p=3.06e-7.

This specification has been described with reference to embodiments, which are illustrated by the accompanying Examples. The invention can, however, be embodied in different forms and should not be construed as limited to the embodiments set forth herein. Given the teaching herein, one of ordinary skill in the art will be able to modify the invention for a desired purpose and such variations are considered within the scope of the disclosure.

SEQUENCE LISTING

| Seq. No. | Gene: |
|---|---|
| Seq. 1 | ANGPTL4 |
| Seq. 2 | ATF3 |
| Seq. 3 | CCL2 |
| Seq. 4 | CDC42EP3 |
| Seq. 5 | CDH1 |
| Seq. 6 | CDKN1A |
| Seq. 7 | CDKN2B |
| Seq. 8 | COL1A2 |
| Seq. 9 | COL3A1 |
| Seq. 10 | COL7A1 |
| Seq. 11 | CTGF |
| Seq. 12 | CTNNB1 |
| Seq. 13 | DLX5 |
| Seq. 14 | EDN1 |
| Seq. 15 | FN1 |
| Seq. 16 | FOXP3 |
| Seq. 17 | FSHB |
| Seq. 18 | FST |
| Seq. 19 | FSTL3 |
| Seq. 20 | GADD45A |
| Seq. 21 | GADD45B |
| Seq. 22 | GNRHR |
| Seq. 23 | GSC |
| Seq. 24 | HAMP |
| Seq. 25 | HEY1 |
| Seq. 26 | HMGA2 |
| Seq. 27 | IBSP |
| Seq. 28 | ID1 |
| Seq. 29 | ID2 |
| Seq. 30 | ID3 |
| Seq. 31 | IL11 |
| Seq. 32 | IL6 |
| Seq. 33 | INPP5D |
| Seq. 34 | ITGB1 |
| Seq. 35 | ITGB5 |
| Seq. 36 | JUN |
| Seq. 37 | JUNB |
| Seq. 38 | LEFTY2 |
| Seq. 39 | MIXL1 |
| Seq. 40 | MMP13 |
| Seq. 41 | MMP2 |
| Seq. 42 | MMP9 |
| Seq. 43 | MSX2 |
| Seq. 44 | MYC |
| Seq. 45 | NKX2-5 |
| Seq. 46 | NODAL |
| Seq. 47 | OVOL1 |
| Seq. 48 | PDGFB |
| Seq. 49 | PMEPA1 |

| Seq. No. | Gene: |
|---|---|
| Seq. 50 | PPARG |
| Seq. 51 | PTGS2 |
| Seq. 52 | PTHLH |
| Seq. 53 | SERPINE1 |
| Seq. 54 | SGK1 |
| Seq. 55 | SKIL |
| Seq. 56 | SLC25A5 |
| Seq. 57 | SMAD4 |
| Seq. 58 | SMAD5 |
| Seq. 59 | SMAD6 |
| Seq. 60 | SMAD7 |
| Seq. 61 | SNAI1 |

| Seq. No. | Gene: |
|---|---|
| Seq. 62 | SNAI2 |
| Seq. 63 | SP7 |
| Seq. 64 | SPP1 |
| Seq. 65 | TAGLN |
| Seq. 66 | TERT |
| Seq. 67 | TGFBR1 |
| Seq. 68 | TIMP1 |
| Seq. 69 | VEGFA |
| Seq. 70 | VIM |
| Seq. 71 | SERPINE1 |

The invention claimed is:

1. A method for determining the activity level of a TGF-β cellular signaling pathway in a subject, comprising:
   identifying target genes for acquiring expression levels of at least three TGF-β target genes derived from a sample isolated from the subject,
      wherein the identified target genes include three or more of genes selected from CDC42EP3, ANGPTL4, ID1, IL11, SERPINE1, JUNB, SKIL, and SMAD7;
   utilizing the expression levels of the at least three TGF-β target genes derived from the sample for determining an activity level of TGF-β transcription factor element in the sample isolated from the subject,
      wherein the at least three TGF-β target genes are selected from the identified target genes; and
   the activity level of TGF-β transcription factor element in the sample is determined by a computerized device having a processor by:
      receiving data on the expression levels of the at least three TGF-β target genes derived from the sample, wherein the TGF-β transcription factor element controls transcription of the at least three TGF-β target genes; and
      calculating the activity level of the TGF-β transcription factor element in the sample using a calibrated pathway model, wherein the calibrated pathway model compares the expression levels of the at least three TGF-β target genes in the sample with expression levels of the at least three TGF-β target genes in the model which define an activity level of TGF-β transcription factor element; and
   determining the activity level of the TGF-β cellular signaling pathway in the sample based on the calculated activity levels of TGF-β transcription factor element in the sample.

2. The method of claim 1, further comprising assigning a TGF-β cellular signaling pathway activity status to the calculated activity level of the TGF-β cellular signaling pathway in the sample, wherein the activity status is indicative of either an active TGF-β cellular signaling pathway or a passive TGF-β cellular signaling pathway.

3. The method of claim 2, further comprising using the activity status of the TGF-β cellular signaling pathway for at least one of diagnosing the presence or absence of a disease or disease state, diagnosing the presence or absence of a particular disease or disease state, diagnosing of a state of advancement of a particular disease or disease state, and designing of a course of treatment of the disease or disease state, wherein the disease is one of an immune disease, cancer, bronchial asthma, heart disease, diabetes, hereditary hemorrhagic telangiectasia, Marfan syndrome, Vascular Ehlers-Danlos syndrome, Loeys-Dietz syndrome, Parkinson's disease, chronic kidney disease, multiple sclerosis, fibrotic disease, liver, lung, or kidney fibrosis, Dupuytren's disease, or Alzheimer's disease.

4. The method of claim 3, wherein the disease is cancer.

5. The method of claim 4, the cancer is breast cancer, lung cancer, colon cancer, pancreatic cancer, or brain cancer.

6. The method of claim 5, wherein the cancer is breast cancer.

7. The method of claim 2, further comprising using the activity status of the TGF-β cellular signaling pathway for administering to the subject a TGF-β inhibitor if the information regarding the activity level of the TGF-β cellular signaling pathway is indicative of an active TGF-β cellular signaling pathway.

8. The method of claim 2, further comprising setting the indication of activity status of the TGF-β cellular signaling pathway at a predetermined cutoff value of odds of the TGF-β cellular signaling pathway being active.

9. The method of claim 1, further comprising displaying the TGF-β cellular signaling pathway activity status.

10. The method of claim 1, wherein the at least three TGF-β target genes are ANGPTL4, CDC42EP3, and at least one of ID1, IL11, SERPINE1, JUNB, SKIL, or SMAD7.

11. The method of claim 1, wherein data on the expression levels of the TGF-β target genes ANGPTL4, CDC42EP3, ID1, SERPINE1, JUNB, SKIL, and SMAD7 is received.

12. The method of claim 11, wherein data on the expression levels of the additional TGF-β target genes CDKN1A, CTGF, GADD45B, VEGFA, and SNAI2 is received.

13. The method of claim 1, wherein the calibrated pathway model is a probabilistic model incorporating conditional probabilistic relationships that compare the expression levels of the at least three TGF-β target genes in the sample with expression levels of the at least three TGF-β target genes in the model which define a level of TGF-β transcription factor element to determine the activity level of TGF-β transcription factor element in the sample.

14. The method of claim 1, wherein the calibrated pathway model is a linear model incorporating relationships that compare the expression levels of the at least three TGF-β target genes in the sample with expression levels of the at least three TGF-β target genes in the model which define a level of TGF-β transcription factor element to determine the activity level of TGF-β transcription factor element in the sample.

15. The method of claim 1, further comprising extracting the sample from the subject.

16. The method of claim 15, further comprising, determining said expression levels of the at least three TGF-β target genes from said sample.

17. The method of claim 1, further comprising determining whether the TGF-β cellular signaling pathway is operating abnormally in the subject based on the calculated activity of the TGF-β cellular signaling pathway in the subject.

18. A computer program product for determining the activity level of a TGF-β cellular signaling pathway in a subject, comprising:
a non-transitory computer readable storage medium having computer readable program code embodied therewith, the computer readable program code executable by at least one processor to:
calculate a level of TGF-β transcription factor element in a sample isolated from a subject, wherein the level of the TGF-β transcription factor element in the sample is calculated by:
utilizing data on the expression levels of at least three TGF-β target genes derived from the sample, wherein the at least three TGF-β target genes are selected from identified target genes including three or more of CDC42EP3, ANGPTL4, ID1, IL11, SERPINE1, JUNB, SKIL, and SMAD7;
calculating the level of TGF-β transcription factor element in the sample using a calibrated pathway model, wherein the calibrated pathway model compares the expression levels of the at least three TGF-β target genes in the sample with expression levels of the at least three TGF-β target genes in the model which define an activity level of the TGF-β transcription factor element; and
calculate the activity level of the TGF-β cellular signaling pathway in the sample based on the calculated TGF-β transcription factor element level in the sample.

19. The computer program product of claim 18, wherein the computer readable program code is executable by at least one processor to assign a TGF-β cellular signaling pathway activity status to the calculated activity level of the TGF-β cellular signaling in the sample, wherein the activity status is indicative of either an active TGF-β cellular signaling pathway or a passive TGF-β cellular signaling pathway.

20. The computer program product of claim 19, wherein the computer readable program code is executable by at least one processor to display the TGF-β signaling pathway activity status.

21. The computer program product of claim 18, wherein the at least three TGF-β target genes are ANGPTL4, CDC42EP3, and at least one of ID1, IL11, SERPINE1, JUNB, SKIL, or SMAD7.

22. The computer program product of claim 18, wherein data on the expression levels of the TGF-β target genes ANGPTL4, CDC42EP3, ID1, SERPINE1, JUNB, SKIL, and SMAD7 is received.

23. The computer program product of claim 22, wherein data on the expression levels of the additional TGF-β target genes CDKN1A, CTGF, GADD45B, VEGFA, and SNAI2 is received.

24. The computer program product of claim 18, wherein the calibrated pathway model is a probabilistic model incorporating conditional probabilistic relationships that compare the expression levels of the at least three TGF-β target genes in the sample with expression levels of the at least three TGF-β target genes in the model which define a level of TGF-β transcription factor element to determine the activity level of the TGF-β transcription factor element in the sample.

25. The computer program product of claim 18, wherein the calibrated pathway model is a linear model incorporating relationships that compare the expression levels of the at least three TGF-β target genes in the sample with expression levels of the at least three TGF-β target genes in the model which define a level of TGF-β transcription factor element to determine the activity level of the TGF-β transcription factor element in the sample.

26. The computer program product of claim 18, further comprising assigning a TGF-β cellular signaling pathway activity status to the calculated activity level of the TGF-β cellular signaling in the sample, wherein the activity status is indicative of either an active TGF-β cellular signaling pathway or a passive TGF-β cellular signaling pathway.

27. The computer program product of claim 26, further comprising using the activity status of the TGF-β cellular signaling pathway for at least one of diagnosing the presence or absence of a disease or disease state, diagnosing the presence or absence of a particular disease or disease state, diagnosing of a state of advancement of a particular disease or disease state, and designing of a course of treatment of the disease or disease state, wherein the disease is one of an immune disease, cancer, bronchial asthma, heart disease, diabetes, hereditary hemorrhagic telangiectasia, Marfan syndrome, Vascular Ehlers-Danlos syndrome, Loeys-Dietz syndrome, Parkinson's disease, chronic kidney disease, multiple sclerosis, fibrotic disease, liver, lung, or kidney fibrosis, Dupuytren's disease, or Alzheimer's disease.

28. The computer program product of claim 27, wherein the disease is cancer.

29. The computer program product of claim 28, the cancer is breast cancer, lung cancer, colon cancer, pancreatic cancer, or brain cancer.

30. The method of claim 29, wherein the cancer is breast cancer.

31. The computer program product of claim 18, wherein the computer readable program code is executable by at least one processor to determine whether the TGF-β cellular signaling pathway is operating abnormally in the subject based on the calculated activity of the TGF-β cellular signaling pathway in the subject.

32. The method of claim 7, wherein the TGF-β inhibitor is Terameprocol, Fresolimumab, Sotatercept, Galunisertib, SB431542, LY2109761, LDN-193189, SB525334, SB505124, GW788388, LY364947, RepSox, LDN-193189 HCl, K02288, LDN-214117, SD-208, EW-7197, ML347, LDN-212854, DMH1, Pirfenidone, Hesperetin, Trabedersen, Lerdelimumab, Metelimumab, trx-SARA, ID11, Ki26894, or SB-431542.

33. A kit for determining the activity level of a TGF-β cellular signaling pathway in a subject, comprising:
one or more components capable of identifying expression levels of at least three TGF-β cellular signaling pathway target genes from a sample of the subject, wherein the at least three TGF-β cellular signaling pathway target genes are selected from identified target genes including three or more genes selected from CDC42EP3, ANGPTL4, Dl, SERPINE1, JUNB, SKIL, or SMAD7; and,
a non-transitory computer readable storage medium having computer readable program code embodied therewith, the computer readable program code executable by at least one processor to:

calculate a level of TGF-β transcription factor element in the sample, wherein the level of the TGF-β transcription factor element in the sample is associated with TGF-β cellular signaling, and wherein the level of the TGF-β transcription factor element in the sample is calculated by:
  utilizing data on the expression levels of the at least three TGF-β target genes derived from the sample;
  calculating the level of the TGF-β transcription factor element in the sample using a calibrated pathway model, wherein the calibrated pathway model compares the expression levels of the at least three TGF-β target genes in the sample with expression levels of the at least three TGF-β target genes in the model which define an activity level of TGF-β transcription factor element; and,
calculate the activity level of the TGF-β cellular signaling pathway in the sample based on the calculated TGF-β transcription factor element level in the sample.

* * * * *

SEQUENCE LISTING

<160> NUMBER OF SEQ ID NOS: 143

<210> SEQ ID NO 1
<211> LENGTH: 1905
<212> TYPE: DNA
<213> ORGANISM: Homo sapiens

<400> SEQUENCE: 1

```
ataaaaaccg tcctcgggcg cggcggggag aagccgagct gagcggatcc tcacacgact      60
gtgatccgat tctttccagc ggcttctgca accaagcggg tcttaccccc ggtcctccgc     120
gtctccagtc ctcgcacctg aaccccaac  gtccccgaga gtccccgaat ccccgctccc     180
aggctaccta agaggatgag cggtgctccg acggccgggg cagccctgat gctctgcgcc     240
gccaccgccg tgctactgag cgctcagggc ggacccgtgc agtccaagtc gccgcgcttt     300
gcgtcctggg acgagatgaa tgtcctggcg cacggactcc tgcagctcgg ccaggggctg     360
cgcgaacacg cggagcgcac ccgcagtcag ctgagcgcg  tggagcggcg cctgagcgcg     420
tgcgggtccg cctgtcaggg aaccgagggg tccaccgacc tcccgttagc ccctgagagc     480
cgggtggacc ctgaggtcct tcacagcctg cagacacaac tcaaggctca gaacagcagg     540
atccagcaac tcttccacaa ggtggcccag cagcagcggc acctggagaa gcagcacctg     600
cgaattcagc atctgcaaag ccagtttggc ctcctggacc acaagcacct agaccatgag     660
gtggccaagc ctgcccgaag aaagaggctg cccgagatgg cccagccagt tgacccggct     720
cacaatgtca gccgcctgca ccggctgccc agggattgcc aggagctgtt ccaggttggg     780
gagaggcaga gtggactatt tgaaatccag cctcaggggt ctccgccatt tttggtgaac     840
tgcaagatga cctcagatgg aggctggaca gtaattcaga ggcgccacga tggctcagtg     900
gacttcaacc ggccctggga agcctacaag gcggggtttg gggatcccca cggcgagttc     960
tggctgggtc tggagaaggt gcatagcatc acggggacc  gcaacagccg cctggccgtg    1020
cagctgcggg actgggatgg caacgccgag ttgctgcagt tctccgtgca cctgggtggc    1080
gaggacacgg cctatagcct gcagctcact gcaccgtgg  ccggccagct gggcgccacc    1140
accgtcccac ccagcggcct ctccgtaccc ttctccactt gggaccagga tcacgacctc    1200
cgcagggaca gaactgcgc  caagagcctc tctggaggct ggtggtttgg cacctgcagc    1260
cattccaacc tcaacggccg tacttccgc  tccatcccac agcagcggca gaagcttaag    1320
aagggaatct tctggaagac ctggcggggc cgctactacc cgctgcaggc caccaccatg    1380
ttgatccagc ccatggcagc agaggcagcc tcctagcgtc ctggctgggc ctggtcccag    1440
gcccacgaaa gacggtgact cttggctctg ccgaggatg  tggccgttcc ctgcctgggc    1500
```

| | |
|---|---|
| agggggctcca aggaggggcc atctggaaac ttgtggacag agaagaagac cacgactgga | 1560 |
| gaagccccct ttctgagtgc aggggggctg catgcgttgc ctcctgagat cgaggctgca | 1620 |
| ggatatgctc agactctaga ggcgtggacc aagggggcatg gagcttcact ccttgctggc | 1680 |
| cagggagttg gggactcaga gggaccactt ggggccagcc agactggcct caatggcgga | 1740 |
| ctcagtcaca ttgactgacg gggaccaggg cttgtgtggg tcgagagcgc cctcatggtg | 1800 |
| ctggtgctgt tgtgtgtagg tcccctgggg acacaagcag gcgccaatgg tatctgggcg | 1860 |
| gagctcacag agttcttgga ataaaagcaa cctcagaaca ctttg | 1905 |

<210> SEQ ID NO 2
<211> LENGTH: 2088
<212> TYPE: DNA
<213> ORGANISM: Homo sapiens

<400> SEQUENCE: 2

| | |
|---|---|
| tccgctccgt tcggccggtt ctcccgggaa gctattaata gcattacgtc agcctgggac | 60 |
| tggcaacacg gagtaaacga ccgcgccgcc agcctgaggg ctataaaagg ggtgatgcaa | 120 |
| cgctctccaa gccacagtcg cacgcagcca ggcgcgcact gcacagctct cttctctcgc | 180 |
| cgccgcccga gcgcaccctt cagcccgcgc gccggccgtg agtcctcggt gctcgcccgc | 240 |
| cggccagaca aacagcccgc ccgaccccgt cccgaccctg gccgccccga gcggagcctg | 300 |
| gagcaaaatg atgcttcaac acccaggcca ggtctctgcc tcggaagtga gtgcttctgc | 360 |
| catcgtcccc tgcctgtccc ctcctgggtc actggtgttt gaggattttg ctaacctgac | 420 |
| gcccttttgtc aaggaagagc tgaggtttgc catccagaac aagcacctct gccaccggat | 480 |
| gtcctctgcg ctggaatcag tcactgtcag cgacagaccc ctcggggtgt ccatcacaaa | 540 |
| agccgaggta gcccctgaag aagatgaaag gaaaagagg cgacgagaaa gaataagat | 600 |
| tgcagctgca aagtgccgaa acaagaagaa ggagaagacg gagtgcctgc agaaagagtc | 660 |
| ggagaagctg gaaagtgtga atgctgaact gaaggctcag attgaggagc tcaagaacga | 720 |
| gaagcagcat ttgatataca tgctcaacct tcatcggccc acgtgtattg tccgggctca | 780 |
| gaatgggagg actccagaag atgagagaaa cctctttatc caacagataa agaaggaac | 840 |
| attgcagagc taagcagtcg tggtatgggg gcgactgggg agtcctcatt gaatcctcat | 900 |
| tttataccca aaaccctgaa gccattggag agctgtcttc ctgtgtacct ctagaatccc | 960 |
| agcagcagag aaccatcaag gcgggagggc ctgcagtgat tcagcaggcc cttcccattc | 1020 |
| tgccccagag tgggtcttgg accagggcaa gtgcatcttt gcctcaactc caggatttag | 1080 |
| gccttaacac actggccatt cttatgttcc agatggcccc cagctggtgt cctgcccgcc | 1140 |
| tttcatctgg attctacaaa aaaccaggat gcccaccgtt aggattcagg cagcagtgtc | 1200 |
| tgtacctcgg gtgggaggga tggggccatc tccttcaccg tggctaccat tgtcactcgt | 1260 |
| aggggatgtg gagtgagaac agcatttagt gaagttgtgc aacggccagg gttgtgcttt | 1320 |
| ctagcaaata tgctgttatg tccagaaatt gtgtgtgcaa gaaaactagg caatgtactc | 1380 |
| ttccgatgtt tgtgtcacac aacactgatg tgactttat atgcttttc tcagatctgg | 1440 |
| tttctaagag ttttggggg cggggctgtc accacgtgca gtatctcaag atattcaggt | 1500 |
| ggccagaaga gcttgtcagc aagaggagga cagaattctc ccagcgttaa cacaaaatcc | 1560 |
| atgggcagta tgatggcagg tcctctgttg caaactcagt tccaaagtca caggaagaaa | 1620 |
| gcagaaagtt caacttccaa aggggttagga ctctccactc aatgtcttag gtcaggagtt | 1680 |
| gtgtctaggc tggaagagcc aaagaatatt ccattttcct ttccttgtgg ttgaaaacca | 1740 |

```
cagtcagtgg agagatgttt ggaaaccaca gtcagtggag cctgggtggt acccaggctt   1800
tagcattatt ggatgtcaat agcattgttt ttgtcatgta gctgttttaa gaaatctggc   1860
ccagggtgtt tgcagctgtg agaagtcact cacactggcc acaaggacgc tggctactgt   1920
ctattaaaat tctgatgttt ctgtgaaatt ctcagagtgt ttaattgtac tcaatggtat   1980
cattacaatt ttctgtaaga gaaatatta cttatttatc ctagtattcc taacctgtca   2040
gaataataaa tattggaacc aagacatggt aaacaaaaaa aaaaaaaa                2088

<210> SEQ ID NO 3
<211> LENGTH: 760
<212> TYPE: DNA
<213> ORGANISM: Homo sapiens

<400> SEQUENCE: 3
gaggaaccga gaggctgaga ctaacccaga acatccaat tctcaaactg aagctcgcac    60
tctcgcctcc agcatgaaag tctctgccgc ccttctgtgc ctgctgctca tagcagccac   120
cttcattccc caagggctcg ctcagccaga tgcaatcaat gccccagtca cctgctgtta   180
taacttcacc aataggaaga tctcagtgca gaggctcgcg agctatagaa gaatcaccag   240
cagcaagtgt cccaaagaag ctgtgatctt caagaccatt gtggccaagg agatctgtgc   300
tgaccccaag cagaagtggg ttcaggattc catggaccac ctggacaagc aaacccaaac   360
tccgaagact tgaacactca ctccacaacc caagaatctg cagctaactt atttttcccct  420 agctttcccc agacaccctg ttttatttta ttataatgaa ttttgtttgt tgatgtgaaa   480
cattatgcct taagtaatgt taattcttat ttaagttatt gatgttttaa gtttatcttt   540
catggtacta gtgttttta gatacagaga cttggggaaa ttgcttttcc tcttgaacca    600
cagttctacc cctgggatgt tttgagggtc tttgcaagaa tcattaatac aaagaatttt   660
ttttaacatt ccaatgcatt gctaaaatat tattgtggaa atgaatattt tgtaactatt   720
acaccaaata aatatatttt tgtacaaaaa aaaaaaaaa                          760

<210> SEQ ID NO 4
<211> LENGTH: 5715
<212> TYPE: DNA
<213> ORGANISM: Homo sapiens

<400> SEQUENCE: 4
cgcgcccacc ggagcccggg ctgagaggga cctggggagc tgcggcctgg ccggggcggc   60
gcactcaggt ggcctcgctt ccctgcgggt caccgcccgc cactcgcaca gctaggtcgg   120
cctgttggga tcgggagagg tgggcgcacg agttttagtg cgggagtccg gggtgcgggc   180
ggagtcctat tgtccccgtg cacccggggcg gcagcacctc cgggtccctc tttaaaccga  240
gcgtccggcg acctttcttt gtgcttaggg agtcgaaagc ggcatcttct ccgagagaag   300
tcgcctactg gggggtggcg ctgggaggt aacaatgggc gcccattgtc ctccgagggt   360
ccaacggtga ccccccccg cgcgcgcgcc cggccaccgg ttggccccgg gccagggcac   420
aggtaccgcg gctgggaggg tcggcccgc tgcccgcgcc ctccgccccg ccccagtgag   480
tccccgcgcc gccggccccg cccgcgccg ccccgccctc gcaggttca gtcctcgcgt    540 ccggccgccc cgcgctcagt gcgcgcacc ttctctcgcg gccggggac cgcagcgcgg    600 ggctagcccg gagacccggc caccggcctg gggcgccttc acgccgtctc ggagcggata   660
atgcggtgag caggcaccac gccggcagac tcggctggat ctgcgcacag cggcagggat   720
```

```
tgcgtgcgcc cgcgggaggc ccggggcagc ggctgggatc ctcagcggcg gccggtttgt    780
cctggttgtg gtcaagactg gatgatgtaa ctggctctct aggaagcctc acttggccgt    840
aacctcagga aggttctctt tgaccccatc tcatttcgaa gccacttctg aagccacttg    900
agaaaaatga tgtgacagtt cctatcaaaa aggattcaga acatatacc atctgtgaag     960
aaagtggccc tttctcccgc ttgcaaaata gacattctca aattccaaaa tgccagccaa   1020
gaccccaatt tacctgaaag cagccaataa caagaaagga aagaaattta aactgaggga   1080
cattctgtct cctgatatga tcagtccccc gcttggagac tttcgccaca ccatccacat   1140
tggcaaagag ggccagcacg atgtctttgg agatatttcc tttcttcaag ggaactacga   1200
gcttttacct ggaaaccagg agaaagcaca cctgggccag ttccctgggc ataatgagtt   1260
cttccgggcc aacagcacct cggactctgt gttcacagaa cgccctccc cggtgctcaa    1320
aaatgccatc tccctcccga ccattggagg atcccaagct ctcatgttgc ccttattgtc   1380
accagtgaca tttaattcca acaggagtc cttcgggcca gcaaagctgc ccaggcttag    1440
ctgcgagccc gtcatggagg aaaaagctca ggagaaaagc agtctgttgg agaatgggac   1500
agtccaccag ggagacacct cgtggggctc cagcggttct gcatctcagt ccagccaagg   1560
cagagacagc cactcctcca gcctgtccga acagtacccc gactggccag ccgaggacat   1620
gtttgaccat cccaccccat gcgagctcat caagggaaag actaagtcag aggagtccct   1680
ctctgacctt acaggttccc tcctctccct gcagcttgat cttgggccct acttttgga    1740
tgaggtgctg aatgtaatgg ataaaaataa gtaacaagat gccaactttt ttccttggg    1800
gtaaaaggta caaaaacaaa ctaaccacag ttgaagagaa gggcttccgg agctgtattt   1860
gcagttttgt gttgggtttt ctaaaataat attcttacaa gtatttttt tacctgttat    1920
gccctgtttg caaaaacaat ttagaaaaaa acaacaaagc aaaacctatc ttggcaaaaa   1980
aaggaagtga gtcagagccc attttcagga ggcattggtg atgttcggct cacatattgt   2040
ttgcagacac acaagaaatc tggcttggcc aggattggca ctagctatga agggctgagc   2100
gagtcacatt aaggaacttc acggaacttt atagcactcc gacattttct gagcaagagg   2160
aagtcaaaat ttatttaaca cctaagcctt tttgtagact cttttctata tattgcttag   2220
gctcaccata gcgaattctc cagtgttaaa acttttctgt tttcacattt gaactttatg   2280
ggttttgggg attttcttgt agttcttata tatccctata tattatatct atattgcaaa   2340
attttgactg tcagctacat gttggtaaga cacaggcaaa gtattactgt aactaagtta   2400
ttttaaaagt taaaatatat ttttacgtgc ctttggcttt ttattgcaga gtctacattt   2460
tatagattct acatcagatg ttgtcactta tttccattgg gattccattg taagctgtgt   2520
atgtgcgtgt ttggaaaagt gtattcatac ttagttttttt tttcttcatc tgttatcata   2580
cttttaacag caaccaataa cggattgtaa agtgtaaagg cacaggttac tcatgatgct   2640
tctgcagaga ctgtgggcta caccacatat gttatttgga aatataggta ttttagtaca   2700
gtacatactt gcattacata ggtacttcaa gcaacacaat aaaaagtaaa tgataaagtg   2760
aacttgcttg tttatagtaa taaacaagac cataagagaa taagtatagc tagagaaatt   2820
gcttctctga aatgtacatg agcccttaag gtaagagatg atttccatct actctcatttt  2880
tgattacttc cttatggttt gagaggctag aaactgagcc tctctacttt tggaaaaatg   2940
aacatgtgag gtcagatttt ttttttttt tttaagtcag cactgatgcc accctctcag    3000
tggtcatttc tgagcatctt cctgacttga acaccttcta cagcaaactc ttgcaagtcc   3060
agtttcatcc ctgtaaggca aatgtctttt cacgcagaaa gtgccatata gacgagataa   3120
```

```
aggcagctaa aacgagggca gtagagagca cttacccgac cccaaggtgc cagagatgcc   3180
ctgaggatgg tggttaagga aacaggagca ggaaatgtac acacagattc ctgtcccttt   3240
gccaactact ccttccccat caaagaaaaa cacttgcaca cagtaactac cagctccttc   3300
tctcaaactt gtatttctcc tggaaatgta tctcagaaat gacctcctct cccaaccact   3360
tcaacgattc tttctttggg tttggggttc ttgcagttct atcatctaaa ataacctttg   3420
gactgcaggt aaaatgcaat taggacaact aaccaagtag acgaaacaag ttcccctagg   3480
caggggtgtc caatatttta gcttccctgg accgcattgg aagaattttc ttgggccaca   3540
tgtaaaacac actaacacta accatagttg atgagcttaa aaaaataaaa atagaaaatt   3600
gcaaaaaaaa aaaaaaaaaa aaatctcaga ctgttttaag aaagtttaaa aatttgtgtt   3660
ggacttcatg cgggccacag gttggacaag cttgccctag ggcattgtgt gctttccgta   3720
acttctcagt tgtatttcgt tatccatgac tctccagtgt tttttctgtt ggaccacacc   3780
cgtcacagtt cacagttcca aagagaaatt tcccagccta ttctaaatct tgttaatgac   3840
gaagagtcca atgtatctca ttatttgtag ccaatttttag actcttttca atacctcccc   3900
cccattttaa ttagtattga tcatattcag tctttcattt tactcttcat ctgtagcgtg   3960
acctcaaggt aaagatgaaa ctatttcatg aaaaggggag gagtatggct gtgcattagc   4020
tctactccct ctctggtaag tactggggag agaacagccc tgccagtact gggtttgata   4080
gattctaaat attaatcaca catcctgcct acagttagcc atttttagttt ctgggagttc   4140 tttcatgtac attttcttcc attaattgaa ttaggtataa ttgagatggc aataaatatg   4200
cccgtattag aaagaggaaa caaagctaca tgcggcttat gattttgttg agtcacttct   4260
cccgaggcag cctttccaat gcctggtccc ttcccctgag agcaggtgga ctgctggtgg   4320
tggctttctt tcctgcagag aggcacttta gacccatacc tgctgtgagc tgaattgatg   4380
ttctcatcct gtgaaccttc tcccactttta acctaattta tctttacttg tttaaagata   4440
aggaaaccca agatgtactt tatttgcaaa ctcaaagcaa atggcgagcc acctgtgacc   4500
cagtaaccag aaaagaaacc atgccatttg tataagtaga gacacttctt gttgaggtag   4560
gcaaggctct tgtgagcgat ttttttcccc tagtgagacc taacaaaaga caagctatat   4620
catttctgcc tgaaattatc tgcttgaaaa gatcaaaata tcaggatact tagctcttca   4680
caaatatgaa gtcattatca catttcactg agccagaaat cactgttaac agcacacaca   4740
aaagactaca ctggttgaac agcaaagaga aacccgggtc tccagaatca cagtttagtc   4800
cttctatatt actgcaagtg acctgttttt tctgaaggct ccccgcaaat gaagtcctgg   4860
aatggaaaaa atccataagt ccataaatta acttgataaa tattttagaa cagacaaaag   4920
aaaatattga gtgatgtagt tctaatcctc ctaatatgga acctggcaag actgaatcat   4980
tttactgtga aatatataaa cacaatagaa tgagccaaca tgatggtttc tctccagtaa   5040
gagtttttct tttggaaatg aggttaacct agccccaaat ctagcaattc tcataaaatc   5100
cgatttagga attagcctcc cagattaatc tgaatgattg acttattttt tcttaggcaa   5160
gtcagtaagc cacccactag acagccatat ccagcaaaat aagagaagtt tccagatgcc   5220
aaatgataag ccaccatcaa cccagcgggg aagccttctg gttggtttgg ctgtatgaga   5280
ttcaggaagg ccagaatacc caaaattatt cacacgacgt taacttattg gtactggcta   5340
agcaatacat gtatttccta aaggaggaga tggtctttg gttgatttat ggacacactt   5400
gtttcatctg actgtaaata tattgcatgc tttattctga tggtgcacta tttcatccag   5460
```

```
caagcttttc atctgagaat gtttaatgtt gaccttattc ttagagcaag tagatctaaa    5520
tatttttcag ctgagttatt agggagtcat tattctgtgg tacaatgctg caaaaagcat    5580
catgtggaag aatgggaact atgcttactt tatgaagtga tgtataacac aatgaaatct    5640
gttttacaac tactgtgctg catttaatta tcttccatttt ttgctgttaa aaaaaaaaaa    5700
tccgttaatg atgtc                                                    5715

<210> SEQ ID NO 5
<211> LENGTH: 4815
<212> TYPE: DNA
<213> ORGANISM: Homo sapiens

<400> SEQUENCE: 5
agtggcgtcg gaactgcaaa gcacctgtga gcttgcggaa gtcagttcag actccagccc      60
gctccagccc ggcccgaccc gaccgcaccc ggcgcctgcc ctcgctcggc gtccccggcc     120
agccatgggc ccttggagcc gcagcctctc ggcgctgctg ctgctgctgc aggtctcctc     180
ttggctctgc caggagccgg agccctgcca ccctggcttt gacgccgaga gctacacgtt     240
cacggtgccc cggcgccacc tggagagagg ccgcgtcctg ggcagagtga attttgaaga     300
ttgcaccggt cgacaaagga cagcctattt ttccctcgac acccgattca agtgggcac     360 agatggtgtg attacagtca aaaggcctct acggtttcat aacccacaga tccatttctt     420
ggtctacgcc tgggactcca cctacagaaa gttttccacc aaagtcacgc tgaatacagt     480
ggggcaccac caccgccccc cgcccatca ggcctccgtt tctggaatcc aagcagaatt     540
gctcacattt cccaactcct ctcctggcct cagaagacag aagagagact gggttattcc     600
tcccatcagc tgcccagaaa atgaaaaagg cccatttcct aaaaacctgg ttcagatcaa     660
atccaacaaa gacaagaag gcaaggtttt ctacagcatc actggccaag agctgacac     720 accccctgtt ggtgtctttta ttattgaaag agaaacagga tggctgaagg tgacagagcc     780
tctggataga gaacgcattg ccacatacac tctcttctct cacgctgtgt catccaacgg     840
gaatgcagtt gaggatccaa tggagatttt gatcacggta accgatcaga atgacaacaa     900
gcccgaattc acccaggagg tctttaaggg gtctgtcatg gaaggtgctc ttccaggaac     960
ctctgtgatg gaggtcacag ccacagacgc ggacgatgat gtgaacacct acaatgccgc    1020
catcgcttac accatcctca gccaagatcc tgagctccct gacaaaaata tgttcaccat    1080
taacaggaac acaggagtca tcagtgtggt caccactggg ctggaccgag agagtttccc    1140
tacgtatacc ctggtggttc aagctgctga ccttcaaggt gagggggttaa gcacaacagc    1200 aacagctgtg atcacagtca ctgacaccaa cgataatcct ccgatcttca atcccaccac    1260
gtacaagggt caggtgcctg agaacgaggc taacgtcgta atcaccacac tgaaagtgac    1320
tgatgctgat gccccccaata cccagcgtg ggaggctgta tacaccatat gaatgatga    1380 tggtggacaa tttgtcgtca ccacaaatcc agtgaacaac gatggcattt tgaaaacagc    1440
aaagggcttg gattttgagg ccaagcagca gtacattcta cacgtagcag tgacgaatgt    1500 ggtaccttttt gaggtctctc tcaccacctc cacagccacc gtcaccgtgg atgtgctgga    1560
tgtgaatgaa gccccatct ttgtgcctcc tgaaaagaga gtggaagtgt ccgaggactt    1620
tggcgtgggc caggaaatca catcctacac tgcccaggag ccagacacat ttatggaaca    1680
gaaaataaca tatcggattt ggagagacac tgccaactgg ctggagatta atccggacac    1740
tggtgccatt tccactcggg ctgagctgga cagggaggat tttgagcacg tgaagaacag    1800
cacgtacaca gccctaatca tagctacaga caatggttct ccagttgcta ctgggaacagg    1860
```

```
gacacttctg ctgatcctgt ctgatgtgaa tgacaacgcc cccataccag aacctcgaac   1920
tatattcttc tgtgagagga atccaaagcc tcaggtcata aacatcattg atgcagacct   1980
tcctcccaat acatctccct tcacagcaga actaacacac ggggcgagtg ccaactggac   2040
cattcagtac aacgacccaa cccaagaatc tatcattttg aagccaaaga tggccttaga   2100
ggtgggtgac tacaaaatca atctcaagct catggataac cagaataaag accaagtgac   2160
caccttagag gtcagcgtgt gtgactgtga aggggccgct ggcgtctgta ggaaggcaca   2220
gcctgtcgaa gcaggattgc aaattcctgc cattctgggg attcttggag gaattcttgc   2280
tttgctaatt ctgattctgc tgctcttgct gtttcttcgg aggagagcgg tggtcaaaga   2340
gcccttactg cccccagagg atgacacccg ggacaacgtt tattactatg atgaagaagg   2400
aggcggagaa gaggaccagg actttgactt gagccagctg cacaggggcc tggacgctcg   2460
gcctgaagtg actcgtaacg acgttgcacc aacccctcatg agtgtccccc ggtatcttcc   2520 ccgcccctgcc aatcccgatg aaattggaaa ttttattgat gaaaatctga agcggctga   2580 tactgacccc acagcccgc cttatgattc tctgctcgtg tttgactatg aaggaagcgg   2640
ttccgaagct gctagtctga gctccctgaa ctcctcagag tcagacaaag accaggacta   2700
tgactacttg aacgaatggg gcaatcgctt caagaagctg gctgacatgt acggaggcgg   2760
cgaggacgac taggggactc gagagaggcg ggccccagac ccatgtgctg ggaaatgcag   2820
aaatcacgtt gctggtggtt tttcagctcc cttcccttga tgagtttc tggggaaaaa   2880 aaagagactg gttagtgatg cagttagtat agctttatac tctctccact ttatagctct   2940
aataagtttg tgttagaaaa gtttcgactt atttcttaaa gctttttttt ttttcccatc   3000
actctttaca tggtggtgat gtccaaaaga tacccaaatt ttaatattcc agaagaacaa   3060
ctttagcatc agaaggttca cccagcacct tgcagatttt cttaaggaat tttgtctcac   3120
ttttaaaaag aagggagaa gtcagctact ctagttctgt tgttttgtgt atataatttt   3180
ttaaaaaaaa tttgtgtgct tctgctcatt actacactgg tgtgtccctc tgccttttt   3240 tttttttaa gacagggtct cattctatcg ccaggctgg agtgcagtgg tgcaatcaca   3300
gctcactgca gccttgtcct cccaggctca agctatcctt gcacctcagc ctcccaagta   3360
gctgggacca caggcatgca ccactacgca tgactaattt tttaaatatt tgagacgggg   3420
tctccctgtg ttacccaggc tggtctcaaa ctcctgggct caagtgatcc tcccatcttg   3480
gcctcccaga gtattgggat tacagacatg agccactgca cctgcccagc tccccaactc   3540
cctgccattt tttaagagac agtttcgctc catcgcccag gctgggatg cagtgatgtg   3600 atcatagctc actgtaacct caaactctgg ggctcaagca gttctcccac cagcctcctt   3660 tttattttt tgtacagatg gggtcttgct atgttgccca agctggtctt aaactcctgg   3720
cctcaagcaa tccttctgcc ttggcccccc aaagtgctgg gattgtgggc atgagctgct   3780
gtgcccagcc tccatgtttt aatatcaact ctcactcctg aattcagttg ctttgcccaa   3840
gataggagtt ctctgatgca gaaattattg ggctctttta gggtaagaag tttgtgtctt   3900
tgtctggcca catcttgact aggtattgtc tactctgaag acctttaatg gcttccctct   3960
ttcatctcct gagtatgtaa cttgcaatgg gcagctatcc agtgacttgt tctgagtaag   4020
tgtgttcatt aatgtttatt tagctctgaa gcaagagtga tatactccag gacttagaat   4080
agtgcctaaa gtgctgcagc caaagacaga gcggaactat gaaaagtggg cttgagatg   4140 gcaggagagc ttgtcattga gcctggcaat ttagcaaact gatgctgagg atgattgagg   4200
```

| | |
|---|---:|
| tgggtctacc tcatctctga aaattctgga aggaatggag gagtctcaac atgtgtttct | 4260 |
| gacacaagat ccgtggtttg tactcaaagc ccagaatccc caagtgcctg cttttgatga | 4320 |
| tgtctacaga aaatgctggc tgagctgaac acatttgccc aattccaggt gtgcacagaa | 4380 |
| aaccgagaat attcaaaatt ccaaattttt ttcttaggag caagaagaaa atgtggccct | 4440 |
| aaaggggttt agttgagggg taggggggtag tgaggatctt gatttggatc tcttttttatt | 4500 |
| taaatgtgaa tttcaacttt tgacaatcaa agaaaagact tttgttgaaa tagctttact | 4560 |
| gtttctcaag tgttttggag aaaaaaatca accctgcaat cacttttttgg aattgtcttg | 4620 |
| attttttcggc agttcaagct atatcgaata tagttctgtg tagagaatgt cactgtagtt | 4680 |
| ttgagtgtat acatgtgtgg gtgctgataa ttgtgtattt tctttggggg tggaaaagga | 4740 |
| aaacaattca agctgagaaa agtattctca aagatgcatt tttataaatt ttattaaaca | 4800 |
| attttgttaa accat | 4815 |

```
<210> SEQ ID NO 6
<211> LENGTH: 2122
<212> TYPE: DNA
<213> ORGANISM: Homo sapiens

<400> SEQUENCE: 6
```

| | |
|---|---:|
| ggtggctatt ttgtccttgg gctgcctgtt ttcagctgct gcaaccacag ggatttcttc | 60 |
| tgttcaggcg ccatgtcaga accggctggg gatgtccgtc agaacccatg cggcagcaag | 120 |
| gcctgccgcc gcctcttcgg cccagtggac agcgagcagc tgagccgcga ctgtgatgcg | 180 |
| ctaatggcgg gctgcatcca ggaggcccgt gagcgatgga acttcgactt tgtcaccgag | 240 |
| acaccactgg agggtgactt cgcctgggag cgtgtgcggg ccttggcct gcccaagctc | 300 |
| taccttccca cggggcccg cgaggccgg gatgagttgg gaggaggcag gcggcctggc | 360 |
| acctcacctg ctctgctgca ggggacagca gaggaagacc atgtggacct gtcactgtct | 420 |
| tgtacccttg tgcctcgctc aggggagcag gctgaagggt ccccaggtgg acctggagac | 480 |
| tctcagggtc gaaaacggcg gcagaccagc atgacagatt tctaccactc caaacgccgg | 540 |
| ctgatcttct ccaagaggaa gccctaatcc gcccacagga agcctgcagt cctggaagcg | 600 |
| cgagggcctc aaaggcccgc tctacatctt ctgccttagt ctcagtttgt gtgtcttaat | 660 |
| tattatttgt gttttaattt aaacacctcc tcatgtacat accctggccg cccccctgccc | 720 |
| cccagcctct ggcattagaa ttatttaaac aaaaactagg cggttgaatg agaggttcct | 780 |
| aagagtgctg ggcattttta ttttatgaaa tactatttaa agcctcctca tcccgtgttc | 840 |
| tccttttcct ctctcccgga ggttgggtgg gccggcttca tgccagctac ttcctcctcc | 900 |
| ccacttgtcc gctgggtggt accctctgga ggggtgtggc tccttcccat cgctgtcaca | 960 |
| ggcggttatg aaattcaccc cctttcctgg acactcagac ctgaattctt tttcatttga | 1020 |
| gaagtaaaca gatggcactt tgaagggggcc tcaccgagtg ggggcatcat caaaaacttt | 1080 |
| ggagtcccct cacctcctct aaggttgggc agggtgaccc tgaagtgagc acagcctagg | 1140 |
| gctgagctgg ggacctggta ccctcctggc tcttgatacc ccctctgtc ttgtgaaggc | 1200 |
| agggggaagg tggggtcctg gagcagacca ccccgcctgc cctcatggcc cctctgacct | 1260 |
| gcactgggga gcccgtctca gtgttgagcc ttttccctct ttggctcccc tgtaccttt | 1320 |
| gaggagcccc agctacccctt cttcccagc tgggctctgc aattcccctc tgctgctgtc | 1380 |
| cctcccccttt gtcctttccc ttcagtaccc tctcagctcc aggtggctct gaggtgcctg | 1440 |
| tcccacccccc acccccagct caatggactg gaaggggaag ggacacacaa gaagaagggc | 1500 |

| | |
|---|---|
| accctagttc tacctcaggc agctcaagca gcgaccgccc cctcctctag ctgtggggt | 1560 |
| gagggtccca tgtggtggca caggcccct tgagtgggt tatctctgtg ttaggggtat | 1620 |
| atgatggggg agtagatctt tctaggaggg agacactggc ccctcaaatc gtccagcgac | 1680 |
| cttcctcatc caccccatcc ctccccagtt cattgcactt tgattagcag cggaacaagg | 1740 |
| agtcagacat tttaagatgg tggcagtaga ggctatggac agggcatgcc acgtgggctc | 1800 |
| atatggggct gggagtagtt gtctttcctg cactaacgt tgagccctg gaggcactga | 1860 |
| agtgcttagt gtacttggag tattggggtc tgaccccaaa caccttccag ctcctgtaac | 1920 |
| atactggcct ggactgtttt ctctcggctc cccatgtgtc ctggttcccg tttctccacc | 1980 |
| tagactgtaa acctctcgag ggcagggacc acccctgta ctgttctgtg tctttcacag | 2040 |
| ctcctcccac aatgctgaat atacagcagg tgctcaataa atgattctta gtgactttac | 2100 |
| ttgtaaaaaa aaaaaaaaaa aa | 2122 |

<210> SEQ ID NO 7
<211> LENGTH: 3878
<212> TYPE: DNA
<213> ORGANISM: Homo sapiens

<400> SEQUENCE: 7

| | |
|---|---|
| ggctccccac tctgccagag cgaggcgggg cagtgaggac tccgcgacgc gtccgcaccc | 60 |
| tgcggccaga gcggctttga gctcggctgc gtccgcgcta ggcgcttttt cccagaagca | 120 |
| atccaggcgc gcccgctggt tcttgagcgc caggaaaagc ccggagctaa cgaccggccg | 180 |
| ctcggccact gcacggggcc ccaagccgca aaggacgac gggagggtaa tgaagctgag | 240 |
| cccaggtctc ctaggaagga gagtgcgc cggagcagcg tgggaaagaa gggaagagtg | 300 |
| tcgttaagtt tacggccaac ggtggattat ccgggccgct gcgcgtctgg gggctgcgga | 360 |
| atgcgcgagg agaacaaggg catgcccagt ggggcggca gcgatgaggg tctggccagc | 420 |
| gccgcggcgc ggggactagt ggagaaggtg cgacagctcc tggaagccgg cgcggatccc | 480 |
| aacggagtca accgtttcgg gaggcgcgcg atccaggtca tgatgatggg cagcgcccgc | 540 |
| gtggcggagc tgctgctgct ccacggcgcg gagcccaact cgcagaccc tgccactctc | 600 |
| acccgaccgg tgcatgatgc tgcccgggag ggcttcctgg acacgctggt ggtgctgcac | 660 |
| cgggccgggg cgcggctgga cgtgcgcgat gcctggggtc gtctgcccgt ggacttggcc | 720 |
| gaggagcggg gccaccgcga cgttgcaggg tacctgcgca cagccacggg ggactgacgc | 780 |
| caggttcccc agccgcccac aacgacttta ttttcttacc caatttccca cccccaccca | 840 |
| cctaattcga tgaaggctgc caacggggag cggcggaaag cctgtaagcc tgcaagcctg | 900 |
| tctgagactc acaggaagga ggagccgacc gggaataacc ttccatacat ttttttcttt | 960 |
| gtcttatctg gccctcgaca ctcaccatga agcgaaacac agagaagcgg atttccaggg | 1020 |
| atatttagga gtgtgtgaca ttccaggggt cgtttgcttt tcagggtttt ctgagggaaa | 1080 |
| gtgcatatga aatccttgac tggacctggt ggctacgaat cttccgatgg atgaatctcc | 1140 |
| cactccagcg ctgagtggga gaaggcagtg attagcactt gggtgacggc agtcgatgcg | 1200 |
| ttcactccaa tgtctgctga ggagttatgg tgaacccaca acttaggccc tagcggcaga | 1260 |
| aaggaaaacc tgaagactga ggacaaagtg gaggagggcc gaggtgggct tcagtaagtc | 1320 |
| cccggcggcg ctttagtttg agcgcatggc aagtcacatg cgtaaacgac actctctgga | 1380 |
| agccctggag accctcgccc aactccacca gatagcagag gggtaagaga ggatgtgcaa | 1440 |

```
gcgacgacag atgctaaaat ccctggatca cgacgctgca gagcaccttt gcacaggatg   1500
ctggcctttg ctcttactac actgaggaga gattcccgcg ggttccgcag gcagactaca   1560
caggatgagg tggtggagtg gagtgagagc aattgtaacg gttaactgta acgttttctt   1620
tcacacacac acacacacac acacacacac atgctaggat gcggaaatcc ccttatgact   1680
tgctactttt tgattttgtg atattttgta ctttttagtt gttcagcaac tgtcttattt   1740
aatggggaga ttttaagtaa cataactagt ggctctcagt taaaatgtga ggaagaacta   1800
cagctcttaa atgtagcaat ggcactgttg caaactcagt gcaaacgcct agattgcttt   1860
cttcttaacc tatttatttc tttgttaaat ttttctgatt gtttcccttta tagagtgtct   1920 cagggtgcag aggtcagact aagaaatatt ccaaatgtct tttagaagat agatgcactt   1980
atgcagtaaa ttatcttggg atagttccca aaagattgct gaaaaagtag attgagtata   2040
aaaacttgaa aatatatgat ggctcgtggg atgtcctact atcactgaac aaactaaagg   2100
tgcactgctt tgggatttaa tttccagggt tgcttgatca ttatatcatt ggaacaactg   2160
atacttcact actttaataa agaattaaca gagattgaac tccaagaggt gggtaatttg   2220
gtttaaaaat acatgttcat gggtttacca ctaactcctg agaaatgtta aaggttcaca   2280
ggggttccct tctctcaatg tttgtaataa ttgctcataa gcaataccag caattcataa   2340
aaactgctta cttatgccat agaaaattaa acacaaagtg tatacatgta ttatgcttct   2400
aaatgctcat tctaccagat acacatttaa aagagaaaaa aggaacagaa acaagtcatt   2460
tgagagtgga gacttataag aaggagtaca tttgagttga atacacaaat ctttacttct   2520
ctaccaattc ctattcccaa aatgaacata ttactgggga aagttagttg agaatcagag   2580
catatgttat tggggaaagg atatgtttat tgacacataa tctgtaccag gtatgcatta   2640
aaatatattt gttaatttaa tatttaaacc tgagagatag gtattgtttc ccagatgagg   2700
acaatgaggc aaagaaatat caagtaactt gccaaaggtt acaagatatt cattccatgg   2760
atgcacaaag aagtgcatct agttccacag ctgattatgg ttgtcttgct tttcttccca   2820
ttgcaccagc ttgtcctcca aaatcatgaa tgatacacat gaagataact ttttttaaaa   2880
aaaagcagaa atacacaatg atctcccttg taagctccta aggtggcttt ctttctctca   2940
acttctagta aatataaacg gtttgtttga aaactatttt aaaatgtcaa caatatggag   3000
aataaccccc cccaacacac ctataaaaac ccaaattttt ggaacaaaga taatggaacc   3060
tccattttca aactgaagca cagggacaga aaatatattt ctagttatca cttaagcact   3120
caatcattag aggctacaag aataatattt ttaaagttac agtattttac aattattaga   3180
aaacattcta tataaagaa gtcagttgat actttaaaat ctcccatttg gtttataaaa   3240
tcccttaatt tgacctctat atcttaaatt ccaagatgtt taaatttgct agttgcatta   3300
tactgggtca tgaaaaatta ccccttgaaa tagatatgaa acatgttact tcatttctgg   3360
tttaaataac ttgtggaatc tttcctaatg acaacctgat attaagggaa actaaagaaa   3420
atgttattgt ggatcccaca gtactatatt acactgtttt ttttgtttgt tttgttagtt   3480 tttttattt aaagcaaacc tcaaacatta ttgggtatca attaccacct ggttgtattg   3540
aaatagtaac ttatcaatgc catgtaaaaa ttaattccat tttcgaagcc acctggcaga   3600
caggtttagc tgtttcatca gcagcctaat atatactgtt aaatttgtta aggatttcac   3660
tttgaaggat acatgcaaaa catatagtta ctattttcat gagtcctgct tctagctcca   3720
ttgtggaata cagaaaatta aatatacctg ttaagttcgt atctaaacct aagacattac   3780
caaggtttgt acaaattcta ctacctgaca tttattccaa gaagatctgg aaagttaaat   3840
```

```
aaatttataa atttaataac aaaaaaaaaa aaaaaaaa                             3878

<210> SEQ ID NO 8
<211> LENGTH: 5411
<212> TYPE: DNA
<213> ORGANISM: Homo sapiens

<400> SEQUENCE: 8
gtgtcccata gtgtttccaa acttggaaag ggcgggggag ggcgggagga tgcggagggc       60
ggaggtatgc agacaacgag tcagagtttc cccttgaaag cctcaaaagt gtccacgtcc      120
tcaaaaagaa tggaaccaat ttaagaagcc agccccgtgg ccacgtccct tcccccattc      180
gctccctcct ctgcgccccc gcaggctcct cccagctgtg gctgcccggg ccccagccc       240 cagccctccc attggtggag gcccttttgg aggcacccta gggccaggga aacttttgcc      300
gtataaatag ggcagatccg ggctttatta ttttagcacc acggcagcag gaggtttcgg      360
ctaagttgga ggtactggcc acgactgcat gcccgcgccc gccaggtgat acctccgccg      420
gtgacccagg ggctctgcga cacaaggagt ctgcatgtct aagtgctaga catgctcagc      480
tttgtggata cgcggacttt gttgctgctt gcagtaacct tatgcctagc aacatgccaa      540
tctttacaag aggaaactgt aagaaagggc ccagccggag atagaggacc acgtggagaa      600
aggggtccac caggcccccc aggcagagat ggtgaagatg gtcccacagg ccctcctggt      660
ccacctggtc ctcctggccc cctggtctc ggtgggaact ttgctgctca gtatgatgga      720
aaaggagttg gacttggccc tggaccaatg ggcttaatgg gacctagagg cccacctggt      780
gcagctggag ccccaggccc tcaaggtttc caaggacctg ctggtgagcc tggtgaacct      840
ggtcaaactg gtcctgcagg tgctcgtggt ccagctggcc ctcctggcaa ggctggtgaa      900
gatggtcacc ctggaaaacc cggacgacct ggtgagagag gagttgttgg accacagggt      960
gctcgtggtt tccctggaac tcctggactt cctggcttca aaggcattag gggacacaat     1020
ggtctggatg gattgaaggg acagcccggt gctcctggtt gaagggtga acctggtgcc     1080 cctggtgaaa atggaactcc aggtcaaaca ggagcccgtg ggcttcctgg tgagagagga     1140
cgtgttggtg ccctggcccc agctggtgcc cgtggcagta tggaagtgt gggtcccgtg     1200 ggtcctgctg gtcccattgg gtctgctggc cctccaggct cccaggtgc cctggcccc     1260 aagggtgaaa ttggagctgt tggtaacgct ggtcctgctg gtcccgccgg tcccgtggt     1320 gaagtgggtc ttccaggcct ctccggcccc gttggacctc ctggtaatcc tggagcaaac     1380
ggccttactg gtgccaaggg tgctgctggc cttcccggcg ttgctgggc tcccggcctc     1440 cctggacccc gcggtattcc tggccctgtt ggtgctgccg gtgctactgg tgccagagga     1500
cttgttggtg agcctggtcc agctggctcc aaaggagaga gcgtaacaa gggtgagccc     1560 ggctctgctg ggccccaagg tcctcctggt cccagtggtg aagaaggaaa gagaggccct     1620
aatggggaag ctggatctgc cggccctcca ggacctctg gctgagagg tagtcctggt     1680 tctcgtggtc ttcctggagc tgatggcaga gctggcgtca tgggccctcc tggtagtcgt     1740
ggtgcaagtg gccctgctgg agtccgagga cctaatggag atgctggtcg ccctgggag     1800 cctggtctca tgggacccag aggtcttcct ggttcccctg gaaatatcgg ccccgctgga     1860
aaagaaggtc ctgtcggcct ccctggcatc gacggcaggc ctggcccaat tggcccagct     1920
ggagcaagag gagagcctgg caacattgga ttccctggac ccaaaggccc cactggtgat     1980
cctggcaaaa acggtgataa aggtcatgct ggtcttgctg gtgctcgggg tgctccaggt     2040
```

```
cctgatggaa caatggtgc tcagggacct cctggaccac agggtgttca aggtggaaaa    2100
ggtgaacagg gtcccctgg tcctccaggc ttccagggtc tgcctggccc ctcaggtccc    2160
gctggtgaag ttggcaaacc aggagaaagg ggtctccatg gtgagtttgg tctccctggt    2220
cctgctggtc aagagggga acgcggtccc ccaggtgaga gtggtgctgc cggtcctact    2280
ggtcctattg gaagccgagg tccttctgga cccccagggc ctgatggaaa caagggtgaa    2340
cctggtgtgg ttggtgctgt gggcactgct ggtccatctg gtcctagtgg actcccagga    2400
gagaggggtg ctgctggcat acctggaggc aagggagaaa agggtgaacc tggtctcaga    2460
ggtgaaattg gtaaccctgg cagagatggt gctcgtggtg ctcctggtgc tgtaggtgcc    2520
cctggtcctg ctggagccac aggtgaccgg ggcgaagctg gggctgctgg tcctgctggt    2580
cctgctggtc ctcggggaag ccctggtgaa cgtggtgagg tcggtcctgc tggccccaat    2640
ggatttgctg gtcctgctgg tgctgctggt caacctggtg ctaaaggaga aagaggagcc    2700
aaagggccta agggtgaaaa cggtgttgtt ggtcccacag gcccgttgg agctgctggc    2760 ccagctggtc caaatggtcc ccccggtcct gctggaagtc gtggtgatgg aggccccccct    2820 ggtatgactg gtttccctgg tgctgctgga cggactggtc cccaggacc ctctggtatt    2880 tctggccctc ctggtccccc tggtcctgct gggaagaag gcttcgtgg tcctcgtggt    2940 gaccaaggtc cagttggccg aactggagaa gtaggtgcag ttggtccccc tggcttcgct    3000
ggtgagaagg gtccctctgg agaggctggt actgctggac ctcctggcac tccaggtcct    3060
cagggtcttc ttggtgctcc tggtattctg ggtctccctg gctcgagagg tgaacgtggt    3120
ctaccaggtg ttgctggtgc tgtgggtgaa cctggtcctc ttggcattgc cggccctcct    3180
ggggcccgtg gtcctcctgg tgctgtgggt agtcctggag tcaacggtgc tcctggtgaa    3240
gctggtcgtg atggcaaccc tgggaacgat ggtccccag tcgcgatgg tcaacccgga    3300 cacaagggag agcgcggtta ccctggcaat attggtcccg ttggtgctgc aggtgcacct    3360
ggtcctcatg gccccgtggg tcctgctggc aaacatggaa accgtggtga aactggtcct    3420
tctggtcctg ttggtcctgc tggtgctgtt ggcccaagag gtcctagtgg cccacaaggc    3480
attcgtggcg ataagggaga gccggtgaa aaggggccca gaggtcttcc tggcttaaag    3540
ggacacaatg gattgcaagg tctgcctggt atcgctggtc accatggtga tcaaggtgct    3600
cctggctccg tggtcctgc tggtcctagg ggccctgctg gtccttctgg ccctgctgga    3660
aaagatggtc gcactggaca tcctggtaca gttggacctg ctggcattcg aggccctcag    3720
ggtcaccaag gccctgctgg ccccctggt cccctggcc ctcctggacc tcaggtgta    3780 agcggtggtg gttatgactt tggttacgat ggagacttct acagggctga ccagcctcgc    3840
tcagcacctt ctctcagacc caaggactat gaagttgatg ctactctgaa gtctctcaac    3900
aaccagattg agaccttct tactcctgaa ggctctagaa agaacccagc tcgcacatgc    3960
cgtgacttga gactcagcca cccagagtgg agcagtggtt actactgat tgaccctaac    4020 caaggatgca ctatggatgc tatcaaagta tactgtgatt tctctactgg cgaaacctgt    4080
atccgggccc aacctgaaaa catcccagcc aagaactggt ataggagctc caaggacaag    4140
aaacacgtct ggctaggaga aactatcaat gctggcagcc agtttgaata taatgtagaa    4200
ggagtgactt ccaaggaaat ggctacccaa cttgccttca tgcgcctgct ggccaactat    4260
gcctctcaga acatcaccta ccactgcaag aacagcattg catacatgga tgaggagact    4320
ggcaacctga aaaggctgt cattctacag ggctctaatg atgttgaact tgttgctgag    4380
ggcaacagca ggttcactta cactgttctt gtagatggct gctctaaaaa gacaaatgaa    4440
```

```
tggggaaaga caatcattga atacaaaaca aataagccat cacgcctgcc cttccttgat      4500
attgcacctt tggacatcgg tggtgctgac caggaattct tgtggacat ggcccagtc        4560 tgtttcaaat aaatgaactc aatctaaatt aaaaagaaa gaaatttgaa aaaactttct       4620 cttgtgccatt tcttcttctt cttttttaac tgaaagctga atccttccat ttcttctgca    4680
catctacttg cttaaattgt gggcaaaaga gaaaagaag gattgatcag agcattgtgc       4740
aatacagttt cattaactcc ttcccccgct cccccaaaaa tttgaatttt ttttcaaca      4800 ctcttacacc tgttatggaa aatgtcaacc tttgtaagaa aaccaaaata aaaattgaaa     4860
aataaaaacc ataaacattt gcaccacttg tggcttttga atatcttcca cagagggaag    4920
tttaaaaccc aaacttccaa aggtttaaac tacctcaaaa cactttccca tgagtgtgat    4980
ccacattgtt aggtgctgac ctagacagag atgaactgag gtccttgttt tgttttgttc     5040
ataatacaaa ggtgctaatt aatagtattt cagatacttg aagaatgttg atggtgctag    5100
aagaatttga gaagaaatac tcctgtattg agttgtatcg tgtggtgtat ttttaaaaa      5160 atttgattta gcattcatat tttccatctt attcccaatt aaaagtatgc agattatttg    5220
cccaaatctt cttcagattc agcatttgtt cttttgccagt tcatttttca tcttcttcca   5280
tggttccaca gaagctttgt ttcttgggca agcagaaaaa ttaaattgta cctatttgt      5340 atatgtgaga tgtttaaata aattgtgaaa aaatgaaat aaagcatgtt tggttttcca    5400
aaagaacata t                                                          5411

<210> SEQ ID NO 9
<211> LENGTH: 5490
<212> TYPE: DNA
<213> ORGANISM: Homo sapiens

<400> SEQUENCE: 9
ggctgagttt tatgacgggc ccggtgctga agggcaggga acaacttgat ggtgctactt       60
tgaactgctt ttcttttctc cttttgcac aaagagtctc atgtctgata tttagacatg      120
atgagctttg tgcaaaaggg gagctggcta cttctcgctc tgcttcatcc cactattatt      180
ttggcacaac aggaagctgt tgaaggagga tgttcccatc ttggtcagtc ctatgcggat     240
agagatgtct ggaagccaga accatgccaa atatgtgtct gtgactcagg atccgttctc    300
tgcgatgaca taatatgtga cgatcaagaa ttagactgcc ccaacccaga aattccattt     360
ggagaatgtt gtgcagtttg cccacagcct ccaactgctc ctactcgccc tcctaatggt   420 caaggaccctc aaggccccaa gggagatcca ggccctcctg gtattcctgg gagaaatggt   480
gaccctggta ttccaggaca accagggtcc cctggttctc ctggcccccc tggaatctgt    540
gaatcatgcc ctactggtcc tcagaactat tctccccagt atgattcata tgatgtcaag   600
tctggagtag cagtaggagg actcgcaggc tatcctggac cagctggccc cccaggccct   660
cccggtcccc ctggtacatc tggtcatcct ggttcccctg atctccagg ataccaagga    720 cccccctggtg aacctgggca agctggtcct tcaggccctc caggacctcc tggtgctata   780
ggtccatctg gtcctgctgg aaaagatgga gaatcaggta gacccggacg acctggagag   840
cgaggattgc ctggacctcc aggtatcaaa ggtccagctg gatacctgg attccctggt    900 atgaaaggac acagaggctt cgatggacga aatggagaaa agggtgaaac aggtgctcct    960
ggattaaagg gtgaaaatgg tcttccaggc gaaaatggag ctcctggacc catgggtcca    1020
agaggggctc ctggtgagcg aggacggcca ggacttcctg gggctgcagg tgctcggggt   1080
```

-continued

```
aatgacggtg ctcgaggcag tgatggtcaa ccaggccctc ctggtcctcc tggaactgcc      1140
ggattccctg gatccctgg tgctaagggt gaagttggac ctgcagggtc tcctggttca       1200
aatggtgccc ctggacaaag aggagaacct ggacctcagg acacgctgg tgctcaaggt       1260 cctcctggcc ctcctgggat taatggtagt cctggtggta aaggcgaaat gggtcccgct      1320
ggcattcctg gagctcctgg actgatggga gcccgggtc ctccaggacc agccggtgct       1380
aatggtgctc ctggactgcg aggtggtgca ggtgagcctg gtaagaatgg tgccaaagga     1440
gagcccggac cacgtggtga acgcggtgag gctggtattc caggtgttcc aggagctaaa    1500
ggcgaagatg caaggatgg atcacctgga gaacctggtg caaatgggct tccaggagct     1560
gcaggagaaa ggggtgcccc tgggttccga ggacctgctg gaccaaatgg catcccagga    1620
gaaaagggtc ctgctggaga gcgtggtgct ccaggccctg cagggcccag aggagctgct    1680
ggagaacctg gcagagatgg cgtccctgga ggtccaggaa tgaggggcat gcccggaagt   1740
ccaggaggac caggaagtga tgggaaacca gggcctcccg gaagtcaagg agaaagtggt   1800
cgaccaggtc ctcctgggcc atctggtccc cgaggtcagc ctggtgtcat gggcttcccc   1860
ggtcctaaag gaaatgatgg tgctcctggt aagaatggag aacgaggtgg ccctggagga   1920
cctggccctc agggtcctcc tggaaagaat ggtgaaactg gacctcaggg accccaggg    1980 cctactgggc ctggtggtga caaaggagac acaggacccc ctggtccaca aggattacaa   2040
ggcttgcctg gtacaggtgg tcctccagga gaaaatggaa aacctgggga accaggtcca   2100
aagggtgatg ccggtgcacc tggagctcca ggaggcaagg gtgatgctgg tgcccctggt   2160
gaacgtggac ctcctggatt ggcagggggcc ccaggactta gaggtggagc tggtcccccct 2220 ggtcccgaag gaggaaaggg tgctgctggt cctcctgggc cacctggtgc tgctggtact   2280
cctggtctgc aaggaatgcc tggagaaaga ggaggtcttg gaagtcctgg tccaaagggt   2340
gacaagggtg aaccaggcgg tccaggtgct gatggtgtcc cagggaaaga tggcccaagg    2400
ggtcctactg gtcctattgg tcctcctggc ccagctggcc agcctggaga taagggtgaa    2460
ggtggtgccc ccggacttcc aggtatagct ggacctcgtg gtagccctgg tgagagaggt    2520
gaaactggcc ctccaggacc tgctggttc cctggtgctc ctggacagaa tggtgaacct     2580
ggtggtaaag gagaaagagg ggctccgggt gagaaaggtg aaggaggccc tcctggagtt    2640
gcaggacccc ctgagggttc tggacctgct ggtcctcctg gtcccaagg tgtcaaaggt     2700 gaacgtggca gtcctggtgg acctggtgct gctggcttcc ctggtgctcg tggtcttcct    2760
ggtcctcctg gtagtaatgg taacccagga ccccaggtc ccagcggttc tccaggcaag    2820
gatgggcccc caggtcctgc gggtaacact ggtgctcctg gcagccctgg agtgtctgga    2880
ccaaaaggtg atgctggcca accaggagag aagggatcgc ctggtgccca gggcccacca    2940
ggagctccag gcccacttgg gattgctggg atcactggag cacggggtct tgcaggacca    3000
ccaggcatgc caggtcctag gggaagccct ggccctcagg gtgtcaaggg tgaaagtggg    3060
aaaccaggag ctaacggtct cagtggagaa cgtggtcccc ctggacccca gggtcttcct    3120
ggtctggctg gtacagctgg tgaacctgga agagatggaa accctggatc agatggtctt    3180
ccaggccgga tggatctcc tggtggcaag ggtgatcgtg tgaaaatgg ctctcctggt     3240 gcccctggcg ctcctggtca tccaggccca cctggtcctg tcggtccagc tggaaagagt    3300
ggtgacagag gagaaagtgg ccctgctggc cctgctggtg ctcccggtcc tgctggttcc    3360
cgaggtgctc ctggtcctca aggcccacgt ggtgacaaag gtgaaacagg tgaacgtgga    3420
gctgctggca tcaaaggaca tcgaggattc cctggtaatc caggtgcccc aggttctcca    3480
```

```
ggccctgctg gtcagcaggg tgcaatcggc agtccaggac ctgcaggccc cagaggacct     3540
gttggaccca gtggacctcc tggcaaagat ggaaccagtg acatccagg tcccattgga      3600 ccaccagggc ctcgaggtaa cagaggtgaa agaggatctg agggctcccc aggccaccca     3660
gggcaaccag gccctcctgg acctcctggt gccctggtc cttgctgtgg tggtgttgga      3720
gccgctgcca ttgctgggat tggaggtgaa aaagctggcg ttttgcccc gtattatgga      3780 gatgaaccaa tggatttcaa aatcaacacc gatgagatta tgacttcact caagtctgtt    3840
aatggacaaa tagaaagcct cattagtcct gatggttctc gtaaaaaccc cgctagaaac    3900
tgcagagacc tgaaattctg ccatcctgaa ctcaagagtg gagaatactg ggttgaccct    3960
aaccaaggat gcaaattgga tgctatcaag gtattctgta atatggaaac tggggaaaca    4020
tgcataagtg ccaatccttt gaatgttcca cggaaacact ggtggacaga ttctagtgct    4080
gagaagaaac acgtttggtt tggagagtcc atggatggtg gttttcagtt tagctacggc    4140
aatcctgaac ttcctgaaga tgtccttgat gtgcagctgg cattccttcg acttctctcc    4200
agccgagctt cccagaacat cacatatcac tgcaaaaata gcattgcata catggatcag    4260
gccagtggaa atgtaaagaa ggcccctgaag ctgatggggt caaatgaagg tgaattcaag    4320
gctgaaggaa atagcaaatt cacctacaca gttctggagg atggttgcac gaaacacact    4380
ggggaatgga gcaaaacagt cttttgaatat cgaacacgca aggctgtgag actacctatt   4440
gtagatattg caccctatga cattggtggt cctgatcaag aatttggtgt ggacgttggc    4500
cctgtttgct ttttataaac caaactctat ctgaaatccc aacaaaaaaa atttaactcc    4560
atatgtgttc ctcttgttct aatcttgtca accagtgcaa gtgaccgaca aaattccagt    4620
tatttatttc caaatgtttt ggaaacagta aatttgaca aagaaaaatg atacttctct     4680
ttttttgctg ttccaccaaa tacaattcaa atgcttttg ttttatttt ttaccaattc       4740 caatttcaaa atgtctcaat ggtgctataa taaataaact tcaacactct ttatgataac    4800
aacactgtgt tatattcttt gaatcctagc ccatctgcag agcaatgact gtgctcacca    4860
gtaaaagata acctttcttt ctgaaatagt caaatacgaa attagaaaag ccctccctat    4920
tttaactacc tcaactggtc agaaacacag attgtattct atgagtccca gaagatgaaa    4980
aaaattttat acgttgataa aacttataaa tttcattgat taatctcctg gaagattggt    5040 ttaaaagaa agtgtaatg caagaattta agaaatatt tttaaagcca caattatttt       5100
aatattggat atcaactgct tgtaaaggtg ctcctctttt ttcttgtcat tgctggtcaa    5160
gattactaat atttgggaag ctttaaaga cgcatgttat ggtgctaatg tactttcact     5220
tttaaactct agatcagaat tgttgacttg cattcagaac ataaatgcac aaaatctgta    5280
catgtctccc atcagaaaga ttcattggca tgccacaggg gattctcctc cttcatcctg    5340
taaaggtcaa caataaaaac caaattatgg ggctgctttt gtcacactag catagagaat    5400
gtgttgaaat ttaactttgt aagcttgtat gtggttgttg atcttttttt tccttacaga    5460
cacccataat aaaatatcat attaaaattc                                     5490
```

<210> SEQ ID NO 10
<211> LENGTH: 9169
<212> TYPE: DNA
<213> ORGANISM: Homo sapiens

<400> SEQUENCE: 10

```
gatgacgctg cggcttctgg tggccgcgct ctgcgccggg atcctggcag aggcgccccg      60
```

-continued

```
agtgcgagcc cagcacaggg agagagtgac ctgcacgcgc ctttacgccg ctgacattgt      120
gttcttactg gatggctcct catccattgg ccgcagcaat ttccgcgagg tccgcagctt      180
tctcgaaggg ctggtgctgc ctttctctgg agcagccagt gcacagggtg tgcgctttgc      240
cacagtgcag tacagcgatg acccacggac agagttcggc ctggatgcac ttggctctgg      300
gggtgatgtg atccgcgcca tccgtgagct tagctacaag gggggcaaca ctcgcacagg      360
ggctgcaatt ctccatgtgg ctgaccatgt cttcctgccc cagctggccc gacctggtgt      420
ccccaaggtc tgcatcctga tcacagacgg gaagtcccag gacctggtgg acacagctgc      480
ccaaaggctg aaggggcagg gggtcaagct atttgctgtg gggatcaaga atgctgaccc      540
tgaggagctg aagcgagttg cctcacagcc caccagtgac ttcttcttct tcgtcaatga      600
cttcagcatc ttgaggacac tactgcccct cgtttcccgg agagtgtgca cgactgctgg      660
tggcgtgcct gtgacccgac ctccggatga ctcgacctct gctccacgag acctggtgct      720
gtctgagcca agcagccaat ccttgagagt acagtggaca gcggccagtg gccctgtgac      780
tggctacaag gtccagtaca ctcctctgac ggggctggga cagccactgc cgagtgagcg      840
gcaggaggtg aacgtcccag ctggtgagac cagtgtgcgg ctgcggggtc tccggccact      900
gaccgagtac caagtgactg tgattgccct ctacgccaac agcatcgggg aggctgtgag      960
cgggacagct cggaccactg ccctagaagg gccggaactg accatccaga ataccacagc     1020
ccacagcctc ctggtggcct ggcggagtgt gccaggtgcc actggctacc gtgtgacatg     1080
gcgggtcctc agtggtgggc ccacacagca gcaggagctg ggccctgggc agggttcagt     1140
gttgctgcgt gacttggagc ctggcacgga ctatgaggtg accgtgagca ccctatttgg     1200
ccgcagtgtg gggcccgcca cttccctgat ggctcgcact gacgcttctg ttgagcagac     1260
cctgcgcccg gtcatcctgg gccccacatc catcctcctt tcctggaact tggtgcctga     1320
ggcccgtggc taccggttgg aatggcggcg tgagactggc ttggagccac cgcagaaggt     1380
ggtactgccc tctgatgtga cccgctacca gttggatggg ctgcagccgg gcactgagta     1440
ccgcctcaca ctctacactc tgctggaggg ccacgaggtg gccacccctg caaccgtggt     1500
tcccactgga ccagagctgc ctgtgagccc tgtaacagac ctgcaagcca ccgagctgcc     1560
cgggcagcgg gtgcgagtgt cctggagccc agtccctggt gccacccagt accgcatcat     1620
tgtgcgcagc acccagggg ttgagcggac cctggtgctt cctgggagtc agacagcatt     1680
cgacttggat gacgttcagg ctgggcttag ctacactgtg cgggtgtctg ctcgagtggg     1740
tccccgtgag ggcagtgcca gtgtcctcac tgtccgccgg gagccggaaa ctccacttgc     1800
tgttccaggg ctgcgggttg tggtgtcaga tgcaacgcga gtgagggtgg cctggggacc     1860
cgtccctgga ccagtggat ttcggattag ctggagcaca ggcagtggtc cggagtccag     1920
ccagacactg cccccagact ctactgccac agacatcaca gggctgcagc ctggaaccac     1980
ctaccaggtg gctgtgtcgg tactgcgagg cagagaggag ggccctgctg cagtcatcgt     2040
ggctcgaacg gacccactgg gcccagtgag gacggtccat gtgactcagg ccagcagctc     2100
atctgtcacc attacctgga ccagggttcc tggcgccaca ggatacaggg tttcctggca     2160
ctcagcccac ggcccagaga atcccagtt ggtttctggg gaggccacgg tggctgagct     2220
ggatggactg gagccagata ctgagtatac ggtgcatgtg agggcccatg tggctggcgt     2280
ggatgggccc cctgcctctg tggttgtgag gactgcccct gagcctgtgg gtcgtgtgtc     2340
gaggctgcag atcctcaatg cttccagcga cgttctacgg atcacctggg tagggtcac      2400 tggagccaca gcttacagac tggcctgggg ccggagtgaa ggcggcccca tgaggcacca     2460
```

```
gatactccca ggaaacacag actctgcaga gatccggggt ctcgaaggtg gagtcagcta    2520
ctcagtgcga gtgactgcac ttgtcgggga ccgcgagggc acacctgtct ccattgttgt    2580
cactacgccg cctgaggctc cgccagccct ggggacgctt cacgtggtgc agcgcgggga    2640
gcactcgctg aggctgcgct gggagccggt gcccagagcg cagggcttcc ttctgcactg    2700
gcaacctgag ggtggccagg aacagtcccg ggtcctgggg cccgagctca gcagctatca    2760
cctggacggg ctggagccag cgacacagta ccgcgtgagg ctgagtgtcc tagggccagc    2820
tggagaaggg ccctctgcag aggtgactgc gcgcactgag tcacctcgtg ttccaagcat    2880
tgaactacgt gtggtggaca cctcgatcga ctcggtgact ttggcctgga ctccagtgtc    2940
cagggcatcc agctacatcc tatcctggcg gccactcaga ggccctggcc aggaagtgcc    3000
tgggtccccg cagacacttc cagggatctc aagctcccag cgggtgacag gctagagcc    3060 tggcgtctct tacatcttct ccctgacgcc tgtcctggat ggtgtgcggg gtcctgaggc    3120
atctgtcaca cagacgccag tgtgcccccg tggcctggcg gatgtggtgt tcctaccaca    3180
tgccactcaa gacaatgctc accgtgcgga ggctacgagg agggtcctgg agcgtctggt    3240
gttggcactt gggcctcttg ggccacaggc agttcaggtt ggcctgctgt cttacagtca    3300
tcggccctcc ccactgttcc cactgaatgg ctcccatgac cttggcatta tcttgcaaag    3360
gatccgtgac atgccctaca tggacccaag tgggaacaac ctgggcacag ccgtggtcac    3420
agctcacaga tacatgttgg caccagatgc tcctgggcgc cgccagcacg taccaggggt    3480
gatggttctg ctagtggatg aacccttgag aggtgacata ttcagcccca tccgtgaggc    3540
ccaggcttct gggcttaatg tggtgatgtt gggaatggct ggagcggacc cagagcagct    3600
gcgtcgcttg gcgccgggta tggactctgt ccagaccttc ttcgccgtgg atgatgggcc    3660
aagcctggac caggcagtca gtggtctggc cacagccctg tgtcaggcat ccttcactac    3720 tcagcccccgg ccagagccct gcccagtgta ttgtccaaag ggccagaagg gggaacctgg    3780
agagatgggc ctgagaggac aagttgggcc tcctggcgac cctggcctcc cgggcaggac    3840
cggtgctccc ggcccccagg ggcccctgg aagtgccact gccaagggcg agaggggctt    3900
ccctggagca gatgggcgtc caggcagccc tggccgcgcc gggaatcctg ggaccccgg    3960 agccctggc ctaaagggct ctccagggtt gcctggccct cgtggggacc cgggagagcg    4020
aggacctcga ggcccaaagg gggagccggg ggctcccgga caagtcatcg gaggtgaagg    4080
acctgggctt cctgggcgga aggggaccc tggaccatcg gcccccctg gacctcgtgg    4140 accactgggg gacccaggac cccgtggccc ccaggggctt cctggaacag ccatgaaggg    4200
tgacaaaggc gatcgtgggg agcggggtcc ccctggacca ggtgaaggtg gcattgctcc    4260
tggggagcct gggctgccgg gtcttccgg aagccctgga ccccaaggcc ccgttggccc    4320
ccctggaaag aaaggagaaa aaggtgactc tgaggatgga gctccaggcc tcccaggaca    4380
acctgggtct ccgggtgagc agggcccacg gggacctcct ggagctattg gccccaaagg    4440
tgaccggggc tttccagggc ccctgggtga ggctggagag aagggcgaac gtggaccccc    4500
aggcccagcg ggatcccggg ggctgccagg ggttgctgga cgtcctggag ccaagggtcc    4560
tgaagggcca ccaggaccca ctggccgcca aggagagaag gggagcctg gtcgccctgg    4620 ggaccctgca gtggtgggac ctgctgttgc tggacccaaa ggagaaaagg gagatgtggg    4680
gcccgctggg cccagaggag ctaccggagt ccaaggggaa cggggcccac ccggcttggt    4740
tcttcctgga gaccctggcc ccaagggaga ccctggagac cggggtccca ttggccttac    4800
```

-continued

```
tggcagagca ggacccccag gtgactcagg gcctcctgga gagaagggag accctgggcg      4860
gcctggcccc ccaggacctg ttggcccccg aggacgagat ggtgaagttg gagagaaagg      4920
tgacgagggt cctccggggtg acccgggttt gcctggaaaa gcaggcgagc gtggccttcg     4980
gggggcacct ggagttcggg ggcctgtggg tgaaaaggga gaccaggag  atcctggaga      5040
ggatggacga aatggcagcc ctggatcatc tggacccaag ggtgaccgtg gggagccggg      5100
tcccccagga cccccgggac ggctggtaga cacaggacct ggagccagag agaagggaga      5160
gcctggggac cgcggacaag agggtcctcg agggcccaag ggtgatcctg gcctccctgg      5220
agccctggg  gaaagggggca ttgaagggtt tcggggaccc  ccaggcccac aggggggaccc  5280
aggtgtccga ggcccagcag gagaaaaggg tgaccggggt cccctgggc  tggatggccg     5340
gagcggactg gatgggaaac caggagccgc tgggccctct gggccgaatg gtgctgcagg      5400
caaagctggg gacccaggga gagacgggct tccaggcctc cgtggagaac agggcctccc     5460
tggcccctct ggtcccccctg gattaccggg aaagccaggc gaggatggca aacctggcct    5520
gaatggaaaa aacggagaac ctggggaccc tggagaagac gggaggaagg gagagaaagg     5580
agattcaggc gcctctggga gagaaggtcg tgatggcccc aagggtgagc gtggagctcc     5640
tggtatcctt ggaccccagg ggcctccagg cctcccaggg ccagtgggcc ctcctggcca     5700
gggttttcct ggtgtcccag gaggcacggg ccccaagggt gaccgtgggg agactggatc     5760
caaaggggag cagggcctcc ctggagagcg tggcctgcga ggagagcctg gaagtgtgcc     5820
gaatgtggat cggttgctgg aaactgctgg catcaaggca tctgccctgc gggagatcgt     5880
ggagacctgg gatgagagct ctggtagctt cctgcctgtg cccgaacggc gtcgaggccc     5940
caaggggggac tcaggcgaac agggcccccc aggcaaggag ggccccatcg gctttcctgg    6000
agaacgcggg ctgaagggcg accgtggaga ccctggccct caggggccac ctggtctggc     6060
ccttggggag aggggccccc ccgggccttc cggccttgcc ggggagcctg gaaagcctgg     6120
tattcccggg ctcccaggca gggctggggg tgtgggagag gcaggaaggc caggagagag     6180
gggagaacgg ggagagaaag gagaacgtgg agaacagggc agagatggcc ctcctggact     6240
ccctggaacc cctgggcccc ccggaccccc tggccccaag gtgtctgtgg atgagccagg     6300
tcctggactc tctggagaac agggaccccc tggactcaag ggtgctaagg gggagccggg     6360
cagcaatggt gaccaaggtc ccaaaggaga caggggtgtg ccaggcatca aggagaccg      6420
gggagagcct ggaccgaggg gtcaggacgg caacccgggt ctaccaggag agcgtggtat     6480
ggctgggcct gaagggaagc cgggtctgca ggtccaaga  ggccccctg gcccagtggg     6540
tggtcatgga gaccctggac cacctggtgc cccgggtctt gctggccctg caggacccca     6600
aggaccttct ggcctgaagg gggagcctgg agagacagga cctccaggac ggggcctgac     6660
tggacctact ggagctgtgg gacttcctgg acccccggc  ccttcaggcc ttgtgggtcc     6720
acagggggtct ccaggtttgc ctggacaagt gggggagaca gggaagccgg gagccccagg     6780
tcgagatggt gccagtggaa agatggaga  cagagggagc cctggtgtgc cagggtcacc     6840
aggtctgcct ggcccctgtcg gacctaaagg agaacctggc cccacgggggg cccctggaca  6900
ggctgtggtc gggctccctg gagcaaaggg agagaaggga gccctggag  gccttgctgg     6960
agacctggtg ggtgagccgg gagccaaagg tgaccgagga ctgccagggc cgcgaggcga     7020
gaagggtgaa gctggccgtg cagggggagcc cggagaccct ggggaagatg gtcagaaagg     7080
ggctccagga cccaaaggtt tcaagggtga cccaggagtc ggggtcccgg gctcccctgg     7140
gcctcctggc cctccaggtg tgaagggaga tctgggcctc cctggcctgc ccggtgctcc     7200
```

-continued

```
tggtgttgtt gggttcccgg gtcagacagg ccctcgagga gagatgggtc agccaggccc    7260
tagtggagag cggggtctgg caggcccccc agggagagaa ggaatcccag accccctggg    7320
gccacctgga ccaccggggt cagtgggacc acctggggcc tctggactca aaggagacaa    7380
gggagaccct ggagtagggc tgcctgggcc ccgaggcgag cgtggggagc caggcatccg    7440
gggtgaagat ggccgccccg gccaggaggg accccgagga ctcacggggc ccctggcag     7500 caggggagag cgtggggaga agggtgatgt tgggagtgca ggactaaagg gtgacaaggg    7560
agactcagct gtgatcctgg ggcctccagg cccacggggt gccaaggggg acatgggtga    7620
acgagggcct cggggcttgg atggtgacaa aggacctcgg ggagacaatg ggaccctgg     7680 tgacaagggc agcaagggag agcctggtga caagggctca gccgggttgc caggactgcg    7740
tggactcctg gaccccagg gtcaacctgg tgcagcaggg atccctggtg acccgggatc     7800
cccaggaaag gatggagtgc ctggtatccg aggagaaaaa ggagatgttg gcttcatggg    7860 tccccgggc ctcaagggtg aacgggagt gaagggagcc tgtggccttg atggagagaa      7920
gggagacaag ggagaagctg gtcccccagg ccgccccggg ctggcaggac acaaaggaga    7980 gatggggag cctggtgtgc cgggccagtc gggggcccct ggcaaggagg gcctgatcgg     8040
tcccaagggt gaccgaggct ttgacgggca gccaggcccc aagggtgacc agggcgagaa    8100
aggggagcgg ggaacccag gaattggggg cttcccaggc cccagtggaa atgatggctc     8160
tgctggtccc ccaggccac ctggcagtgt tggtcccaga ggccccgaag gacttcaggg     8220
ccagaagggt gagcgaggtc ccccggaga gagagtggtg ggggctcctg gggtccctgg     8280
agctcctggc gagagagggg agcaggggcg gccagggcct gccggtcctc gaggcgagaa    8340
gggagaagct gcactgacgg aggatgacat ccggggcttt gtgcgccaag agatgagtca    8400
gcactgtgcc tgccagggcc agttcatcgc atctggatca cgacccctcc ctagttatgc    8460
tgcagacact gccggctccc agctccatgc tgtgcctgtg ctccgcgtct ctcatgcaga    8520
ggaggaagag cgggtacccc ctgaggatga tgagtactct gaatactccg agtattctgt    8580
ggaggagtac caggaccctg aagctccttg ggatagtgat gacccctgtt ccctgccact    8640
ggatgagggc tcctgcactg cctacaccct gcgctgtac catcgggctg tgacaggcag    8700
cacagaggcc tgtcaccctt ttgtctatgg tggctgtgga gggaatgcca accgttttgg    8760
gacccgtgag gcctgcgagc gccgctgccc acccccgggtg gtccagagcc aggggacagg    8820
tactgcccag gactgaggcc cagataatga gctgagattc agcatccctt ggaggagtcg    8880
gggtctcagc agaaccccac tgtccctccc cttggtgcta gaggcttgtg tgcacgtgag    8940
cgtgcgtgtg cacgtccgtt atttcagtga cttggtcccg tgggtctagc cttccccct    9000 gtggacaaac cccattgtg gctcctgcca ccctggcaga tgactcactg tggggggtg     9060 gctgtgggca gtgagcggat gtgactggcg tctgacccgc ccttgaccc aagcctgtga    9120 tgacatggtg ctgattctgg ggggcattaa agctgctgtt ttaaaaggc                9169
```

<210> SEQ ID NO 11
<211> LENGTH: 2358
<212> TYPE: DNA
<213> ORGANISM: Homo sapiens

<400> SEQUENCE: 11

```
aaactcacac aacaactctt ccccgctgag aggagacagc cagtgcgact ccaccctcca      60
gctcgacgga agccgccccg ccgacagcc ccgagacgac agcccggcgc gtcccggtcc       120
```

```
ccacctccga ccaccgccag cgctccaggc cccgccgctc cccgctcgcc gccaccgcgc    180
cctccgctcc gcccgcagtg ccaaccatga ccgccgccag tatgggcccc gtccgcgtcg    240
ccttcgtggt cctcctcgcc ctctgcagcc ggccggccgt cggccagaac tgcagcgggc    300
cgtgccggtg cccggacgag ccggcgccgc gctgccggc gggcgtgagc ctcgtgctgg    360
acggctgcgg ctgctgccgc gtctgcgcca agcagctggg cgagctgtgc accgagcgcg    420
acccctgcga cccgcacaag ggcctcttct gtgacttcgg ctccccggcc aaccgcaaga    480
tcggcgtgtg caccgccaaa gatggtgctc cctgcatctt cggtggtacg gtgtaccgca    540
gcggagagtc cttccagagc agctgcaagt accagtgcac gtgcctggac ggggcggtgg    600
gctgcatgcc cctgtgcagc atggacgttc gtctgcccag ccctgactgc cccttcccga    660
ggagggtcaa gctgcccggg aaatgctgcg aggagtgggt gtgtgacgag cccaaggacc    720
aaaccgtggt tgggcctgcc ctcgcggctt accgactgga agacacgttt ggcccagacc    780
caactatgat tagagccaac tgcctggtcc agaccacaga gtggagcgcc tgttccaaga    840
cctgtgggat gggcatctcc acccgggtta ccaatgacaa cgcctcctgc aggctagaga    900
agcagagccg cctgtgcatg gtcaggcctt gcgaagctga cctggaagag aacattaaga    960
agggcaaaaa gtgcatccgt actcccaaaa tctccaagcc tatcaagttt gagctttctg   1020
gctgcaccag catgaagaca taccgagcta aattctgtgg agtatgtacc gacggccgat   1080
gctgcacccc ccacagaacc accacccgc cggtggagtt caagtgccct gacggcgagg   1140
tcatgaagaa gaacatgatg ttcatcaaga cctgtgcctg ccattacaac tgtcccggag   1200
acaatgacat ctttgaatcg ctgtactaca ggaagatgta cggagacatg gcatgaagcc   1260
agagagtgag agacattaac tcattagact ggaacttgaa ctgattcaca tctcattttt   1320
ccgtaaaaat gatttcagta gcacaagtta tttaaatctg tttttctaac tgggggaaaa   1380
gattcccacc caattcaaaa cattgtgcca tgtcaaacaa atagtctatc aaccccagac   1440
actggtttga agaatgttaa gacttgacag tggaactaca ttagtacaca gcaccagaat   1500
gtatattaag gtgtggcttt aggagcagtg ggagggtacc agcagaaagg ttagtatcat   1560
cagatagcat cttatacgag taatatgcct gctatttgaa gtgtaattga gaggaaaat   1620 tttagcgtgc tcactgacct gcctgtagcc ccagtgacag ctaggatgtg cattctccag   1680
ccatcaagag actgagtcaa gttgttcctt aagtcagaac agcagactca gctctgacat   1740
tctgattcga atgacactgt tcaggaatcg gaatcctgtc gattagactg gacagcttgt   1800
ggcaagtgaa tttgcctgta acaagccaga tttttaaaa tttatattgt aaatattgtg   1860
tgtgtgtgtg tgtgtgtata tatatatata tgtacagtta tctaagttaa tttaaagttg   1920
tttgtgcctt tttatttttg tttttaatgc tttgatattt caatgttagc ctcaatttct   1980
gaacaccata ggtagaatgt aaagcttgtc tgatcgttca aagcatgaaa tggatactta   2040
tatggaaatt ctgctcagat agaatgacag tccgtcaaaa cagattgttt gcaaggggga   2100
ggcatcagtg tccttggcag gctgatttct aggtaggaaa tgtggtagcc tcactttaa   2160 tgaacaaatg gcctttatta aaaactgagt gactctatat agctgatcag ttttttcacc   2220
tggaagcatt tgtttctact ttgatatgac tgttttcgg acagtttatt tgttgagagt   2280
gtgaccaaaa gttacatgtt tgcacctttc tagttgaaaa taaagtgtat atttttcta    2340 taaaaaaaaa aaaaaaaa                                                 2358
```

<210> SEQ ID NO 12
<211> LENGTH: 3256

<212> TYPE: DNA
<213> ORGANISM: Homo sapiens

<400> SEQUENCE: 12

| | | | | | |
|---|---|---|---|---|---|
| aggatacagc | ggcttctgcg | cgacttataa | gagctccttg | tgcggcgcca | ttttaagcct | 60 |
| ctcggtctgt | ggcagcagcg | ttggcccggc | cccgggagcg | gagagcgagg | ggaggcggag | 120 |
| acggaggaag | gtctgaggag | cagcttcagt | ccccgccgag | ccgccaccgc | aggtcgagga | 180 |
| cggtcggact | cccgcggcgg | gaggagcctg | ttccctgag | ggtatttgaa | gtataccata | 240 |
| caactgtttt | gaaaatccag | cgtggacaat | ggctactcaa | gctgatttga | tggagttgga | 300 |
| catggccatg | gaaccagaca | gaaaagcggc | tgttagtcac | tggcagcaac | agtcttacct | 360 |
| ggactctgga | atccattctg | gtgccactac | cacagctcct | tctctgagtg | gtaaaggcaa | 420 |
| tcctgaggaa | gaggatgtgg | atacctccca | agtcctgtat | gagtgggaac | agggatttc | 480 |
| tcagtccttc | actcaagaac | aagtagctga | tattgatgga | cagtatgcaa | tgactcgagc | 540 |
| tcagagggta | cgagctgcta | tgttccctga | gacattagat | gagggcatgc | agatcccatc | 600 |
| tacacagttt | gatgctgctc | atcccactaa | tgtccagcgt | ttggctgaac | catcacagat | 660 |
| gctgaaacat | gcagttgtaa | acttgattaa | ctatcaagat | gatgcagaac | ttgccacacg | 720 |
| tgcaatccct | gaactgacaa | aactgctaaa | tgacgaggac | caggtggtgg | ttaataaggc | 780 |
| tgcagttatg | gtccatcagc | tttctaaaaa | ggaagcttcc | agacacgcta | tcatgcgttc | 840 |
| tcctcagatg | gtgtctgcta | ttgtacgtac | catgcagaat | acaaatgatg | tagaaacagc | 900 |
| tcgttgtacc | gctgggacct | tgcataacct | ttcccatcat | cgtgagggct | tactggccat | 960 |
| ctttaagtct | ggaggcattc | ctgccctggt | gaaaatgctt | ggttcaccag | tggattctgt | 1020 |
| gttgttttat | gccattacaa | ctctccacaa | cctttatta | catcaagaag | gagctaaaat | 1080 |
| ggcagtgcgt | ttagctggtg | ggctgcagaa | aatggttgcc | ttgctcaaca | aaacaaatgt | 1140 |
| taaattcttg | gctattacga | cagactgcct | tcaaattta | gcttatggca | accaagaaag | 1200 |
| caagctcatc | atactggcta | gtggtggacc | ccaagcttta | gtaaatataa | tgaggaccta | 1260 |
| tacttacgaa | aaactactgt | ggaccacaag | cagagtgctg | aaggtgctat | ctgtctgctc | 1320 |
| tagtaataag | ccggctattg | tagaagctgg | tggaatgcaa | gctttaggac | ttcacctgac | 1380 |
| agatccaagt | caacgtcttg | ttcagaactg | tctttggact | ctcaggaatc | tttcagatgc | 1440 |
| tgcaactaaa | caggaaggga | tggaaggtct | ccttgggact | cttgttcagc | ttctgggttc | 1500 |
| agatgatata | aatgtggtca | cctgtgcagc | tggaattctt | tctaacctca | cttgcaataa | 1560 |
| ttataagaac | aagatgatgg | tctgccaagt | gggtggtata | gaggctcttg | tgcgtactgt | 1620 |
| ccttcgggct | ggtgacaggg | aagacatcac | tgagcctgcc | atctgtgctc | ttcgtcatct | 1680 |
| gaccagccga | caccaagaag | cagagatggc | ccagaatgca | gttcgccttc | actatggact | 1740 |
| accagttgtg | gttaagctct | tacacccacc | atcccactgg | cctctgataa | aggctactgt | 1800 |
| tggattgatt | cgaaatcttg | ccctttgtcc | cgcaaatcat | gcacctttgc | gtgagcaggg | 1860 |
| tgccattcca | cgactagttc | agttgcttgt | tcgtgcacat | caggataccc | agcgccgtac | 1920 |
| gtccatgggt | gggacacagc | agcaatttgt | ggaggggtc | cgcatggaag | aaatagttga | 1980 |
| aggttgtacc | ggagcccttc | acatcctagc | tcgggatgtt | cacaaccgaa | ttgttatcag | 2040 |
| aggactaaat | accattccat | tgtttgtgca | gctgctttat | tctcccattg | aaaacatcca | 2100 |
| aagagtagct | gcaggggtcc | tctgtgaact | tgctcaggac | aaggaagctg | cagaagctat | 2160 |
| tgaagctgag | ggagccacag | ctcctctgac | agagttactt | cactctagga | atgaaggtgt | 2220 |

```
ggcgacatat gcagctgctg ttttgttccg aatgtctgag gacaagccac aagattacaa    2280
gaaacggctt tcagttgagc tgaccagctc tctcttcaga acagagccaa tggcttggaa    2340
tgagactgct gatcttggac ttgatattgg tgcccaggga gaaccccttg gatatcgcca    2400
ggatgatcct agctatcgtt cttttcactc tggtggatat ggccaggatg ccttgggtat    2460
ggaccccatg atggaacatg agatgggtgg ccaccaccct ggtgctgact atccagttga    2520
tgggctgcca gatctggggc atgcccagga cctcatggat gggctgcctc caggtgacag    2580
caatcagctg gcctggtttg atactgacct gtaaatcatc ctttaggagt aacaatacaa    2640
atggattttg ggagtgactc aagaagtgaa gaatgcacaa gaatggatca caagatggaa    2700
tttatcaaac cctagccttg cttgttaaat tttttttttt tttttttttaa gaatatctgt    2760 aatggtactg actttgcttg ctttgaagta gctctttttt tttttttttt ttttttttg     2820 cagtaactgt tttttaagtc tctcgtagtg ttaagttata gtgaatactg ctacagcaat    2880
ttctaatttt taagaattga gtaatggtgt agaacactaa ttcataatca ctctaattaa    2940
ttgtaatctg aataaagtgt aacaattgtg tagccttttt gtataaaata gacaaataga    3000
aaatggtcca attagtttcc ttttttaatat gcttaaaata agcaggtgga tctatttcat   3060
gtttttgatc aaaaactatt tgggatatgt atgggtaggg taaatcagta agaggtgtta    3120
tttggaacct tgttttggac agtttaccag ttgccttttta tcccaaagtt gttgtaacct   3180
gctgtgatac gatgcttcaa gagaaaatgc ggttataaaa aatggttcag aattaaactt    3240
ttaattcatt cgattg                                                    3256

<210> SEQ ID NO 13
<211> LENGTH: 1424
<212> TYPE: DNA
<213> ORGANISM: Homo sapiens

<400> SEQUENCE: 13
agcagtcagc cggccggaga cagagacttc acgactccca gtctcctcct cgccgcggcc      60
gccgcctcct ccttctctcc tcctcctctt cctcctcctc cctcgctccc acagccatgt     120
ctgcttagac cagagcagcc ccacagccaa ctagggcagc tgccgccgcc acaacagcaa     180
ggacagccgc tgccgccgcc cgtgagcgat gacaggagtg tttgacagaa gggtccccag     240
catccgatcc ggcgacttcc aagctccgtt ccagacgtcc gcagctatgc accatccgtc     300
tcaggaatcg ccaactttgc ccgagtcttc agctaccgat tctgactact acagccctac     360 gggggagcc ccgcacggct actgctctcc tacctcggct tcctatggca agctctcaa       420 cccctaccag tatcagtatc acggcgtgaa cggctccgcc gggagctacc cagccaaagc     480
ttatgccgac tatagctacg ctagctccta ccaccagtac ggcggcgcct acaaccgcgt     540
cccaagcgcc accaaccagc cagagaaaga agtgaccgag cccgaggtga aatggtgaa      600 tgcaaaccaa agaaagttc gtaaaccag gactatttat ccagctttc agctggccgc       660 attacagaga aggtttcaga agactcagta cctcgccttg ccggaacgcg ccgagctggc     720
cgcctcgctg ggattgacac aaacacaggt gaaaatctgg tttcagaaca aagatccaa     780 gatcaagaag atcatgaaaa acggggagat gccccggag cacagtccca gctccagcga    840
cccaatggcg tgtaactcgc cgcagtctcc agcggtgtgg agccccagg gctcgtcccg    900 ctcgctcagc caccaccctc atgcccaccc tccgacctcc aaccagtccc cagcgtccag   960
ctacctggag aactctgcat cctggtacac aagtgcagcc agctcaatca attcccacct  1020
gccgccgccg ggctccttac agcacccgct ggcgctggcc tccgggacac tctattagat  1080
```

```
gggctgctct ctcttactct cttttttggg actactgtgt tttgctgttc tagaaaatca    1140
taaagaaagg aattcatatg gggaagttcg gaaaactgaa aaagattcat gtgtaaagct    1200 ttttttttgca tgtaagttat tgcatttcaa agacccccc cttttttttac agaggacttt   1260 ttttgcgcaa ctgtgacac tttcaatggt gccttgaaat ctatgacctc aacttttcaa    1320
aagacttttt tcaatgttat tttagccatg taaataagtg tagatagagg aattaaactg   1380
tatattctgg ataaataaaa ttatttcgac catgaaaagc ggaa                    1424

<210> SEQ ID NO 14
<211> LENGTH: 2109
<212> TYPE: DNA
<213> ORGANISM: Homo sapiens

<400> SEQUENCE: 14
ggagctgttt acccccactc taataggggt tcaatataaa aagccggcag agagctgtcc    60
aagtcagacg cgcctctgca tctgcgccag gcgaacgggt cctgcgcctc ctgcagtccc    120
agctctccac cgccgcgtgc gcctgcagac gctccgctcg ctgccttctc tcctggcagg    180
cgctgccttt tctccccgtt aaagggcac ttgggctgaa ggatcgcttt gagatctgag     240
gaacccgcag cgctttgagg gacctgaagc tgttttttctt cgttttcctt tgggttcagt   300
ttgaacggga ggttttttgat ccctttttttt cagaatggat tatttgctca tgattttctc   360
tctgctgttt gtggcttgcc aaggagctcc agaaacagtc ttaggcgctg agctcagcgc    420
ggtgggtgag aacggcgggg agaaacccac tcccagtcca ccctggcggc tccgccggtc    480
caagcgctgc tcctgctcgt ccctgatgga taaagagtgt gtctacttct gccacctgga    540
catcatttgg gtcaacactc ccgagcacgt tgttccgtat ggacttggaa gccctaggtc    600
caagagagcc ttggagaatt tacttcccac aaaggcaaca gaccgtgaaa atagatgcca    660
atgtgctagc caaaaagaca agaagtgctg gaattttttgc caagcaggaa aagaactcag   720
ggctgaagac attatggaga aagactggaa taatcataag aaaggaaaag actgttccaa    780
gcttgggaaa aagtgtatttt atcagcagtt agtgagagga agaaaaatca gaagaagttc    840
agaggaacac ctaagacaaa ccaggtcgga gaccatgaga aacagcgtca aatcatcttt    900
tcatgatccc aagctgaaag gcaagccctc cagagagcgt tatgtgaccc acaaccgagc    960
acattggtga cagaccttcg gggcctgtct gaagccatag cctccacgga gagccctgtg   1020
gccgactctg cactctccac cctggctggg atcagagcag gagcatcctc tgctggttcc    1080
tgactggcaa aggaccagcg tcctcgttca aacattcca agaaaggtta aggagttccc    1140
ccaaccatct tcactggctt ccatcagtgg taactgcttt ggtctcttct ttcatctggg    1200
gatgacaatg gacctctcag cagaaacaca cagtcacatt cgaattcggg tggcatcctc    1260
cggagagaga gagaggaagg agattccaca caggggtgga gtttctgacg aaggtcctaa    1320
gggagtgttt gtgtctgact caggcgcctg gcacatttca gggagaaact ccaaagtcca    1380
cacaaagatt ttctaaggaa tgcacaaatt gaaaacacac tcaaaagaca aacatgcaag    1440
taaagaaaaa aaaagaaag acttttgttt aaatttgtaa aatgcaaaac tgaatgaaac     1500
tgttactacc ataatcagg atatgtttca tgaatatgag tctacctcac ctatattgca    1560
ctctggcaga agtatttccc acatttaatt attgcctccc caaactcttc ccaccctgc    1620 tgcccctcc tccatccccc atactaaatc ctagcctcgt agaagtctgg tctaatgtgt    1680
cagcagtaga tataatattt tcatggtaat ctactagctc tgatccataa gaaaaaaaag   1740
```

```
atcattaaat caggagattc cctgtccttg attttttggag acacaatggt atagggttgt    1800
ttatgaaata tattgaaaag taagtgtttg ttacgcttta aagcagtaaa attattttcc    1860
tttatataac cggctaatga agaggttgg attgaatttt gatgtactta ttttttata      1920 gatatttata ttcaaacaat ttattcctta tatttaccat gttaaatatc tgtttgggca    1980
ggccatattg gtctatgtat ttttaaaata tgtatttcta aatgaaattg agaacatgct    2040
ttgttttgcc tgtcaaggta atgactttag aaaataaata ttttttttcct tactgtaaaa   2100 aaaaaaaaa                                                            2109

<210> SEQ ID NO 15
<211> LENGTH: 8272
<212> TYPE: DNA
<213> ORGANISM: Homo sapiens

<400> SEQUENCE: 15
gcccgcgccg gctgtgctgc acaggggag gagagggaac cccaggcgcg agcgggaaga       60
ggggacctgc agccacaact tctctggtcc tctgcatccc ttctgtccct ccacccgtcc    120
ccttccccac cctctggccc ccaccttctt ggaggcgaca accccgggga ggcattagaa    180 gggattttc ccgcaggttg cgaagggaag caaacttggt ggcaacttgc ctcccggtgc     240
gggcgtctct cccccaccgt ctcaacatgc ttaggggtcc ggggcccggg ctgctgctgc    300
tggccgtcca gtgcctgggg acagcggtgc cctccacggg agcctcgaag agcaagaggc    360
aggctcagca aatggttcag ccccagtccc cggtggctgt cagtcaaagc aagcccggtt    420
gttatgacaa tggaaaacac tatcagataa atcaacagtg ggagcggacc tacctaggca    480
atgcgttggt ttgtacttgt tatggaggaa gccgaggttt taactgcgag agtaaacctg    540
aagctgaaga gacttgcttt gacaagtaca ctgggaacac ttaccgagtg ggtgacactt    600
atgagcgtcc taaagactcc atgatctggg actgtacctg catcgggcct gggcgaggga    660
gaataagctg taccatcgca aaccgctgcc atgaagggg tcagtcctac aagattggtg    720
acacctggag gagaccacat gagactggtg gttacatgtt agagtgtgtg tgtcttggta    780
atggaaaagg agaatggacc tgcaagccca tagctgagaa gtgttttgat catgctgctg    840
ggacttccta tgtggtcgga gaaacgtggg agaagcccta ccaaggctgg atgatggtag    900
attgtacttg cctgggagaa ggcagcggac gcatcacttg cacttctaga aatagatgca    960
acgatcagga cacaaggaca tcctatagaa ttggagacac ctggagcaag aaggataatc   1020
gaggaaacct gctccagtgc atctgcacag gcaacggccg aggagagtgg aagtgtgaga   1080
ggcacacctc tgtgcagacc acatcgagcg atctggccc cttcaccgat gttcgtgcag    1140
ctgtttacca accgcagcct caccccccagc ctcctcccta tggccactgt gtcacagaca   1200
gtggtgtggt ctactctgtg gggatgcagt ggctgaagac acaaggaaat aagcaaatgc    1260
tttgcacgtg cctgggcaac ggagtcagct gccaagagac agctgtaacc cagacttacg    1320
gtggcaactc aaatgggaga ccatgtgtct taccattcac ctacaatggc aggacgttct    1380
actcctgcac cacagaaggg cgacaggacg acatctttg gtgcagcaca acttcgaatt    1440
atgagcagga ccagaaatac tcttttctgca cagaccacac tgttttggtt cagactcgag    1500
gaggaaattc caatggtgcc ttgtgccact tccccttcct atacaacaac cacaattaca   1560
ctgattgcac ttctgagggc agaagagaca acatgaagtg gtgtgggacc acacagaact    1620
atgatgccga ccagaagttt gggttctgcc ccatggctgc ccacgaggaa atctgcacaa    1680
ccaatgaagg ggtcatgtac cgcattggag atcagtggga taagcagcat gacatgggtc    1740
```

```
acatgatgag gtgcacgtgt gttgggaatg gtcgtgggga atggacatgc attgcctact    1800
cgcagcttcg agatcagtgc attgttgatg acatcactta caatgtgaac gacacattcc    1860
acaagcgtca tgaagagggg cacatgctga actgtacatg cttcggtcag ggtcggggca    1920
ggtggaagtg tgatcccgtc gaccaatgcc aggattcaga gactgggacg ttttatcaaa    1980
ttggagattc atgggagaag tatgtgcatg gtgtcagata ccagtgctac tgctatggcc    2040
gtggcattgg ggagtggcat tgccaacctt tacagaccta tccaagctca agtggtcctg    2100
tcgaagtatt tatcactgag actccgagtc agcccaactc ccaccccatc cagtggaatg    2160
caccacagcc atctcacatt tccaagtaca ttctcaggtg gagacctaaa aattctgtag    2220
gccgttggaa ggaagctacc ataccaggcc acttaaactc ctacaccatc aaaggcctga    2280
agcctggtgt ggtatacgag ggccagctca tcagcatcca gcagtacggc caccaagaag    2340
tgactcgctt tgacttcacc accaccagca ccagcacacc tgtgaccagc aacaccgtga    2400
caggagagac gactcccttt tctcctcttg tggccacttc tgaatctgtg accgaaatca    2460
cagccagtag ctttgtggtc tcctgggtct cagcttccga caccgtgtcg ggattccggg    2520
tggaatatga gctgagtgag gagggagatg agccacagta cctggatctt ccaagcacag    2580
ccacttctgt gaacatccct gacctgcttc ctggccgaaa atacattgta aatgtctatc    2640
agatatctga ggatggggag cagagtttga tcctgtctac ttcacaaaca acagcgcctg    2700
atgcccctcc tgacccgact gtggaccaag ttgatgacac ctcaattgtt gttcgctgga    2760
gcagacccca ggctcccatc acagggtaca gaatagtcta ttcgccatca gtagaaggta    2820
gcagcacaga actcaacctt cctgaaactg caaactccgt caccctcagt gacttgcaac    2880
ctggtgttca gtataacatc actatctatg ctgtggaaga aaatcaagaa agtacacctg    2940
ttgtcattca acaagaaacc actggcaccc cacgctcaga tacagtgccc tctcccaggg    3000
acctgcagtt tgtggaagtg acagacgtga aggtcaccat catgtggaca ccgcctgaga    3060
gtgcagtgac cggctaccgt gtggatgtga tccccgtcaa cctgcctggc gagcacgggc    3120
agaggctgcc catcagcagg aacacctttg cagaagtcac cggcctgtcc cctgggatca    3180
cctattactt caaagtcttt gcagtgagcc atggagggga gagcaagcct ctgactgctc    3240
aacagacaac caaactggat gctcccacta acctccagtt tgtcaatgaa actgattcta    3300
ctgtcctggt gagatggact ccacctcggg cccagataac aggataccga ctgaccgtgg    3360
gccttacccg aagaggacag cccaggcagt acaatgtggg tccctctgtc tccaagtacc    3420
cactgaggaa tctgcagcct gcatctgagt acaccgtatc cctcgtggcc ataaagggca    3480
accaagagag ccccaaagcc actggagtct ttaccacact gcagcctggg agctctattc    3540
caccttacaa caccgaggtg actgagacca ccattgtgat cacatggacg cctgctccaa    3600
gaattggttt taagctgggt gtacgaccaa gccagggagg agaggcacca cgagaagtga    3660
cttcagactc aggaagcatc gttgtgtccg gcttgactcc aggagtagaa tacgtctaca    3720
ccatccaagt cctgagagat ggacaggaaa gagatgcgcc aattgtaaac aaagtggtga    3780
caccattgtc tccaccaaca aacttgcatc tggaggcaaa ccctgacact ggagtgctca    3840
cagtctcctg ggagaggagc accaccccag acattactgg ttatagaatt accacaaccc    3900
ctacaaacgg ccagcaggga aattctttgg aagaagtggt ccatgctgat cagagctcct    3960 gcactttga taacctgagt cccggcctgg agtacaatgt cagtgtttac actgtcaagg    4020
atgacaagga aagtgtccct atctctgata ccatcatccc agctgttcct cctcccactg    4080
```

```
acctgcgatt caccaacatt ggtccagaca ccatgcgtgt cacctgggct ccaccccat    4140 ccattgattt aaccaacttc ctggtgcgtt actcacctgt gaaaaatgag gaagatgttg   4200
cagagttgtc aatttctcct tcagacaatg cagtggtctt aacaaatctc ctgcctggta   4260
cagaatatgt agtgagtgtc tccagtgtct acgaacaaca tgagagcaca cctcttagag   4320
gaagacagaa aacaggtctt gattccccaa ctggcattga cttttctgat attactgcca   4380
actcttttac tgtgcactgg attgctcctc gagccaccat cactggctac aggatccgcc   4440
atcatcccga gcacttcagt gggagacctc gagaagatcg ggtgccccac tctcggaatt   4500
ccatcaccct caccaacctc actccaggca cagagtatgt ggtcagcatc gttgctctta   4560
atggcagaga ggaaagtccc ttattgattg ccaacaatc aacagtttct gatgttccga    4620
gggacctgga agttgttgct gcgaccccca ccagcctact gatcagctgg gatgctcctg   4680
ctgtcacagt gagatattac aggatcactt acggagagac aggaggaaat agccctgtcc   4740
aggagttcac tgtgcctggg agcaagtcta cagctaccat cagcggcctt aaacctggag   4800
ttgattatac catcactgtg tatgctgtca ctggccgtgg agacagcccc gcaagcagca   4860
agccaatttc cattaattac cgaacagaaa ttgacaaacc atcccagatg caagtgaccg   4920
atgttcagga caacagcatt agtgtcaagt ggctgccttc aagttcccct gttactggtt   4980
acagagtaac caccactccc aaaaatggac caggaccaac aaaaactaaa actgcaggtc   5040
cagatcaaac agaaatgact attgaaggct tgcagcccac agtggagtat gtggttagtg   5100
tctatgctca gaatccaagc ggagagagtc agcctctggt tcagactgca gtaaccacta   5160
ttcctgcacc aactgacctg aagttcactc aggtcacacc cacaagcctg agcgcccagt   5220
ggacaccacc caatgttcag ctcactggat atcgagtgcg ggtgaccccc aaggagaaga   5280
ccggaccaat gaaagaaatc aaccttgctc ctgacagctc atccgtggtt gtatcaggac   5340
ttatggtggc caccaaatat gaagtgagtg tctatgctct taaggacact ttgacaagca   5400
gaccagctca gggagttgtc accactctgg agaatgtcag cccaccaaga agggctcgtg   5460
tgacagatgc tactgagacc accatcacca ttagctggag aaccaagact gagacgatca   5520
ctggcttcca agttgatgcc gttccagcca atggccagac tccaatccag agaaccatca   5580
agccagatgt cagaagctac accatcacag gtttacaacc aggcactgac tacaagatct   5640
acctgtacac cttgaatgac aatgctcgga gctcccctgt ggtcatcgac gcctccactg   5700
ccattgatgc accatccaac ctgcgtttcc tggccaccac acccaattcc ttgctggtat   5760
catggcagcc gccacgtgcc aggattaccg gctacatcat caagtatgag aagcctgggt   5820
ctcctcccag agaagtggtc cctcggcccc gccctggtgt cacagaggct actattactg   5880
gcctggaacc gggaaccgaa tatacaattt atgtcattgc cctgaagaat aatcagaaga   5940
gcgagcccct gattggaagg aaaaagacag acgagcttcc ccaactggta accttccac    6000 accccaatct tcatggacca gagatcttgg atgttccttc cacagttcaa aagaccccctt   6060 tcgtcaccca ccctgggtat gacactggaa atggtattca gcttcctggc acttctggtc   6120
agcaacccag tgttgggcaa caaatgatct ttgaggaaca tggttttagg cggaccacac   6180
cgcccacaac ggccaccccc ataaggcata ggccaagacc atacccgccg aatgtaggtg   6240
aggaaatcca aattggtcac atccccaggg aagatgtaga ctatcacctg tacccacacg   6300
gtccgggact caatccaaat gcctctacag gacaagaagc tctctctcag acaaccatct   6360
catgggcccc attccaggac acttctgagt acatcatttc atgtcatcct gttggcactg   6420
atgaagaacc cttacagttc agggttcctg gaacttctac cagtgccact ctgacaggcc   6480
```

-continued

| | |
|---|---|
| tcaccagagg tgccacctac aacatcatag tggaggcact gaaagaccag cagaggcata | 6540 |
| aggttcggga agaggttgtt accgtgggca actctgtcaa cgaaggcttg aaccaaccta | 6600 |
| cggatgactc gtgctttgac ccctacacag tttcccatta tgccgttgga gatgagtggg | 6660 |
| aacgaatgtc tgaatcaggc tttaaactgt tgtgccagtg cttaggcttt ggaagtggtc | 6720 |
| atttcagatg tgattcatct agatggtgcc atgacaatgg tgtgaactac aagattggag | 6780 |
| agaagtggga ccgtcaggga gaaaatggcc agatgatgag ctgcacatgt cttgggaacg | 6840 |
| gaaaaggaga attcaagtgt gaccctcatg aggcaacgtg ttatgatgat gggaagacat | 6900 |
| accacgtagg agaacagtgg cagaaggaat atctcggtgc catttgctcc tgcacatgct | 6960 |
| ttggaggcca gcgggctgg cgctgtgaca actgccgcag acctgggggt gaacccagtc | 7020 |
| ccgaaggcac tactgccag tcctacaacc agtattctca gagataccat cagagaacaa | 7080 |
| acactaatgt taattgccca attgagtgct tcatgccttt agatgtacag gctgacagag | 7140 |
| aagattcccg agagtaaatc atctttccaa tccagaggaa caagcatgtc tctctgccaa | 7200 |
| gatccatcta aactggagtg atgttagcag acccagctta gagttcttct ttctttctta | 7260 |
| agccctttgc tctggaggaa gttctccagc ttcagctcaa ctcacagctt ctccaagcat | 7320 |
| caccctggga gttcctgag ggttttctca taaatgaggg ctgcacattg cctgttctgc | 7380 |
| ttcgaagtat tcaataccgc tcagtatttt aaatgaagtg attctaagat ttggtttggg | 7440 |
| atcaatagga aagcatatgc agccaaccaa gatgcaaatg ttttgaaatg atatgaccaa | 7500 |
| aattttaagt aggaaagtca cccaaacact tctgctttca cttaagtgtc tggcccgcaa | 7560 |
| tactgtagga acaagcatga tcttgttact gtgatatttt aaatatccac agtactcact | 7620 |
| ttttccaaat gatcctagta attgcctaga aatatctttc tcttacctgt tatttatcaa | 7680 |
| tttttcccag tatttttata cggaaaaaat tgtattgaaa acacttagta tgcagttgat | 7740 |
| aagaggaatt tggtataatt atggtgggtg attatttttt atactgtatg tgccaaagct | 7800 |
| ttactactgt ggaaagacaa ctgtttaat aaaagattta cattccacaa cttgaagttc | 7860 |
| atctatttga tataagacac cttcggggga ataattcct gtgaatattc tttttcaatt | 7920 |
| cagcaaacat ttgaaaatct atgatgtgca agtctaattg ttgatttcag tacaagattt | 7980 |
| tctaaatcag ttgctacaaa aactgattgg ttttttgtcac ttcatctctt cactaatgga | 8040 |
| gatagcttta cactttctgc tttaatagat ttaagtggac cccaatattt attaaaattg | 8100 |
| ctagtttacc gttcagaagt ataatagaaa taatctttag ttgctctttt ctaaccattg | 8160 |
| taattcttcc cttcttccct ccacctttcc ttcattgaat aaacctctgt tcaaagagat | 8220 |
| tgcctgcaag ggaaataaaa atgactaaga tattaaaaaa aaaaaaaaa aa | 8272 |

<210> SEQ ID NO 16
<211> LENGTH: 2397
<212> TYPE: DNA
<213> ORGANISM: Homo sapiens

<400> SEQUENCE: 16

| | |
|---|---|
| gcacacactc atcgaaaaaa atttggatta ttagaagaga gaggtctgcg gcttccacac | 60 |
| cgtacagcgt ggttttcctt ctcggtataa aagcaaagtt gttttttgata cgtgacagtt | 120 |
| tcccacaagc caggctgatc cttttctgtc agtccacttc accaagcctg cccttggaca | 180 |
| aggacccgat gccaaccccc aggcctggca agccctcggc ccttccttg gcccttggcc | 240 |
| catccccagg agcctcgccc agctggaggg ctgcacccaa agcctcagac ctgctggggg | 300 |

```
cccggggccc aggggggaacc ttccagggcc gagatcttcg aggcggggcc catgcctcct      360
cttcttcctt gaaccccatg ccaccatcgc agctgcagct gcccacactg cccctagtca      420
tggtggcacc ctccggggca cggctgggcc ccttgcccca cttacaggca ctcctccagg      480
acaggccaca tttcatgcac cagctctcaa cggtggatgc ccacgccgg accctgtgc        540
tgcaggtgca cccctggag agcccagcca tgatcagcct cacaccaccc accaccgcca       600
ctggggtctt ctccctcaag gcccggcctg gcctcccacc tgggatcaac gtggccagcc     660
tggaatgggt gtccagggag ccggcactgc tctgcacctt cccaaatccc agtgcaccca     720
ggaaggacag cacccttcg gctgtgcccc agagctccta cccactgctg gcaaatggtg      780
tctgcaagtg gcccggatgt gagaaggtct tcgaagagcc agaggacttc ctcaagcact    840
gccaggcgga ccatcttctg gatgagaagg gcagggcaca atgtctcctc cagagagaga   900
tggtacagtc tctggagcag cagctggtgc tggagaagga gaagctgagt gccatgcagg   960
cccacctggc tgggaaaatg gcactgacca aggcttcatc tgtggcatca tccgacaagg  1020
gctcctgctg catcgtagct gctggcagcc aaggccctgt cgtcccagcc tggtctggcc  1080
cccgggaggc ccctgacagc ctgtttgctg tccggaggca cctgtggggt agccatggaa  1140
acagcacatt cccagagttc ctccacaaca tggactactt caagttccac aacatgcgac  1200
ccccttcac ctacgccacg ctcatccgct gggccatcct ggaggctcca gagaagcagc   1260
ggacactcaa tgagatctac cactggttca cacgcatgtt tgccttcttc agaaaccatc  1320
ctgccacctg gaagaacgcc atccgccaca acctgagtct gcacaagtgc tttgtgcggg  1380
tggagagcga gaagggggct gtgtggaccg tggatgagct ggagttccgc aagaaacgga  1440
gccagaggcc cagcaggtgt tccaacccta cacctggccc ctgacctcaa gatcaaggaa  1500
aggaggatgg acgaacaggg gccaaactgg tgggaggcag aggtggtggg ggcagggatg  1560
ataggccctg gatgtgccca cagggaccaa gaagtgaggt ttccactgtc ttgcctgcca  1620
gggcccctgt tccccgctg gcagccaccc cctcccccat catatccttt gcccaaggc   1680
tgctcagagg ggccccggtc ctggccccag ccccacctc cgccccagac acacccca    1740
gtcgagccct gcagccaaac agagccttca caaccagcca cacagagcct gcctcagctg  1800
ctcgcacaga ttacttcagg gctggaaaag tcacacagac acacaaaatg tcacaatcct  1860
gtccctcact caacacaaac cccaaaacac agagagcctg cctcagtaca ctcaaacaac  1920
ctcaaagctg catcatcaca caatcacaca caagcacagc cctgacaacc cacacacccc  1980
aaggcacgca cccacagcca gcctcagggc ccacaggggc actgtcaaca caggggtgtg  2040
cccagaggcc tacacagaag cagcgtcagt accctcagga tctgaggtcc caacacgtgc  2100
tcgctcacac acacggcctg ttagaattca cctgtgtatc tcacgcatat gcacacgcac  2160
agcccccag tgggtctctt gagtcccgtg cagacacaca cagccacaca cactgccttg   2220
ccaaaaatac cccgtgtctc ccctgccact cacctcactc ccattccctg agccctgatc  2280
catgcctcag cttagactgc agaggaacta ctcatttatt tgggatccaa ggcccccaac  2340
ccacagtacc gtccccaata aactgcagcc gagctcccca caaaaaaaaa aaaaaaa     2397
```

<210> SEQ ID NO 17
<211> LENGTH: 1936
<212> TYPE: DNA
<213> ORGANISM: Homo sapiens

<400> SEQUENCE: 17

```
acagctcttg ccaggcaagg cagccgacca caggtgagtc ttggcatcta ccgttttcaa      60
```

```
gtgaccagga tgaagacact ccagttttc ttccttttct gttgctgaa agcaatctgc      120 tgcaatagct gtgagctgac caacatcacc attgcaatag agaaagaaga atgtcgtttc    180
tgcataagca tcaacaccac ttggtgtgct ggctactgct acaccaggga tctggtgtat    240
aaggacccag ccaggcccaa aatccagaaa acatgtacct tcaaggaact ggtatacgaa    300
acagtgagag tgcccggctg tgctcaccat gcagattcct tgtatacata cccagtggcc    360
acccagtgtc actgtggcaa gtgtgacagc gacagcactg attgtactgt gcgaggcctg    420
gggcccagct actgctcctt tggtgaaatg aaagaataaa gatcagtgga catttcaggc    480
cacataccct tgtcctgaag gaccaagata ttcaaaaagt ctgtgtgtgt gcaatgtgcc    540
caggggacaa accactggat caggggattc agactctact gatccctggt ctactggcag    600
agggaactct gggaattgag agtgctgggg gccaggactc catcatgatt cagtctctata   660 ttcctaggtc tgatttcata aggtttattc agtcttaact cacagacttg tgcctggttt    720 cttcttttaaa aatcttagaa atcttctcag gcaatgcctc tctcttaggg ggaaacataa   780
gcctagaagg aggaagcagt aatgggagtg agtgaaagaa ctaactgcag cagtcttctg    840
gtagactctt gggccctcta gagcaaggtc agcatcttca gcattgtagc gtcaatgcct    900
agcactctgc ctggaactta gaaacacaac aatgacttct ttagatcaga aggtcaagg    960 gtagaaaata ctggaagacg atgtttgagg taagctgatg aggctgcccg cagccacacc   1020
agtcccatga agttagtgg catcagttcc acctcgcctt ttctccagca catggagtat   1080
tgagacatga tgtatctttc tgaattgttt ggtacagatg gggagtaaca gagctcaaga   1140
tttccaagct attactacca agcctgttag ttaagggcaa aggcaagaaa ttgtaatttg   1200
gggctgtgga aattagcctg cctctattca ttacttaaac aaattgatca catgctacta   1260
ggctcctgca aaactccttt ttgagataaa gggaaaaaac caaactatct caccctaccc    1320
tccctaggat ccacttcttt ggaatgacaa aggatttgaa agtaggtttg aaagcagttt    1380
cagcaattta ataaatataa ttaatttgtc tacaaatata tttgtataaa taaatagctc    1440
ctttagaaag aattagccat gggggacgag gggaaactgc tgttttctag gatcctgtct    1500
acatcaatct tctatttat ccatccatgt tctcccaaat ctgtgctttc tttcaacagg     1560
ttatatatta aaactatttc atgagttgat ttcttttaaa cgtgttaact gtcttagtta    1620
tgcactcagt ttcacactca tattgtttaa ctaatttatt taaatcttat ttttttaata    1680
aagatgctag ccaccagagt cacaggcttg gattgtttta tgtacaaaca gatgacttag    1740
atattctgta ttttataata ttagtggaat gaaatcttaa aatataattc ccagtgtttc    1800
tataaatatt acctttcctt atctttggag atattaaaaa taattttgtt ggatttctga    1860
agtgttttgt cacttaaatt tcctgtcatt ttttgaagac attttctgat gtaatttggg    1920
agaaaaaaag cataga                                                    1936
```

<210> SEQ ID NO 18
<211> LENGTH: 1834
<212> TYPE: DNA
<213> ORGANISM: Homo sapiens

<400> SEQUENCE: 18

```
ttgggaaggg tttccagaag gtgggaaatg tcacctgatt cacactgaac ttttgaaagc      60
tccccacccc caaggagccg cgcacaccct cgctcgcggc cgccctccca cagccccaca    120
cactgggaga ccgcccaccg caaaccgcgg agaccccgt ctagatttaa agcgcggctg     180
```

```
cgcccggctt ctgacgtcca ttgaatcgcg cgggcggccg gcggcgagcg cggggctgcg      240
ccgggatcgc tgcgccctcc gccgctggcc tctgcgacgc gcgccgctcg cccgagccac      300
ccgccgccgc gccggctccc cgcgccgctg cgctcctcgc cccgcgcctg cccccaggat      360
ggtccgcgcg aggcaccagc cgggtgggct ttgcctcctg ctgctgctgc tctgccagtt      420
catggaggac cgcagtgccc aggctgggaa ctgctggctc cgtcaagcga agaacggccg      480
ctgccaggtc ctgtacaaga ccgaactgag caaggaggag tgctgcagca ccggccggct      540
gagcacctcg tggaccgagg aggacgtgaa tgacaacaca ctcttcaagt ggatgatttt      600
caacgggggc gcccccaact gcatcccctg taaagaaacg tgtgagaacg tggactgtgg      660
acctgggaaa aaatgccgaa tgaacaagaa gaacaaaccc cgctgcgtct gcgccccgga      720
ttgttccaac atcacctgga agggtccagt ctgcgggctg gatgggaaaa cctaccgcaa      780
tgaatgtgca ctcctaaagg caagatgtaa agagcagcca gaactggaag tccagtacca      840
aggcagatgt aaaagacttt gtcgggatgt tttctgtcca ggcagctcca catgtgtggt      900
ggaccagacc aataatgcct actgtgtgac ctgtaatcgg atttgcccag agcctgcttc      960
ctctgagcaa tatctctgtg gaatgatgg agtcacctac tccagtgcct gccacctgag      1020
aaaggctacc tgcctgctgg gcagatctat tggattagcc tatgagggaa agtgtatcaa      1080
agcaaagtcc tgtgaagata tccagtgcac tggtgggaaa aaatgtttat gggatttcaa      1140
ggttgggaga ggccggtgtt ccctctgtga tgagctgtgc cctgacagta agtcggatga      1200
gcctgtctgt gccagtgaca atgccactta tgccagcgag tgtgccatga aggaagctgc      1260
ctgctcctca ggtgtgctac tggaagtaaa gcactccgga tcttgcaact ccatttcgga      1320
agacaccgag gaagaggagg aagatgaaga ccaggactac agctttccta tatcttctat      1380
tctagagtgg taaactctct ataagtgttc agtgttgaca tagcctttgt gcaaaaaaaa      1440 aaaaaaaaa aagaaaaag aaaaaagaa aaatatattg tccatactgt aaataagtgt      1500
atgcttattt atttggggg aaaactatac attaaaggac cttgtcccta aagctctctc      1560
ccaggccacc ttgttactca ttggacacgg agaggcattc attgtgaggt ctactggatg      1620
aggcccatag ttgagacttg tagacatta tttatactgt gtcatgtttt ataattata      1680 cataaaatgt ctggttgact gtataccttg tttttgaaga aatttattcg tgaaaggaag      1740
agcagttgtt atttattgtg aggtctcttg cttgtaaagt aaaagctttt tttccttgta      1800
aaccatttaa gtccattcct tactattcac tcac                                1834

<210> SEQ ID NO 19
<211> LENGTH: 2525
<212> TYPE: DNA
<213> ORGANISM: Homo sapiens

<400> SEQUENCE: 19
gggaagtcgg tgccgctgcc gtctctgcgt tcgccatgcg tcccggggcg ccagggccac       60
tctggcctct gccctggggg gccctggctt gggccgtggg cttcgtgagc tccatgggct      120
cggggaaccc cgcgcccggt ggtgtttgct ggctccagca gggccaggag gccacctgca      180
gcctggtgct ccagactgat gtcacccggg ccgagtgctg tgcctccggc aacattgaca      240
ccgcctggtc caacctcacc cacccgggga acaagatcaa cctcctcggc ttcttgggcc      300
ttgtccactg ccttccctgc aaagattcgt gcgacggcgt ggagtgcggc ccgggcaagg      360
cgtgccgcat gctggggggc cgcccgcgct gcgagtgcgc cccgactgc tcggggctcc      420 cggcgcggct gcaggtctgc ggctcagacg gcgccaccta ccgcgacgag tgcgagctgc      480
```

```
gcgccgcgcg ctgccgcggc cacccggacc tgagcgtcat gtaccggggc cgctgccgca      540
agtcctgtga gcacgtggtg tgcccgcggc cacagtcgtg cgtcgtggac cagacgggca      600
gcgcccactg cgtggtgtgt cgagcggcgc cctgccctgt gcctccagc cccggccagg       660 agctttgcgg caacaacaac gtcacctaca tctcctcgtg ccacatgcgc caggccacct      720
gcttcctggg ccgctccatc ggcgtgcgcc acgcgggcag ctgcgcaggc acccctgagg      780
agccgccagg tggtgagtct gcagaagagg aagagaactt cgtgtgagcc tgcaggacag      840
gcctgggcct ggtgcccgag gccccccatc atccctgtt atttattgcc acagcagagt       900
ctaatttata tgccacggac actccttaga gcccggattc ggaccacttg gggatcccag      960
aacctccctg acgatatcct ggaaggactg aggaagggag gcctgggggc cggctggtgg     1020
gtgggataga cctgcgttcc ggacactgag cgcctgattt agggcccttc tctaggatgc     1080
cccagcccct accctaagac ctattgccgg ggaggattcc acacttccgc tcctttgggg     1140
ataaacctat taattattgc tactatcaag agggctgggc attctctgct ggtaattcct     1200
gaagaggcat gactgctttt ctcagcccca agcctctagt ctgggtgtgt acggagggtc     1260
tagcctgggt gtgtacggag ggtctagcct gggtgagtac ggagggtcta gcctgggtga     1320
gtacggaggg tctagcctgg gtgagtacgg agggtctagc ctgggtgtgt atggaggatc     1380
tagcctgggt gagtatggag ggtctagcct gggtgagtat ggagggtcta gcctgggtgt     1440
gtatggaggg tctagcctgg gtgagtatgg agggtctagc ctgggtgtgt atggagggtc     1500
tagcctgggt gagtatggag ggtctagcct gggtgtgtac ggagggtcta gtctgagtgc     1560
gtgtggggac ctcagaacac tgtgacctta gcccagcaag ccaggcccctt catgaaggcc    1620 aagaaggctg ccaccattcc ctgccagccc aagaactcca gcttccccac tgcctctgtg     1680
tgcccctttg cgtcctgtga aggccattga gaaatgccca gtgtgccccc tgggaaaggg    1740
cacggcctgt gctcctgaca cgggctgtgc ttggccacag aaccacccag cgtctcccct     1800
gctgctgtcc acgtcagttc atgaggcaac gtcgcgtggt ctcagacgtg gagcagccag     1860
cggcagctca gagcagggca ctgtgtccgg cggagccaag tccactctgg gggagctctg     1920
gcggggacca cgggccactg ctcacccact ggccccgagg ggggtgtaga cgccaagact     1980
cacgcatgtg tgacatccgg agtcctggag ccgggtgtcc cagtggcacc actaggtgcc     2040
tgctgcctcc acagtgggt tcacacccag ggctccttgg tccccacaa cctgccccgg       2100 ccaggcctgc agacccagac tccagccaga cctgcctcac ccaccaatgc agccggggct     2160
ggcgacacca gccaggtgct ggtcttgggc cagttctccc acgacggctc accctcccct     2220
ccatctgcgt tgatgctcag aatcgcctac ctgtgcctgc gtgtaaacca cagcctcaga    2280
ccagctatgg ggagaggaca acacggagga tatccagctt ccccggtctg gggtgaggaa     2340
tgtggggagc ttgggcatcc tcctccagcc tcctccagcc cccaggcagt gccttacctg    2400
tggtgcccag aaaagtgccc ctaggttggt gggtctacag gagcctcagc caggcagccc     2460
accccaccct ggggccctgc ctcaccaagg aaataaagac tcaagccatt taaaaaaaaa    2520
aaaaa                                                                2525
```

<210> SEQ ID NO 20
<211> LENGTH: 1398
<212> TYPE: DNA
<213> ORGANISM: Homo sapiens

<400> SEQUENCE: 20

-continued

| | |
|---|---|
| ggagagcggg gcccttttgtc ctccagtggc tggtaggcag tggctgggag gcagcggccc | 60 |
| aattagtgtc gtgcggcccg tggcgaggcg aggtccgggg agcgagcgag caagcaaggc | 120 |
| gggaggggtg gccggagctg cggcggctgg cacaggagga ggagcccggg cgggcgaggg | 180 |
| gcggccggag agcgccaggg cctgagctgc cggagcggcg cctgtgagtg agtgcagaaa | 240 |
| gcaggcgccc gcgcgctagc cgtggcagga gcagcccgca cgccgcgctc tctccctggg | 300 |
| cgacctgcag tttgcaatat gactttggag gaattctcgg ctggagagca gaagaccgaa | 360 |
| aggatggata aggtggggga tgccctggag gaagtgctca gcaaagccct gagtcagcgc | 420 |
| acgatcactg tcggggtgta cgaagcggcc aagctgctca acgtcgaccc cgataacgtg | 480 |
| gtgttgtgcc tgctggcggc ggacgaggac gacgacagag atgtggctct gcagatccac | 540 |
| ttcaccctga tccaggcgtt ttgctgcgag aacgacatca acatcctgcg cgtcagcaac | 600 |
| ccgggccggc tggcggagct cctgctcttg gagaccgacg ctggccccgc ggcgagcgag | 660 |
| ggcgccgagc agcccccgga cctgcactgc gtgctggtga cgaatccaca ttcatctcaa | 720 |
| tggaaggatc ctgccttaag tcaacttatt tgttttttgcc gggaaagtcg ctacatggat | 780 |
| caatgggttc cagtgattaa tctccctgaa cggtgatggc atctgaatga aaataactga | 840 |
| accaaattgc actgaagttt ttgaaatacc tttgtagtta ctcaagcagt tactccctac | 900 |
| actgatgcaa ggattacaga aactgatgcc aaggggctga gtgagttcaa ctacatgttc | 960 |
| tgggggcccg gagatagatg actttgcaga tggaaagagg tgaaaatgaa gaaggaagct | 1020 |
| gtgttgaaac agaaaaataa gtcaaaagga acaaaaatta caaagaacca tgcaggaagg | 1080 |
| aaaactatgt attaatttag aatggttgag ttacattaaa ataaaccaaa tatgttaaag | 1140 |
| tttaagtgtg cagccatagt ttgggtattt ttggtttata tgccctcaag taaaagaaaa | 1200 |
| gccgaaaggg ttaatcatat ttgaaaacca tattttattg tattttgatg agatattaaa | 1260 |
| ttctcaaagt tttattataa attctactaa gttattttat gacatgaaaa gttatttatg | 1320 |
| ctataaattt tttgaaacac aatacctaca ataaactggt atgaataatt gcatcatttc | 1380 |
| aaaaaaaaaa aaaaaaaa | 1398 |

<210> SEQ ID NO 21
<211> LENGTH: 1393
<212> TYPE: DNA
<213> ORGANISM: Homo sapiens

<400> SEQUENCE: 21

| | |
|---|---|
| tcagatcgcc gaagcgtcgg actaccgttg gtttccgcaa cttcctggat tatcctcgcc | 60 |
| aaggactttg caatatattt ttccgccttt tctggaagga tttcgctgct tcccgaaggt | 120 |
| cttggacgag cgctctagct ctgtgggaag gttttgggct ctctggctcg gattttgcaa | 180 |
| tttctccctg gggactgccg tggagccgca tccactgtgg attataattg caacatgacg | 240 |
| ctggaagagc tcgtggcgtg cgacaacgcg gcgcagaaga tgcagacggt gaccgccgcg | 300 |
| gtggaggagc ttttggtggc cgctcagcgc caggatcgcc tcacagtggg ggtgtacgag | 360 |
| tcggccaagt tgatgaatgt ggacccagac agcgtggtcc tctgcctctt ggccattgac | 420 |
| gaggaggagg aggatgacat cgccctgcaa atccacttca cgctcatcca gtccttctgc | 480 |
| tgtgacaacg acatcaacat cgtgcgggtg tcgggcatgc agcgcctggc gcagctcctg | 540 |
| ggagagccgg ccgagaccca gggcaccacc gaggcccgag acctgcattg tctcctggtc | 600 |
| acgaaccctc acacgacgc ctggaagagc cacggcttgg tggaggtggc cagctactgc | 660 |
| gaagaaagcc ggggcaacaa ccagtgggtc ccctacatct ctcttcagga acgctgaggc | 720 |

```
ccttcccagc agcagaatct gttgagttgc tgccacaaac aaaaaataca ataaatattt    780
gaaccccctc cccccagca caacccccc aacccacgag gaccatcggg                 840
ggcagagtcg ttggagactg aagaggaaga ggaggaggag aaggggagtg agcggccgcc    900
cccagggcgg agatccagga gctggcggcc gccgatccga tggagaaggg gggacccagg    960
ccagcaggag acaggacccc cgaagctgag gccttgggat ggagcagaag ccggagtggc   1020
ggggcacgct gccgccttcc ccatcacgga gggtccagac tgtccactcg ggggtggagt   1080
gagactgact gcaagcccca ccctccttga gactggagct ggcgtctgca tacgagagac   1140
ttggttgaac ttggttggtc cttgtctgca ccctcgacaa gaccacactt tgggacttgg   1200
gagctggggc tgaagttgct ctgtacccat gaactcccag tttgcgaatt atagagacaa   1260
tctattttgt tacttgcact tgttattcga accactgaga gcgagatggg aagcatagat   1320
atctatattt ttatttctac tatgagggcc ttgtaataaa tttctaaagc ctctgaaaaa   1380
aaaaaaaaaa aaa                                                      1393
```

<210> SEQ ID NO 22
<211> LENGTH: 5843
<212> TYPE: DNA
<213> ORGANISM: Homo sapiens

<400> SEQUENCE: 22

```
ttggttgctg gtccacttac aaacactttt catatttgta tgtctttcca atggttatcc     60
tgttttgttc atttcaggca tatggccctg atcagattaa ctgacatgat gtatatgcaa    120
agccttttga gttcttcaga aaaataaatt atcttattca agactgattg cttataagga    180
acttattata gctaatatag taggcacaat ttttttttg taattctcct agatgagtca     240
gaacttagtt ttgacgtagg taaaaatttt atggtcacaa atctcaggtg tgagaaaatc    300
tctttccttg atactctata taatagagg atataaatat ttcaagtctg gaagtagtga    360
gagaagctgg taattctgga catatagtga cagtcaaaaa ggagctcagg tacaggactg    420
gtctaagctg ctcaagattc aggagacagc cagtacacag agaagctgag gagatacata    480
agatatatct aaaacattta tctaaccttc tgtggtaaca agctccttaa aggggctgga    540
tgatgttgtg ttcactttt atcaccagca aaggctaaga taatgtatat agtaaatatt    600
tagtaactat ttattaaata aataaatatt taagacagaa taaacaagta taataaatga    660
accaataaga atgcaccatc taagtcaaaa tagccacttt tatccttaac attgtacctg    720 cttggctgc tgcagaagca aacttgttgg cattagacaa atcaagctgg tgatttaata    780
aattccaatg taagtcttac cagtattgat gaataactat ccagcactca ccatgaaagt    840
taaagaaaca acacagaaaa agttcctaag tggtcccaat ttgaaatgat cagataacct    900 ataaagaac atattcatat tatactaaca taaacacata taaatgcact tacagcagtt    960
acacagtatt ctcttcaata actagtttcc ttatgcatta atgtgtaata acagcaacta   1020
caatatttag ataattataa aaaccaaggc aataatttaa aaactgatta accgttttac   1080
tctaacttaa gcatggattg gatcagtaag attgattaat aaatttgaat gcagtcagtt   1140
ggattgattc taatttaaag ttttaatttg ttgtagaata attttaagtg aatatatttg   1200
tccagtgttc gagtgctcaa cagtgtgttt gaaaaggaaa acaaagaaat gttttgtaga   1260
aatgtgttaa ttccttaaga caatggattt taattggatc tagttgtttt cattttctt   1320 cattatcatt atacatctgt atgttggaca gaacactaac actaaatagt ttttagaaaa   1380
```

```
attttttaaa gttatttaaa tcataatatc atgactgact tttaaattca aaattaggct  1440
gtgactatcc ttcttcactt aggaagagtg ttgtgaaagc cagaccatct gctgaggtgc  1500
tacagttaca tgtggccctc agaatgcatt tggcctgctc tgttttagca ctctgttgga  1560
ttaccaatac acaaaacaag ttaaccttga tctttcacat taagtatctc agggacaaaa  1620
tttgacatac gtctaaacct gtgacgtttc catctaaaga aggcagaaat aaaacaggac  1680
tttagattcg gttacaataa aatatcagat gcaccagaga cacaaggctt gaagctctgt  1740
cctgggaaaa tatggcaaac agtgcctctc ctgaacagaa tcaaaatcac tgttcagcca  1800
tcaacaacag catcccactg atgcagggca acctccccac tctgaccttg tctggaaaga  1860
tccgagtgac ggttactttc ttcctttttc tgctctctgc gacctttaat gcttctttct  1920
tgttgaaact tcagaagtgg acacagaaga aagagaaagg gaaaaagctc tcaagaatga  1980
agctgctctt aaaacatctg accttagcca acctgttgga gactctgatt gtcatgccac  2040
tggatgggat gtggaacatt acagtccaat ggtatgctgg agagttactc tgcaaagttc  2100
tcagttatct aaagcttttc tccatgtatg ccccagcctt catgatggtg gtgatcagcc  2160
tggaccgctc cctggctatc acgaggcccc tagctttgaa aagcaacagc aaagtcggac  2220
agtccatggt tggcctggcc tggatcctca gtagtgtctt tgcaggacca cagttataca  2280
tcttcaggat gattcatcta gcagacagct ctggacagac aaaagttttc tctcaatgtg  2340
taacacactg cagttttcca caatggtggc atcaagcatt ttataacttt ttcaccttca  2400
gctgcctctt catcatccct cttttcatca tgctgatctg caatgcaaaa atcatcttca  2460
ccctgacacg ggtccttcat caggaccccc acgaactaca actgaatcag tccaagaaca  2520
atataccaag agcacggctg aagactctaa aaatgacggt tgcatttgcc acttcattta  2580
ctgtctgctg gactccctac tatgtcctag gaatttggta ttggtttgat cctgaaatgt  2640
taaacaggtt gtcagaccca gtaaatcact tcttctttct ctttgccttt ttaaacccat  2700
gctttgatcc acttatctat ggatattttt ctctgtgatt gatagactac acaagaagtc  2760
atatgaagaa gggtaaggta atgaatctct ccatctggga atgattaaca caaatgttgg  2820
agcatgttta catacaaaca aagtaggatt tacacttaag ttatcattct tttagaaact  2880
cagtcttcag agcctcaatt attaaggaaa agtcttcagg aaaaatacta aaatattttc  2940
tcttcctcat aagcttctaa attaatctct gccttttctg acctcatata acacattatg  3000
taggtttctt atcactttct ctttgcataa taatgtacta atatttaaaa taccttcagc  3060
ctaaggcaca aggatgccaa aaaaacaaag gtgagaaacc acaacacagg tctaaactca  3120
gcatgctttg gtgagttttt ctccaaaagg ggcatattag caattagagt tgtatgctat  3180
ataatacata gagcacagag ccctttgccc ataatatcaa ctttccctcc tatagttaaa  3240
aagaaaaaaa atgaatctat ttttctcttt ggcttcaaaa gcattctgac atttggagga  3300
gtcagtaacc aatcccacca accactccag caacctgaca agactatgag tagttctcct  3360
tcatcctatt tatgtggtac aggttgtgaa gtatctctat ataaagggaa attttagagg  3420
ggttaggatt tggacagggg tttagaacat tcctctaagc tatctagtct gtggagtttg  3480
tggcaattaa ttgccataaa ataacaatgt ttccaaatgc aactaagaaa atactcatag  3540
tgagtacgct ctatgcatag tatgacttct attttaatgt gaagaatttt ttgtctctct  3600
cctgatctta ctaaatccat atttcataaa taactgagaa taattaaaac aaaattaagc  3660
aaatgcacaa gcaaaaagat gcttgataca caaaaggaac tctggagaga aaactacagc  3720
ttcagtctgt acagatcaaa gaagacagaa catgtcaggg gaaggaggga aagatcttga  3780
```

```
tgcagggttt cttaacctgc agtctatgca caacactata tttccatgta atgttttat    3840 ttcagcccta tttgtattat tttgtgcatt taaaaaacac aatcttaagg ggatagacta    3900
gactgccaca gcagcccatg gcacaactaa cacctactga tattcacatt aaatagtatg    3960
gtttccaaaa tatgtctgca caacaagacc tctttatgta attcaggctt gtgtctacct    4020
cttccatgaa aaatggaaag ggatgaaaat aatgggagta taatacccat ttaatgtgaa    4080
aaacataaga gtcttaaaag aaattaagcc atttaacatt ttttaaatag gtaagatacc    4140
attatattta tatgagctat gtactgccac aaaaaaagat gaaatgtaat ttctaaatac    4200
tccaggtgtg tggtattatg gaaagcaaat tgccaactaa tggcacgtcc tttctttctt    4260
tgattttctc ctctcatact tcagttttat agtgttgtgt tgttgttttt ttcatatcct    4320
accttacttt ccaattctgt ctcaattgaa ctccctctgt ctactcactc tttcattcat    4380
agcttctttt ccattaaact catacccttta attaaccaat tcatggccca gttctacagt    4440
tgaattggac aaggctaaaa ttctgtagtg tgctaaaatg ctcaagttgg cacataaacc    4500
cattccaaga ttttatagtt cttgtagata acacagggat gtagataagt tgaaacaaaa    4560
ccagtgtcct ctaagtctct atcatatact tattcctaaa ctgataattc ttacttctgg    4620
atttaaaatc aaaaataaca cacttgtaca gatacaatct aagggcttta tcacacacgt    4680
gttaacgaat gtatctcagc ttggttcttc ttgtgtgctc attatggatc tctctgtctt    4740
aggaattgcc tcaggcattt ttttttttta cacattaact aaagggctat tcgaaatctt    4800
gactcagggg ttcttaacct acatttcatg caaaaaatat atatatttca atgtatttt    4860 tattttagtc ctatttgtat tattttatgc atttaaaaac acagtcctga gagggatgga    4920
ccagactgcc acagcagctc atagcacaaa aaaaggttaa gaagtcctag ttgactttgt    4980
atatatataa agaaatctat tacaataaaa atataacata atctattcat ctatttatat    5040
gcaaacataa aaatgtaaat attgaaacaa gattgcttca atatgcttat tgttttcaaa    5100
ccaacaaact ctcttaaggt tcaatatgta ataaaaaaca taacacaaat aattattcta    5160
tatgaatatt atggttcata aattataatg tataatctat acattataat gtaatatata    5220
aactaaaatt tatggcacaa aagataaata tggctttgaa attaaagata ttccactcaa    5280
cagacaatat ttcatatttg atattacaat catttatttt atgtcctatt ataataaaag    5340
gtgaggactc cttgtaaaaa aggaaatgtt ccacagagtc aatctaatat atcagatatt    5400
ggagattcta tcttggtttc tcttccttta cttagcctat aaaactagtt aaaaatggaa    5460
tttcttttag caattcagtt tagtacagga gtgacattaa ctaatgacaa taaattaaac    5520
aaagcctaca ttagttcaat ttaagcctat tcaacagaaa tatagaaata tagtagctaa    5580
aaaaatactc tgggaaggt accacaaaca ttatctacca gggaacatag cataaattag    5640
tctgaaattt cctgagagtg actttgtctt agaacttagg tggtagtcat gaagagataa    5700 tgttttagg cagttaaaat acttctagaa ctccatctat tttacctgtg gtccactttc    5760
ctacattgaa ccaatgcctt gggcttctct aattactata cattgtgctc atatgaataa    5820
aagaaatttt aaaagaaaaa aaa                                           5843
```

<210> SEQ ID NO 23
<211> LENGTH: 1217
<212> TYPE: DNA
<213> ORGANISM: Homo sapiens

<400> SEQUENCE: 23

```
aggggggcggg gaggggcgca gggctgcgcg ctcgccggcg ctctctttcg gtttggtcgg      60
cggctggagg agagtggacc ccccccacttt aaggctctgt cctcggcgcg ttcccgccgc     120
cccccggtcc cgacgcgggg ctcggggatg cccgccagca tgttcagcat cgacaacatc     180
ctagccgccc ggccgcgctg caaggactcg gtgttgccgg tggcgcacag cgcggcggct     240
cccgtcgtct tcccggccct gcacggggac tcgctctacg gcgccagcgg cggcgcctcc     300
tcggactatg cgccttcta cccgcgcccc gtgccccccg gcggcgcggg cctcccggcc     360
gcggtcagcg gctcccgcct cggctacaac aactacttct acgggcagct gcacgtgcag     420
gcggcgcccg tgggcccggc ctgctgcggg gccgtgccgc cgctgggcgc ccagcagtgc     480
tcctgcgtcc cgacgccccc aggctacgag ggccccggtt cggtgctggt gtccccggta     540
ccgcaccaga tgctgcccta catgaacgtg gcacgctgt cgcgcaccga gctgcagctt     600
ctcaaccagc tgcactgtcg gcggaagcgg cggcaccgca ccatcttcac tgacgagcag     660
ctcgaagctc tcgagaacct cttccaggag accaagtacc cggacgtggg cacgcgcgag     720
cagctggccc ggaaagtgca cctccgcgag agaaagtgg aggtctggtt taagaaccgc     780
cgcgccaaat ggaggcggca gaagcggtcc tcatcagagg agtcggagaa cgcggagaag     840
tggaacaaga cgtcgtcgtc gaaggcgtca ccggagaaga gggaagagga aggtaaaagc     900
gatttggact cggacagctg acggccgcgg gacacttgcc cgtattactt acctaactcg     960
aaggacttgc acagacagac gatgctactt tcttgcacac gcgctgcctt gcggaggggg    1020
gtcgagaaag aggaacgagg agctgtaaat agtgtacaga gccgggaggg tcggcgtctg    1080
gggtcagggc gcgcacagcc cagcagcccg aggccgcccg cgactagccc ccaccgtagt    1140
atttatagtt aaattaaggg tgacagtaca ataaagtgat ggcgatgtaa aaaaaaaaa    1200
aaaaaaaaaa aaaaaaa                                                 1217
```

<210> SEQ ID NO 24
<211> LENGTH: 430
<212> TYPE: DNA
<213> ORGANISM: Homo sapiens

<400> SEQUENCE: 24

```
gactgtcact cggtcccaga caccagagca agctcaagac ccagcagtgg gacagccaga     60
cagacggcac gatggcactg agctcccaga tctgggccgc ttgcctcctg ctcctcctcc    120
tcctcgccag cctgaccagt ggctctgttt tcccacaaca gacgggacaa cttgcagagc    180
tgcaacccca ggacagagct ggagccaggg ccagctggat gcccatgttc cagaggcgaa    240
ggaggcgaga cacccacttc cccatctgca ttttctgctg cggctgctgt catcgatcaa    300
agtgtgggat gtgctgcaag acgtagaacc tacctgccct gccccgtcc cctcccttcc    360
ttatttattc ctgctgcccc agaacatagg tcttggaata aaatggctgg ttcttttgtt    420
ttccaaaaaa                                                          430
```

<210> SEQ ID NO 25
<211> LENGTH: 2319
<212> TYPE: DNA
<213> ORGANISM: Homo sapiens

<400> SEQUENCE: 25

```
ttccccactc cccgccctc cccagggccc tgggaagggg ctcagcgtgg gaaaggatgg      60
ttgagttttc accagaggca aagcgtgagc gggatcagtt tgtgcggaac gcaagcagcc    120
gagagcggag aggcgccgct gtagttaact cctcccctgcc cgccgcgccg accctcccca    180
```

```
ggaaccccca gggagccagc atgaagcgag ctcaccccga gtacagctcc tcggacagcg    240
agctggacga gaccatcgag gtggagaagg agagtgcgga cgagaatgga aacttgagtt    300
cggctctagg ttccatgtcc ccaactacat cttcccagat tttggccaga aaagacgga    360 gaggaataat tgagaagcgc cgacgagacc ggatcaataa cagtttgtct gagctgagaa    420
ggctggtacc cagtgctttt gagaagcagg gatctgctaa gctagaaaaa gccgagatcc    480
tgcagatgac cgtggatcac ctgaaaatgc tgcatacggc aggagggaaa ggttactttg    540
acgcgcacgc ccttgctatg gactatcgga gtttgggatt tcgggaatgc ctggcagaag    600
ttgcgcgtta tctgagcatc attgaaggac tagatgcctc tgacccgctt cgagttcgac    660
tggtttcgca tctcaacaac tacgcttccc agcgggaagc cgcgagcggc gcccacgcgg    720
gcctcggaca cattccctgg gggaccgtct tcggacatca cccgcacatc gcgcacccgc    780
tgttgctgcc ccagaacggc cacgggaacg cgggcaccac ggcctcaccc acggaaccgc    840
accaccaggg caggctgggc tcggacacatc cggaggcgcc tgctttgcga gcgcccccta    900
gcggcagcct cggaccggtg ctccctgtgg tcacctccgc ctccaaactg tcgccgcctc    960
tgctctcctc agtggcctcc ctgtcggcct tccccttctc tttcggctcc ttccacttac   1020
tgtctcccaa tgcactgagc ccttcagcac ccacgcaggc tgcaaacctt ggcaagccct   1080
atagaccttg ggggacggag atcggagctt tttaaagaac tgatgtagaa tgagggaggg   1140
gaaagtttaa atcccagct gggctggact gttgccaaca tcaccttaaa gtcgtcagta    1200
aaagtaaaaa ggaaaaaggt acactttcag ataattttt ttttaaagac taaaggtttg    1260
ttggtttact tttatctttt ttaatgtttt tttcatcatg tcatgtatta gcagttttta   1320
aaaactagtt gttaaatttt gttcaagaca ttaaattgaa atagtgagta taagccaaca   1380
ctttgtgata ggtttgtact gtgcctaatt tactttgtaa accagaatga ttccgttttt   1440
gcctcaaaat ttggggaatc ttaacattta gtattttttgg tctgttttc tccttgtata   1500 gttatggtct gttttagaa ttaattttcc aaaccactat gcttaatgtt aacatgattc   1560
tgtttgttaa tattttgaca gattaaggtg ttgtataaat aatattcttt tgggggagg   1620 ggaactatat tgaattttat atttctgagc aaagcgttga caaatcagat gatcagcttt   1680
atccaagaaa gaagactagt aaattgtctg cctcctatag cagaaaggtg aatgtacaaa   1740
ctgttggtgg ccctgaatcc atctgaccag ctgctgtat ctgccaggac tggcagttct    1800
gatttagtta ggagagagcc gctgataggt taggtctcat ttggagtgtt ggtggaaagg   1860
aaactgaagg taattgaata gaatacgcct gcatttacca gccccagcaa cacaaagaat   1920
ttttaatcac acggatctca aattcacaaa tgttaacatg gataagtgat catggtgtgc   1980
gagtggtcaa ttgagtagta cagtggaaac tgttaaatgc ataacctaat ttcctgggga   2040
ctgccatatt ttcttttaac tggaaatttt tatgtgagtt ttccttttgg tgcatggaac   2100
tgtggttgcc aaggtattta aaagggcttt cctgcctcct tctctttgat ttatttaatt   2160
tgatttgggc tataaaatat catttttcag gtttattctt ttagcaggtg tagttaaacg   2220
acctccactg aactgggttt gacctctgtt gtactgatgt gttgtgacta aataaaaaag   2280
aaagaacaaa gtaaaaaaaa aaaaaaaaa aaaaaaaa                            2319
```

<210> SEQ ID NO 26
<211> LENGTH: 4150
<212> TYPE: DNA
<213> ORGANISM: Homo sapiens

<400> SEQUENCE: 26

```
cttgaatctt ggggcaggaa ctcagaaaac ttccagcccg ggcagcgcgc gcttggtgca      60
agactcagga gctagcagcc cgtcccctc cgactctccg gtgccgccgc tgcctgctcc     120
cgccacccta ggaggcgcgg tgccacccac tactctgtcc tctgcctgtg ctccgtgccc    180
gaccctatcc cggcggagtc tccccatcct cctttgcttt ccgactgccc aaggcacttt   240
caatctcaat ctcttctctc tctctctctc tctctctctc tctctctctc              300
tctctctctc gcagggtggg gggaagagga ggaggaattc tttccccgcc taacatttca    360
agggacacaa ttcactccaa gtctcttccc tttccaagcc gcttccgaag tgctcccggt    420
gcccgcaact cctgatccca acccgcgaga ggagcctctg cgacctcaaa gcctctcttc    480
cttctccctc gcttccctcc tcctcttgct acctccacct ccaccgccac ctccacctcc    540
ggcacccacc caccgccgcc gccgccaccg gcagcgcctc ctcctctcct cctcctcctc    600
ccctcttctc tttttggcag ccgctggacg tccggtgttg atggtggcag cggcggcagc    660
ctaagcaaca gcagccctcg cagcccgcca gctcgcgctc gccccgccgg cgtccccagc    720
cctatcacct catctcccga aaggtgctgg gcagctccgg ggcggtcgag gcgaagcggc    780
tgcagcggcg gtagcggcgg cgggaggcag gatgagcgca cgcggtgagg gcgcggggca    840
gccgtccact tcagcccagg gacaacctgc cgccccagcg cctcagaaga gaggacgcgg    900
ccgcccagg aagcagcagc aagaaccaac cggtgagccc tctcctaaga gacccagggg     960
aagacccaaa ggcagcaaaa acaagagtcc ctctaaagca gctcaaaaga aagcagaagc   1020
cactggagaa aaacggccaa gaggcagacc taggaaatgg ccacaacaag ttgttcagaa   1080
gaagcctgct caggaggaaa ctgaagagac atcctcacaa gagtctgccg aagaggacta   1140
gggggcgcca acgttcgatt tctacctcag cagcagttgg atcttttgaa gggagaagac   1200
actgcagtga ccacttattc tgtattgcca tggtcttttcc actttcatct ggggtggggt   1260
ggggtggggt ggggggaggg ggggtggggt gggagaaaat cacataacct taaaaaggac   1320
tatattaatc accttctttg taatcccttc acagtcccag gtttagtgaa aaactgctgt   1380
aaacacaggg gacacagctt aacaatgcaa cttttaatta ctgttttctt ttttcttaac   1440
ctactaatag tttgttgatc tgataagcaa gagtgggcgg gtgagaaaaa ccgaattggg   1500
tttagtcaat cactgcactg catgcaaaca agaaacgtgt cacacttgtg acgtcgggca   1560
ttcatatagg aagaacgcgg tgtgtaacac tgtgtacacc tcaaatacca ccccaaccca   1620
ctccctgtag tgaatcctct gtttagaaca ccaaagataa ggactagata ctactttctc   1680
tttttcgtat aatcttgtag acacttactt gatgattttt aactttttat ttctaaatga   1740
gacgaaatgc tgatgtatcc tttcattcag ctaacaaact agaaaaggtt atgttcattt   1800
ttcaaaaagg gaagtaagca aacaaatatt gccaactctt ctatttatgg atatcacaca   1860
tatcagcagg agtaataaat ttactcacag cacttgtttt caggacaaca cttcattttc   1920
aggaaatcta cttcctacag agccaaaatg ccatttagca ataaataaca cttgtcagcc   1980
tcagagcatt taaggaaact agacaagtaa aattatcctc tttgtaattt aatgaaaagg   2040
tacaacagaa taatgcatga tgaactcacc taattatgag gtgggaggag cgaaatctaa   2100
atttcttttg ctatagttat acatcaattt aaaaagcaaa aaaaaaaag ggggggcaa     2160
tctctctctg tgtcttctc tctctctctt cctctccctc tctcttttca ttgtgtatca    2220
gtttccatga aagacctgaa taccacttac ctcaaattaa gcatatgtgt tacttcaagt   2280
aatacgtttt gacataagat ggttgaccaa ggtgcttttc ttcggcttga gttcaccatc   2340
```

```
tcttcattca aactgcactt ttagccagag atgcaatata tccccactac tcaatactac    2400
ctctgaatgt tacaacgaat ttacagtcta gtacttatta catgctgcta tacacaagca    2460
atgcaagaaa aaaacttact gggtaggtga ttctaatcat ctgcagttct ttttgtacac    2520
ttaattacag ttaaagaagc aatctcctta ctgtgtttca gcatgactat gtattttcct    2580
atgttttttt aattaaaaat ttttaaaata cttgtttcag cttctctgct agatttctac    2640
attaacttga aaattttta accaagtcgc tcctaggttc ttaaggataa ttttcctcaa     2700
tcacactaca catcacacaa gatttgactg taatatttaa atattaccct ccaagtctgt    2760
acctcaaatg aattctttaa ggagatggac taattgactt gcaaagacct acctccagac    2820
ttcaaaagga atgaacttgt tacttgcagc attcatttgt tttttcaatg tttgaaatag    2880
ttcaaactgc agctaaccct agtcaaaact attttttgtaa aagacatttg atagaaagga    2940
acacgttttt acatactttt gcaaaataag taaataataa ataaaataaa agccaacctt    3000
caaagaaact tgaagctttg taggtgagat gcaacaagcc ctgcttttgc ataatgcaat    3060
caaaaatatg tgttttttaag attagttgaa tataagaaaa tgcttgacaa atattttcat    3120
gtattttaca caaatgtgat ttttgtaata tgtctcaacc agatttattt taaacgcttc    3180
ttatgtagag tttttatgcc tttctctcct agtgagtgtg ctgactttt aacatggtat     3240 tatcaactgg gccaggaggt agtttctcat gacggctttt gtcagtatgg cttttagtac    3300
tgaagccaaa tgaaactcaa aaccatctct cttccagctg cttcagggag gtagtttcaa    3360
aggccacata cctctctgag actggcagat cgctcactgt tgtgaatcac caaaggagct    3420
atggagagaa ttaaaactca acattactgt taactgtgcg ttaaataagc aaataaacag    3480
tggctcataa aaataaaagt cgcattccat atctttggat gggccttta gaaacctcat     3540 tggccagctc ataaaatgga agcaattgct catgttggcc aaacatggtg caccgagtga    3600
tttccatctc tggtaaagtt acactttat tccctgtatg ttgtacaatc aaaacacact     3660
actacctctt aagtcccagt atacctcatt tttcatactg aaaaaaaaag cttgtggcca    3720
atggaacagt aagaacatca taaaattttt atatatatag tttattttg tgggagataa     3780 atttatagg actgttcttt gctgttgttg gtcgcagcta cataagactg gacatttaac     3840
ttttctacca tttctgcaag ttaggtatgt ttgcaggaga aaagtatcaa gacgtttaac    3900
tgcagttgac tttctccctg ttcctttgag tgtcttctaa ctttattctt tgttctttat    3960
gtagaattgc tgtctatgat tgtactttga atcgcttgct tgttgaaaat atttctctag    4020
tgtattatca ctgtctgttc tgcacaataa acataacagc ctctgtgatc cccatgtgtt    4080
ttgattcctg ctctttgtta cagttccatt aaatgagtaa taaagtttgg tcaaaacaga    4140
aaaaaaaaaa                                                           4150

<210> SEQ ID NO 27
<211> LENGTH: 1595
<212> TYPE: DNA
<213> ORGANISM: Homo sapiens

<400> SEQUENCE: 27
gagtgagtga gagggcagag gaaatactca atctgtgcca ctcactgcct tgagcctgct      60
tcctcactcc aggactgcca gaggaagcaa tcaccaaaat gaagactgct ttaattttgc     120
tcagcatttt gggaatggcc tgtgctttct caatgaaaaa tttgcatcga agagtcaaaa     180
tagaggattc tgaagaaaat ggggtcttta agtacaggcc acgatattat ctttacaagc     240
```

```
atgcctactt ttatcctcat ttaaaacgat ttccagttca gggcagtagt gactcatccg   300
aagaaaatgg agatgacagt tcagaagagg aggaggaaga agaggagact tcaaatgaag   360
gagaaaacaa tgaagaatcg aatgaagatg aagactctga ggctgagaat accacacttt   420
ctgctacaac actgggctat ggagaggacg ccacgcctgg cacagggtat acagggttag   480
ctgcaatcca gcttcccaag aaggctgggg atataacaaa taaagctaca aaagagaagg   540
aaagtgatga agaagaagag gaggaagagg aaggaaatga aaacgaagaa agcgaagcag   600
aagtggatga aaacgaacaa ggcataaacg gcaccagtac caacagcaca gaggcagaaa   660
acggcaacgg cagcagcgga ggagacaatg agaagaagg ggaagaagaa agtgtcactg   720
gagccaatgc agaagacacc acagagaccg gaaggcaggg caagggcacc tcgaagacaa   780
caacctctcc aaatggtggg tttgaaccta caaccccacc acaagtctat agaaccactt   840 ccccacctt tgggaaaacc accaccgttg aatacgaggg ggagtacgaa tacacgggcg   900
ccaatgaata cgacaatgga tatgaaatct atgaaagtga aacgggggaa cctcgtgggg   960
acaattaccg agcctatgaa gatgagtaca gctactttaa aggacaaggc tacgatggct  1020
atgatggtca gaattactac caccaccagt gaagctccag cctgggatga attcatccat  1080
tctggctttg catccggcta ccattttcga agttcaactc aggaaggtgc aatataacaa  1140
atgtgcatat tataatgagg aatggtacta ccgttccaga ttttctgtaa ttgcttctgc  1200
aaagtaatag gcttcttgtc ccttttttt ctggcatgtt atggaatgat cattgtaaat  1260
caggaccatt tatcaagcag tacaccaact cataagatca aatttcattg aatggtttga  1320
ggttgtagct ctataaatag tagttttttaa catgcctgta gtattgctaa ctgcaaaaac  1380
atactctttg tacaagaagt gcttctaaga atttcattga cattaatgac actgtataca  1440
ataaatgtgt agtttcttaa tcgcactacc tatgcaacac tgtgtattag gtttatcatc  1500
ctcatgtatt tttatgtgac ctgtatgtat attctaatct acgagtttta tcacaaataa  1560
aaatgcaatc cttcaaatgt gttataatta aaaaa                              1595

<210> SEQ ID NO 28
<211> LENGTH: 1000
<212> TYPE: DNA
<213> ORGANISM: Homo sapiens

<400> SEQUENCE: 28
actctcattc cacgttctta actgttccat tttccgtatc tgcttcgggc ttccacctca    60
tttttttcgc tttgcccatt ctgtttcagc cagtcgccaa gaatcatgaa agtcgccagt   120
ggcagcaccg ccaccgccgc cgcgggcccc agctgcgcgc tgaaggccgg caagacagcg   180
agcggtgcgg gcgaggtggt gcgctgtctg tctgagcaga gcgtggccat ctcgcgctgc   240 gccggggcg ccggggcgcg cctgcctgcc ctgctggacg agcagcaggt aaacgtgctg   300
ctctacgaca tgaacggctg ttactcacgc ctcaaggagc tggtgcccac cctgccccag   360
aaccgcaagg tgagcaaggt ggagattctc cagcacgtca tcgactacat cagggacctt   420
cagttggagc tgaactcgga atccgaagtt ggaaccccg ggggccgagg gctgccggtc   480
cgggctccgc tcagcaccct caacggcgag atcagcgccc tgacgccga gcggcatgc   540 gttcctgcgg acgatcgcat cttgtgtcgc tgaagcgcct ccccagggac cggcggacc   600 ccagccatcc aggggcaag aggaattacg tgctctgtgg gtctccccca acgcgcctcg   660
ccggatctga gggagaacaa gaccgatcgg cggccactgc gcccttaact gcatccagcc   720
tggggctgag gctgaggcac tggcgaggag agggcgctcc tctctgcaca cctactagtc   780
```

| | |
|---|---|
| accagagact ttaggggggtg ggattccact cgtgtgtttc tattttttga aaagcagaca | 840 |
| ttttaaaaaa tggtcacgtt tggtgcttct cagatttctg aggaaattgc tttgtattgt | 900 |
| atattacaat gatcaccgac tgaaaatatt gttttacaat agttctgtgg ggctgttttt | 960 |
| ttgttattaa acaaataatt tagatggtgg taaaaaaaaa | 1000 |

<210> SEQ ID NO 29
<211> LENGTH: 1402
<212> TYPE: DNA
<213> ORGANISM: Homo sapiens

<400> SEQUENCE: 29

| | |
|---|---|
| ggggacgaag ggaagctcca gcgtgtggcc ccggcgagtg cggataaaag ccgccccgcc | 60 |
| gggctcgggc ttcattctga gccgagcccg gtgccaagcg cagctagctc agcaggcggc | 120 |
| agcggcggcc tgagcttcag ggcagccagc tccctcccgg tctcgccttc cctcgcggtc | 180 |
| agcatgaaag ccttcagtcc cgtgaggtcc gttaggaaaa acagcctgtc ggaccacagc | 240 |
| ctgggcatct cccggagcaa aacccctgtg gacgacccga tgagcctgct atacaacatg | 300 |
| aacgactgct actccaagct caaggagctg gtgcccagca tcccccagaa caagaaggtg | 360 |
| agcaagatgg aaatcctgca gcacgtcatc gactacatct tggacctgca gatcgccctg | 420 |
| gactcgcatc ccactattgt cagcctgcat caccagagac ccgggcagaa ccaggcgtcc | 480 |
| aggacgccgc tgaccaccct caacacggat atcagcatcc tgtccttgca ggcttctgaa | 540 |
| ttcccttctg agttaatgtc aaatgacagc aaagcactgt gtggctgaat aagcggtgtt | 600 |
| catgatttct tttattcttt gcacaacaac aacaacaaca aattcacgga atcttttaag | 660 |
| tgctgaactt attttttcaac catttcacaa ggaggacaag ttgaatggac cttttttaaaa | 720 |
| agaaaaaaaa aatggaagga aaactaagaa tgatcatctt cccagggtgt tctcttactt | 780 |
| ggactgtgat attcgttatt tatgaaaaag actttttaaat gcccttttctg cagttggaag | 840 |
| gttttctttta tatactattc ccaccatggg gagcgaaaac gttaaaatca caaggaattg | 900 |
| cccaatctaa gcagacttttg cctttttttca aaggtggagc gtgaatacca gaaggatcca | 960 |
| gtattcagtc acttaaatga agtcttttgg tcagaaatta ccttttttgac acaagcctac | 1020 |
| tgaatgctgt gtatatattt atatataaat atatctattt gagtgaaacc ttgtgaactc | 1080 |
| tttaattaga gttttcttgt atagtggcag agatgtctat ttctgcattc aaaagtgtaa | 1140 |
| tgatgtactt attcatgcta aacttttttat aaaagtttag ttgtaaactt aacccttttta | 1200 |
| tacaaaataa atcaagtgtg tttattgaat ggtgattgcc tgctttattt cagaggacca | 1260 |
| gtgctttgat ttttattatg ctatgttata actgaaccca ataaataca agttcaaatt | 1320 |
| tatgtagact gtataagatt ataataaaac atgtctgaag tcaaaaaaaa aaaaaaaaa | 1380 |
| aaaaaaaaaa aaaaaaaaaa aa | 1402 |

<210> SEQ ID NO 30
<211> LENGTH: 1252
<212> TYPE: DNA
<213> ORGANISM: Homo sapiens

<400> SEQUENCE: 30

| | |
|---|---|
| gatctgggggt gctgccagga aaaagcaaat tctggaagtt aatggttttg agtgattttt | 60 |
| aaatcccttgc tggcggagag gcccgcctct ccccggtatc agcgcttcct cattctttga | 120 |
| atccgcggct ccgcggtctt cggcgtcaga ccagccggag gaagcctgtt tgcaatttaa | 180 |

```
gcgggctgtg aacgcccagg gccggcgggg gcagggccga ggcggccat tttgaataaa      240
gaggcgtgcc ttccaggcag gctctataag tgaccgccgc ggcgagcgtg cgcgcgttgc      300
aggtcactgt agcgggactt cttttggttt tctttctctt tggggcacct ctggactcac      360
tccccagcat gaaggcgctg agccggtgc gcggctgcta cgaggcggtg tgctgcctgt      420
cggaacgcag tctggccatc gcccgggggcc gagggaaggg cccggcagct gaggagccgc      480
tgagcttgct ggacgacatg aaccactgct actcccgcct gcgggaactg gtacccggag      540
tcccgagagg cactcagctt agccaggtgg aaatcctaca gcgcgtcatc gactacattc      600
tcgacctgca ggtagtcctg gccgagccag cccctggacc ccctgatggc ccccaccttc      660
ccatccagac agccgagctc actccggaac ttgtcatctc caacgacaaa aggagctttt      720
gccactgact cggccgtgtc ctgacacctc cagaacgcag gtgctggcgc ccgttctgcc      780
tgggaccccg ggaacctctc ctgccggaag ccggacggca gggatgggcc ccaacttcgc      840
cctgcccact tgacttcacc aaatcccttc ctggagacta aacctggtgc tcaggagcga      900
aggactgtga acttgtggcc tgaagagcca gagctagctc tggccaccag ctgggcgacg      960
tcaccctgct cccaccccac ccccaagttc taaggtctct tcagagcgtg gaggtgtgga     1020
aggagtggct gctctccaaa ctatgccaag gcggcggcag agctggtctt ctggtctcct     1080
tggagaaagg ttctgttgcc ctgatttatg aactctataa tagagtatat aggttttgta     1140
ccttttttac aggaaggtga cttctgtaa caatgcgatg tatattaaac tttttataaa     1200
agttaacatt ttgcataata aacgattttt aaacacttga aaaaaaaaa aa              1252

<210> SEQ ID NO 31
<211> LENGTH: 2381
<212> TYPE: DNA
<213> ORGANISM: Homo sapiens

<400> SEQUENCE: 31
actgccgcgg ccctgctgct cagggcacat gcctcccctc cccaggccgc ggcccagctg       60
accctcgggg ctccccggc agcggacagg gaagggttaa aggcccccgg ctccctgccc      120
cctgccctgg ggaaccccctg gcccctgtggg gacatgaact gtgtttgccg cctggtcctg      180
gtcgtgctga gcctgtggcc agatacagct gtcgcccctg ggccaccacc tggcccccct      240
cgagtttccc cagaccctcg ggccgagctg gacagcaccg tgctcctgac ccgctctctc      300
ctggcggaca cgcggcagct ggctgcacag ctgagggaca aattcccagc tgacggggac      360
cacaacctgg attccctgcc cacccctggcc atgagtgcgg gggcactggg agctctacag      420
ctcccaggtg tgctgacaag gctgcgagcg gacctactgt cctacctgcg gcacgtgcag      480
tggctgcgcc gggcaggtgg ctcttccctg aagaccctgg agcccgagct gggcaccctg      540
caggcccgac tggaccggct gctgcgccgg ctgcagctcc tgatgtcccg cctggccctg      600
ccccagccac ccccggaccc gccggcgccc ccgctggcgc ccccctcctc agcctggggg      660
ggcatcaggg ccgcccacgc catcctgggg gggctgcacc tgacacttga ctgggccgtg      720
aggggactgc tgctgctgaa gactcggctg tgacccgggg cccaaagcca ccaccgtcct      780
tccaaagcca gatcttattt attatttat ttcagtactg ggggcgaaac agccaggtga      840
tccccccgcc attatctccc cctagttaga gacagtcctt ccgtgaggcc tgggggggcat      900
ctgtgcctta tttatactta tttatttcag gagcagggt gggaggcagg tggactcctg      960
ggtccccgag gaggaggga ctggggtccc ggattcttgg gtctccaaga agtctgtcca     1020
cagacttctg ccctggctct tccccatcta ggcctgggca ggaacatata ttatttattt     1080
```

```
aagcaattac tttttcatgtt ggggtgggga cggaggggaa agggaagcct gggttttttgt    1140 acaaaaatgt gagaaacctt tgtgagacag agaacaggga attaaatgtg tcatacatat    1200
ccacttgagg gcgatttgtc tgagagctgg ggctggatgc ttgggtaact ggggcagggc    1260
aggtggaggg gagacctcca ttcaggtgga ggtcccgagt gggcggggca gcgactggga    1320
gatgggtcgg tcacccagac agctctgtgg aggcagggtc tgagccttgc ctggggcccc    1380
gcactgcata gggccttttg tttgttttttt gagatggagt ctcgctctgt tgcctaggct    1440
ggagtgcagt gaggcaatct gaggtcactg caacctccac ctcccgggtt caagcaattc    1500
tcctgcctca gcctcccgat tagctgggat tacaggtgtg caccaccatg cccagctaat    1560
tatttatttc ttttgtattt ttagtagaga cagggtttca ccatgttggc caggctggtt    1620
tcgaactcct gacctcaggt gatcctcctg cctcggcctc ccaaagtgct gggattacag    1680
gtgtgagcca ccacacctga cccataggtc ttcaataaat atttaatgga aggttccaca    1740
agtcaccctg tgatcaacag tacccgtatg ggacaaagct gcaaggtcaa gatggttcat    1800
tatggctgtg ttcaccatag caaactggaa acaatctaga tatccaacag tgagggttaa    1860
gcaacatggt gcatctgtgg atagaacgcc acccagccgc ccggagcagg gactgtcatt    1920
cagggaggct aaggagagag gcttgcttgg gatatagaaa gatatcctga cattggccag    1980
gcatggtggc tcacgcctgt aatcctggca ctttgggagg acgaagcgag tggatcactg    2040
aagtccaaga gttcgagacc ggcctgcgag acatggcaaa accctgtctc aaaaaagaaa    2100
gaatgatgtc ctgacatgaa acagcaggct acaaaaccac tgcatgctgt gatcccaatt    2160
ttgtgttttt ctttctatat atggattaaa acaaaaatcc taagggaaa tacgccaaaa    2220 tgttgacaat gactgtctcc aggtcaaagg agagaggtgg gattgtgggt gacttttaat    2280
gtgtatgatt gtctgtattt tacagaattt ctgccatgac tgtgtatttt gcatgacaca    2340
ttttaaaaat aataaacact atttttagaa taacagaaaa a                       2381
```

<210> SEQ ID NO 32
<211> LENGTH: 1201
<212> TYPE: DNA
<213> ORGANISM: Homo sapiens

<400> SEQUENCE: 32

```
aatattagag tctcaacccc caataaatat aggactggag atgtctgagg ctcattctgc      60
cctcgagccc accgggaacg aaagagaagc tctatctccc ctccaggagc ccagctatga     120
actccttctc cacaagcgcc ttcggtccag ttgccttctc cctggggctg ctcctggtgt     180
tgcctgctgc cttccctgcc ccagtacccc caggagaaga ttccaaagat gtagccgccc     240
cacacagaca gccactcacc tcttcagaac gaattgacaa acaaattcgg tacatcctcg     300
acggcatctc agccctgaga aaggagacat gtaacaagag taacatgtgt gaaagcagca     360
aagaggcact ggcagaaaac aacctgaacc ttccaaagat ggctgaaaaa gatggatgct     420
tccaatctgg attcaatgag gagacttgcc tggtgaaaat catcactggt cttttggagt     480
ttgaggtata cctagagtac ctccagaaca gatttgagag tagtgaggaa caagccagag     540
ctgtgcagat gagtacaaaa gtcctgatcc agttcctgca gaaaaaggca agaatctag     600 atgcaataac caccccctgac ccaaccacaa atgccagcct gctgacgaag ctgcaggcac     660
agaaccagtg gctgcaggac atgacaactc atctcattct gcgcagcttt aaggagttcc     720
tgcagtccag cctgagggct cttcggcaaa tgtagcatgg gcacctcaga ttgttgttgt     780
```

| | |
|---|---|
| taatgggcat tccttcttct ggtcagaaac ctgtccactg ggcacagaac ttatgttgtt | 840 |
| ctctatggag aactaaaagt atgagcgtta ggacactatt ttaattattt ttaatttatt | 900 |
| aatatttaaa tatgtgaagc tgagttaatt tatgtaagtc atatttatat ttttaagaag | 960 |
| taccacttga acatttttat gtattagttt tgaaataata atggaaagtg gctatgcagt | 1020 |
| ttgaatatcc tttgtttcag agccagatca tttcttggaa agtgtaggct tacctcaaat | 1080 |
| aaatggctaa cttatacata tttttaaaga aatatttata ttgtatttat ataatgtata | 1140 |
| aatggttttt ataccaataa atggcatttt aaaaaattca gcaaaaaaaa aaaaaaaaa | 1200 |
| a | 1201 |

<210> SEQ ID NO 33
<211> LENGTH: 5294
<212> TYPE: DNA
<213> ORGANISM: Homo sapiens

<400> SEQUENCE: 33

| | |
|---|---|
| ctagggcatg gcatcccacg tgggtgtcag cacggccgca gaagaaccac ttctctggcc | 60 |
| cacccatgcc tgctaggcca tgcttcttca gaagtggcca caactctcct gacgtctcca | 120 |
| gagccggtca ttccacccag ggggacttca gctgccactg gacacttcaa ttgtacgctg | 180 |
| cgaccagttg ccaggaagga gagggctggc aagagagccg cggcagccgt ggcagggtgt | 240 |
| aggggacggt ggacgccag ggcccccccc tctctctctt tctctctctc tctcttgctt | 300 |
| ggtttctgta atgaggaagt tctccgcagc tcagtttcct ttccctcact gagcgcctga | 360 |
| aacaggaagt cagtcagtta agctggtggc agcagccgag gccaccaaga ggcaacgggc | 420 |
| ggcaggttgc agtggagggg cctccgctcc cctcggtggt gtgtgggtcc tgggggtgcc | 480 |
| tgccggcccg gccgaggagg cccacgccca ccatggtccc ctgctggaac catggcaaca | 540 |
| tcacccgctc caaggcggag gagctgcttt ccaggacagg caaggacggg agcttcctcg | 600 |
| tgcgtgccag cgagtccatc tcccgggcat acgcgctctg cgtgctgtat cggaattgcg | 660 |
| tttacactta cagaattctg cccaatgaag atgataaatt cactgttcag gcatccgaag | 720 |
| gcgtctccat gaggttcttc accaagctgg accagctcat cgagttttac aagaaggaaa | 780 |
| acatggggct ggtgacccat ctgcaatacc ctgtgccgct ggaggaagag gacacaggcg | 840 |
| acgaccctga ggaggacaca gtagaaagtg tcgtgtctcc acccgagctg ccccaagaa | 900 |
| acatcccgct gactgccagc tcctgtgagg ccaaggaggt tccttttttca aacgagaatc | 960 |
| cccgagcgac cgagaccagc cggccgagcc tctccgagac attgttccag cgactgcaaa | 1020 |
| gcatggacac cagtgggctt ccagaagagc atcttaaggc catccaagat tatttaagca | 1080 |
| ctcagctcgc ccaggactct gaatttgtga agacagggtc cagcagtctt cctcacctga | 1140 |
| agaaactgac cacactgctc tgcaaggagc tctatggaga agtcatccgg accctcccat | 1200 |
| ccctggagtc tctgcagagg ttatttgacc agcagctctc cccgggcctc cgtccacgtc | 1260 |
| ctcaggttcc tggtgaggcc aatcccatca acatggtgtc caagctcagc caactgacaa | 1320 |
| gcctgttgtc gtccattgaa gacaaggtca aggccttgct gcacgagggt cctgagtctc | 1380 |
| cgcaccggcc ctcccttatc cctccagtca cctttgaggt gaaggcagag tctctgggga | 1440 |
| ttcctcagaa aatgcagctc aaagtcgacg ttgagtctgg gaaactgatc attaagaagt | 1500 |
| ccaaggatgg ttctgaggac aagttctaca gccacaagaa aatcctgcag ctcattaagt | 1560 |
| cacagaaaatt tctgaataag ttggtgatct tggtggaaac agagaaggag aagatcctgc | 1620 |
| ggaaggaata tgttttttgct gactccaaaa agagagaagg cttctgccag ctccctgcagc | 1680 |

```
agatgaagaa caagcactca gagcagccgg agcccgacat gatcaccatc ttcatcggca    1740
cctggaacat gggtaacgcc ccccctccca agaagatcac gtcctggttt ctctccaagg    1800
ggcagggaaa gacgcgggac gactctgcgg actacatccc ccatgacatt tacgtgatcg    1860
gcacccaaga ggaccccctg agtgagaagg agtggctgga gatcctcaaa cactccctgc    1920
aagaaatcac cagtgtgact tttaaaacag tcgccatcca cacgctctgg aacatccgca    1980
tcgtggtgct ggccaagcct gagcacgaga accggatcag ccacatctgt actgacaacg    2040
tgaagacagg cattgcaaac acactgggga caagggagc cgtgggggtg tcgttcatgt     2100
tcaatggaac ctccttaggg ttcgtcaaca gccacttgac ttcaggaagt gaaaagaaac    2160
tcaggcgaaa ccaaaactat atgaacattc tccggttcct ggccctgggc gacaagaagc    2220
tgagtccctt taacatcact caccgcttca cgcacctctt ctggtttggg gatcttaact    2280
accgtgtgga tctgcctacc tgggaggcag aaaccatcat ccagaaaatc aagcagcagc    2340
agtacgcaga cctcctgtcc cacgaccagc tgctcacaga gaggagggag cagaaggtct    2400
tcctacactt cgaggaggaa gaaatcacgt ttgccccaac ctaccgtttt gagagactga    2460
ctcgggacaa atacgcctac accaagcaga aagcgacagg gatgaagtac aacttgcctt    2520
cctggtgtga ccgagtcctc tggaagtctt atccctggt gcacgtggtg tgtcagtctt     2580
atggcagtac cagcgacatc atgacgagtg accacagccc tgtctttgcc acatttgagg    2640
caggagtcac ttcccagttt gtctccaaga acggtcccgg gactgttgac agccaaggac    2700
agattgagtt tctcaggtgc tatgccacat tgaagaccaa gtcccagacc aaattctacc    2760
tggagttcca ctcgagctgc ttggagagtt ttgtcaagag tcaggaagga gaaaatgaag    2820
aaggaagtga gggggagctg gtggtgaagt ttggtgagac tcttccaaag ctgaagccca    2880
ttatctctga ccctgagtac ctgctagacc agcacatcct catcagcatc aagtcctctg    2940
acagcgacga atcctatggc gagggctgca ttgcccttcg gttagaggcc acagaaacgc    3000
agctgcccat ctacacgcct ctcacccacc atggggagtt gacaggccac ttccaggggg    3060
agatcaagct gcagacctct cagggcaaga cgagggagaa gctctatgac tttgtgaaga    3120
cggagcgtga tgaatccagt gggccaaaga ccctgaagag cctcaccagc cacgaccca    3180 tgaagcagtg ggaagtcact agcagggccc ctccgtgcag tggctccagc atcactgaaa    3240
tcatcaaccc caactacatg ggagtggggc cctttgggcc accaatgccc ctgcacgtga    3300
agcagacctt gtcccctgac cagcagccca cagcctggag ctacgaccag ccgcccaagg    3360
actccccgct ggggccctgc aggggagaaa gtcctccgac acctcccggc cagccgccca    3420
tatcacccaa gaagttttta ccctcaacag caaaccgggg tctccctccc aggacacagg    3480
agtcaaggcc cagtgacctg gggaagaacg caggggacac gctgcctcag gaggacctgc    3540
cgctgacgaa gcccgagatg tttgagaacc ccctgtatgg gtccctgagt tccttcccta    3600
agcctgctcc caggaaggac caggaatccc ccaaaatgcc gcggaaggaa ccccgccct    3660 gcccggaacc cggcatcttg tcgcccagca tcgtgctcac caaagcccag gaggctgatc    3720
gcggcgaggg gccccggcaag caggtgcccg cgccccggct gcgctccttc acgtgctcat    3780
cctctgccga gggcagggcg gccggcgggg acaagagcca agggaagccc aagacccggg    3840
tcagctccca ggccccggtg ccggccaaga ggcccatcaa gccttccaga tcggaaatca    3900
accagcagac cccgcccacc ccgacgccgc ggccgccgct gccagtcaag agcccggcgg    3960
tgctgcacct ccagcactcc aagggccgcg actaccgcga caacaccgag ctcccgcatc    4020
```

| | |
|---|---|
| acggcaagca ccggccggag gaggggccac cagggcctct aggcaggact gccatgcagt | 4080 |
| gaagccctca gtgagctgcc actgagtcgg gagcccagag gaacggcgtg aagccactgg | 4140 |
| accctctccc gggacctcct gctggctcct cctgcccagc ttcctatgca aggctttgtg | 4200 |
| ttttcaggaa agggcctagc ttctgtgtgg cccacagagt tcactgcctg tgagacttag | 4260 |
| caccaagtgc tgaggctgga agaaaaacgc acaccagacg ggcaacaaac agtctgggtc | 4320 |
| cccagctcgc tcttggtact tgggacccca gtgcctcgtt gagggcgcca ttctgaagaa | 4380 |
| aggaactgca gcgccgattt gagggtggag atatagataa taataatatt aataataata | 4440 |
| atggccacat ggatcgaaca ctcatgatgt gccaagtgct gtgctaagtg ctttacgaac | 4500 |
| attcgtcata tcaggatgac ctcgagagct gaggctctag ccacctaaaa ccacgtgccc | 4560 |
| aaacccacca gtttaaaacg gtgtgtgttc ggaggggtga agcattaag aagcccagtg | 4620 |
| ccctcctgga gtgagacaag ggctcggcct taaggagctg aagagtctgg gtagcttgtt | 4680 |
| tagggtacaa gaagcctgtt ctgtccagct tcagtgacac aagctgcttt agctaaagtc | 4740 |
| ccgcgggttc cggcatggct aggctgagag cagggatcta cctggcttct cagttctttg | 4800 |
| gttggaagga gcaggaaatc agctcctatt ctccagtgga gagatctggc ctcagcttgg | 4860 |
| gctagagatg ccaaggcctg tgccaggttc cctgtgccct cctcgaggtg ggcagccatc | 4920 |
| accagccaca gttaagccaa gcccccaac atgtattcca tcgtgctggt agaagagtct | 4980 |
| ttgctgttgc tcccgaaagc cgtgctctcc agcctggctg ccaggagggg tgggcctctt | 5040 |
| ggttccaggc tcttgaaata gtgcagcctt ttcttcctat ctctgtggct ttcagctctg | 5100 |
| cttccttggt tattaggaga atagatgggt gatgtctttc cttatgttgc ttttcaaca | 5160 |
| tagcagaatt aatgtaggga gctaaatcca gtggtgtgtg tgaatgcaga agggaatgca | 5220 |
| ccccacattc ccatgatgga agtctgcgta accaataaat tgtgccttc tcactcaaaa | 5280 |
| aaaaaaaaaa aaaa | 5294 |

<210> SEQ ID NO 34
<211> LENGTH: 3879
<212> TYPE: DNA
<213> ORGANISM: Homo sapiens

<400> SEQUENCE: 34

| | |
|---|---|
| atcagacgcg cagaggaggc ggggccgcgg ctggtttcct gccggggggc ggctctgggc | 60 |
| cgccgagtcc cctcctcccg cccctgagga ggaggagccg ccgccacccg ccgcgcccga | 120 |
| cacccgggag gccccgccag cccgcgggag aggcccagcg ggagtcgcgg aacagcaggc | 180 |
| ccgagcccac cgcgccgggc cccggacgcc gcgcggaaaa gatgaattta caaccaattt | 240 |
| tctggattgg actgatcagt tcagtttgct gtgtgtttgc tcaaacagat gaaaatagat | 300 |
| gtttaaaagc aaatgccaaa tcatgtggag aatgtataca agcagggcca aattgtgggt | 360 |
| ggtgcacaaa ttcaacattt ttacaggaag gaatgcctac ttctgcacga tgtgatgatt | 420 |
| tagaagcctt aaaaagaag ggttgccctc cagatgacat agaaaatccc agaggctcca | 480 |
| aagatataaa gaaaataaa aatgtaacca accgtagcaa aggaacagca gagaagctca | 540 |
| agccagagga tattactcag atccaaccac agcagttggt tttgcgatta agatcagggg | 600 |
| agccacagac atttacatta aaattcaaga gagctgaaga ctatcccatt gacctctact | 660 |
| accttatgga cctgtcttac tcaatgaaag acgatttgga gaatgtaaaa agtcttggaa | 720 |
| cagatctgat gaatgaaatg aggaggatta cttcggactt cagaattgga tttggctcat | 780 |
| tgtgtggaaaa gactgtgatg ccttacatta gcacaacacc agctaagctc aggaacccct | 840 |

-continued

```
gcacaagtga acagaactgc accagcccat ttagctacaa aaatgtgctc agtcttacta    900
ataaaggaga agtatttaat gaacttgttg gaaaacagcg catatctgga aatttggatt    960
ctccagaagg tggtttcgat gccatcatgc aagttgcagt ttgtggatca ctgattggct   1020
ggaggaatgt tacacggctg ctggtgtttt ccacagatgc cgggtttcac tttgctggag   1080
atgggaaact tggtggcatt gttttaccaa atgatggaca atgtcacctg gaaaataata   1140
tgtacacaat gagccattat tatgattatc cttctattgc tcaccttgtc cagaaactga   1200
gtgaaaataa tattcagaca attttttgcag ttactgaaga atttcagcct gtttacaagg   1260
agctgaaaaa cttgatccct aagtcagcag taggaacatt atctgcaaat tctagcaatg   1320
taattcagtt gatcattgat gcatacaatt ccctttcctc agaagtcatt ttggaaaacg   1380
gcaaattgtc agaaggcgta acaataagtt acaaatctta ctgcaagaac ggggtgaatg   1440
gaacagggga aaatggaaga aaatgttcca atatttccat tggagatgag gttcaatttg   1500
aaattagcat aacttcaaat aagtgtccaa aaaaggattc tgacagcttt aaaattaggc   1560
ctctgggctt tacggaggaa gtagaggtta ttcttcagta catctgtgaa tgtgaatgcc   1620
aaagcgaagg catccctgaa agtcccaagt gtcatgaagg aaatgggaca tttgagtgtg   1680
gcgcgtgcag gtgcaatgaa gggcgtgttg gtagacattg tgaatgcagc acagatgaag   1740
ttaacagtga agacatggat gcttactgca ggaaagaaaa cagttcagaa atctgcagta   1800
acaatggaga gtgcgtctgc ggacagtgtg tttgtaggaa gagggataat acaaatgaaa   1860
tttattctgg caaattctgc gagtgtgata atttcaactg tgatagatcc aatggcttaa   1920
tttgtggagg aaatggtgtt tgcaagtgtc gtgtgtgtga gtgcaacccc aactacactg   1980
gcagtgcatg tgactgttct ttggatacta gtacttgtga agccagcaac ggacagatct   2040
gcaatggccg gggcatctgc gagtgtggtg tctgtaagtg tacagatccg aagtttcaag   2100
ggcaaacgtg tgagatgtgt cagacctgcc ttggtgtctg tgctgagcat aaagaatgtg   2160
ttcagtgcag agccttcaat aaaggagaaa agaaagacac atgcacacag gaatgttcct   2220
attttaacat taccaaggta gaaagtcggg acaaattacc ccagccggtc caacctgatc   2280
ctgtgtccca ttgtaaggag aaggatgttg acgactgttg gttctatttt acgtattcag   2340
tgaatgggaa caacgaggtc atggttcatg ttgtggagaa tccagagtgt cccactggtc   2400
cagacatcat tccaattgta gctggtgtgg ttgctgggaat tgttcttatt ggccttgcat   2460
tactgctgat atggaagctt ttaatgataa ttcatgacag aagggagttt gctaaatttg   2520
aaaaggagaa aatgaatgcc aaatgggaca cgggtgaaaa tcctatttat aagagtgccg   2580
taacaactgt ggtcaatccg aagtatgagg gaaaatgagt actgccgtg caaatcccac   2640
aacactgaat gcaaagtagc aatttccata gtcacagtta ggtagcttta gggcaatatt   2700
gccatggttt tactcatgtg caggttttga aaatgtacaa tatgtataat ttttaaaatg   2760
ttttattatt ttgaaaataa tgttgtaatt catgccaggg actgacaaaa gacttgagac   2820
aggatggtta ctcttgtcag ctaaggtcac attgtgcctt tttgacccttt tcttcctgga   2880
ctattgaaat caagcttatt ggattaagtg atatttctat agcgattgaa agggcaatag   2940
ttaaagtaat gagcatgatg agagtttctg ttaatcatgt attaaaactg attttttagct   3000
ttacaaatat gtcagtttgc agttatgcag aatccaaagt aaatgtcctg ctagctagtt   3060
aaggattgtt ttaaatctgt tattttgcta tttgcctgtt agacatgact gatgacatat   3120
ctgaaagaca agtatgttga gagttgctgg tgtaaaaatac gtttgaaata gttgatctac   3180
```

-continued

| aaaggccatg | ggaaaaattc | agagagttag | gaaggaaaaa | ccaatagctt | taaaacctgt | 3240 |
| gtgccatttt | aagagttact | taatgtttgg | taacttttat | gccttcactt | tacaaattca | 3300 |
| agccttagat | aaaagaaccg | agcaattttc | tgctaaaaag | tccttgattt | agcactattt | 3360 |
| acatacaggc | catactttac | aaagtatttg | ctgaatgggg | accttttgag | ttgaatttat | 3420 |
| tttattattt | ttattttgtt | taatgtctgg | tgctttctgt | caccctcttct | aatctttttaa | 3480 |
| tgtatttgtt | tgcaattttg | gggtaagact | tttttttatga | gtacttttc | tttgaagttt | 3540 |
| tagcggtcaa | tttgcctttt | taatgaacat | gtgaagttat | actgtggcta | tgcaacagct | 3600 |
| ctcacctacg | cgagtcttac | tttgagttag | tgccataaca | gaccactgta | tgtttacttc | 3660 |
| tcaccatttg | agttgcccat | cttgtttcac | actagtcaca | ttcttgtttt | aagtgccttt | 3720 |
| agttttaaca | gttcactttt | tacagtgcta | tttactgaag | ttatttatta | aatatgccta | 3780 |
| aaatacttaa | atcggatgtc | ttgactctga | tgtatttat | caggttgtgt | gcatgaaatt | 3840 |
| tttatagatt | aaagaagttg | aggaaaagca | aaaaaaaa | | | 3879 |

<210> SEQ ID NO 35
<211> LENGTH: 3392
<212> TYPE: DNA
<213> ORGANISM: Homo sapiens

<400> SEQUENCE: 35

| gcggagccag | cccctcccct | acccggagca | gcccgctggg | gccgtcccga | gcggcgacac | 60 |
| actaggagtc | ccggccggcc | agccagggca | gccgcggtcc | cgggactcgg | ccgtgagtgc | 120 |
| tgcgggacga | atggtggcgg | cggggcgcgg | gccagcgcgg | gcgccgtgag | ccggagctgc | 180 |
| gcgcggggca | tgcggctgcg | gcccccggcc | ctcggccccc | gcgctccggc | cccagccccg | 240 |
| gccgccggcc | cccgcggagt | gcagcgaccg | cgccgccgct | gagggaggcg | ccccaccatg | 300 |
| ccgcgggccc | cggcgccgct | gtacgcctgc | ctcctggggc | tctgcgcgct | cctgccccgg | 360 |
| ctcgcaggtc | tcaacatatg | cactagtgga | agtgccacct | catgtgaaga | atgtctgcta | 420 |
| atccacccaa | aatgtgcctg | gtgctccaaa | gaggacttcg | gaagcccacg | gtccatcacc | 480 |
| tctcggtgtg | atctgagggc | aaaccttgtc | aaaaatggct | gtggaggtga | gatagagagc | 540 |
| ccagccagca | gcttccatgt | cctgaggagc | ctgcccctca | gcagcaaggg | ttcgggctct | 600 |
| gcaggctggg | acgtcattca | gatgacacca | caggagattg | ccgtgaacct | ccggcccggt | 660 |
| gacaagacca | ccttccagct | acaggttcgc | caggtggagg | actatcctgt | ggacctgtac | 720 |
| tacctgatgg | acctctccct | gtccatgaag | gatgacttgg | acaatatccg | gagcctgggc | 780 |
| accaaactcg | cggaggagat | gaggaagctc | accagcaact | tccggttggg | atttgggtct | 840 |
| tttgttgata | aggacatctc | tccttttctcc | tacacggcac | cgaggtacca | gaccaatccg | 900 |
| tgcattggtt | acaagttgtt | tccaaattgc | gtccctcct | ttgggttccg | ccatctgctg | 960 |
| cctctcacag | acagagtgga | cagcttcaat | gaggaagttc | ggaaacagag | ggtgtcccgg | 1020 |
| aaccgagatg | cccctgaggg | gggctttgat | gcagtactcc | aggcagccgt | ctgcaaggag | 1080 |
| aagattggct | ggcgaaagga | tgcactgcat | ttgctggtgt | tcacaacaga | tgatgtgccc | 1140 |
| cacatcgcat | tggatggaaa | atttgggagc | ctggtcagc | cacacgatgg | ccagtgccac | 1200 |
| ctgaacgagg | ccaacgagta | cactgcatcc | aaccagatgg | actatccatc | ccttgccttg | 1260 |
| cttggagaga | aattggcaga | gaacaacatc | aacctcatct | ttgcagtgac | aaaaaaccat | 1320 |
| tatatgctgt | acaagaattt | tacagccctg | ataccctggaa | caacggtgga | gatttttagat | 1380 |
| ggagactcca | aaaatattat | tcaactgatt | attaatgcat | acaatagtat | ccggtctaaa | 1440 |

| | |
|---|---|
| gtggagttgt cagtctggga tcagcctgag gatcttaatc tcttctttac tgctacctgc | 1500 |
| caagatgggg tatcctatcc tggtcagagg aagtgtgagg gtctgaagat tggggacacg | 1560 |
| gcatcttttg aagtatcatt ggaggcccga agctgtccca gcagacacac ggagcatgtg | 1620 |
| tttgccctgc ggccggtggg attccggac agcctggagg tggggtcac ctacaactgc | 1680 |
| acgtgcggct gcagcgtggg gctggaaccc aacagtgcca ggtgcaacgg gagcgggacc | 1740 |
| tatgtctgcg gcctgtgtga gtgcagcccc ggctacctgg caccaggtg cgagtgccag | 1800 |
| gatggggaga accagagcgt gtaccagaac ctgtgccggg aggcagaggg caagccactg | 1860 |
| tgcagcgggc gtggggactg cagctgcaac cagtgctcct gcttcgagag cgagttcggc | 1920 |
| aagatctatg ggcctttctg tgagtgcgac aacttctcct gtgccaggaa caagggagtc | 1980 |
| ctctgctcag gccatggcga gtgtcactgc ggggaatgca agtgccatgc aggttacatc | 2040 |
| ggggacaact gtaactgctc gacagacatc agcacatgcc ggggcagaga tggccagatc | 2100 |
| tgcagcgagc gtgggcactg tctctgtggg cagtgccaat gcacggagcc gggggccttt | 2160 |
| ggggagatgt gtgagaagtg ccccacctgc ccggatgcat gcagcaccaa gagagattgc | 2220 |
| gtcgagtgcc tgctgctcca ctctgggaaa cctgacaacc agacctgcca cagcctatgc | 2280 |
| agggatgagg tgatcacatg ggtggacacc atcgtgaaag atgaccagga ggctgtgcta | 2340 |
| tgtttctaca aaaccgccaa ggactgcgtc atgatgttca cctatgtgga gctccccagt | 2400 |
| gggaagtcca acctgaccgt cctcagggag ccagagtgtg gaaacacccc caacgccatg | 2460 |
| accatcctcc tggctgtggt cggtagcatc ctccttgttg ggcttgcact cctggctatc | 2520 |
| tggaagctgc ttgtcaccat ccacgaccgg aggagtttg caaagtttca gagcgagcga | 2580 |
| tccagggccc gctatgaaat ggcttcaaat ccattataca gaaagcctat ctccacgcac | 2640 |
| actgtggact tcaccttcaa caagttcaac aaatcctaca atggcactgt ggactgatgt | 2700 |
| ttccttctcc gaggggctgg agcggggatc tgatgaaaag gtcagactga acgccttgc | 2760 |
| acggctgctc ggcttgatca cagctcccta ggtaggcacc acagagaaga ccttctagtg | 2820 |
| agcctgggcc aggagcccac agtgcctgta caggaaggtg cctggccatg tcacctggct | 2880 |
| gctaggccag agccatgcca ggctgcgtcc ctccgagctt gggataaagc aaggggacct | 2940 |
| tggcactctc agctttccct gccacatcca gcttgttgtc ccaatgaaat actgagatgc | 3000 |
| tgggctgtct ctcccttcca ggaatgctgg gcccccagcc tggccagaca agacgactgt | 3060 |
| caggaagggt cggagtctgt aaaaccagca tacagtttgg cttttttcac attgatcatt | 3120 |
| tttatatgaa ataaaagat cctgcattta tggtgtagtt ctgagtcctg agacttttcc | 3180 |
| gcgtgatggc tatgccttgc acacaggtgt tggtgatggg gctgttgaga tgcctgttga | 3240 |
| aggtacatcg tttgcaaatg tcagtttcct ctcctgtccg tgtttgttta gtactttat | 3300 |
| aatgaaaaga aacaagattg tttgggattg gaagtaaaga ttaaaaccaa aagaatttgt | 3360 |
| gtttgtctga taaaaaaaaa aaaaaaaaaa aa | 3392 |

<210> SEQ ID NO 36
<211> LENGTH: 3338
<212> TYPE: DNA
<213> ORGANISM: Homo sapiens
<400> SEQUENCE: 36

| | |
|---|---|
| gacatcatgg gctatttta gggttgact ggtagcagat aagtgttgag ctcgggctgg | 60 |
| ataagggctc agagttgcac tgagtgtggc tgaagcagcg aggcgggagt ggaggtgcgc | 120 |

```
ggagtcaggc agacagacag acacagccag ccagccaggt cggcagtata gtccgaactg    180
caaatcttat tttcttttca ccttctctct aactgcccag agctagcgcc tgtggctccc    240
gggctggtgt ttcgggagtg tccagagagc ctggtctcca gccgccccg ggaggagagc     300 cctgctgccc aggcgctgtt gacagcggcg gaaagcagcg gtacccacgc gcccgccggg    360
ggaagtcggc gagcggctgc agcagcaaag aactttcccg gctgggagga ccggagacaa    420
gtggcagagt cccggagcga acttttgcaa gcctttcctg cgtcttaggc ttctccacgg    480
cggtaaagac cagaaggcgg cggagagcca cgcaagagaa gaaggacgtg cgctcagctt    540
cgctcgcacc ggttgttgaa cttgggcgag cgcgagccgc ggctgccggg cgccccctcc    600
ccctagcagc ggaggagggg acaagtcgtc ggagtccggg cggccaagac ccgccgccgg    660
ccggccactg cagggtccgc actgatccgc tccgcgggga gagccgctgc tctgggaagt    720
gagttcgcct gcggactccg aggaaccgct gcgcccgaag agcgctcagt gagtgaccgc    780
gacttttcaa agccgggtag cgcgcgcgag tcgacaagta agagtgcggg aggcatctta    840
attaaccctg cgctccctgg agcgagctgg tgaggagggc gcagcgggga cgacagccag    900
cgggtgcgtg cgctcttaga gaaactttcc ctgtcaaagg ctccgggggg cgcgggtgtc    960
ccccgcttgc cagagccctg ttgcggcccc gaaacttgtg cgcgcagccc aaactaacct    1020
cacgtgaagt gacggactgt tctatgactg caaagatgga aacgaccttc tatgacgatg    1080
ccctcaacgc ctcgttcctc ccgtccgaga gcggaccttta tggctacagt aaccccaaga   1140
tcctgaaaca gagcatgacc ctgaacctgg ccgacccagt ggggagcctg aagccgcacc    1200
tccgcgccaa gaactcggac ctcctcacct gcccgacgt ggggctgctc aagctggcgt     1260
cgcccgagct ggagcgcctg ataatccagt ccagcaacgg gcacatcacc accacgccga    1320
cccccaccca gttcctgtgc cccaagaacg tgacagatga gcaggagggc ttcgccgagg    1380
gcttcgtgcg cgccctggcc gaactgcaca gccagaacac gctgcccagc gtcacgtcgg    1440
cggcgcagcc ggtcaacggg gcaggcatgg tggctcccgc ggtagcctcg gtggcagggg    1500
gcagcggcag cggcggcttc agcgccagcc tgcacagcga gccgccggtc tacgcaaacc    1560
tcagcaactt caacccaggc gcgctgagca gcggcggcgg ggcgccctcc tacggcgcgg    1620
ccggcctggc cttcccgcg caaccccagc agcagcagca gccgccgcac cacctgcccc     1680
agcagatgcc cgtgcagcac ccgcggctgc aggcccctgaa ggaggagcct cagacagtgc    1740
ccgagatgcc cggcgagaca cggccctgt ccccatcga catggagtcc caggagcgga      1800
tcaaggcgga gaggaagcgc atgaggaacc gcatcgctgc ctccaagtgc cgaaaaagga    1860
agctggagag aatcgccgg ctggaggaaa aagtgaaaac cttgaaagct cagaactcgg     1920
agctggcgtc caccggccaac atgctcaggg aacaggtggc acagcttaaa cagaaagtca    1980
tgaaccacgt taacagtggg tgccaactca tgctaacgca gcagttgcaa acattttgaa    2040
gagagaccgt cgggggctga ggggcaacga agaaaaaaaa taacacagag agacagactt    2100
gagaacttga caagttgcga cggagagaaa aaagaagtgt ccgagaacta agccaaggg     2160 tatccaagtt ggactgggtt cgtcctgac ggcgcccca gtgtgcacga gtgggaagga      2220
cttggcgcgc cctcccttgg cgtggagcca gggagcggcc gctgcgggc tgccccgctt     2280 tgcggacggg ctgtccccgc gcgaacggaa cgttggactt ttcgttaaca ttgaccaaga    2340
actgcatgga cctaacattc gatctcattc agtattaaag gggggagggg gaggggtta     2400 caaactgcaa tagagactgt agattgcttc tgtagtactc cttaagaaca caaagcgggg    2460
ggagggttgg ggaggggcgg caggagggag gtttgtgaga gcgaggctga gcctacagat    2520
```

```
gaactctttc tggcctgcct tcgttaactg tgtatgtaca tatatatatt ttttaatttg    2580
atgaaagctg attactgtca ataaacagct tcatgccttt gtaagttatt tcttgtttgt    2640
ttgtttgggt atcctgccca gtgttgtttg taaataagag atttggagca ctctgagttt    2700
accatttgta ataagtata taattttttt atgttttgtt tctgaaaatt ccagaaagga    2760
tatttaagaa aatacaataa actattggaa agtactcccc taacctcttt tctgcatcat    2820
ctgtagatac tagctatcta ggtggagttg aaagagttaa gaatgtcgat taaaatcact    2880
ctcagtgctt cttactatta agcagtaaaa actgttctct attagacttt agaaataaat    2940
gtacctgatg tacctgatgc tatggtcagg ttatactcct cctcccccag ctatctatat    3000
ggaattgctt accaaaggat agtgcgatgt tcaggaggc tggaggaagg ggggttgcag     3060
tggagaggga cagcccactg agaagtcaaa catttcaaag tttggattgt atcaagtggc    3120
atgtgctgtg accatttata atgttagtag aaattttaca ataggtgctt attctcaaag    3180
caggaattgg tggcagattt tacaaaagat gtatccttcc aatttggaat cttctctttg    3240
acaattccta gataaaaaga tggcctttgc ttatgaatat ttataacagc attcttgtca    3300
caataaatgt attcaaatac caaaaaaaaa aaaaaaa                              3338
```

<210> SEQ ID NO 37
<211> LENGTH: 1832
<212> TYPE: DNA
<213> ORGANISM: Homo sapiens

<400> SEQUENCE: 37

```
gagcggccag gccagcctcg gagccagcag ggagctggga gctggggaa acgacgccag      60 gaaagctatc gcgccagaga gggcgacggg ggctcgggaa gcctgacagg gcttttgcgc    120
acagctgccg gctggctgct acccgcccgc gccagccccc gagaacgcgc gaccaggcac    180
ccagtccggt caccgcagcg gagagctcgc cgctcgctgc agcgaggccc ggagcggccc    240
cgcagggacc ctccccagac cgcctgggcc gcccggatgt gcactaaaat ggaacagccc    300
ttctaccacg acgactcata cacagctacg ggatacggcc gggcccctgg tggcctctct    360
ctacacgact acaaactcct gaaaccgagc ctggcggtca acctggccga cccctaccgg    420
agtctcaaag cgcctggggc tcgcggaccc ggcccagagg gcggcggtgg cggcagctac    480
ttttctggtc agggctcgga caccggcgcg tctctcaagc tcgcctcttc ggagctggaa    540
cgcctgattg tccccaacag caacggcgtg atcacgacga cgcctacacc cccgggacag    600
tacttttacc cccgcggggg tggcagcggt ggaggtgcag ggggcgcagg gggcggcgtc    660
accgaggagc aggagggctt cgccgacggc tttgtcaaag ccctggacga tctgcacaag    720
atgaaccacg tgacaccccc caacgtgtcc ctgggcgcta ccgggggggcc cccggctggg    780 cccggggggcg tctacgccgg cccggagcca cctcccgttt acaccaacct cagcagctac    840
tccccagcct ctgcgtcctc gggaggcgcc gggctgccg tcgggaccgg agctcgtac     900 ccgacgacca ccatcagcta cctcccacac gcgccgccct tcgccggtgg ccacccggcg    960
cagctgggct tgggccgcgg cgcctccacc ttcaaggagg aaccgcagac cgtgccggag    1020
gcgcgcagcc gggacgccac gccgcccgtg tcccccatca acatgaagga ccaagagcgc    1080
atcaaagtgg agcgcaagcg gctgcgcaac cggctggcgg ccaccaagtg ccggaagcgg    1140
aagctggagc gcatcgcgcg cctggaggac aaggtgaaga cgctcaaggc cgagaacgcg    1200
gggctgtcga gtaccgccgg cctcctccgg gagcaggtgg cccagctcaa acagaaggtc    1260
```

```
atgacccacg tcagcaacgg ctgtcagctg ctgcttgggg tcaagggaca cgccttctga      1320
acgtcccctg cccctttacg dacaccccct cgcttggacg gctgggcaca cgcctcccac      1380
tggggtccag ggagcaggcg gtgggcaccc accctgggac ctaggggcgc cgcaaaccac      1440
actggactcc ggccctccta ccctgcgccc agtccttcca cctcgacgtt tacaagcccc      1500
cccttccact ttttttgta tgttttttt ctgctggaaa cagactcgat tcatattgaa        1560
tataatatat ttgtgtattt aacagggagg ggaagagggg gcgatcgcgg cggagctggc      1620
cccgccgcct ggtactcaag cccgcgggga cattgggaag gggaccccg cccctgccc         1680 tcccctctct gcaccgtact gtggaaaaga aacacgcact tagtctctaa agagtttatt      1740
ttaagacgtg tttgtgtttg tgtgtgtttg ttcttttat tgaatctatt taagtaaaaa        1800
aaaaattggt tctttaaaaa aaaaaaaaa aa                                      1832

<210> SEQ ID NO 38
<211> LENGTH: 2187
<212> TYPE: DNA
<213> ORGANISM: Homo sapiens

<400> SEQUENCE: 38
gtcctttcta gacagccccc tcctccaggc tcagggacct gtctggctgt gagctcccag        60
gaggtcccag gggtgtgacc tccctccctc cctccctccc tcttcccttc accccaggcc       120
agcccagggc cagctataaa gctggcccag cctggctctc agcacaccca gctgcctgag       180
accctccttc aacctcccta gaggacagcc ccactctgcc tcctgctccc ccagggcagc       240
accatgtggc cctgtggct ctgctgggca ctctgggtgc tgcccctggc tggccccggg         300
gcggccctga ccgaggagca gctcctgggc agcctgctgc ggcagctgca gctcagcgag       360 gtgccgtac tggacagggc cgacatggag aagctggtca tccccgccca cgtgagggcc        420
cagtatgtag tcctgctgcg gcgcagccac ggggaccgct cccgcggaaa gaggttcagc       480
cagagcttcc gagaggtggc cggcaggttc ctggcgtcgg aggccagcac acacctgctg       540
gtgttcggca tggagcagcg gctgccgccc aacagcgagc tggtgcaggc cgtgctgcgg       600
ctcttccagg agccggtccc caaggccgcg ctgcacaggc acgggcggct gtccccgcgc       660
agcgcccagg cccgggtgac cgtcgagtgg ctgcgcgtcc gcgacgacgg ctccaaccgc       720
acctccctca tcgactccag gctggtgtcc gtccacgaga gcggctggaa ggccttcgac       780
gtgaccgagg ccgtgaactt ctggcagcag ctgagccggc cccggcagcc gctgctgcta       840
caggtgtcgg tgcagaggga gcatctgggc ccgctgcgt ccggcgccca caagctggtc        900
cgctttgcct cgcaggggc gccagccggg cttggggagc cccagctgga gctgcacacc       960
ctggacctca gggactatgg agctcagggc gactgtgacc ctgaagcacc aatgaccgag      1020
ggcacccgct gctgccgcca ggagatgtac attgacctgc aggggatgaa gtgggccaag      1080
aactgggtgc tggagccccc gggcttcctg gcttacgagt gtgtgggcac ctgccagcag      1140
cccccggagg ccctggcctt caattggcca tttctggggc cgcgacagtg tatcgcctcg      1200
gagactgcct cgctgcccat gatcgtcagc atcaaggagg gaggcaggac caggccccag      1260
gtggtcagcc tgcccaacat gagggtgcag aagtgcagct gtgcctcgga tggggcgctc      1320
gtgccaagga ggctccagcc ataggcgcct ggtgtatcca ttgagccctc taactgaacg      1380
tgtgcataga ggtggtctta atgtaggtct taactttata cttagcaagt tactccatcc      1440
caatttagtg ctcctgtgtg accttcgccc tgtgtccttc catttcctgt ctttcccgtc      1500
catcacccat cctaagcact tacgtgagta aataatgcag ctcagatgct gagctctagt      1560
```

```
aggaaatgct ggcatgctga ttacaagata cagctgagca atgcacacat tttcagctgg   1620
gagtttctgt tctctggcaa attcttcact gagtctggaa caataatacc ctatgattag   1680
aactggggaa acagaactga attgctgtgt tatatgagga attaaaacct tcaaatctct   1740
atttccccca aatactgacc cattctggac ttttgtaaac atacctaggc ccctgttccc   1800
ctgagagggt gctaagagga aggatgaagg gcttcaggct gggggcagtg gacagggaat   1860
tgggatacct ggattctggt tctgacaggg ccacaagcta ggatctctaa caaacgcaga   1920
aggctttggc tcgtcatttc ctcttaaaaa ggaggagctg gcttcagct ctaagaactt   1980 cattgccctg gggatcagac agcccctacc taccctgcc cactcctctg gagactgagc   2040
cttgcccgtg catatttagg tcatttccca cactgtctta gagaacttgt caccagaaac   2100
cacatgtatt tgcatgtttt ttgttaattt agctaaagca attgaatgta gatactcaga   2160
agaaataaaa aatgatgttt cactctg                                       2187

<210> SEQ ID NO 39
<211> LENGTH: 2048
<212> TYPE: DNA
<213> ORGANISM: Homo sapiens

<400> SEQUENCE: 39
cctggcccgg gagggtataa gtgcggcccg cgccctccg agcggcgcgc tgggttccgg     60
agcgatggcc acagccgagt cccgtgcgct ccagtttgcc gagggcgccg cgtttccagc    120
gtaccgggcc cccacgccg gcggggcgct cctgccgccc ccgagccctg cggcagccct    180
gctccctgcg ccgcccgcgg gccccggccc agcgaccttt gcgggcttcc tcggccggga    240
ccccgggccg gccccgccgc ccccgccag cctgggctcg cctgcgcccc ccaaaggcgc    300
ggccgccccg tcggcgtcgc agcgccgcaa gcgcacgtct ttcagcgccg aacagctgca    360
gctgctggag ctcgtcttcc gccggacccg gtaccccgac atccacttgc gcgagcgcct    420
ggccgcgctc accctgctcc ccgagtccag gatccagctt ttatttttctc ccctcttcca   480 ggtatggttc cagaacaggc gtgccaagtc tcggcgtcag agtgggaaat ccttccaacc    540
tttggctagg ccggagatta tcctcaacca ctgtgctcct ggaactgaaa cgaaatgtct    600
gaagccccag ctgcctcttg aggtagatgt gaactgcctg cccgaaccaa acggggttgg    660 aggggggcatc tctgactcta gctcccaagg tcagaatttt gaaacctgtt cccctctctc    720
tgaagacatt ggttcaaagc tggactcatg ggaggaacac atcttttctg cctttggtaa    780
cttttgagga ttctgggaga attcgggata agctctgagg agccatgact gacagcctgg    840
gagagacaca tcagcatact gtcctttctg acttccatgc taaggacatg tccttgttaa    900
ccttgatgat ggttttgaca gcacctctca catttgaagg taccccgcca ctttgtcaat    960
gacgttttaa gcccacactc ccaccccaga gttcccgcat tcgtttttac ctgtgttctc   1020
tccaagcctg cacattccat tggtctgcat ccctatgcct tcttgccagg cctgtttta    1080 gttttttggac tggttgttca gaactcatta ttttcttcac aagaatgcct cagcttgact   1140
cagtttcccc ttgtgtttga cagctgccat tttctcctgg tccctccaag gcttataatc   1200
ttaaagtcac tctaccccgt ctcttcaacc ctcatcctag gttattact ttttaaaatt   1260 gggcctgtca tcttcacgtt caatcatagc tccaatgact ctgcatgcag attatttcga   1320
cagccccctt gcctctagct tctcaactac ttaaaaaaaa ttaccctctg tgggccaggt   1380
gcagtggctc actcctgcaa tctcagcact ttgggaggcc gagtgggtgg atcacctgaa   1440
```

```
gtcaggagtt caagaccagc ctggccaata tggcgaaacc ccatctctgc taaaaatata    1500
aaacttagct gggcacggtg acgggagcct gtagtcccag ctactcagga ggctgaggca    1560
ggagaatcac ttgagcctgg gaggtggagg ttgcagtgat ctaagatcgt gccactgcac    1620
ttcagcctgg gagacagagg gaggctctca aaaaaaaaaa aaaaaaaaaa aaaaattact    1680
ctatggttct gtggtagcct ccagttgcta ccaaattata aaaagctttc agttaccctc    1740
ccagataact gatatcatcc ttagcctgca ggacagctat gcaaatctga aggtcaacta    1800
tccacaatat atgctttggt cttaaagtca ctcctttcag ttttgaacca aattcatacc    1860
ttttgctttc aaaacactcg aggactcccc acctgccttc tgaagtctga aattttctct    1920
aagtaatcct gattttgcac ctgttacttc gatcactcca ttacccttag cacttgttat    1980
tgtacttcct gtgcaagttt tgtggattat aaatgtctt tcacaaatgt aaaaaaaaa    2040 aaaaaaaa                                                             2048

<210> SEQ ID NO 40
<211> LENGTH: 2735
<212> TYPE: DNA
<213> ORGANISM: Homo sapiens

<400> SEQUENCE: 40
acaacagtcc ccaggcatca ccattcaaga tgcatccagg ggtcctggct gccttcctct      60
tcttgagctg gactcattgt cgggccctgc cccttcccag tggtggtgat gaagatgatt     120
tgtctgagga agacctccag tttgcagagc gctacctgag atcatactac catcctacaa     180
atctcgcggg aatcctgaag gagaatgcag caagctccat gactgagagg ctccgagaaa     240
tgcagtcttt cttcggctta gaggtgactg gcaaacttga cgataacacc ttagatgtca     300
tgaaaaagcc aagatgcggg gttcctgatg tgggtgaata caatgttttc cctcgaactc     360
ttaaatggtc caaaatgaat ttaacctaca gaattgtgaa ttacacccct gatatgactc     420
attctgaagt cgaaaaggca ttcaaaaaag ccttcaaagt ttggtccgat gtaactcctc     480
tgaattttac cagacttcac gatggcattg ctgacatcat gatctctttt ggaattaagg     540
agcatggcga cttctaccca tttgatgggc cctctggcct gctggctcat gcttttcctc     600
ctgggccaaa ttatggagga gatgcccatt ttgatgatga tgaaacctgg acaagtagtt     660
ccaaaggcta caacttgttt cttgttgctg cgcatgagtt cggccactcc ttaggtcttg     720
accactccaa ggaccctgga gcactcatgt ttcctatcta cacctacacc ggcaaaagcc     780
actttatgct tcctgatgac gatgtacaag ggatccagtc tctctatggt ccaggagatg     840
aagaccccaa ccctaaacat ccaaaaacgc cagacaaatg tgacccttcc ttatcccttg     900
atgccattac cagtctccga ggagaaacaa tgatctttaa agacagattc ttctggcgcc     960
tgcatcctca gcaggttgat gcggagctgt ttttaacgaa atcattttgg ccagaacttc    1020
ccaaccgtat tgatgctgca tatgagcacc cttctcatga cctcatcttc atcttcagag    1080
gtagaaaatt ttgggctctt aatggttatg acattctgga aggttatccc aaaaaaatat    1140
ctgaactggg tcttccaaaa gaagttaaga agataagtgc agctgttcac tttgaggata    1200
caggcaagac tctcctgttc tcaggaaacc aggtctggag atatgatgat actaaccata    1260
ttatggataa agactatccg agactaatag aagaagactt cccaggaatt ggtgataaag    1320
tagatgctgt ctatgagaaa aatggttata tctattttt caacggaccc atacagtttg    1380
aatacagcat ctggagtaac cgtattgttc gcgtcatgcc agcaaattcc attttgtggt    1440
gttaagtgtc ttttaaaaa ttgttatta aatcctgaag agcatttggg gtaatacttc    1500
```

```
cagaagtgcg gggtagggga agaagagcta tcaggagaaa gcttggttct gtgaacaagc    1560
ttcagtaagt tatctttgaa tatgtagtat ctatatgact atgcgtggct ggaaccacat    1620
tgaagaatgt tagagtaatg aaatggagga tctctaaaga gcatctgatt cttgttgctg    1680
tacaaaagca atggttgatg atacttccca caccacaaat gggacacatg gtctgtcaat    1740
gagagcataa tttaaaaata tatttataag gaaattttac aagggcataa agtaaataca    1800
tgcatataat gaataaatca ttcttactaa aagtataaaa atagtatgaa aatgaaatt     1860 tgggagagcc atacataaaa gaaataaacc aaaggaaaat gtctgtaata atagactgta    1920
acttccaaat aaataatttt cattttgcac tgaggatatt cagatgtatg tgcccttctt    1980
cacacagaca ctaacgaaat atcaaagtca ttaaagacag gagacaaaag agcagtggta    2040
agaatagtag atgtggcctt tgaattctgt ttaattttca cttttggcaa tgactcaaag    2100
tctgctctca tataagacaa atattccttt gcatattata aaggataaag aaggatgatg    2160
tctttttatt aaaatatttc aggttcttca gaagtcacac attacaaagt taaaattgtt    2220
atcaaaatag tctaaggcca tggcatccct ttttcataaa ttatttgatt atttaagact    2280
aaaagttgca ttttaaccct atttaccta gctaattatt taattgtcca gtttgtcttg     2340
gatatatagg ctattttcta aagacttgta tagcatgaaa taaaatatat cttataaagt    2400
ggaagtatgt atattaaaaa agagacatcc aaatttttt ttaaagcagt ctactagatt     2460
gtgatccctt gagatatgga aggatgcctt tttttctctg catttaaaaa aatcccccag    2520
cacttcccac agtgcctatt gatacttggg gagggtgctt ggcacttatt gaatatatga    2580
tcggccatca agggaagaac tattgtgctc agagacactg ttgataaaaa ctcaggcaaa    2640
gaaaatgaaa tgcatatttg caagtgtat taggaagtgt ttatgttgtt tataataaaa     2700
atatattttc aacagacaaa aaaaaaaaaa aaaaa                               2735
```

<210> SEQ ID NO 41
<211> LENGTH: 3549
<212> TYPE: DNA
<213> ORGANISM: Homo sapiens

<400> SEQUENCE: 41

```
acatctggcg gctgccctcc cttgtttccg ctgcatccag acttcctcag gcggtggctg      60
gaggctgcgc atctggggct ttaaacatac aaagggattg ccaggacctg cggcggcggc    120
ggcggcggcg ggggctgggg cgcggggggcc ggaccatgag ccgctgagcc gggcaaaccc    180
caggccaccg agccagcgga ccctcggagc gcagccctgc gccgcggagc aggctccaac    240
caggcggcga ggcggccaca cgcaccgagc cagcgacccc cgggcgacgc gcggggccag    300
ggagcgctac gatggaggcg ctaatggccc ggggcgcgct cacgggtccc ctgagggcgc    360
tctgtctcct gggctgcctg ctgagccacg ccgccgccgc gccgtcgccc atcatcaagt    420
tccccggcga tgtcgccccc aaaacggaca aagagttggc agtgcaatac ctgaacacct    480
tctatggctg ccccaaggag agctgcaacc tgtttgtgct gaaggacaca ctaaagaaga    540
tgcagaagtt cttggactg cccccagacag gtgatcttga ccagaatacc atcgagacca    600
tgcggaagcc acgctgcggc aacccagatg tggccaacta caacttcttc cctcgcaagc    660
ccaagtggga caagaaccag atcacataca ggatcattgg ctacacacct gatctggacc    720
cagagacagt ggatgatgcc tttgctcgtg ccttccaagt ctggagcgat gtgaccccac    780
tgcggttttc tcgaatccat gatggagagg cagacatcat gatcaacttt ggccgctggg    840
```

-continued

```
agcatggcga tggatacccc tttgacggta aggacggact cctggctcat gccttcgccc    900
caggcactgg tgttggggga gactcccatt ttgatgacga tgagctatgg accttgggag    960
aaggccaagt ggtccgtgtg aagtatggga acgccgatgg ggagtactgc aagttcccct   1020
tcttgttcaa tggcaaggag tacaacagct gcactgatac cggccgcagc gatggcttcc   1080
tctggtgctc caccacctac aactttgaga aggatggcaa gtacggcttc tgtccccatg   1140
aagccctgtt caccatgggc ggcaacgctg aaggacagcc ctgcaagttt ccattccgct   1200
tccagggcac atcctatgac agctgcacca ctgagggccg cacggatggc taccgctggt   1260
gcggcaccac tgaggactac gaccgcgaca agaagtatgg cttctgccct gagaccgcca   1320
tgtccactgt tggtgggaac tcagaaggtg ccccctgtgt cttccccttc actttcctgg   1380
gcaacaaata tgagagctgc accagcgccg ccgcagtga cggaaagatg tggtgtgcga   1440
ccacagccaa ctacgatgat gaccgcaagt ggggcttctg ccctgaccaa gggtacagcc   1500
tgttcctcgt ggcagcccac gagtttggcc acgccatggg gctggagcac tcccaagacc   1560
ctggggccct gatggcaccc atttacacct acaccaagaa cttccgtctg tccaggatg    1620
acatcaaggg cattcaggag ctctatgggg cctctcctga cattgacctt ggcaccggcc   1680
ccaccccac gctgggccct gtcactcctg agatctgcaa acaggacatt gtatttgatg    1740
gcatcgctca gatccgtggt gagatcttct tcttcaagga ccggttcatt tggcggactg   1800
tgacgccacg tgacaagccc atggggcccc tgctggtggc cacattctgg cctgagctcc   1860
cggaaaagat tgatgcggta cgaggcccc acaggagga aaggctgtg ttctttgcag      1920
ggaatgaata ctggatctac tcagccagca ccctggagcg agggtacccc aagccactga   1980
ccagcctggg actgccccct gatgtccagc gagtggatgc cgcctttaac tggagcaaaa   2040
acaagaagac atacatcttt gctggagaca aattctggag atacaatgag gtgaagaaga   2100
aaatggatcc tggcttcccc aagctcatcg cagatgcctg gaatgccatc cccgataacc   2160
tggatgccgt cgtggacctg cagggcgcg gtcacagcta cttcttcaag ggtgcctatt    2220
acctgaagct ggagaaccaa gtctgaaga gcgtgaagtt tggaagcatc aaatccgact    2280
ggctaggctg ctgagctggc cctggctccc acaggccctt cctctccact gccttcgata   2340
caccgggcct ggagaactag agaaggaccc ggaggggcct ggcagccgtg ccttcagctc   2400
tacagctaat cagcattctc actcctacct ggtaatttaa gattccagag agtggctcct   2460
cccggtgccc aagaatagat gctgactgta ctcctcccag gcgcccttc ccctccaat     2520
cccaccaacc ctcagagcca cccctaaaga gatactttga tattttcaac gcagccctgc   2580
tttgggctgc cctggtgctg ccacacttca ggctcttctc ctttcacaac cttctgtggc   2640
tcacagaacc cttggagcca atggagactg tctcaagagg gcactggtgg cccgacagcc   2700
tggcacaggg cagtgggaca gggcatggcc aggtggccac tccagacccc tggcttttca   2760
ctgctggctg cctagaacc tttcttacat tagcagtttg ctttgtatgc actttgtttt    2820
tttctttggg tcttgttttt tttttccact tagaaattgc atttcctgac agaaggactc   2880
aggttgtctg aagtcactgc acagtgcatc tcagcccaca tagtgatggt tcccctgttc   2940
actctactta gcatgtccct accgagtctc ttctccactg gatggaggaa aaccaagccg   3000
tggcttcccg ctcagccctc cctgcccctc ccttcaacca ttcccatgg gaaatgtcaa    3060
caagtatgaa taaagacacc tactgagtgg ccgtgtttgc catctgtttt agcagagcct   3120
agacaagggc cacagaccca gccagaagcg gaaacttaaa aagtccgaat ctctgctccc   3180
tgcagggcac aggtgatggt gtctgctgga aaggtcagag cttccaaagt aaacagcaag   3240
```

```
agaacctcag ggagagtaag ctctagtccc tctgtcctgt agaaagagcc ctgaagaatc    3300
agcaattttg ttgctttatt gtggcatctg ttcgaggttt gcttcctctt taagtctgtt    3360
tcttcattag caatcatatc agttttaatg ctactactaa caatgaacag taacaataat    3420 atcccctca attaatagag tgctttctat gtgcaaggca cttttcacgt gtcacctatt     3480
ttaacctttc caaccacata aataaaaaag gccattatta gttgaaaaaa aaaaaaaaa     3540 aaaaaaaaa                                                             3549
```

<210> SEQ ID NO 42
<211> LENGTH: 2387
<212> TYPE: DNA
<213> ORGANISM: Homo sapiens

<400> SEQUENCE: 42

```
agacacctct gccctcacca tgagcctctg gcagcccctg gtcctggtgc tcctggtgct     60
gggctgctgc tttgctgccc ccagacagcg ccagtccacc cttgtgctct ccctggaga    120 cctgagaacc aatctcaccg acaggcagct ggcagaggaa tacctgtacc gctatggtta    180
cactcgggtg gcagagatgc gtggagagtc gaaatctctg gggcctgcgc tgctgcttct    240
ccagaagcaa ctgtccctgc cgagaccggt gagctggat agcgccacgc tgaaggccat     300
gcgaacccca cggtgcgggg tcccagacct gggcagattc caaacctttg agggcgacct    360
caagtggcac caccacaaca tcacctattg gatccaaaac tactcggaag acttgccgcg    420
ggcggtgatt gacgacgcct ttgccccgcg cttcgcactg tggagcgcgg tgacgccgct    480
caccttcact cgcgtgtaca gccgggacgc agacatcgtc atccagtttg tgtcgcgga    540 gcacggagac gggtatccct cgacgggaa ggacgggctc ctggcacacg cctttcctcc    600
tggccccggc attcagggag acgcccattt cgacgatgac gagttgtggt ccctgggcaa    660
gggcgtcgtg gttccaactc ggtttggaaa cgcagatggc gcggcctgcc acttccctt     720 catcttcgag ggccgctcct actctgcctg caccaccgac ggtcgctccg acggcttgcc    780
ctggtgcagt accacggcca actacgacac cgacgaccgg tttggcttct gccccagcga    840
gagactctac acccaggacg gcaatgctga tgggaaaccc tgccagtttc cattcatctt    900
ccaaggccaa tcctactccg cctgcaccac ggacggtcgc tccgacggct accgctggtg    960
cgccaccacc gccaactacg accgggacaa gctcttcggc ttctgcccga cccgagctga   1020
ctcgacggtg atggggggca actcggcggg ggagctgtgc gtcttcccct tcactttcct   1080
gggtaaggag tactcgacct gtaccagcga gggccgcgga gatgggcgcc tctggtgcgc   1140
taccacctcg aactttgaca gcgacaagaa gtggggcttc tgcccggacc aaggatacag   1200
tttgttcctc gtggcggcgc atgagttcgg ccacgcgctg gcttagatc attcctcagt    1260 gccggaggcg ctcatgtacc ctatgtaccg cttcactgag gggcccccct gcataagga    1320 cgacgtgaat ggcatccggc acctctatgg tcctcgccct gaacctgagc cacggcctcc    1380
aaccaccacc acaccgcagc ccacggctcc cccgacggtc tgccccaccg acccccac     1440 tgtccacccc tcagagcgcc ccacagctgg ccccacaggt cccccctcag ctggccccac    1500
aggtcccccc actgctggcc cttctacggc cactactgtg cctttgagtc cggtggacga    1560
tgcctgcaac gtgaacatct tcgacgccat cgcggagatt gggaaccagc tgtatttgtt    1620
caaggatggg aagtactggc gattctctga gggcaggggg agccggccgc agggcccctt    1680
ccttatcgcc gacaagtggc ccgcgctgcc ccgcaagctg gactcggtct ttgaggagcg    1740
```

```
gctctccaag aagcttttct tcttctctgg gcgccaggtg tgggtgtaca caggcgcgtc    1800
ggtgctgggc ccgaggcgtc tggacaagct gggcctggga ccgacgtggg cccaggtgac    1860
cggggccctc cggagtggca gggggaagat gctgctgttc agcgggcggc gcctctggag    1920
gttcgacgtg aaggcgcaga tggtggatcc ccggagcgcc agcaggtgga ccggatgtt    1980
ccccggggtg cctttggaca cgcacgacgt cttccagtac cgagagaaag cctatttctg    2040
ccaggaccgc ttctactggc gcgtgagttc ccggagtgag ttgaaccagg tggaccaagt    2100
gggctacgtg acctatgaca tcctgcagtg ccctgaggac tagggctccc gtcctgcttt    2160
ggcagtgcca tgtaaatccc cactgggacc aaccctgggg aaggagccag tttgccggat    2220
acaaactggt attctgttct ggaggaaagg gaggagtgga ggtgggctgg ccctctctt    2280
ctcacctttg tttttgttg gagtgttct aataaacttg gattctctaa cctttaaaaa    2340
aaaaaaaaaa aaaaaaaaa aaaaaaaaa aaaaaaaaa aaaaaa                    2387
```

<210> SEQ ID NO 43
<211> LENGTH: 2224
<212> TYPE: DNA
<213> ORGANISM: Homo sapiens

<400> SEQUENCE: 43

```
tcccgtctcc gcagcaaaaa agtttgagtc gccgctgccg ggttgccagc ggagtcgcgc    60
gtcgggagct acgtagggca gagaagtcat ggcttctccg tccaaaggca atgacttgtt    120
ttcgcccgac gaggagggcc cagcagtggt ggccggacca ggcccggggc ctggggcgc    180
cgaggggcc gcggaggagc gccgcgtcaa ggtctccagc ctgcccttca gcgtggaggc    240
gctcatgtcc gacaagaagc cgcccaagga ggcgtccccg ctgccggccg aaagcgcctc    300
ggccggggcc accctgcggc cactgctgct gtcggggcac ggcgctcggg aagcgcacag    360
ccccgggccg ctggtgaagc ccttcgagac cgcctcggtc aagtcggaaa attcagaaga    420
tggagcggcg tggatgcagg aacccggccg atattcgccg ccgccaagac atatgagccc    480
taccacctgc accctgagga acacaagac caatcggaag ccgcgcacgc cctttaccac    540
atcccagctc ctcgccctgg agcgcaagtt ccgtcagaaa cagtacctct ccattgcaga    600
gcgtgcagag ttctccagct ctctgaacct cacagagacc caggtcaaaa tctggttcca    660
gaaccgaagg gccaaggcga aaagactgca ggaggcagaa ctggaaaagc tgaaaatggc    720
tgcaaaacct atgctgccct ccagcttcag tctccctttc cccatcagct cgcccctgca    780
ggcagcgtcc atatatggag catcctaccc gttccataga cctgtgcttc ccatcccgcc    840
tgtgggactc tatgccacgc cagtgggata tggcatgtac cacctgtcct aaggaagacc    900
agatcaatag actccatgat ggatgcttgt ttcaaagggt ttcctctccc tctccacgaa    960
ggcagtacca gccagtactc ctgctctgct aaccctgcgt gcaccaccct aagcggctag    1020
gctgacaggg ccacacgaca tagctgaaat ttgttctgta ggcggaggca ccaagccctg    1080
ttttcttggt gtaatcttcc agatgccccc ttttccttc acaaagattg gctctgatgg    1140
ttttatgta taaatatata tataataa aatataatac atttttatac agcagacgta    1200
aaaattcaaa ttattttaaa aggcaaaatt tatatacata tgtgcttttt ttctatatct    1260
caccttccca aaagacactg tgtaagtcca tttgttgtat ttcttaaag agggagacaa    1320
attatttgca aaatgtgcta aagtcaatga tttttacggg attattgact tctgcttatg    1380
gaaaacaaag aaacagacac aatgcacaca gaaaatatta gatatggaga gattattcaa    1440
agtgaagggg acacatcata tttctgcatt ttacttgcat taaaagaaac ctctttatat    1500
```

```
actacagttg ttcctatctc tcccccgccc cccaccgccc caccacacac atattttaa    1560 agttttcct ttttaagaa tattttgta agaccaatac ctgggatgag aagaatcctg    1620
agactgcctg gaggtgaggt agaaaattag aaatacttcc taattcttct caaggctgtt    1680
ggtaacttta tttcagataa ttggagagta aaatgttaaa acctgttgag aggaattgat    1740
ggtttctgag aaatactagg tacattcatc ctcacagatt gcaaaggtga tttgggtggg    1800
ggtttagtaa ttttctgctt aaaaaatgag tatcttgtaa ccattaccta tatgctaaat    1860
attcttgaac aattagtaga tccagaaaga aaaaaaaata tgctttctct gtgtgtgtac    1920
ctgttgtatg tcctaaactt attagaaaat tttatatact tttttacatg ttgggggca    1980 gaaggtaaag ccatgttttg acttggtgaa aatgggattg tcaaacagcc cattaagttc    2040
cctggtattt caccttcctg tccatctgtc ccctccctcc ggtataccct tatccctttg    2100
aaagggtgct tgtacaattt gatatatttt attgaagagt tatctcttat tctgaattaa    2160
attaagcatt tgttttattg cagtaaagtt tgtccaaact cacaattaaa aaaaaaaaa    2220 aaaa    2224

<210> SEQ ID NO 44
<211> LENGTH: 2379
<212> TYPE: DNA
<213> ORGANISM: Homo sapiens

<400> SEQUENCE: 44
gacccccgag ctgtgctgct cgcggccgcc accgccgggc cccggccgtc cctggctccc      60
ctcctgcctc gagaagggca gggcttctca gaggcttggc gggaaaaaga acggagggag     120
ggatcgcgct gagtataaaa gccggttttc ggggctttat ctaactcgct gtagtaattc     180
cagcgagagg cagagggagc gagcgggcgg ccggctaggt ggaagagcc gggcgagcag     240 agctgcgctg cgggcgtcct gggaaggagg atcggagcg aatagggggc ttcgcctctg     300
gcccagccct cccgctgatc ccccagccag cggtccgcaa cccttgccgc atccacgaaa     360
ctttgcccat agcagcgggc gggcactttg cactggaact acaacaccc gagcaaggac     420 gcgactctcc cgacgcgggg aggctattct gcccatttgg ggacacttcc ccgccgctgc     480
caggacccgc ttctctgaaa ggctctcctt gcagctgctt agacgctgga ttttttcgg     540 gtagtggaaa accagcagcc tcccgcgacg atgcccctca acgttagctt caccaacagg     600
aactatgacc tcgactacga ctcggtgcag ccgtatttct actgcgacga ggaggagaac     660
ttctaccagc agcagcagca gagcgagctg cagccccgg cgcccagcga ggatatctgg     720
aagaaattcg agctgctgcc cacccccgcc ctgtccccta gccgccgctc cgggctctgc     780 tcgcctcct acgttgcggt cacccccttc tcccttcggg gagacaacga cggcggtggc     840
gggagcttct ccacggccga ccagctggag atggtgaccg agctgctggg aggagacatg     900
gtgaaccaga gtttcatctg cgacccggac gacgagacct tcatcaaaaa catcatcatc     960
caggactgta tgtggagcgg cttctcggcc gccgccaagc tcgtctcaga aagctggcc    1020 tcctaccagg ctgcgcgcaa agacagcggc agcccgaacc ccgccgcgcg ccacagcgtc    1080
tgctccacct ccagcttgta cctgcaggat ctgagcgccg ccgcctcaga gtgcatcgac    1140
ccctcggtgg tcttcccta ccctctcaac gacagcagct cgcccaagtc ctgcgcctcg    1200
caagactcca gcgccttctc tccgtcctcg gattctctgc tctcctcgac ggagtcctcc    1260
ccgcagggca gccccgagcc cctggtgctc catgaggaga caccgccac caccagcagc    1320
```

```
gactctgagg aggaacaaga agatgaggaa gaaatcgatg ttgtttctgt ggaaaagagg    1380
caggctcctg gcaaaaggtc agagtctgga tcaccttctg ctggaggcca cagcaaacct    1440
cctcacagcc cactggtcct caagaggtgc cacgtctcca cacatcagca caactacgca    1500
gcgcctccct ccactcggaa ggactatcct gctgccaaga gggtcaagtt ggacagtgtc    1560
agagtcctga gacagatcag caacaaccga aaatgcacca gccccaggtc ctcggacacc    1620
gaggagaatg tcaagaggcg aacacacaac gtcttggagc gccagaggag gaacgagcta    1680
aaacggagct tttttgccct gcgtgaccag atcccggagt tggaaaacaa tgaaaaggcc    1740
cccaaggtag ttatccttaa aaaagccaca gcatacatcc tgtccgtcca agcagaggag    1800
caaaagctca tttctgaaga ggacttgttg cggaaacgac gagaacagtt gaaacacaaa    1860
cttgaacagc tacggaactc ttgtgcgtaa ggaaaagtaa ggaaaacgat tccttctaac    1920
agaaatgtcc tgagcaatca cctatgaact tgtttcaaat gcatgatcaa atgcaacctc    1980
acaaccttgg ctgagtcttg agactgaaag atttagccat aatgtaaact gcctcaaatt    2040
ggactttggg cataaaagaa cttttttatg cttaccatct tttttttttc tttaacagat    2100
ttgtatttaa gaattgtttt taaaaaattt taagatttac acaatgtttc tctgtaaata    2160
ttgccattaa atgtaaataa ctttaataaa acgtttatag cagttacaca gaatttcaat    2220
cctagtatat agtacctagt attataggta ctataaaccc taattttttt tatttaagta    2280
cattttgctt tttaaagttg attttttct attgttttta gaaaaaataa aataactggc    2340
aaatatatca ttgagccaaa tcttaaaaaa aaaaaaaaa                           2379
```

<210> SEQ ID NO 45
<211> LENGTH: 1669
<212> TYPE: DNA
<213> ORGANISM: Homo sapiens

<400> SEQUENCE: 45

```
gctcctgtca tcgaggcccc tggcccaatg gcaggctgag tcccctcct ctggcctggt      60
cccgcctctc ctgccccttg tgctcagcgc tacctgctgc ccggacacat ccagagctgg    120
ccgacgggtg cgcgggcggg cggcggcacc atgcagggaa gctgccaggg gccgtgggca    180
gcgccgcttt ctgccgccca cctggcgctg tgagactggc gctgccacca tgttccccag    240
ccctgctctc acgcccacgc ccttctcagt caaagacatc ctaaacctgg aacagcagca    300
gcgcagcctg gctgccgccg gagagctctc tgcccgcctg gaggcgaccc tggcgccctc    360
ctcctgcatg ctgccgcct tcaagccaga ggcctacgct gggcccgagg cggctgcgcc    420
gggcctccca gagctgcgcg cagagctggg ccgcgcgcct tcaccggcca agtgtgcgtc    480
tgcctttccc gccgccccg ccttctatcc acgtgcctac agcgaccccg acccagccaa    540
ggaccctaga gccgaaaaga aagagctgtg cgcgctgcag aaggcggtgg agctggagaa    600
gacagaggcg gacaacgcgg agcggccccg ggcgcgacgg cggaggaagc cgcgcgtgct    660
cttctcgcag gcgcaggtct atgagctgga gcggcgcttc aagcagcagc ggtacctgtc    720
ggcccccgaa cgcgaccagc tggccagcgt gctgaaactc acgtccacgc aggtcaagat    780
ctggttccag aaccgcgct acaagtgcaa gcggcagcgg caggaccaga ctctggagct    840
ggtggggctg ccccgccgc gccgccgcc tgcccgcagg atcgcggtgc cagtgctggt    900
gcgcgatggc aagccatgcc tagggactgg ggcccctac gcgcctgcct acggcgtggg    960
cctcaatccc tacggttata acgcctaccc cgcctatccg ggttacgcg gcgcggcctg   1020
cagccctggc tacagctgca ctgccgctta cccgccggg ccttccccag cgcagccggc   1080
```

```
cactgccgcc gccaacaaca acttcgtgaa cttcggcgtc ggggacttga atgcggttca      1140
gagccccggg attccgcaga gcaactcggg agtgtccacg ctgcatggta tccgagcctg      1200
gtagggaagg gacccgcgtg gcgcgaccct gaccgatccc acctcaacag ctccctgact      1260
ctcgggggga aaggggctc ccaacatgac cctgagtccc ctggattttg cattcactcc       1320
tgcggagacc taggaacttt ttctgtccca cgcgcgtttg ttcttgcgca cgggagagtt      1380
tgtggcggcg attatgcagc gtgcaatgag tgatcctgca gcctggtgtc ttagctgtcc      1440
ccccaggagt gccctccgag agtccatggg caccccggt tggaactggg actgagctcg       1500
ggcacgcagg gcctgagatc tggccgccca ttccgcgagc cagggccggg cgcccgggcc      1560
tttgctatct cgccgtcgcc cgcccacgca cccacccgta tttatgtttt tacctattgc      1620
tgtaagaaat gacgatcccc ttcccattaa agagagtgcg ttgaccccg                  1669

<210> SEQ ID NO 46
<211> LENGTH: 2086
<212> TYPE: DNA
<213> ORGANISM: Homo sapiens

<400> SEQUENCE: 46
ataagggctg gaggtgctgc tttcaggcct ggccagccca ccatgcacgc ccactgcctg        60
cccttccttc tgcacgcctg gtgggcccta ctccaggcgg gtgctgcgac ggtggccact       120
gcgctcctgc gtacgcgggg gcagccctcg tcgccatccc ctctggcgta catgctgagc       180
ctctaccgcg acccgctgcc gagggcagac atcatccgca gcctacaggc agaagatgtg       240
gcagtggatg ggcagaactg gacgtttgct tttgacttct ccttcctgag ccaacaagag       300
gatctggcat gggctgagct ccggctgcag ctgtccagcc ctgtggacct ccccactgag       360
ggctcacttg ccattgagat tttccaccag ccaaagcccg acacagagca ggcttcagac       420
agctgcttag agcggtttca gatggaccta ttcactgtca ctttgtccca ggtcaccttt       480
tccttgggca gcatggtttt ggaggtgacc aggcctctct ccaagtggct gaagcaccct       540
ggggccctgg agaagcagat gtccagggta gctggagagt gctggccgcg gccccccaca       600
ccgcctgcca ccaatgtgct ccttatgctc tactccaacc tctcgcagga gcagaggcag       660
ctgggtgggt ccaccttgct gtgggaagcc gagagctcct ggcggggccca ggagggacag      720 ctgtcctggg agtggggcaa gaggcaccgt cgacatcact tgccagacag aagtcaactg       780
tgtcggaagg tcaagttcca ggtggacttc aacctgatcg gatgggctc ctggatcatc       840 tacccccaagc agtacaacgc ctatcgctgt gagggcgagt gtcctaatcc tgttggggag      900
gagtttcatc cgaccaacca tgcatacatc cagagtctgc tgaaacgtta ccagccccac      960
cgagtccctt ccacttgttg tgccccagtg aagaccaagc cgctgagcat gctgtatgtg      1020
gataatggca gagtgctcct agatcaccat aaagacatga tcgtggaaga atgtgggtgc      1080
ctctgatgac atcctggagg gagactggat ttgcctgcac tctggaaggc tgggaaactc      1140
ctggaagaca tgataaccat ctaatccagt aaggagaaac agagaggggc aaagttgctc      1200
tgcccaccag aactgaagag gaggggctgc ccactctgta aatgaagggc tcagtggagt      1260
ctggccaagc acagaggctg ctgtcaggaa gaggaggaa gaagcctgtg caggggctg       1320 gctggatgtt ctctttactg aaaagacagt ggcaaggaaa agcacaagtg catgagttct      1380
ttactggatt ttttaaaaac ctgtgaaccc cccgaaactg tatgtgaaag ttgagacata      1440
tgtgcatgta ttttggaggt gggatgaagt cacctatagc tttcatgtat tctccaaagt      1500
```

-continued

| | |
|---|---|
| agtctgtgtg tgacctgtcc ccctccccaa agattaagga tcactgtata gattaaaaag | 1560 |
| agtccgtcaa tctcattgcc tcaggctggg ttgggggagc cccacagctt tctggctggc | 1620 |
| cagtggcaat ctactggcct tgtccagagg ctcactggag tggttctctg ctaatgagct | 1680 |
| gtacaacaat aaagccattg tctagttctc ctgggccagc tggtgcctgt gaaggcagag | 1740 |
| gcaggaactc atccaagagg accggccatg ttgggttaca gaagacatcc ctgcgtcagt | 1800 |
| ctgcttcggc agacacagcc tgagtttgtt aaagttggtg acaatccacc tcagtctctc | 1860 |
| aatgtgtgct attaatgagg cctctgagct tcctatccag cagtggtgaa ggccttgccc | 1920 |
| tgggtggcaa gatacttgct ctatggtcac agctcagcca ctggaagctg tgcgacctca | 1980 |
| ggtgagcaat tcactgtcca gtctccactt gtaaaaggaa cgctggtgaa tcctaatgca | 2040 |
| ttcatattaa atgtctgttg tcaggctcag aagagccatg agcttt | 2086 |

<210> SEQ ID NO 47
<211> LENGTH: 3039
<212> TYPE: DNA
<213> ORGANISM: Homo sapiens

<400> SEQUENCE: 47

| | |
|---|---|
| aataaagcgt gaacccgtcc gtccggctcg cactttaaga cttcccgagc ggcggcgggg | 60 |
| acgccagtcg agccgggaga cgcttacctg ccgcttcccc gcgccgcccg gtgcacctgg | 120 |
| ccgcaaggga cctcgttctc agggaagacg gcgacattcc gcggaggtgg aaccgccgcg | 180 |
| cgccgtccgg gctcggacct tccccggaac gtggggcgc cttagcgact ccttccctgt | 240 |
| tgtgcccccg ttcccggcgt tcagcccggc cccgcaaagg tgggacggct cccggcttca | 300 |
| gttacggaag cggccgtgt ccagcgacga gggttcgaaa atgccccgcg cgttcctggt | 360 |
| gaagaagccg tgcgtctcca cgtgcaagag gaactggagc gagctccccg acgaggagcg | 420 |
| cggcgagatc tacgtgccag tcagcctggg cttctgccca ccacagccct accggagcc | 480 |
| ggaaccctct gtggccgaac ccccttcctg cccgctggct tgaacatga gccttcgaga | 540 |
| ctctagctac agcatggccc ccgggccctg tgtggtggcc cagctgccct ctgaagacat | 600 |
| gggccacttg acagaccccc agagcagaga ccatggcttc ctgcgcacca agatgaaggt | 660 |
| gaccctgggg acagtcccca gtggagacct gttcacctgc cgtgtctgcc agaaggcctt | 720 |
| cacctaccag cgcatgctga accgccacat gaagtgtcac aacgacgtca agaggcacct | 780 |
| ctgcacgtac tgcgggaagg gcttcaatga caccttcgac ctcaagagac acgtccgaac | 840 |
| tcacactggc gtgcggccct acaagtgcag cctgtgtgac aaggccttca cgcagcgctg | 900 |
| ctctctggag tctcacctca gaagatcca tggtgtgcag cagaagtacg cgtacaagga | 960 |
| gcggcgggcc aagctgtacg tgtgtgagga gtgcggctgc acatctgaga gccaggaggg | 1020 |
| ccacgtcctg cacctgaagg agcaccaccc tgacagcccg ctgctgcgca agacctccaa | 1080 |
| gaaggtggcc gtggcactac agaacactgt cacttccctg ctgcagggca gccccacct | 1140 |
| gtgagtggct cgagccctgg gggtgctcct ggaagcccca agagcatcca ggattgcctc | 1200 |
| ccagctgcct ggccagccca cctcctgca acctctcacc cgaacaccag tgatcaggac | 1260 |
| tggagccccc gtgccttggt ctcccccctg ggcacgtg ctcactcagg cccagcaatg | 1320 |
| acctctgctc atttttgcat ttttgactta tgggccgagg ctgttctgag cctgggaaga | 1380 |
| tgtacctatg tcaagagaag ggatgaggcc aagctgcct tcaattagaa gcagccgccc | 1440 |
| acagagacag gcactgtgtg cctggcagca ggacttccta cccagaggag gttcgagcta | 1500 |
| ggatcccact gccccgcct ctcagcacag ggcagggct gcaggtcccc agtggacatc | 1560 |

```
agagtcaaaa gcactggcaa agggtacccc tgcaaacaac tgtggtgggg gctggcagca    1620 gacccccac  ctggcagggc ttctaatgct cagggttctg gagggctctg tccttccggc    1680
aaggagaggc acacatgtgt gcccagccgt gtgtgtgcgt gtgcttgtgt gtgtgcactg    1740
ctgtgtgtgt gtgcacgcac aggaagcctt tccacatatc acctcatttc taagaaataa    1800
actacaaggt gccaagaagg ttttatttcc ttttattttt taaagatgac aaatgtacag    1860
atgttaatat atttttggtg ccaatggcga tgttttaag  agtgggatgg agctggcttt    1920
tctccattcc cgtgcgcttc tatttatcct ggacatttca aacctcctct gtgccttggc    1980
tctgggcggg ggctgcccca acccacccc  gttctttgta cgtgctgaga cagccactag    2040
aagatcttcc tccagcggcg ccctggacgg ctgctcctgc aacagcccca tggcatcttc    2100
tgctcttccc tcccggctct gccctgcaca tcctgttgag ccaagcccca gtgacccgga    2160
gagctggcct gatgctgaga gtgtgtcctc ctggggcttt aggggcagg  aaggtgggac    2220 gaatgacgat gccatccac  tacctgaagc actaggacac tcttgcaggg ccaggctgga    2280
agaccggccc ttttcttggt tgagtcaaaa gccttagcac agtggcaaaa aatgggacag    2340
aatgatgacc agcaccctcag aaacttccag agggaggaga ggatttgatg ctaccaaat    2400 tgtatctgtt gccttttttc tgactttttc acctgaccag gctgggtttt ggagtggctg    2460
tggggagacc cgtcctggct ggctggctgg ctcccttgct cccttgctgc agctgggaaa    2520
ggggttctgg gtgtaaagag gtgtgcgtct tgtgggccaa agggaaaaac aggcagggt     2580 cagagccagc ctgccagagg caaatgcaaa agaggtcccc agaacacagc cagctgggca    2640
gccccttaaa gccaaacccc acctgaagca gaaccacttt ggcctcccct gcccaaaatg    2700
ggtagtgtct acacgtcccc gggctcaggc tcaggcccag cctgggctg  acctgagagg    2760 aaggctcctt cctggactgc cctctgaaat gtgtatagat tgattctaaa atctcttgtt    2820
tcacttgact ttagagtgtc tgggacgctg ctgtattctg aaagtcacat agcacacagt    2880
aatgttatct ggaagctctg ttttttgttta catttctgta tccctgggtt gactgccaat    2940
ccgaggccgt catgaagctc tgtgttgtct gttttatttt ataaccttcc tctcaactat    3000
taaaattaga gatctaatgt ttaaaaaaaa aaaaaaaaa                           3039

<210> SEQ ID NO 48
<211> LENGTH: 3393
<212> TYPE: DNA
<213> ORGANISM: Homo sapiens

<400> SEQUENCE: 48
cctgcctgcc tccctgcgca cccgcagcct ccccgctgc  ctccctaggg ctcccctccg      60
gccgccagcg cccattttc  attccctaga tagagatact tgcgcgcac  acacatacat     120 acgcgcgcaa aaaggaaaaa aaaaaaaaaa agcccaccct ccagcctcgc tgcaaagaga     180
aaaccggagc agccgcagct cgcagctcgc agctcgcagc ccgcagcccg cagaggacgc     240
ccagagcggc gagcgggcgg gcagacggac cgacggactc gcgccgcgtc cacctgtcgg     300
ccgggcccag ccgagcgcgc agcgggcacg ccgcgcgcgc ggagcagccg tgcccgccgc     360
ccgggccccg cgccagggcg cacacgctcc cgccccccta cccggcccgg gcgggagttt     420
gcacctctcc ctgcccgggt gctcgagctg ccgttgcaaa gccaactttg gaaaaagttt     480 tttggggag  acttgggcct tgaggtgccc agctccgcgc tttccgattt tgggggcctt     540
tccagaaaat gttgcaaaaa agctaagccg gcgggcagag gaaaacgcct gtagccggcg     600
```

| | |
|---|---|
| agtgaagacg aaccatcgac tgccgtgttc cttttcctct tggaggttgg agtccctgg | 660 |
| gcgcccccac acggctagac gcctcggctg gttcgcgacg cagcccccg gccgtggatg | 720 |
| ctcactcggg ctcgggatcc gcccaggtag cggcctcgga cccaggtcct gcgcccaggt | 780 |
| cctcccctgc ccccagcga cggagccggg gccggggcg gcggcgcccg ggggccatgc | 840 |
| gggtgagccg cggctgcaga ggcctgagcg cctgatcgcc gcggacccga gccgagccca | 900 |
| cccccctccc cagcccccca ccctggccgc ggggcggcg cgctcgatct acgcgtccgg | 960 |
| ggccccgcgg ggccgggccc ggagtcggca tgaatcgctg ctgggcgctc ttcctgtctc | 1020 |
| tctgctgcta cctgcgtctg gtcagcgccg aggggaccc cattcccgag gagctttatg | 1080 |
| agatgctgag tgaccactcg atccgctcct ttgatgatct ccaacgcctg ctgcacggag | 1140 |
| accccggaga ggaagatggg gccgagttgg acctgaacat gacccgctcc cactctggag | 1200 |
| gcgagctgga gagcttggct cgtggaagaa ggagcctggg ttccctgacc attgctgagc | 1260 |
| cggccatgat cgccgagtgc aagacgcgca ccgaggtgtt cgagatctcc cggcgcctca | 1320 |
| tagaccgcac caacgccaac ttcctggtgt ggccgccctg tgtggaggtg cagcgctgct | 1380 |
| ccggctgctg caacaaccgc aacgtgcagt gccgcccac ccaggtgcag ctgcgacctg | 1440 |
| tccaggtgag aaagatcgag attgtgcgga agaagccaat ctttaagaag ccacggtga | 1500 |
| cgctggaaga ccacctggca tgcaagtgtg agacagtggc agctgcacgg cctgtgaccc | 1560 |
| gaagcccggg gggttcccag gagcagcgag ccaaaacgcc ccaaactcgg gtgaccattc | 1620 |
| ggacggtgcg agtccgccgg ccccccaagg gcaagcaccg gaaattcaag cacacgcatg | 1680 |
| acaagacggc actgaaggag acccttggag cctaggggca tcggcaggag agtgtgtggg | 1740 |
| cagggttatt taatatggta tttgctgtat tgcccccatg gggtccttgg agtgataata | 1800 |
| ttgtttccct cgtccgtctg tctcgatgcc tgattcggac ggccaatggt gcttcccca | 1860 |
| ccctccacg tgtccgtcca cccttccatc agcgggtctc ctcccagcgg cctccggcgt | 1920 |
| cttgcccagc agctcaagaa gaaaaagaag gactgaactc catcgccatc ttcttccctt | 1980 |
| aactccaaga acttgggata agagtgtgag agagactgat ggggtcgctc tttgggggaa | 2040 |
| acgggctcct tcccctgcac ctggcctggg ccacacctga gcgctgtgga ctgtcctgag | 2100 |
| gagccctgag gacctctcag catagcctgc ctgatccctg aaccctggc cagctctgag | 2160 |
| gggaggcacc tccaggcagg ccaggctgcc tcggactcca tggctaagac cacagacggg | 2220 |
| cacacagact ggagaaaacc cctcccacgg tgcccaaaca ccagtcacct cgtctccctg | 2280 |
| gtgcctctgt gcacagtggc ttcttttcgt tttcgttttg aagacgtgga ctcctcttgg | 2340 |
| tgggtgtggc cagcacacca agtggctggg tgccctctca ggtgggttag agatggagtt | 2400 |
| tgctgttgag gtggctgtag atggtgacct gggtatcccc tgcctcctgc cacccccttcc | 2460 |
| tccccacact ccactctgat tcacctcttc ctctggttcc tttcatctct ctacctccac | 2520 |
| cctgcatttt cctcttgtcc tggcccttca gtctgctcca ccaagggct cttgaacccc | 2580 |
| ttattaaggc cccagatgat cccagtcact cctctctagg gcagaagact agaggccagg | 2640 |
| gcagcaaggg acctgctcat catattccaa cccagccacg actgccatgt aaggttgtgc | 2700 |
| agggtgtgta ctgcacaagg acattgtatg cagggagcac tgttcacatc atagataaag | 2760 |
| ctgatttgta tatttattat gacaatttct ggcagatgta ggtaaagagg aaaaggatcc | 2820 |
| ttttcctaat tcacacaaag acttccttgt gactggctgt gcccctgatg cagcctgtgg | 2880 |
| cttggagtgg ccaaatagga gggagactgt ggtaggggca gggaggcaac actgctgtcc | 2940 |
| acatgacctc catttcccaa agtcctctgc tccagcaact gcccttccag gtgggtgtgg | 3000 |

| | |
|---|---|
| gacacctggg agaaggtctc caagggaggg tgcagccctc ttgcccgcac ccctccctgc | 3060 |
| ttgcacactt ccccatcttt gatccttctg agctccacct ctggtggctc ctcctaggaa | 3120 |
| accagctcgt gggctgggaa tgggggagag aagggaaaag atccccaaga cccctgggg | 3180 |
| tgggatctga gctcccacct cccttcccac ctactgcact ttcccccttc ccgccttcca | 3240 |
| aaacctgctt ccttcagttt gtaaagtcgg tgattatatt tttgggggct ttccttttat | 3300 |
| tttttaaatg taaaatttat ttatattccg tatttaaagt tgtaaaaaaa aataaccaca | 3360 |
| aaacaaaacc aaatgaaaaa aaaaaaaaaa aaa | 3393 |

<210> SEQ ID NO 49
<211> LENGTH: 4934
<212> TYPE: DNA
<213> ORGANISM: Homo sapiens

<400> SEQUENCE: 49

| | |
|---|---|
| aaacccgatc tccttggact tgaatgagga ggaggaggcg gcggcggcgg cggcggcgga | 60 |
| ggcgctcggc tggggaaagc tagcggcaga ggctcagccc cggcggcagc gcgcgccccg | 120 |
| ctgccagccc attttccgga cgccaccccgc gggcactgcc gacgccccg gggctgccga | 180 |
| ggggaggccg ggggggcgca gcggagcgcg gtcccgcgca ctgagccccg cggcgccccg | 240 |
| ggaacttggc ggcgacccga gccggcgag ccggggcgcg cctcccccgc cgcgcgcctc | 300 |
| ctgcatgcgg ggccccagct ccgggcgccg gccggagccc ccccggccg ccccgagcc | 360 |
| ccccgcgccc cgccgccgcgc cgccgcgccg tccatgcacc gcttgatggg ggtcaacagc | 420 |
| accgccgccg ccgccgccgg gcagcccaat gtctcctgca cgtgcaactg caaacgctct | 480 |
| ttgttccaga gcatggagat cacggagctg gagtttgttc agatcatcat catcgtggtg | 540 |
| gtgatgatgg tgatggtggt ggtgatcacg tgcctgctga gccactacaa gctgtctgca | 600 |
| cggtccttca tcagccggca cagccagggg cggaggagag aagatgccct gtcctcagaa | 660 |
| ggatgcctgt ggccctcgga gagcacagtg tcaggcaacg gaatcccaga gccgcaggtc | 720 |
| tacgccccgc ctcggcccac cgaccgcctg gccgtgccgc cttcgcccca gcgggagcgc | 780 |
| ttccaccgct tccagcccac ctatccgtac ctgcagcacg agatcgacct gccacccacc | 840 |
| atctcgctgt cagacgggga ggagccccca ccctaccagg gccctgcac cctccagctt | 900 |
| cgggaccccg agcagcagct ggaactgaac cgggagtcgg tgcgcgcacc cccaaacaga | 960 |
| accatcttcg acagtgacct gatggatagt gccaggctgg gcggcccctg ccccccagc | 1020 |
| agtaactcgg gcatcagcgc cacgtgctac ggcagcggcg ggcgcatgga ggggcgccg | 1080 |
| cccacctaca gcgaggtcat cggccactac ccggggtcct ccttccagca ccagcagagc | 1140 |
| agtgggccgc cctccttgct ggaggggacc cggctccacc acacacacat cgcgcccta | 1200 |
| gagagcgcag ccatctggag caaagagaag gataaacaga aggacacccc tctctagggt | 1260 |
| ccccaggggg gccgggctgg ggctgcgtag gtgaaaggc agaacactcc gcgcttctta | 1320 |
| gaagaggagt gagaggaagg cgggggcgc agcaacgcat cgtgtggccc tcccctccca | 1380 |
| cctccctgtg tataaatatt tacatgtgat gtctggtctg aatgcacaag ctaagagagc | 1440 |
| ttgcaaaaaa aaaagaaaa aagaaaaaaa aaaccacgt tctttgttg agctgtgtct | 1500 |
| tgaaggcaaa agaaaaaaaa tttctacagt agtctttctt gtttctagtt gagctgcgtg | 1560 |
| cgtgaatgct tatttctttt tgtttatgat aatttcactt aacttaaaag acatatttgc | 1620 |
| acaaaaccctt tgtttaaaga tctgcaatat tatatatata aatatatata agataagaga | 1680 |

```
aactgtatgt gcgagggcag gagtatttttt gtattagaag aggcctatta aaaaaaaaag   1740
ttgttttctg aactagaaga ggaaaaaaat ggcaattttt gagtgccaag tcagaaagtg   1800
tgtattacct tgtaaagaaa aaaattacaa agcagggtt tagagttatt tatataaatg    1860
ttgagatttt gcactatttt ttaatataaa tatgtcagtg cttgcttgat ggaaacttct   1920
cttgtgtctg ttgagacttt aagggagaaa tgtcggaatt tcagagtcgc ctgacggcag   1980
agggtgagcc cccgtggagt ctgcagagag gccttggcca ggagcggcgg gctttcccga   2040
ggggccactg tccctgcaga gtggatgctt ctgcctagtg acaggttatc accacgttat   2100
atattcccta ccgaaggaga caccttttcc cccctgaccc agaacagcct ttaaatcaca   2160
agcaaaatag gaaagttaac cacggaggca ccgagttcca ggtagtggtt ttgcctttcc   2220
caaaaatgaa aataaactgt taccgaagga attagttttt cctcttcttt tttccaactg   2280
tgaaggtccc cgtggggtgg agcatggtgc ccctcacaag ccgcagcggc tggtgcccgg   2340
gctaccaggg acatgccaga gggctcgatg acttgtctct gcagggcgct ttggtggttg   2400
ttcagctggc taaaggttca ccggtgaagg caggtgcggt aactgccgca ctggacccta   2460
ggaagcccca ggtattcgca atctgacctc ctcctgtctg tttcccttca cggatcaatt   2520
ctcacttaag aggccaataa acaacccaac atgaaaaggt gacaagcctg ggtttctccc   2580
aggataggtg aaagggttaa aatgagtaaa gcagttgagc aaacaccaac ccgagcttcg   2640
ggcgcagaat tcttcacctt ctcttcccct ttccatctcc tttcccgcg gaaacaacgc    2700
ttcccttctg gtgtgtctgt tgatctgtgt tttcatttac atctctctta gactccgctc   2760
ttgttctcca ggttttcacc agatagattt ggggttggcg ggacctgctg gtgacgtgca   2820
ggtgaaggac aggaagggc atgtgagcgt aaatagaggt gaccagagga gagcatgagg    2880
ggtgggctt gggacccac cggggccagt ggctggagct tgacgtcttt cctccccatg     2940
ggggtgggag ggccccagc tggaagagca gactcccagc tgctacccc tcccttccca     3000
tgggagtggc tttccatttt gggcagaatg ctgactagta gactaacata aaagatataa   3060
aaggcaataa ctattgtttg tgagcaactt ttttataact tccaaaacaa aaacctgagc   3120
acagttttga agttctagcc actcgagctc atgcatgtga acgtgtgct ttacgaaggt    3180
ggcagctgac agacgtgggc tctgcatgcc gccagcctag tagaaagttc tcgttcattg   3240
gcaacagcag aacctgcctc tccgtgaagt cgtcagccta aaatttgttt ctctcttgaa   3300
gaggattctt tgaaaaggtc ctgcagagaa atcagtacag gttatcccga aggtacaag    3360
gacgcacttg taaagatgat taaaacgtat cttttccttta tgtgacgcgt ctctagtgcc   3420
ttactgaaga agcagtgaca ctcccgtcgc tcggtgagga cgttcccgga cagtgcctca   3480
ctcacctggg actggtatcc cctcccaggg tccaccaagg gctcctgctt ttcagacacc   3540
ccatcatcct cgcgcgtcct caccctgtct ctaccaggga ggtgcctagc ttggtgaggt   3600
tactcctgct cctccaacct ttttttgcca aggtttgtac acgactccca tctaggctga   3660
aaacctagaa gtggaccttg tgtgtgtgca tggtgtcagc ccaaagccag gctgagacag   3720
tcctcatatc ctcttgagcc aaactgtttg ggtctcgttg cttcatggta tggtctggat   3780
ttgtgggaat ggctttgcgt gagaaagggg aggagagtgg ttgctgccct cagccggctt   3840
gaggacagag cctgtccctc tcatgacaac tcagtgttga agcccagtgt cctcagcttc   3900
atgtccagtg gatggcagaa gttcatgggg tagtggcctc tcaaaggctg ggcgcatccc   3960
aagacagcca gcaggttgtc tctggaaacg accagagtta agctctcggc ttctctgctg   4020
agggtgcacc ctttcctcta gatggtagtt gtcacgttat cttttgaaaac tcttggactg   4080
```

```
ctcctgagga ggccctcttt tccagtagga agttagatgg gggttctcag aagtggctga      4140
ttggaagggg acaagcttcg tttcaggggt ctgccgttcc atcctggttc agagaaggcc      4200
gagcgtggct ttctctagcc ttgtcactgt ctccctgcct gtcaatcacc acctttcctc      4260
cagaggagga aaattatctc ccctgcaaag cccggttcta cacagatttc acaaattgtg      4320
ctaagaaccg tccgtgttct cagaaagccc agtgtttttg caaagaatga aaagggaccc      4380
catatgtagc aaaaatcagg ctgggggag agccgggttc attccctgtc ctcattggtc       4440
gtccctatga attgtacgtt tcagagaaat ttttttttcct atgtgcaaca cgaagcttcc    4500
agaaccataa aatatcccgt cgataaggaa agaaaatgtc gttgttgttg tttttctgga     4560
aactgcttga atcttgctg tactatagag ctcagaagga cacagcccgt cctcccctgc       4620
ctgcctgatt ccatggctgt tgtgctgatt ccaatgcttt cacgttggtt cctggcgtgg     4680
gaactgctct cctttgcagc cccatttccc aagctctgtt caagttaaac ttatgtaagc      4740
tttccgtggc atgcggggcg cgcacccacg tccccgctgc gtaagactct gtatttggat      4800
gccaatccac aggcctgaag aaactgcttg ttgtgtatca gtaatcatta gtggcaatga     4860
tgacattctg aaaagctgca atacttatac aataaatttt acaattcttt ggaatgagaa     4920
aaaaaaaaaa aaaa                                                        4934

<210> SEQ ID NO 50
<211> LENGTH: 1818
<212> TYPE: DNA
<213> ORGANISM: Homo sapiens

<400> SEQUENCE: 50
ggcgcccgcg cccgcccccg cgccgggccc ggctcggccc gacccggctc cgccgcgggc        60
aggcggggcc cagcgcactc ggagcccgag cccgagccgc agccgccgcc tggggcgctt       120
gggtcggcct cgaggacacc ggagaggggc gccacgccgc cgtggccgca gaaatgacca      180
tggttgacac agagatgcca ttctggccca ccaactttgg gatcagctcc gtggatctct      240
ccgtaatgga agaccactcc cactcctttg atatcaagcc cttcactact gttgacttct      300
ccagcatttc tactccacat tacgaagaca ttccattcac aagaacagat ccagtggttg      360
cagattacaa gtatgacctg aaacttcaag agtaccaaag tgcaatcaaa gtggagcctg      420
catctccacc ttattattct gagaagactc agctctacaa taagcctcat gaagagcctt      480
ccaactccct catggcaatt gaatgtcgtg tctgtggaga taaagcttct ggatttcact      540
atggagttca tgcttgtgaa ggatgcaagg gtttcttccg gagaacaatc agattgaagc      600
ttatctatga cagatgtgat cttaactgtc ggatccacaa aaaaagtaga aataaatgtc      660
agtactgtcg gtttcagaaa tgccttgcag tggggatgtc tcataatgcc atcaggtttg      720
ggcggatgcc acaggccgag aaggagaagc tgttggcgga gatctccagt gatatcgacc      780
agctgaatcc agagtccgct gacctccggg ccctggcaaa catttgtat gactcataca      840 taaagtcctt cccgctgacc aaagcaaagg cgagggcgat cttgacagga agacaacag      900 acaaatcacc attcgttatc tatgacatga attccttaat gatgggagaa gataaaatca     960
agttcaaaca catcaccccc ctgcaggagc agagcaaaga ggtggccatc cgcatctttc    1020
agggctgcca gtttcgctcc gtggaggctg tgcaggagat cacagagtat gccaaaagca   1080
ttcctggttt tgtaaatctt gacttgaacg accaagtaac tctcctcaaa tatgagtcc      1140 acgagatcat ttacacaatg ctggcctcct tgatgaataa agatgggtt ctcatatccg      1200
```

| | |
|---|---|
| agggccaagg cttcatgaca agggagtttc taaagagcct gcgaaagcct tttggtgact | 1260 |
| ttatggagcc caagtttgag tttgctgtga agttcaatgc actggaatta gatgacagcg | 1320 |
| acttggcaat atttattgct gtcattattc tcagtggaga ccgcccaggt ttgctgaatg | 1380 |
| tgaagcccat tgaagacatt caagacaacc tgctacaagc cctggagctc agctgaagc | 1440 |
| tgaaccaccc tgagtcctca cagctgtttg ccaagctgct ccagaaaatg acagacctca | 1500 |
| gacagattgt cacggaacac gtgcagctac tgcaggtgat caagaagacg gagacagaca | 1560 |
| tgagtcttca cccgctcctg caggagatct acaaggactt gtactagcag agagtcctga | 1620 |
| gccactgcca acatttccct tcttccagtt gcactattct gagggaaaat ctgacaccta | 1680 |
| agaaatttac tgtgaaaaag cattttaaaa agaaaggtt ttagaatatg atctatttta | 1740 |
| tgcatattgt ttataaagac acatttacaa tttacttta atattaaaaa ttaccatatt | 1800 |
| atgaaattgc tgatagta | 1818 |

<210> SEQ ID NO 51
<211> LENGTH: 4507
<212> TYPE: DNA
<213> ORGANISM: Homo sapiens

<400> SEQUENCE: 51

| | |
|---|---|
| gaccaattgt catacgactt gcagtgagcg tcaggagcac gtccaggaac tcctcagcag | 60 |
| cgcctccttc agctccacag ccagacgccc tcagacagca aagcctaccc ccgcgccgcg | 120 |
| ccctgcccgc cgctgcgatg ctcgcccgcg ccctgctgct gtgcgcggtc ctggcgctca | 180 |
| gccatacagc aaatccttgc tgttcccacc catgtcaaaa ccgaggtgta tgtatgagtg | 240 |
| tgggatttga ccagtataag tgcgattgta cccggacagg attctatgga gaaaactgct | 300 |
| caacaccgga atttttgaca agaataaaat tatttctgaa acccactcca aacacagtgc | 360 |
| actacatact tacccacttc aagggatttt ggaacgttgt gaataacatt cccttccttc | 420 |
| gaaatgcaat tatgagttat gtgttgcatc ccagatcaca tttgattgac agtccaccaa | 480 |
| cttacaatgc tgactatggc tacaaaagct gggaagcctt ctctaacctc tcctattata | 540 |
| ctagagcccct tcctcctgtg cctgatgatt gcccgactcc cttgggtgtc aaaggtaaaa | 600 |
| agcagcttcc tgattcaaat gagattgtgg aaaaattgct tctaagaaga agttcatcc | 660 |
| ctgatcccca gggctcaaac atgatgtttg cattctttgc ccagcacttc acgcatcagt | 720 |
| ttttcaagac agatcataag cgagggccag cttttcacca cgggctgggc catggggtgg | 780 |
| acttaaatca tatttacggt gaaactctgg ctagacagcg taaactgcgc cttttcaagg | 840 |
| atggaaaaat gaaatatcag ataattgatg gagagatgta tcctcccaca gtcaaagata | 900 |
| ctcaggcaga gatgatctac cctcctcaag tccctgagca tctacggttt gctgtggggc | 960 |
| aggaggtctt tggtctggtg cctggtctga tgatgtatgc acaatctgg ctgcgggaac | 1020 |
| acaacagagt atgcgatgtg cttaaacagg agcatcctga tggggtgat gagcagttgt | 1080 |
| tccagacaag caggctaata ctgataggag agactattaa gattgtgatt gaagattatg | 1140 |
| tgcaacactt gagtggctat cacttcaaac tgaaatttga cccagaacta ctttcaaca | 1200 |
| aacaattcca gtaccaaaat cgtattgctg ctgaatttaa caccctctat cactggcatc | 1260 |
| cccttctgcc tgacaccttt caaattcatg accagaaata aactatcaa cagtttatct | 1320 |
| acaacaactc tatattgctg gaacatggaa tttcccagtt tgttgaatca ttcaccaggc | 1380 |
| aaattgctgg caggggttgct ggtggtagga atgttccacc cgcagtacag aaagtatcac | 1440 |
| aggcttccat tgaccagagc aggcagatga ataccagtc ttttaatgag taccgcaaac | 1500 |

```
gctttatgct gaagccctat gaatcatttg aagaacttac aggagaaaag gaaatgtctg   1560
cagagttgga agcactctat ggtgacatcg atgctgtgga gctgtatcct gcccttctgg   1620
tagaaaagcc tcggccagat gccatctttg gtgaaaccat ggtagaagtt ggagcaccat   1680
tctccttgaa aggacttatg ggtaatgtta tatgttctcc tgcctactgg aagccaagca   1740
cttttggtgg agaagtgggt tttcaaatca tcaacactgc ctcaattcag tctctcatct   1800
gcaataacgt gaagggctgt ccctttactt cattcagtgt tccagatcca gagctcatta   1860
aaacagtcac catcaatgca agttcttccc gctccggact agatgatatc aatcccacag   1920
tactactaaa agaacgttcg actgaactgt agaagtctaa tgatcatatt tatttattta   1980
tatgaaccat gtctattaat ttaattattt aataatattt atattaaact ccttatgtta   2040
cttaacatct tctgtaacag aagtcagtac tcctgttgcg gagaaaggag tcatacttgt   2100
gaagactttt atgtcactac tctaaagatt ttgctgttgc tgttaagttt ggaaaacagt   2160
ttttattctg ttttataaac cagagagaaa tgagttttga cgtcttttta cttgaatttc   2220
aacttatatt ataagaacga agtaaagat gtttgaatac ttaaacactg tcacaagatg   2280
gcaaaatgct gaaagttttt acactgtcga tgtttccaat gcatcttcca tgatgcatta   2340
gaagtaacta atgtttgaaa ttttaaagta cttttggtta ttttttctgtc atcaaacaaa   2400 aacaggtatc agtgcattat taaatgaata tttaaattag acattaccag taatttcatg   2460 tctactttt aaaatcagca atgaaacaat aatttgaaat ttctaaattc atagggtaga   2520
atcacctgta aaagcttgtt tgatttctta aagttattaa acttgtacat ataccaaaaa   2580
gaagctgtct tggatttaaa tctgtaaaat cagtagaaat tttactacaa ttgcttgtta   2640
aaatatttta taagtgatgt tccttttca ccaagagtat aaaccttttt agtgtgactg   2700
ttaaaacttc cttttaaatc aaaatgccaa atttattaag gtggtggagc cactgcagtg   2760
ttatcttaaa ataagaatat tttgttgaga tattccagaa tttgtttata tggctggtaa   2820
catgtaaaat ctatatcagc aaaagggtct acctttaaaa taagcaataa caaagaagaa   2880
aaccaaatta ttgttcaaat ttaggtttaa acttttgaag caaacttttt tttatccttg   2940
tgcactgcag gcctggtact cagattttgc tatgaggtta atgaagtacc aagctgtgct   3000
tgaataatga tatgttttct cagattttct gttgtacagt ttaatttagc agtccatatc   3060
acattgcaaa agtagcaatg acctcataaa atacctcttc aaaatgctta aattcatttc   3120
acacattaat tttatctcag tcttgaagcc aattcagtag gtgcattgga atcaagcctg   3180
gctacctgca tgctgttcct tttctttct tcttttagcc attttgctaa gagacacagt   3240
cttctcatca cttcgtttct cctatttgt tttactagtt ttaagatcag agttcacttt   3300
ctttggactc tgcctatatt ttcttacctg aacttttgca agttttcagg taaacctcag   3360
ctcaggactg ctatttagct cctcttaaga agattaaaag agaaaaaaaa aggccctttt   3420
aaaaatagta tacacttatt ttaagtgaaa agcagagaat tttatttata gctaatttta   3480
gctatctgta accaagatgg atgcaaagag gctagtgcct cagagagaac tgtacggggt   3540
ttgtgactgg aaaaagttac gttcccattc taattaatgc cctttcttat ttaaaaacaa   3600
aaccaaatga tatctaagta gttctcagca ataataataa tgacgataat acttcttttc   3660
cacatctcat tgtcactgac atttaatggt actgtatatt acttaattta ttgaagatta   3720
ttatttatgt cttattagga cactatggtt ataaactgtg tttaagccta caatcattga   3780
tttttttttg ttatgtcaca atcagtatat tttctttggg gttacctctc tgaatattat   3840
```

-continued

| | |
|---|---|
| gtaaacaatc caaagaaatg attgtattaa gatttgtgaa taaattttta gaaatctgat | 3900 |
| tggcatattg agatatttaa ggttgaatgt ttgtccttag gataggccta tgtgctagcc | 3960 |
| cacaaagaat attgtctcat tagcctgaat gtgccataag actgaccttt taaaatgttt | 4020 |
| tgagggatct gtggatgctt cgttaatttg ttcagccaca atttattgag aaaatattct | 4080 |
| gtgtcaagca ctgtgggttt taatattttt aaatcaaacg ctgattacag ataatagtat | 4140 |
| ttatataaat aattgaaaaa aattttcttt tgggaagagg gagaaaatga aataaatatc | 4200 |
| attaaagata actcaggaga atcttcttta caattttacg tttagaatgt ttaaggttaa | 4260 |
| gaaagaaata gtcaatatgc ttgtataaaa cactgttcac tgttttttt aaaaaaaaaa | 4320 |
| cttgatttgt tattaacatt gatctgctga caaaacctgg gaatttgggt tgtgtatgcg | 4380 |
| aatgtttcag tgcctcagac aaatgtgtat ttaacttatg taaaagataa gtctggaaat | 4440 |
| aaatgtctgt ttatttttgt actatttaaa aattgacaga tcttttctga agaaaaaaaa | 4500 |
| aaaaaaa | 4507 |

<210> SEQ ID NO 52
<211> LENGTH: 1331
<212> TYPE: DNA
<213> ORGANISM: Homo sapiens

<400> SEQUENCE: 52

| | |
|---|---|
| cctgcatctt tttggaagga ttcttttat aaatcagaaa gtgttcgagg ttcaaaggtt | 60 |
| tgcctcggag cgtgtgaaca ttcctccgct cggttttcaa ctcgcctcca acctgcgccg | 120 |
| cccggccagc atgtctcccc gcccgtgaag cggggctgcc gcctccctgc cgctccggct | 180 |
| gccactaacg acccgccctc gccgccacct ggccctcctg atcgacgaca cacgcacttg | 240 |
| aaacttgttc tcagggtgtg tggaatcaac tttccggaag caaccagccc accagaggag | 300 |
| gtcccgagcg cgagcggaga cgatgcagcg gagactggtt cagcagtgga gcgtcgcggt | 360 |
| gttcctgctg agctacgcgg tgccctcctg cgggcgctcg gtgagggtc tcagccgccg | 420 |
| cctcaaaaga gctgtgtctg aacatcagct cctccatgac aaggggaagt ccatccaaga | 480 |
| tttacggcga cgattcttcc ttcaccatct gatcgcagaa atccacacag ctgaaatcag | 540 |
| agctacctcg gaggtgtccc ctaactccaa gccctctccc aacacaaaga accacccgt | 600 |
| ccgatttggg tctgatgatg agggcagata cctaactcag gaaactaaca aggtggagac | 660 |
| gtacaaagag cagccgctca agacacctgg gaagaaaaag aaaggcaagc ccgggaaacg | 720 |
| caaggagcag gaaaagaaaa aacggcgaac tcgctctgcc tggttagact ctggagtgac | 780 |
| tgggagtggg ctagaagggg accacctgtc tgacacctcc acaacgtcgc tggagctcga | 840 |
| ttcacggagg cattgaaatt ttcagcgagg accttccaag gacatattgc aggattctgt | 900 |
| aatagtgaac atatggaaag tattagaaat atttattgtc tgtaaatact gtaaatgcat | 960 |
| tggaataaaa ctgtctcccc cattgctcta tgaaactgca cattggtcat tgtgaatatt | 1020 |
| ttttttttgc caaggctaat ccaattatta ttatcacatt taccataatt tattttgtcc | 1080 |
| attgatgtat ttattttgta aatgtatctt ggtgctgctg aatttctata ttttttgtaa | 1140 |
| cataatgcac tttagatata catatcaagt atgttgataa atgacacaat gaagtgtctc | 1200 |
| tatttttgtgg ttgattttaa tgaatgccta aatataatta tccaaattga ttttccttg | 1260 |
| tgcatgtaaa ataacagta ttttaaattt gtaaagaatg tctaataaaa tataatctaa | 1320 |
| ttacatcatg a | 1331 |

<210> SEQ ID NO 53
<211> LENGTH: 3207
<212> TYPE: DNA
<213> ORGANISM: Homo sapiens

<400> SEQUENCE: 53

| | | | | | |
|---|---|---|---|---|---|
| ggcccacaga | ggagcacagc | tgtgtttggc | tgcagggcca | agagcgctgt | caagaagacc | 60 |
| cacacgcccc | cctccagcag | ctgaattcct | gcagctcagc | agccgccgcc | agagcaggac | 120 |
| gaaccgccaa | tcgcaaggca | cctctgagaa | cttcaggatg | cagatgtctc | cagccctcac | 180 |
| ctgcctagtc | ctgggcctgg | cccttgtctt | tggtgaaggg | tctgctgtgc | accatccccc | 240 |
| atcctacgtg | gcccacctgg | cctcagactt | cggggtgagg | gtgtttcagc | aggtggcgca | 300 |
| ggcctccaag | gaccgcaacg | tggttttctc | accctatggg | gtggcctcgg | tgttggccat | 360 |
| gctccagctg | acaacaggag | gagaaaccca | gcagcagatt | caagcagcta | tgggattcaa | 420 |
| gattgatgac | aagggcatgg | cccccgccct | ccggcatctg | tacaaggagc | tcatgggcc | 480 |
| atggaacaag | gatgagatca | gcaccacaga | cgcgatcttc | gtccagcggg | atctgaagct | 540 |
| ggtccagggc | ttcatgcccc | acttcttcag | gctgttccgg | agcacggtca | gcaagtgga | 600 |
| cttttcagag | gtggagagag | ccagattcat | catcaatgac | tgggtgaaga | cacacacaaa | 660 |
| aggtatgatc | agcaacttgc | ttgggaaagg | agccgtggac | cagctgacac | ggctggtgct | 720 |
| ggtgaatgcc | ctctacttca | acggccagtg | gaagactccc | ttccccgact | ccagcaccca | 780 |
| ccgccgcctc | ttccacaaat | cagacggcag | cactgtctct | gtgcccatga | tggctcagac | 840 |
| caacaagttc | aactatactg | agttcaccac | gcccgatggc | cattactacg | acatcctgga | 900 |
| actgccctac | cacggggaca | ccctcagcat | gttcattgct | gccccttatg | aaaagagt | 960 |
| gcctctctct | gccctcacca | acattctgag | tgcccagctc | atcagccact | ggaaaggcaa | 1020 |
| catgaccagg | ctgccccgcc | tcctggttct | gcccaagttc | tccctggaga | ctgaagtcga | 1080 |
| cctcaggaag | cccctagaga | acctgggaat | gaccgacatg | ttcagacagt | ttcaggctga | 1140 |
| cttcacgagt | ctttcagacc | aagagcctct | ccacgtcgcg | caggcgctgc | agaaagtgaa | 1200 |
| gatcgaggtg | aacgagagtg | gcacggtggc | ctcctcatcc | acagctgtca | tagtctcagc | 1260 |
| ccgcatggcc | cccgaggaga | tcatcatgga | cagacccttc | ctctttgtgg | tccggcacaa | 1320 |
| ccccacagga | acagtccttt | tcatgggcca | agtgatggaa | ccctgaccct | ggggaaagac | 1380 |
| gccttcatct | gggacaaaac | tggagatgca | tcgggaaaga | agaaactccg | aagaaaagaa | 1440 |
| ttttagtgtt | aatgactctt | tctgaaggaa | gagaagacat | ttgccttttg | ttaaaagatg | 1500 |
| gtaaaccaga | tctgtctcca | agaccttggc | ctctccttgg | aggaccttta | ggtcaaactc | 1560 |
| cctagtctcc | acctgagacc | ctgggagaga | agtttgaagc | acaactccct | taaggtctcc | 1620 |
| aaaccagacg | tgacgcctg | cgggaccatc | tgggcacct | gcttccaccc | gtctctctgc | 1680 |
| ccactcgggt | ctgcagacct | ggttcccact | gaggcccttt | gcaggatgga | actacggggc | 1740 |
| ttacaggagc | ttttgtgtgc | ctggtagaaa | ctatttctgt | tccagtcaca | ttgccatcac | 1800 |
| tcttgtactg | cctgccaccg | cggaggaggc | tggtgacagg | ccaaaggcca | gtggaagaaa | 1860 |
| caccctttca | tctcagagtc | cactgtggca | ctggccaccc | ctccccagta | cagggtgct | 1920 |
| gcaggtggca | gagtgaatgt | ccccccatcat | gtggcccaac | tctcctggcc | tggccatctc | 1980 |
| cctccccaga | aacagtgtgc | atgggttatt | ttggagtgta | ggtgacttgt | ttactcattg | 2040 |
| aagcagattt | ctgcttcctt | ttatttttat | aggaatagag | gaagaaatgt | cagatgcgtg | 2100 |
| cccagctctt | cacccccaa | tctcttggtg | gggaggggtg | tacctaaata | tttatcatat | 2160 |

| | |
|---|---|
| ccttgccctt gagtgcttgt tagagagaaa gagaactact aaggaaaata atattattta | 2220 |
| aactcgctcc tagtgtttct tgtggtctg tgtcaccgta tctcaggaag tccagccact | 2280 |
| tgactggcac acaccctcc ggacatccag cgtgacggag cccacactgc caccttgtgg | 2340 |
| ccgcctgaga ccctcgcgcc ccccgcgccc ctcttttttcc ccttgatgga aattgaccat | 2400 |
| acaatttcat cctccttcag gggatcaaaa ggacggagtg gggggacaga gactcagatg | 2460 |
| aggacagagt ggtttccaat gtgttcaata gatttaggag cagaaatgca aggggctgca | 2520 |
| tgacctacca ggacagaact ttccccaatt acagggtgac tcacagccgc attggtgact | 2580 |
| cacttcaatg tgtcatttcc ggctgctgtg tgtgagcagt ggacacgtga gggggggtg | 2640 |
| ggtgagagag acaggcagct cggattcaac taccttagat aatatttctg aaaacctacc | 2700 |
| agccagaggg tagggcacaa agatggatgt aatgcacttt gggaggccaa ggcgggagga | 2760 |
| ttgcttgagc ccaggagttc aagaccagcc tgggcaacat accaagaccc ccgtctcttt | 2820 |
| aaaaatatat atatttttaaa tatacttaaa tatatatttc taatatcttt aaatatatat | 2880 |
| atatatttta aagaccaatt tatgggagaa ttgcacacag atgtgaaatg aatgtaatct | 2940 |
| aatagaagcc taatcagccc accatgttct ccactgaaaa atcctctttc tttggggttt | 3000 |
| ttctttcttt cttttttgat tttgcactgg acggtgacgt cagccatgta caggatccac | 3060 |
| aggggtggtg tcaaatgcta ttgaaattgt gttgaattgt atgcttttc acttttgata | 3120 |
| aataaacatg taaaaatgtt tcaaaaaaat aataaaataa ataaatacga agaatatgtc | 3180 |
| aggacagtca aaaaaaaaaa aaaaaaa | 3207 |

<210> SEQ ID NO 54
<211> LENGTH: 2414
<212> TYPE: DNA
<213> ORGANISM: Homo sapiens

<400> SEQUENCE: 54

| | |
|---|---|
| ttttttataa ggccgagcgc gcggcctggc gcagcatacg ccgagccggt ctttgagcgc | 60 |
| taacgtctttt ctgtctcccc gcggtggtga tgacggtgaa aactgaggct gctaagggca | 120 |
| ccctcactta ctccaggatg aggggcatgg tggcaattct catcgctttc atgaagcaga | 180 |
| ggaggatggg tctgaacgac tttattcaga agattgccaa taactcctat gcatgcaaac | 240 |
| accctgaagt tcagtccatc ttgaagatct cccaacctca ggagcctgag cttatgaatg | 300 |
| ccaaccctc tcctccacca agtccttctc agcaaatcaa ccttggcccg tcgtccaatc | 360 |
| ctcatgctaa accatctgac tttcacttct tgaaagtgat cggaaagggc agttttggaa | 420 |
| aggttcttct agcaagacac aaggcagaag aagtgttcta tgcagtcaaa gttttacaga | 480 |
| agaaagcaat cctgaaaaag aaagaggaga agcatattat gtcggagcgg aatgttctgt | 540 |
| tgaagaatgt gaagcaccct ttcctggtgg gccttcactt ctctttccag actgctgaca | 600 |
| aattgtactt tgtcctagac tacattaatg gtggagagtg gttctaccat ctccagaggg | 660 |
| aacgctgctt cctggaacca cgggctcgtt tctatgctgc tgaaatagcc agtgccttgg | 720 |
| gctacctgca ttcactgaac atcgtttata gagacttaaa accagagaat attttgctag | 780 |
| attcacaggg acacattgtc cttactgact tcggactctg caaggagaac attgaacaca | 840 |
| acagcacaac atccaccttc tgtggcacgc cggagtatct cgcacctgag gtgcttcata | 900 |
| agcagcctta tgacaggact gtggactggt ggtgctgggg agctgtcttg tatgagatgc | 960 |
| tgtatggcct gccgccttttt tatagccgaa acacagctga aatgtacgac aacattctga | 1020 |
| acaagcctct ccagctgaaa ccaaatatta caaattccgc aagacacctc ctggagggcc | 1080 |

| | |
|---|---|
| tcctgcagaa ggacaggaca aagcggctcg gggccaagga tgacttcatg gagattaaga | 1140 |
| gtcatgtctt cttctcctta attaactggg atgatctcat taataagaag attactcccc | 1200 |
| cttttaaccc aaatgtgagt gggcccaacg acctacggca ctttgacccc gagtttaccg | 1260 |
| aagagcctgt ccccaactcc attggcaagt cccctgacag cgtcctcgtc acagccagcg | 1320 |
| tcaaggaagc tgccgaggct ttcctaggct tttcctatgc gcctcccacg gactcttcc | 1380 |
| tctgaaccct gttagggctt ggttttaaag gattttatgt gtgtttccga atgttttagt | 1440 |
| tagccttttg gtggagccgc cagctgacag gacatcttac aagagaattt gcacatctct | 1500 |
| ggaagcttag caatcttatt gcacactgtt cgctggaagc ttttgaaga gcacattctc | 1560 |
| ctcagtgagc tcatgaggtt ttcatttta ttcttcctc caacgtggtg ctatctctga | 1620 |
| aacgagcgtt agagtgccgc cttagacgga ggcaggagtt tcgttagaaa gcggacgctg | 1680 |
| ttctaaaaaa ggtctcctgc agatctgtct gggctgtgat gacgaatatt atgaaatgtg | 1740 |
| ccttttctga agagattgtg ttagctccaa agcttttcct atcgcagtgt ttcagttctt | 1800 |
| tatttcct tgtggatatg ctgtgtgaac cgtcgtgtga gtgtggtatg cctgatcaca | 1860 |
| gatggatttt gttataagca tcaatgtgac acttgcagga cactacaacg tgggacattg | 1920 |
| tttgtttctt ccatatttgg aagataaatt tatgtgtaga ctttttgta agatacggtt | 1980 |
| aataactaaa atttattgaa atggtcttgc aatgactcgt attcagatgc ttaaagaaag | 2040 |
| cattgctgct acaaatattt ctatttag aaagggtttt tatggaccaa tgccccagtt | 2100 |
| gtcagtcaga gccgttggtg ttttcattg tttaaaatgt cacctgtaaa atgggcatta | 2160 |
| tttatgtttt ttttttgca ttcctgataa ttgtatgtat tgtataaaga acgtctgtac | 2220 |
| attgggttat aacactagta tatttaaact tacaggctta tttgtaatgt aaaccaccat | 2280 |
| tttaatgtac tgtaattaac atggttataa tacgtacaat ccttccctca tcccatcaca | 2340 |
| caactttttt tgtgtgtgat aaactgattt tggtttgcaa taaaaccttg aaaaatattt | 2400 |
| acatataaaa aaaa | 2414 |

<210> SEQ ID NO 55
<211> LENGTH: 7202
<212> TYPE: DNA
<213> ORGANISM: Homo sapiens

<400> SEQUENCE: 55

| | |
|---|---|
| gatgtgtgtg gggttcggag ccgcgccggc acagccgaag ggagcgggcg agcggcgacg | 60 |
| gcggcggcgg cgggcacaga ttaattaaaa gaagaatgaa ctataatcct tgaagataac | 120 |
| tgggcaattt tttaagtcgg aggctgttct tactggtgtg aggatttaca cacgtcttca | 180 |
| gtttttcagc acagaccagc agaccatcat ttttagagga aatactccct ctgccctcct | 240 |
| ttttggtttc cttggtggta aagattaaat ttggttgcat cattttgact tgtgtttgag | 300 |
| tctagatttt atggcacaag gaatggcata aactttcat gtgttttggt taaacaaac | 360 |
| cagaccattg cattgacccct ggacatcttt aattgagaaa ttggtaactt tattttaata | 420 |
| tgtatatctg aagaattcaa gaaaacaaag gcatcctcag aggtgtgcct cttttcttta | 480 |
| ttattagagg caaaacgaac aattttatag gatttgtagt gaaattatac cagattataa | 540 |
| ggagaaccaa aactaagtcg caaaatttat taatttaagg ggctctcgct ttgaaagttt | 600 |
| gagagtaagt tacgataggc attttgtatcc attcattact ttcctctttt caaataagca | 660 |
| actaaataga aatgctaatc tcagacttaa ttatttaaca gaagagtgta ccatggaaaa | 720 |

```
cctccagaca aatttctcct tggttcaggg ctcaactaaa aaactgaatg ggatgggaga      780
tgatggcagc cccccagcga aaaaatgat aacggacatt catgcaaatg aaaaacgat       840 aaacaaggtg ccaacagtta agaaggaaca cttggatgac tatggagaag caccagtgga    900
aactgatgga gagcatgtta agcgaacctg tacttctgtt cctgaaactt tgcatttaaa    960
tcccagtttg aaacacacat tggcacaatt ccatttaagt agtcagagct cgctgggtgg   1020
accagcagca ttttctgctc ggcattccca agaaagcatg tcgcctactg tatttctgcc   1080
tcttccatca cctcaggttc ttcctggccc attgctcatc ccttcagata gctccacaga   1140
actcactcag actgtgttgg aaggggaatc tatttcttgt tttcaagttg gaggagaaaa   1200
gagactctgt ttgccccaag tcttaaattc tgttctccga gaatttacac tccagcaaat   1260
aaatacagtg tgtgatgaac tgtacatata ttgttcaagg tgtacttcag accagcttca   1320
tatcttaaag gtactgggca tacttccatt caatgcccca tcctgtgggc tgattacatt   1380
aactgatgca caaagattat gtaatgcttt attgcggcca cgaacttttc ctcaaaatgg   1440
tagcgtactt cctgctaaaa gctcattggc ccagttaaag gaaactggca gtgcctttga   1500
agtggagcat gaatgcctag gcaaatgtca gggtttattt gcaccccagt tttatgttca   1560
gcctgatgct ccgtgtattc aatgtctgga gtgttgtgga atgtttgcac ccagacgtt    1620 tgtgatgcat tctcacagat cacctgacaa agaacttgc cactggggct ttgaatcagc    1680
taaatggcat tgctatcttc atgtgaacca aaaatactta ggaacacctg aagaaaagaa   1740
actgaagata atttttagaag aaatgaagga aagtttagc atgagaagtg aaagagaaa    1800 tcaatccaag acagatgcac catcaggaat ggaattacag tcatggtatc ctgttataaa   1860
gcaggaaggt gaccatgttt ctcagacaca ttcatttta cacccccagct actacttata   1920 catgtgtgat aaagtggttg ccccaaatgt gtcacttact tctgctgtat cccagtctaa   1980
agagctcaca aagacagagg caagtaagtc catatcaaga cagtcagaga aggctcacag   2040
tagtggtaaa cttcaaaaaa cagtgtctta tccagatgtc tcacttgagg aacaggagaa   2100
aatggattta aaaacaagta gagaattatg tagccgttta gatgcatcaa tctcaaataa   2160
ttctacaagt aaaaggaaat ctgagtctgc cacttgcaac ttagtcagag acataaaacaa  2220 agtgggaatt ggccttgttg ctgccgcttc atctccgctt cttgtgaaag atgtcatttg   2280
tgaggatgat aagggaaaaa tcatggaaga agtaatgaga acttatttaa acaacagga    2340 aaaactaaac ttgattttgc aaaagaagca acaacttcag atggaagtaa aaatgttgag   2400
tagttcaaaa tctatgaagg aactcactga agaacagcag aatttacaga aagagcttga   2460
atctttgcag aatgaacatg ctcaaagaat ggaagaattt tatgttgaac agaaagactt   2520
agagaaaaaa ttggagcaga taatgaagca aaaatgtacc tgtgactcaa atttagaaaa   2580
agacaaagag gctgaatatg caggacagtt ggcagaactg aggcagagat tggaccatgc   2640
tgaggccgat aggcaagaac tccaagatga actcagacag gaacgggaag caagacagaa   2700
gttagagatg atgataaaag agctaaagct gcaaattctg aaatcatcaa agactgctaa   2760
agaatagaaa ctgttaaaga gattcatctg tgtattactg acaaggtttt ttttgtttgt   2820
tgcttgcttt ggtaattgaa ttctgaagaa tttatctgca tgacgataac taggcattct   2880
atccatttgt agatcagaga agtgaagag attatatatt agtacttaaa tttttacatt    2940
ttccaaatga atgaaaatgt atgtttcttt gtacttttt aaaaaaatca gcttagtaac    3000
aatactatat ggtttcaact agtaggtaat ctgcttatat ttctaatgca aacttaacaa   3060
ttgtgtactt tttaaaagct gcaatatgtg ttggaaaata gctgtggtca attttgttat   3120
```

```
ccatatttca gactcaattt tagatacaat ggtggcttta tattttaagt atatagagct   3180
actcaaggag ttgaatctcc ccttttctca ttaacacaat ttttctaagt tgatatggtg   3240
tactcattaa catacaccaa atttactttt actttgttca gattgtggaa tgaatttcca   3300
ccagttctct tcttttaat gtgtaccta ggaggaattt tactgaggtt atagcatacc   3360
ccatgagcac agtggggaag aagaatgtgt tgttatgtgc tgctgctaaa cagaagcagc   3420
agttgtaatt tgttttcag tttaaatgtg ttatagtta gatttttttt taagcagcaa   3480
cttttcaaaa ataaaatgtg ataatttctg aacttttgtt tgtgttgtta atagtggtgt   3540
gaaaatatta acgttcttga gaaaaactga taccactgtt gtgtatcagt ttctatacaa   3600
tccataatcc tcctgtacag tttttacatg tagttatgag tcttactaaa atttatataa   3660
tggacttgtt ttccttaag ttgtaaaatg ttaaacacct tgaaggttat tttgacttc   3720 tgtatgttta aatgttgtct taccaaaatt tgcacgaatg gaccattttc atttactact   3780
taatatcaaa atcaggaatt tacagtcaac tgatagtaca tgataggtgc atataggaca   3840
gtttagttac ctgctactaa aagattttta gataagtttt agaagataaa ggaattccat   3900
agtttcagga gggacaacat cttctgcact ttttttttgc acagaaaagt ctgtcattct   3960
ctaatggcaa atttcatatt tgttaattct tggctcaaaa tatattaggt aaaattctta   4020
gatctgtttt taagggagt ttcctgaaac tatcattaat tgacattatt accccatgga   4080
ttttatggga taataaatgt ttttcatgtt ctcttataag atactatgta tgaaattact   4140
tcagagagct atatttattt taaaataaat tagctagggt taaggttata ttctatttcc   4200
agcatagaag gtagataatc taatggtgta gaaagaatca ctaggttgtc atttaaccag   4260
ttattttcat attttgctta atagtacata tccaaaaaga attttgtact tccccaaatg   4320
taatttattt actaaattga gtataaccta aatgtgtgtt ttctatttc catttaaatt   4380 ttgctatatt aagactaatt taattcgttg agtcttggaa tcttctcaag gaggaacaaa   4440
tattaaaatg acatgtagaa acaaattttt tttttttttt tttttttttt tttttgaga   4500 cagagtctcg ctgtctccca ggctggagtt cagtggtgca atctcggctc actgcaagct   4560
ctgcctcctg ggttcaagcc attctcctgc ctcagcctcc cgagtagctg ggactacagg   4620 caccaccac cactcccggc taattttag aaacaaatat ttaaaatgac atattctccc   4680
aatacaatct atttagatct ggagaaggaa aaatcagata tttatgatat agttttattt   4740
taattttgaa ttatttgtgt cacagctcag cttttggaa gacaaactca aacacctata   4800
atttcattta tatttctaat tcacttggaa cctttctgct ttatgttacc tagaaaatga   4860
taatttgttt aacccaaaac ttctaaaata aattgcttaa tccttgaaat atgttattgg   4920
aaaattttaa gcagtgctta aacaccatta aattattatg aacttgtaat tcagaattga   4980
gtaaagaaat attttttcta gtccttcata tattgaaaac ttgccacatg acattgtatc   5040
gtcttcattt tccagaagat gcgttggtgt gccataggtt tctaacttcc ttgaaaatag   5100
ttttttaagt caattgtaaa tatacgtatt attgttaaaa gtaactttaa actgcaacac   5160
atagcttcaa aacaatatag agattttgta ataccttata agtggagttg gctaaaatac   5220
cttatccata taaaacttat tctattcttt gcatgcttat tttgtgtgtt ggttgctagc   5280
ttaaagtttg atttgttgtt actctttgtg tgccaaattc actaggcaag cggattttc   5340 ctcagacttc aaaaaataat tcttttaaga aaaatgtaa aatgtttat tctaaaaagc   5400 tgcattaaag ggacaaccta taaaaagttt tgctagctca tctttagaag gaagaaagaa   5460
```

```
tattagcttg ggtgatgttt aatttgggtg gcgatagttt ctgtaggcta aactttatga   5520
gaaaagtgta cctactctat aaaggtaata aatgtaaaac ctcttgctgt tattgaggaa   5580
gctcttcaac tacccctaaat ttcacaaatg taacttataa cactatgaaa agatttgacc  5640
aacaatttac gtttgctgtg tgctttagtt tttgtttaag catattcttt tgcttgaatt   5700
tctgtgttca tgagagttag ggtgttttat gcttcttgaa ctaattttat aacatattta   5760
atatattacc agttaagata taaaatcatt tgtacatagc gaattgtaaa gcagctatta   5820
aagtaggtga aataaagtat atatttgccg gttatccata tcttttagaa gtcctgacag   5880
aacaaccagt ttatttgcac ataggtagct tctgtttgaa ggaaggtaaa gttataagga   5940
aactcaaata ctataagatg tgtcaaggta tttctccaga attaattgca aagctagtgc   6000
tgaaggattt taatcagctt ctaaaatttt cttctcaata aggcatatgt tttgattact   6060
tagggaagat tcctcatttt tatttgccct ttatgcattt aatccacatg ataggacatt   6120
aaaaattaat ataagaaaaa atcgtgctca tactgtacat ctgtttctgt gcttggaact   6180
acttgttaat agttttatc gaagctgtca gcaataaggg acataaaact gctgtattat    6240
acattgtgga attgaataaa cagcctaatt ttttttttct agtatagggt acttaagcat   6300
ttccactttt ggaagaaaag tgtattagta ttttatattg catttcattt aaaaggacag   6360
tttttttttt tttttgtaa atccattcat tgaaatggtt tctaaactgt ataatgtaat    6420
ttggagccta tttagtaata gaattaaatg tcctatgtag tgctacaatt tttgaattag   6480
aaagtgatca aatgtaagaa aaaaatttaa aaattcagcc cagaaaacaa aatagtgtat   6540
taaattagtt taatgtaaaa ggaatttata agattttttt cctcaatata gatacctcac   6600
ttgaaaagaa agcacagcat acttaaagta gttctagtaa acatgtccta gaaaacagtt   6660
gctaaatgta ggacatcttt tgaggaatta gtttatgaga aataaaattt tacttgtttt   6720
tactatcctg ttagaagtat ttgtttatcc tgataatttt aagccaacat agtagtctta   6780
aattactttt gaatttctaa tctgtgaagg cagtaaatga aatatctgtt ctgcaactgt   6840
tgaaacaaat aattggctac attgaccata attaaagtta aaattttgcc aatgatgtac   6900
agttttatgg ttaaagttgc tgtggttggt tgcattacat gacacagaaa actgtcctct   6960
acctcacgtg aaataaatat tttatatggt tttactaaaa ataagactca tgtatctggt   7020
cacctagttt acaaattttg aattatattt attgaaacat gacatactgt gctctgagct   7080
tatacctcaa ttgtattttg tgctgttttc catttttcatg ccttgtaaat aacttgtata   7140
gattgtggat caaatactaa ataaaaactt ttaatgccaa ttaaatttga ttcaagttaa   7200
aa                                                                  7202

<210> SEQ ID NO 56
<211> LENGTH: 1351
<212> TYPE: DNA
<213> ORGANISM: Homo sapiens

<400> SEQUENCE: 56
agctccggct cccctatat aaatcggcca tttgcttcgc tccgccccgc agcgccggag      60
tcaaagccgg ttcccggccc agtcccgtcc tgcagcagtc tgcctcctct ttcaacatga    120
cagatgccgc tgtgtccttc gccaaggact tcctggcagg tggagtggcc gcagccatct    180
ccaagacggc ggtagcgccc atcgagcggg tcaagctgct gctgcaggtg cagcatgcca    240
gcaagcagat cactgcagat aagcaataca aaggcattat agactgcgtg gtccgtattc    300
ccaaggagca gggagttctg tccttctggc gcggtaacct ggccaatgtc atcagatact    360
```

| | | | |
|---|---|---|---|
| tccccaccca | ggctcttaac | ttcgccttca aagataaata caagcagatc ttcctgggtg | 420 |
| gtgtggacaa | gagaacccag | ttttggctct actttgcagg gaatctggca tcgggtggtg | 480 |
| ccgcaggggc | cacatccctg | tgttttgtgt accctcttga ttttgcccgt acccgtctag | 540 |
| cagctgatgt | gggtaaagct | ggagctgaaa gggaattccg aggcctcggt gactgcctgg | 600 |
| ttaagatcta | caaatctgat | gggattaagg gcctgtacca aggctttaac gtgtctgtgc | 660 |
| agggtattat | catctaccga | gccgcctact tcggtatcta tgacactgca aagggaatgc | 720 |
| ttccggatcc | caagaacact | cacatcgtca tcagctggat gatcgcacag actgtcactg | 780 |
| ctgttgccgg | gttgacttcc | tatccatttg acactgttcg ccgccgcatg atgatgcagt | 840 |
| cagggcgcaa | aggaactgac | atcatgtaca caggcacgct tgactgctgg cggaagattg | 900 |
| ctcgtgatga | aggaggcaaa | gctttttttca agggtgcatg gtccaatgtt ctcagaggca | 960 |
| tgggtggtgc | ttttgtgctt | gtcttgtatg atgaaatcaa gaagtacaca aagttatttt | 1020 |
| cctaggattt | ttccccctgt | gaacaggcat gttgtattat ataacatatc ttgagcattc | 1080 |
| ttgacagact | cctggctgtc | agtttctcag tggcaactat ttactggttg aaaatgggaa | 1140 |
| gcaataatat | tcatctgacc | agtttttctct taaagccatt tccatgatga tgatgatggg | 1200 |
| actcaattgt | attttttatt | tcagtcactc ctgataaata acaaatttgg agaaataaaa | 1260 |
| atatctaaaa | taattttgt | ctgcagtata ttttcatata aaaatgcata tttgagtgct | 1320 |
| acattcgaat | aaatactacc | ttttttagtga a | 1351 |

<210> SEQ ID NO 57
<211> LENGTH: 8789
<212> TYPE: DNA
<213> ORGANISM: Homo sapiens

<400> SEQUENCE: 57

| | | | |
|---|---|---|---|
| atgctcagtg | gcttctcgac | aagttggcag caacaacacg ccctggtcg tcgtcgccgc | 60 |
| tgcggtaacg | gagcggtttg | ggtggcggag cctgcgttcg cgccttcccg ctctcctcgg | 120 |
| gaggcccttc | ctgctctccc | ctaggctccg cggccgccca gggggtggga gcgggtgagg | 180 |
| ggagccaggc | gcccagcgag | agaggccccc cgccgcaggg cggcccggga gctcgaggcg | 240 |
| gtccggcccg | cgcgggcagc | ggcgcggcgc tgaggagggg cggcctggcc gggacgcctc | 300 |
| ggggcggggg | ccgaggagct | ctccgggccg ccggggaaag ctacgggccc ggtgcgtccg | 360 |
| cggaccagca | gcgcgggaga | gcggactccc ctcgccaccg cccgagccca ggttatcctg | 420 |
| aatacatgtc | taacaatttt | ccttgcaacg ttagctgttg ttttcactg tttccaaagg | 480 |
| atcaaaattg | cttcagaaat | tggagacata tttgatttaa aaggaaaaac ttgaacaaat | 540 |
| ggacaatatg | tctattacga | atacaccaac aagtaatgat gcctgtctga gcattgtgca | 600 |
| tagtttgatg | tgccatagac | aaggtggaga gagtgaaaca tttgcaaaaa gagcaattga | 660 |
| aagtttggta | agaagctga | aggagaaaaa agatgaattg gattcttaa taacagctat | 720 |
| aactacaaat | ggagctcatc | ctagtaaatg tgttaccata cagagaacat ggatgggag | 780 |
| gcttcaggtg | gctggtcgga | aaggatttcc tcatgtgatc tatgcccgtc tctggaggtg | 840 |
| gcctgatctt | cacaaaaatg | aactaaaaca tgttaaatat tgtcagtatg cgtttgactt | 900 |
| aaaatgtgat | agtgtctgtg | tgaatccata tcactacgaa cgagttgtat cacctggaat | 960 |
| tgatctctca | ggattaacac | tgcagagtaa tgctccatca gtatgatgg tgaaggatga | 1020 |
| atatgtgcat | gactttgagg | gacagccatc gttgtccact gaaggacatt caattcaaac | 1080 |

```
catccagcat ccaccaagta atcgtgcatc gacagagaca tacagcaccc cagctctgtt      1140
agccccatct gagtctaatg ctaccagcac tgccaacttt cccaacattc ctgtggcttc      1200
cacaagtcag cctgccagta tactgggggg cagccatagt gaaggactgt tgcagatagc      1260
atcagggcct cagccaggac agcagcagaa tggatttact ggtcagccag ctacttacca      1320
tcataacagc actaccacct ggactggaag taggactgca ccatacacac ctaatttgcc      1380
tcaccaccaa aacggccatc ttcagcacca cccgcctatg ccgccccatc ccggacatta      1440
ctggcctgtt cacaatgagc ttgcattcca gcctcccatt tccaatcatc ctgctcctga      1500
gtattggtgt tccattgctt actttgaaat ggatgttcag gtaggagaga catttaaggt      1560
tccttcaagc tgccctattg ttactgttga tggatacgtg gacccttctg gaggagatcg      1620
cttttgtttg ggtcaactct ccaatgtcca caggacagaa gccattgaga gagcaaggtt      1680
gcacataggc aaaggtgtgc agttggaatg taaaggtgaa ggtgatgttt gggtcaggtg      1740
ccttagtgac cacgcggtct ttgtacagag ttactactta gacagagaag ctgggcgtgc      1800
acctggagat gctgttcata agatctaccc aagtgcatat ataaaggtct ttgatttgcg      1860
tcagtgtcat cgacagatgc agcagcaggc ggctactgca caagctgcag cagctgccca      1920
ggcagcagcc gtggcaggaa acatccctgg cccaggatca gtaggtggaa tagctccagc      1980
tatcagtctg tcagctgctg ctggaattgg tgttgatgac cttcgtcgct tatgcatact      2040
caggatgagt tttgtgaaag gctggggacc ggattaccca agacagagca tcaaagaaac      2100
accttgctgg attgaaattc acttacaccg ggccctccag ctcctagacg aagtacttca      2160
taccatgccg attgcagacc cacaaccttt agactgaggt cttttaccgt tggggcccctt     2220 aaccttatca ggatggtgga ctacaaaata caatcctgtt tataatctga agatatattt      2280
cacttttgtt ctgcttatc ttttcataaa gggttgaaaa tgtgtttgct gccttgctcc       2340
tagcagacag aaactggatt aaaacaattt ttttttttcct cttcagaact tgtcaggcat     2400
ggctcagagc ttgaagatta ggagaaacac attcttatta attcttcacc tgttatgtat      2460
gaaggaatca ttccagtgct agaaaattta gccctttaaa acgtcttaga gccttttatc      2520
tgcagaacat cgatatgtat atcattctac agaataatcc agtattgctg attttaaagg     2580
cagagaagtt ctcaaagtta attcacctat gttatttttgt gtacaagttg ttattgttga    2640
acatacttca aaataatgt gccatgtggg tgagttaatt ttaccaagag taactttact      2700
ctgtgtttaa aaagtaagtt aataatgtat tgtaatcttt catccaaaat atttttttgca    2760 agttatatta gtgaagatgg tttcaattca gattgtcttg caacttcagt tttattttttg    2820 ccaaggcaaa aaactcttaa tctgtgtgta tattgagaat cccttaaaat taccagacaa      2880
aaaaatttaa aattacgttt gttattccta gtggatgact gttgatgaag tatacttttc      2940
ccctgttaaa cagtagttgt attcttctgt atttctaggc acaaggttgg ttgctaagaa      3000
gcctataaga ggaatttctt ttccttcatt catagggaaa ggttttgtat tttttaaaac      3060
actaaaagca gcgtcactct acctaatgtc tcactgttct gcaaaggtgg caatgcttaa     3120
actaaataat gaataaactg aatattttgg aaactgctaa attctatgtt aaatactgtg      3180
cagaataatg gaaacattac agttcataat aggtagtttg gatattttg tacttgatttt     3240 gatgtgactt ttttttggtat aatgtttaaa tcatgtatgt tatgatattg tttaaaattc    3300 agttttttgta tcttggggca agactgcaaa cttttttata tcttttggtt attctaagcc    3360 cttttgccatc aatgatcata tcaattggca gtgactttgt atagagaatt taagtagaaa    3420
agttgcagat gtattgactg taccacagac acaatatgta tgctttttac ctagctggta    3480
```

```
gcataaataa aactgaatct caacatacaa agttgaattc taggtttgat ttttaagatt    3540
tttttttct tttgcactttt tgagtccaat ctcagtgatg aggtaccttc tactaaatga    3600
caggcaacag ccagttctat tgggcagctt tgttttttc cctcacactc taccgggact    3660
tccccatgga cattgtgtat catgtgtaga gttggttttt ttttttttta attttattt    3720
tactatagca gaaatagacc tgattatcta caagatgata aatagattgt ctacaggata    3780
aatagtatga aataaaatca aggattatct ttcagatgtg tttacttttg cctggagaac    3840
ttttagctat agaaacacatt gtgtgatgat agtcctcctt atatcacctg aatgaacac    3900
agcttctact gccttgctca gaaggtctt taaatagacc atcctagaaa ccactgagtt    3960
tgcttatttc tgtgatttaa acatagatct tgatccaagc tacatgactt ttgtctttaa    4020
ataacttatc taccacctca tttgtactct tgattactta caattctttt cagtaaacac    4080
ctaattttct tctgtaaaag tttggtgatt taagtttat tggcagtttt ataaaaagac    4140
atcttctcta gaaattgcta actttaggtc cattttactg tgaatgagga ataggagtga    4200
gttttagaat aacagatttt taaaaatcca gatgatttga ttaaaacctt aatcatacat    4260
tgacataatt cattgcttct tttttttgag atatggagtc ttgctgtgtt gcccaggcag    4320
gagtgcagtg gtatgatctc agctcactgc aacctctgcc tcccgggttc aactgattct    4380
cctgcctcag cctccctggt agctaggatt acaggtgccc gccaccatgc ctggctaact    4440
tttgtagttt tagtagagac ggggttttgc ctgttggcca ggctggtctt gaactcctga    4500
cctcaagtga tccatccacc ttggcctccc aaagtgctgg gattacgggc gtgagccact    4560
gtccctggcc tcattgttcc cttttctact ttaaggaaag ttttcatgtt taatcatctg    4620
gggaaagtat gtgaaaaata tttgttaaga agtatctctt tggagccaag ccacctgtct    4680
tggtttcttt ctactaagag ccataaagta tagaaatact tctagttgtt aagtgcttat    4740
atttgtacct agatttagtc acacgctttt gagaaaacat ctagtatgtt atgatcagct    4800
attcctgaga gcttggttgt taatctatat ttctatttct tagtggtagt catctttgat    4860
gaataagact aaagattctc acaggtttaa aattttatgt ctactttaag ggtaaaatta    4920
tgaggttatg gttctgggtg ggttttctct agctaattca tatctcaaag agtctcaaaa    4980
tgttgaattt cagtgcaagc tgaatgagag atgagccatg tacacccacc gtaagacctc    5040
attccatgtt tgtccagtgc ctttcagtgc attatcaaag ggaatccttc atggtgttgc    5100
ctttatttc cggggagtag atcgtgggat atagtctatc tcatttttaa tagtttaccg    5160
cccctggtat acaaagataa tgacaataaa tcactgccat ataaccttgc ttttttccaga    5220
aacatggctg ttttgtattg ctgtaaccac taaataggtt gcctatacca ttcctcctgt    5280
gaacagtgca gatttacagg ttgcatggtc tggcttaagg agagccatac ttgagacatg    5340
tgagtaaact gaactcatat tagctgtgct gcatttcaga cttaaaatcc attttttgtgg    5400
ggcagggtgt ggtgtgtaaa gggggtgtt tgtaatacaa gttgaaggca aaataaaatg    5460
tcctgtctcc cagatgatat acatcttatt attttttaaag tttattgcta attgtaggaa    5520
ggtgagttgc aggtatcttt gactatggtc atctggggaa ggaaaatttt acattttact    5580
attaatgctc cttaagtgtc tatggaggtt aaagaataaa atggtaaatg tttctgtgcc    5640
tggtttgatg gtaactggtt aatagttact caccatttta tgcagagtca cattagttca    5700
cacccttttct gagagccttt tgggagaagc agttttattc tctgagtgga acagagttct    5760
ttttgttgat aatttctagt ttgctcccctt cgttattgcc aactttactg gcattttatt    5820
```

-continued

```
taatgatagc agattgggaa aatggcaaat ttaggttacg gaggtaaatg agtatatgaa      5880
agcaattacc tctaaagcca gttaacaatt attttgtagg tggggtacac tcagcttaaa      5940
gtaatgcatt ttttttccc gtaaaggcag aatccatctt gttgcagata gctatctaaa       6000
taatctcata tcctcttttg caaagactac agagaatagg ctatgacaat cttgttcaag      6060
cctttccatt tttttccctg ataactaagt aatttctttg aacataccaa gaagtatgta      6120
aaaagtccat ggccttattc atccacaaag tggcatccta ggcccagcct tatccctagc      6180
agttgtccca gtgctgctag gttgcttatc ttgtttatct ggaatcactg tggagtgaaa      6240
ttttccacat catccagaat tgccttattt aagaagtaaa acgttttaat ttttagcctt      6300
tttttggtgg agttatttaa tatgtatatc agaggatata ctagatggta acatttcttt      6360
ctgtgcttgg ctatctttgt ggacttcagg ggcttctaaa acagacagga ctgtgttgcc      6420
tttactaaat ggtctgagac agctatggtt ttgaattttt agttttttt ttttaaccca       6480 cttccctcc tggtctcttc cctctctgat aattaccatt catatgtgag tgttagtgtg       6540 cctccttta gcattttctt cttctctttc tgattcttca tttctgactg cctaggcaag       6600
gaaaccagat aaccaaactt actagaacgt tctttaaaac acaagtacaa actctgggac      6660
aggacccaag acactttcct gtgaagtgct gaaaaagacc tcattgtatt ggcatttgat      6720
atcagtttga tgtagcttag agtgcttcct gattcttgct gagtttcagg tagttgagat      6780
agagagaagt gagtcatatt catatttcc cccttagaat aatattttga aaggtttcat       6840
tgcttccact tgaatgctgc tcttacaaaa actggggtta caagggttac taaattagca      6900
tcagtagcca gaggcaatac cgttgtctgg aggacaccag caaacaacac acaacaaagc      6960
aaaacaaacc ttgggaaact aaggccattt gttttgtttt ggtgtcccct ttgaagccct      7020
gccttctggc cttactcctg tacagatatt tttgacctat aggtgccttt atgagaattg      7080
agggtctgac atcctgcccc aaggagtagc taaagtaatt gctagtgttt tcagggattt      7140
taacatcaga ctgaatgaa tgaatgaaac ttttgtcct tttttttct gttttttttt         7200 ttctaatgta gtaaggacta aggaaaacct ttggtgaaga caatcatttc tctctgttga      7260
tgtggatact tttcacaccg tttatttaaa tgctttctca ataggtccag agccagtgtt      7320
cttgttcaac ctgaaagtaa tggctctggg ttgggccaga cagttgcact ctctagtttg      7380
ccctctgcca caaatttgat gtgtgacctt tgggcaagtc attatcttc tctgggcctt       7440 agttgcctca tctgtaaaat gagggagttg gagtagatta attattccag ctctgaaatt      7500
ctaagtgacc ttggctacct tgcagcagtt ttggatttct tccttatctt tgttctgctg      7560 tttgagggg cttttacttt atttccatgt tattcaaagg agactaggct tgatattta        7620 ttactgttct tttatggaca aaaggttaca tagtatgccc ttaagactta attttaacca      7680
aaggcctagc accaccttag gggctgcaat aaacacttaa cgcgcgtgcg cacgcgcgcg      7740
cgcacacaca cacacacaca cacacacaca cacaggtcag agtttaaggc tttcgagtca      7800
tgacattcta gcttttgaat tgcgtgcaca cacacacgca cgcacacact ctggtcagag      7860
tttattaagg ctttcgagtc atgacattat agcttttgag ttggtgtgtg tgacaccacc      7920
ctcctaagtg gtgtgtgctt gtaatttttt ttttcagtga aaatggattg aaaacctgtt      7980
gttaatgctt agtgatatta tgctcaaaac aaggaaattc ccttgaaccg tgtcaattaa      8040
actggtttat atgactcaag aaaacaatac cagtagatga ttattaactt tattcttggc      8100 tcttttagg tccattttga ttaagtgact tttggctgga tcattcagag ctctcttcta       8160
gcctaccctt ggatgagtac aattaatgaa attcatattt tcaaggacct gggagccttc      8220
```

| | |
|---|---|
| cttggggctg ggttgagggt gggggggttgg ggagtcctgg tagaggccag ctttgtggta | 8280 |
| gctggagagg aagggatgaa accagctgct gttgcaaagg ctgcttgtca ttgatagaag | 8340 |
| gactcacggg cttggattga ttaagactaa acatggagtt ggcaaacttt cttcaagtat | 8400 |
| tgagttctgt tcaatgcatt ggacatgtga tttaagggaa aagtgtgaat gcttatagat | 8460 |
| gatgaaaacc tggtgggctg cagagcccag tttagaagaa gtgagttggg ggttggggac | 8520 |
| agatttggtg gtggtatttc ccaactgttt cctcccctaa attcagagga atgcagctat | 8580 |
| gccagaagcc agagaagagc cactcgtagc ttctgctttg gggacaactg gtcagttgaa | 8640 |
| agtcccagga gttcctttgt ggctttctgt atacttttgc ctggttaaag tctgtggcta | 8700 |
| aaaaatagtc gaacctttct tgagaactct gtaacaaagt atgttttga ttaaaagaga | 8760 |
| aagccaacta aaaaaaaaaa aaaaaaaa | 8789 |

<210> SEQ ID NO 58
<211> LENGTH: 7014
<212> TYPE: DNA
<213> ORGANISM: Homo sapiens

<400> SEQUENCE: 58

| | |
|---|---|
| atccgggtcc tgggcgagcg ggcgccgtgc gcgtgtcccg cggccgagct gctaataaag | 60 |
| ttgcagcgag gagaagcgca gcgacggcgt cgggagagcg cgcctagccg gctcgcgaaa | 120 |
| aggaagctgt tgaagttatt gaagtacctg ttgctatatt ctaagaaatt aaaatgtcca | 180 |
| gaaatctgcc tctgacttga cccaatgaaa aagcatatg gcacttgtga agataaatgt | 240 |
| tactcctccc ttttttaattg gaacttctgc ttaggacctg tgtatgacgt ttcacctgtg | 300 |
| atctgttctt tcggtagcca ctgactttga gttacaggaa ggtctccgaa gatttgtgtc | 360 |
| aaatgacgtc aatggccagc ttgttttctt ttactagtcc agcagtaaag cgattgttgg | 420 |
| gctggaaaca aggtgatgag gaggagaaat gggcagaaaa ggcagttgat gctttggtga | 480 |
| agaaactaaa aaagaaaaag ggtgccatgg aggaactgga gaaagccttg agcagtccag | 540 |
| gacagccgag taaatgtgtc actattccca gatctttaga tggacgcctg caggtttctc | 600 |
| acagaaaagg cttaccccat gttatatatt gtcgtgtttg gcgctggccg gatttgcaga | 660 |
| gtcatcatga gctaaagccg ttggatattt gtgaatttcc ttttggatct aagcaaaaag | 720 |
| aagtttgtat caacccatac cactataaga gagtggagag tccagtctta cctccagtat | 780 |
| tagtgcctcg tcataatgaa ttcaatccac aacacagcct tctggttcag tttaggaacc | 840 |
| tgagccacaa tgaaccacac atgccacaaa atgccacgtt tccagattct ttccaccagc | 900 |
| ccaacaacac tccttttccc ttatctccaa acagccctta tccccttct cctgctagca | 960 |
| gcacatatcc caactcccca gcaagttctg gaccaggaag tccatttcag ctcccagctg | 1020 |
| atacgcctcc tcctgcctat atgccacctg atgatcagat gggtcaagat aattcccagc | 1080 |
| ctatggatac aagcaataat atgattcctc agattatgcc cagtatatcc agcagggatg | 1140 |
| ttcagcctgt tgcctatgaa gagcctaaac attggtgttc aatagtctac tatgaattaa | 1200 |
| acaatcgtgt tggagaagct tttcatgcat cttctactag tgtgttagta gatggattca | 1260 |
| cagatccttc aaataacaaa agtagattct gcttgggttt tttgtcaaat gttaatcgta | 1320 |
| attcgacaat tgaaaacact aggcgacata ttggaaaagg tgttcatctg tactatgttg | 1380 |
| gtggagaggt gtatgcggaa tgcctcagtg acagcagcat atttgtacag gtaggaact | 1440 |
| gcaactttca tcatggcttt catcccacca ctgtctgtaa gattcccagc agctgcagcc | 1500 |

```
tcaaaatttt taacaatcag gagtttgctc agcttctggc tcaatctgtc aaccatgggt    1560
ttgaggcagt atatgagctc accaaaatgt gtaccattcg gatgagtttt gtcaagggtt    1620
ggggagcaga atatcaccgg caggatgtaa ccagcacccc atgttggatt gagattcatc    1680
ttcatgggcc tcttcagtgg ctggataaag tccttactca gatgggctcc cctctgaacc    1740
ccatatcttc tgttcataa tgcagaagta ttcttttcaa ttatattgtt agtggacttg    1800
ttttaatttt agagaaactt tgagtacaga tactgtgagc ttacattgaa aacagatatt    1860
acagcttatt tttctaca taattgtgac caatacattt gtattttgtg atgaatctac    1920
atttgtttgt attcatgttc atgtgattaa ctcttagaag tgttgtaaaa gatgcagagt    1980
aagtattatg ccccagttca gaaatttggc attgatctta aactggaaca tgcttttact    2040
ttattgccct aacaattttt tattaaattt atttgaaaat gcatcacatg atgaaaaatt    2100
atagtagctt ataagagggc atatacagtg aagagtaagt tttccctcct actctcgatc    2160
ttccagaagc tgtacttta ccagtttctt tgtcccacca acttaaaaaa aaaaagtaca    2220
attcattgtt ttgcaaaagt gtatggtagg ggcttaaaag aaactataaa gttttatttg    2280
aatgaacact atgcactgct gtaactggta gtgttcagta aaagcaaaat gatagttttc    2340
tagatgacat aaaatttaca tttaatacag ataagtgttc ttcagtgtaa tgtgacttca    2400
tgctatatat cttttgtaag acatttcctt ttttaaaaaa attttgcaa ataactgatc    2460 tcaagtatat gtcatttact caaaatctgt cataagcatt actttatagc tagtgacagt    2520
gcatgcacag ccttgttcaa ctatgtttgc tgcttttgga caatgttgca agaactctat    2580
ttttgacatg cattaatctt ttattttgca ctttatgggt tgacagtttt tagcataacc    2640
tttgataaaa tacactcaag tgacttggac ttagatgctt atccttacgt ccttggtacc    2700 tttttgtat taacaaacac tgcaatttat agattacatt tgtaggaagt tatgcttttt    2760
tctggttttt gttttacttt caacctaggt tataagactg ttattctata gctccaactt    2820
aaggtgcctt tttaattccc tacagtttta tgggtgttat cagtgctgga gaatcatgta    2880
gttaatccca ttgctcttac aagtgtcagc ttacttgtat cagcctccct acgcaaggac    2940
ctatgcactg gagccgtagg aggctcttca gttgggcccc aaggataagg ctactgattt    3000
gatactaaat gaatcagcag tggatgtagg gatagctgat tttaaaacac tcggctgggc    3060
acagtggctc acacctgtaa tcccagcact tgggaggct gaggcaggca gatcatgatg    3120
tcaggagttt gagaccagcc tggccaatat ggtgaaaccc tgtctctaca aaaatacaa    3180 aaattagctg gcatggtgg tgcgtgcctg aagtcccagc tactcgggaa gctgaggcag    3240
aagaatcact tgaacctggg aggcggaggt tgtggtgagc cgagatcgca ccactgcact    3300
ccagcctggg cgacagagcg agactctgcc tcaaaaaca aaacaaaaca aaacactcac    3360
ccatcaacga atatagactc ttctctcatt tatcgatgat cctctttttc cattttttaa    3420
gtacttatgt ggaagctagt ctcccaaaac acaatcttta gagagaaaag acatgaacga    3480
actccaaaat atccatttaa tcaatcatgt ttttggcttt ggataaagaa ctttgaacca    3540 gttttttct caggagctgt caaatggaca cttaattatg acatgagaat gaagaaatta    3600
ttttggaaaa aaaaaatgac ctaatttacc tatcagtgaa agctttattt tctggtgcct    3660
tttgaaagta tatggagtca tatcattctt ctgtttaaaa tgttagtttg gtttgacttt    3720
ccactttgtc ctttctgctc ttgtgaagaa aaaaaaagc attttcgagg aaagaattat    3780
gcaatttctt ttgttttctg tgtcattatt tattgctttt tcaatgtgca gccagtggat    3840
ggttttagtt ctttcagatg aactgccatt tgtgtttcag ctcacagttc tttgctgggt    3900
```

```
aaaagaaata ctttctgaca gtcacctgag ccttaaatgt aagtattaca tgacatgcat    3960
tctgtttctt ccagagttct gtctgccaca cgaaagagaa tatttgctta cttgatagaa    4020
ctttggcatt ttcatcattc ttttacttaa ccaggcttat ggcatgatct ctggaacaaa    4080
tttgtaggaa aaaattactc caattgaatg actgatgtat gtaatcaact tcattgggct    4140
gcagtaaact agtggaaatt agagagttgt tttattggtg ttttctactg tgagttaatt    4200
aaaaattgtt tttatttggg gtcattatgt cacagtcttg agttaacaag atcttacgtg    4260
attggccttt tctttgtttt ctcttaggag ttgtgtctca tgaatgacag tactaaagct    4320
attaacaact aagagtttga cagagaacta taagcctgtt gtatctccta aaagttgtca    4380
actccccacc cttggacttt aaatgaaaat tttattcagt ccagctattc ttacagtccc    4440
taaggatttt catatatcta tgtataggag ataaaatttg ctagtaagat ttttaaaaac    4500
tggctagtga aggaaagta cctctgaaag aaaccatttt agcaaattat ggttatatgt     4560
tttaatttaa tctacagaat gttttatagt aaaattctag caccactaga ataatcacat    4620
agcatgtaca atatatttat gctggctgaa aagacagaat ctgggaataa taaaattgca    4680
accagtttgg taatgcaaac agcagaatag aatgaaatct cagtaatgaa ttaaagcaac    4740
aaaaagatat tgattggcaa aaagcaagat ataagagatt catttgctta acatttctac    4800
ataatattta tggtctggtc agtattggtc tggtcagtat tgcctggctg acgtgaaatg    4860
taaactagta ggcgtgttat tgatctgcta aaactaaccc tcttttttaag aggagattta    4920 aggaagacgt caatcaaaat gtcaaatatg tgtgtcagaa tataataat ttttcacatt     4980 gtattgttgc tatataaaaa aataataga attggttggg tttctgaggt gaaatccaga    5040
gtaagagtac tagacagttc aacaagccac atctaatggc acagatagag gatgtagcta    5100 ttttataccct ttcataacat ttgagagtaa gatatccttc aggatgtgaa gtgattatta   5160
agtactcata cctgaaatct gttgtcaaga ttagaactgg ggttcatgtt aaaaaccttc    5220
catattacct gagggtaccct gtggggaaca gttccttccc ctgtgtggta gtattttgtt   5280
ggaagagaat gtttatacaa aaatgaaatt tcttccaaca gcagagaaac tctaaaaagt    5340
ttgatagtac ctatcaaagt gctgtacttc tgtgatagag aacatctgat gtaccaattt    5400
agatctattt ctttatactt tttctaatca attgcttaat agtactttgg atgattatca    5460
cctttgccac ttaaaatata taaatatcct ttttacttca tgaggaagga agaattttt    5520 gataattact gagttcagcc ttttgtgatg acttatattt tggacttaca ttttaacttt    5580
aaagaatgtc agatcccttc tttgtcttac tagttaaatc ctcacctaat ctcttgggta    5640
tgaatataaa tgtgtgtcat cgttatattg ttcagctaga tgagcaagta tcttagggta    5700
gtaggtagcc tggtggtttt agaagtgttt ggtgattttt atggagagag ttttcctaag    5760
tggtggttta taggtggtat cagatattat tagggcagct ttttggggag taatctcagg    5820
tctcccagag cagcagcatt tttctcattg atataagtaa gattcttagg agcttttctt    5880
atcacacaag atgcctgaat cgaatgtgag aattgaaggc atttcttctg cataaacaaa    5940
gaattctacc tgctggacag aaacctggaa agttctttgg aattcgctga attacagttt    6000
agtatgtcct gattacagag tgacaatatt tatcaagcct tgttatatt ggattatctt     6060 ctctcttaaa atacaactgt attataattg aaatgacagc ccaaaattgg atggtttacc    6120
aaaaccaatg aaagggattt cacacatcaa ttttatttc tgttttgaag agcacatgct     6180
atataataat tgctagtagc aactgcagta aaacaggtga taagttattt tctctgaaaa    6240
```

```
gatccagtcc tagagcagga ttcttcgatc attcatggca gagtgaaaaa ggtttgtatg    6300
gttcttgtcc aaataactca gttcttaaaa ttcttaaaat gatcgtaaac cattatcctt    6360
taaaggttta tttgaagatg ctgttaaagt acagaatttt gtgtacaggt agatttttcc    6420
gtccctcatt aatagtgcct tcttaattaa tacagactgg tgttagctat aacaaaactc    6480
cagtaaggcc aaagaatccc aagttctttg tggaaaaaaa aaaaaaatct tttagggtca    6540
gattttccct tctaatatca ttgaagatga tgttgcattg attattcat aaagtatttt     6600 aactatagga actctagaag ataatggtta ggcaagtgat tttttttta aatatggttg     6660 gcgtaagttg tattttgaaa ttcacttatt ttaaaatcga agaggattgt aatcatggaa    6720
atagaatgtt tgtatctacc tgcccacatt ttcttaaaaa gatatttcat atacagataa    6780
tgaagaccaa gctagtggct gcactgtagg tctgctgctt atttgtattt gttgtgcttc    6840
tgtttatgtt gtagaagctg aaattctagc aacatgcttc aattctgtta ttttgatact    6900
tatgaaaatg tattaggttt tactatattg tgcttttgaa agccataact cttaagaact    6960
ttgtttttgc atattgtttg ctaattcttt actttaataa acctcaaaac ctgc          7014

<210> SEQ ID NO 59
<211> LENGTH: 2886
<212> TYPE: DNA
<213> ORGANISM: Homo sapiens

<400> SEQUENCE: 59
cgatcgaggg agctgagccg agagaaagag ccgccgggcg ctgcctcgcc agacctcgct      60 gggacccegg ggccaccggg aggcactttt gtggaggggg gaggggggggc gacctcggca    120 gcctcggcgc acgaagcgtc cgagggcagc gtggggcggg ctgcgacctc tgcatcggtg    180
gactgcattt ttaattaagg attcccagca gctctttggg attttacag cttccactca     240 tgtgttgaca cccgcgtcca ggagaaactc gctccaagtg catctagcgc ctgggacctg    300
agacggcgtt ggccttcgt gcatgcaaat ccagggattt aggttttgtt tgggattttcc    360 ttttctttct ttccttttt ttttcttttt gcagggagta agaagggagc tgggggtatc     420
aacaagcctg cctttcggat cctgcgggaa aagcccatgt agttaagcgc tttggtttaa    480
aaaaaaggca aggtaaaggc agggcttttcc agacacattt aggggttcgc gcgagcgctt    540
tgtgctcatg gaccagccgc acaacttttg aaggctcgcc ggcccatgtg gggtcttttct   600 ggcggcgcgc cgcctgcagc cccctaaag cgcggggggct ggagttgttg agcagccccg     660
ccgctgtggt ccatgtagcc gctggccgcg cgcggactgc ggctcggcgt gcgcgtgttc    720
ccggccgtcc cgcctcggcg agctccctca tgttgtcgcc ctgcgcgcc ccttcgacga     780 caggctgtgc gcggtctgca cggcgctccg cggcggagct tcatgtgggg ctgcgacccg    840
cgcagccggc gcctcgctga gggaacggac ccccggtaac cggagaccgc ctcccccca     900 cccctggcgc caaaggatat cgtatgttca ggtccaaacg ctcggggctg gtgcggcgac    960
tttggcgaag tcgtgtggtc cccgaccggg aggaaggcgg cagcggcggc ggcggtggcg   1020
gcgacgagga tgggagcttg ggcagccgag ctgagccggc cccgcgggca agagagggcg   1080
gaggctgcgg ccgctccgaa gtccgccggg tagccccgcg cgcggcccgg gacgcagtgg   1140
gacagcgagg cgcccagggc gcggggaggc gccggcgcgc aggggcccc cgaggcccga    1200 tgtcggagcc aggggccggc gctgggagct ccctgctgga cgtggcgagc cgggaggcc    1260 cgggctggct gcccgagagt gactgcgaga cggtgacctg ctgtctcttt tcggagcggg   1320
acgccgccgg cgcgccccgg gacgccagcg accccctggc cggggcggcc ctggagccgg   1380
```

```
cgggcggcgg gcggagtcgc gaagcgcgct cgcggctgct gctgctggag caggaactca    1440
aaaccgtcac gtactcgctg ctgaagcggc tcaaggagcg ctcgctggac acgctgctgg    1500
aggcggtgga gtcccgcggc ggcgtgccgg gcggctgcgt gctggtgccg cgcgccgacc    1560
tccgcctggg cggccagccc gcgccgccgc agctgctgct cggccgcctc tttcgctggc    1620
ccgacctgca gcacgccgtg gagctgaagc ccctgtgcgg ctgccacagc ttcgccgccg    1680
ccgccgacgg ccctaccgtg tgctgcaacc cctaccactt cagccggctc tgcgggcccg    1740
aatctccgcc acctccctac tctcggctgt ctcctcgcga cgagtacaag ccactggatc    1800
tgtccgattc cacattgtct tacactgaaa cggaggctac caactccctc atcactgctc    1860
cgggtgaatt ctcagacgcc agcatgtctc cggacgccac caagccgagc cactggtgca    1920
gcgtggcgta ctgggagcac cggacgcgcg tgggccgcct ctatgcggtg tacgaccagg    1980
ccgtcagcat cttctacgac ctacctcagg gcagcggctt ctgcctgggc agctcaacc    2040 tggagcagcg cagcgagtcg gtgcggcgaa cgcgcagcaa gatcggcttc ggcatcctgc    2100
tcagcaagga gcccgacggc gtgtgggcct acaaccgcgg cgagcacccc atcttcgtca    2160
actccccgac gctggacgcg cccggcgccc gcgccctggt cgtgcgcaag gtgcccccg    2220 gctactccat caaggtgttc gacttcgagc gctcgggcct gcagcacgcg cccgagcccg    2280
acgccgccga cggcccctac gaccccaaca cgtccgcat cagcttcgcc aagggctggg    2340
ggccctgcta ctcccggcag ttcatcacct cctgcccctg ctggctggag atcctcctca    2400
acaaccccag atagtggcgg ccccggcggg aggggcgggt gggaggccgc ggccaccgcc    2460
acctgccggc ctcgagaggg gccgatgccc agagacacag cccccacgga caaaaccccc    2520
cagatatcat ctacctagat ttaatataaa gtttttatata ttatatggaa atatatatta    2580
tacttgtaat tatggagtca ttttttacaat gtaattattt atgtatggtg caatgtgtgt    2640
atatggacaa aacaagaaag acgcactttg gcttataatt cttttcaatac agatatattt    2700 tctttctctt cctccttcct cttccttact ttttatatat atatataaag aaaatgatac    2760
agcagagcta ggtggaaaag cctgggtttg gtgtatggtt tttgagatat taatgcccag    2820
acaaaaagct aataccagtc actcgataat aaagtattcg cattatagtt tttttaaaa    2880 aaaaaa                                                               2886
```

<210> SEQ ID NO 60
<211> LENGTH: 3088
<212> TYPE: DNA
<213> ORGANISM: Homo sapiens

<400> SEQUENCE: 60

```
cggagagccg cgcagggcgc gggccgcgcg gggtggggca gccggagcgc aggcccccga      60
tccccggcgg gcgccccggg gccccgcgc gcgccccggc ctccgggaga ctggcgcatg     120
ccacggagcg cccctcgggc cgccgccgct cctgccccggg ccctgctgc tgctgctgtc    180 gcctgcgcct gctgccccaa ctcggcgccc gacttcttca tggtgtgcgg aggtcatgtt    240
cgctccttag caggcaaacg acttttctcc tcgcctcctc gccccgcatg ttcaggacca    300
aacgatctgc gctcgtccgg cgtctctgga ggagccgtgc gcccggcggc gaggacgagg    360
aggagggcgc agggggaggt ggaggaggag gcgagctgcg gggagaaggg gcgacggaca    420
gccgagcgca tggggccggt ggcggcggcc cgggcagggc tggatgctgc ctgggcaagg    480
cggtgcgagg tgccaaaggt caccaccatc cccacccgcc agccgcgggc gccggcgcgg    540
```

-continued

```
ccgggggcgc cgaggcggat ctgaaggcgc tcacgcactc ggtgctcaag aaactgaagg      600
agcggcagct ggagctgctg ctccaggccg tggagtcccg cggcgggacg cgcaccgcgt      660
gcctcctgct gcccggccgc ctggactgca ggctgggccc gggggcgccc gccggcgcgc      720
agcctgcgca gccgccctcg tcctactcgc tccccctcct gctgtgcaaa gtgttcaggt      780
ggccggatct caggcattcc tcggaagtca agaggctgtg ttgctgtgaa tcttacggga      840
agatcaaccc cgagctggtg tgctgcaacc cccatcacct tagccgactc tgcgaactag      900
agtctccccc ccctccttac tccagatacc cgatggattt tctcaaacca actgcagact      960
gtccagatgc tgtgccttcc tccgctgaaa caggggaac gaattatctg cccctgggg     1020
ggctttcaga ttcccaactt cttctggagc ctggggatcg gtcacactgg tgcgtggtgg     1080
catactggga ggagaagacg agagtgggga ggctctactg tgtccaggag ccctctctgg     1140
atatcttcta tgatctacct caggggaatg gcttttgcct cggacagctc aattcggaca     1200
acaagagtca gctggtgcag aaggtgcgga gcaaaatcgg ctgcggcatc cagctgacgc     1260
gggaggtgga tggtgtgtgg gtgtacaacc gcagcagtta ccccatcttc atcaagtccg     1320
ccacactgga caacccggac tccaggacgc tgttggtaca caaggtgttc cccggtttct     1380
ccatcaaggc tttcgactac gagaaggcgt acagcctgca gcggcccaat gaccacgagt     1440
ttatgcagca gccgtggacg ggctttaccg tgcagatcag cttctgtgaag gctggggcc     1500
agtgctacac ccgccagttc atcagcagct gcccgtgctg gctagaggtc atcttcaaca     1560
gccggtagcc gcgtgcggag gggacagagc gtgagctgag caggccacac ttcaaactac     1620
tttgctgcta atattttcct cctgagtgct tgcttttcat gcaaactctt tggtcgtttt     1680
ttttttgttt gttggttggt tttcttcttc tcgtcctcgt ttgtgttctg ttttgtttcg     1740
ctctttgaga aatagcttat gaaaagaatt gttgggggtt tttttggaag aagggggcagg     1800
tatgatcggc aggacaccct gataggaaga ggggaagcag aaatccaagc accaccaaac     1860
acagtgtatg aagggggcg gtcatcattt cacttgtcag gagtgtgtgt gagtgtgagt     1920
gtgcggctgt gtgtgcacgc gtgtgcagga gcggcagatg gggagacaac gtgctctttg     1980
ttttgtgtct cttatggatg tccccagcag agaggtttgc agtcccaagc ggtgtctctc     2040
ctgccccttg gacacgctca gtggggcaga ggcagtacct gggcaagctg gcggctgggg     2100
tcccagcagc tgccaggagc acggctctgt ccccagcctg ggaaagcccc tgcccctcct     2160
ctccctcatc aaggacacgg gcctgtccac aggcttctga gcagcgagcc tgctagtggc     2220
cgaaccagaa ccaattattt tcatccttgt cttattccct tcctgccagc cctgccatt     2280
gtagcgtctt tcttttttgg ccatctgctc ctggatctcc ctgagatggg cttcccaagg     2340
gctgccgggg cagcccctc acagtattgc tcacccagtg ccctctcccc tcagcctctc     2400
ccctgcctgc cctggtgaca tcaggttttt cccggactta gaaaaccagc tcagcactgc     2460
ctgctcccat cctgtgtgtt aagctctgct attaggccag caagcgggga tgtccctggg     2520
agggacatgc ttagcagtcc ccttccctcc aagaaggatt tggtccgtca taacccaagg     2580
taccatccta ggctgacacc taactcttct ttcatttctt ctacaactca tacactcgta     2640
tgatacttcg acactgttct tagctcaatg agcatgttta gactttaaca taagctattt     2700
ttctaactac aaaggtttaa atgaacaaga gaagcattct cattggaaat ttagcattgt     2760
agtgctttga gagagaaagg actcctgaaa aaaacctga gatttattaa agaaaaaaat     2820
gtatttttatg ttatatataa atatattatt acttgtaaat ataagacgt tttataagca     2880
tcattattta tgtattgtgc aatgtgtata aacaagaaaa ataaagaaaa gatgcacttt     2940
```

```
gctttaatat aaatgcaaat aacaaatgcc aaattaaaaa agataaacac aagattggtg    3000 ttttttttcta tgggtgttat cacctagctg aatgtttttc taaaggagtt tatgttccat    3060
taaacgattt ttaaaatgta cacttgaa                                       3088
```

<210> SEQ ID NO 61
<211> LENGTH: 1722
<212> TYPE: DNA
<213> ORGANISM: Homo sapiens

<400> SEQUENCE: 61

```
attcattgcg ccgcggcacg gcctagcgag tggttcttct gcgctactgc tgcgcgaatc      60
ggcgacccca gtgcctcgac cactatgccg cgctctttcc tcgtcaggaa gccctccgac     120
cccaatcgga agcctaacta cagcgagctg caggactcta atccagagtt taccttccag     180
cagccctacg accaggccca cctgctggca gccatcccac ctccggagat cctcaacccc     240
accgcctcgc tgccaatgct catctgggac tctgtcctgg cgcccaagc ccagccaatt      300 gcctgggcct cccttcggct ccaggagagt cccagggtgg cagagctgac ctccctgtca     360
gatgaggaca gtgggaaagg ctcccagccc ccagcccac cctcaccggc tccttcgtcc      420
ttctcctcta cttcagtctc ttccttggag gccgaggcct atgctgcctt cccaggcttg     480
ggccaagtgc ccaagcagct ggcccagctc tctgaggcca aggatctcca ggctcgaaag     540
gccttcaact gcaaatactg caacaaggaa tacctcagcc tgggtgccct caagatgcac     600
atccgaagcc acacgctgcc ctgcgtctgc ggaacctgcg ggaaggcctt ctctaggccc     660
tggctgctac aaggccatgt ccggacccac actggcgaga agcccttctc ctgtccccac     720
tgcagccgtg ccttcgctga ccgctccaac ctgcgggccc acctccagac ccactcagat     780
gtcaagaagt accagtgcca ggcgtgtgct cggaccttct cccgaatgtc cctgctccac     840
aagcaccaag agtccggctg ctcaggatgt ccccgctgac cctcgaggct ccctcttcct     900
ctccatacct gccctgcct gacagccttc cccagctcca gcaggaagga ccccacatcc      960
ttctcactgc catggaattc cctcctgagt gccccacttc tggccacatc agccccacag    1020
gactttgatg aagaccattt tctggttctg tgtcctctgc ctgggctctg gaagaggcct    1080
tcccatggcc atttctgtgg agggagggca gctggccccc agccctgggg gattcctgag    1140
ctggcctgtc tgcgtgggtt tttgtatcca gagctgtttg gatacagctg ctttgagcta    1200
caggacaaag gctgacagac tcactgggaa gctcccaccc cactcagggg accccactcc    1260
cctcacacac acccccccac aaggaaccct caggccaccc tccacgaggt gtgactaact    1320
atgcaataat ccaccccag gtgcagcccc agggcctgcg gaggcggtgg cagactagag      1380
tctgagatgc cccgagccca ggcagctatt tcagcctcct gtttggtggg gtggcacctg    1440
tttcccgggc aatttaacaa tgtctgaaaa gggactgtga gtaatggctg tcacttgtcg    1500
ggggcccaag tggggtgctc tggtctgacc gatgtgtctc ccagaactat tctggggcc      1560 cgacaggtgg gcctgggagg aagatgttta catttttaaa ggtacactgg tatttatatt    1620
tcaaacattt tgtatcaagg aaacgttttg tatagttata tgtacagttt attgatattc    1680
aataaagcag ttaatttata tattaaaaaa aaaaaaaaaa aa                       1722
```

<210> SEQ ID NO 62
<211> LENGTH: 2112
<212> TYPE: DNA
<213> ORGANISM: Homo sapiens

<400> SEQUENCE: 62

```
aaaacgggct cagttcgtaa aggagccggg tgacttcaga ggcgccggcc cgtccgtctg      60
ccgcacctga gcacggcccc tgcccgagcc tggcccgccg cgatgctgta gggaccgccg     120
tgtcctcccg ccggaccgtt atccgcgccg ggcgcccgcc agacccgctg gcaagatgcc     180
gcgctccttc ctggtcaaga agcatttcaa cgcctccaaa aagccaaact acagcgaact     240
ggacacacat acagtgatta tttccccgta tctctatgag agttactcca tgcctgtcat     300
accacaacca gagatcctca gctcaggagc atacagcccc atcactgtgt ggactaccgc     360
tgctccattc cacgcccagc tacccaatgg cctctctcct ctttccggat actcctcatc     420
tttgggcga gtgagtcccc ctcctccatc tgacacctcc tccaaggacc acagtggctc     480
agaaagcccc attagtgatg aagaggaaag actacagtcc aagctttcag accccccatgc    540
cattgaagct gaaaagtttc agtgcaattt atgcaataag acctattcaa cttttttctgg   600
gctggccaaa cataagcagc tgcactgcga tgcccagtct agaaaatctt tcagctgtaa    660
atactgtgac aaggaatatg tgagcctggg cgccctgaag atgcatattc ggacccacac     720
attaccttgt gtttgcaaga tctgcggcaa ggcgttttcc agaccctggt tgcttcaagg     780
acacattaga actcacacgg gggagaagcc ttttcttgc cctcactgca acagagcatt     840
tgcagacagg tcaaatctga gggctcatct gcagacccat tctgatgtaa agaaatacca     900
gtgcaaaaac tgctccaaaa ccttctccag aatgtctctc ctgcacaaac atgaggaatc     960
tggctgctgt gtagcacact gagtgacgca atcaatgttt actcgaacag aatgcatttc    1020
ttcactccga agccaaatga caaataaagt ccaaaggcat tttctcctgt gctgaccaac    1080
caaataatat gtatagacac acacacatat gcacacacac acacacacac ccacagagag    1140
agagctgcaa gagcatggaa ttcatgtgtt taaagataat cctttccatg tgaagtttaa    1200
aattactata tatttgctga tggctagatt gagagaataa aagacagtaa cctttctctt    1260
caaagataaa atgaaaagca cattgcatct tttcttccta aaaaaatgca aagatttaca    1320
ttgctgccaa atcatttcaa ctgaaaagaa cagtattgct ttgtaataga gtctgtaata    1380
ggatttccca taggaagaga tctgccagac gcgaactcag gtgccttaaa aagtattcca    1440
agtttactcc attacatgtc ggttgtctgg ttgccattgt tgaactaaag cctttttttg    1500
attacctgta gtgctttaaa gtatattttt aaagggagg aaaaaaataa caagaacaaa    1560
acacaggaga atgtattaaa agtattttg ttttgttttg ttttgccaa ttaacagtat     1620
gtgccttggg ggaggaggga aagattagct ttgaacattc ctggcgcatg ctccattgtc    1680
ttactatttt aaaacatttt aataatttt gaaaattaat taaagatggg aataagtgca    1740
aaagaggatt cttacaaatt cattaatgta cttaaactat ttcaaatgca taccacaaat    1800
gcaataatac aatacccctt ccaagtgcct ttttaaattg tatagttgat gagtcaatgt    1860
aaatttgtgt ttatttttat atgattgaat gagttctgta tgaaactgag atgttgtcta    1920
tagctatgtc tataaacaac ctgaagactt gtgaaatcaa tgtttctttt ttaaaaaaca    1980
atttttcaagt tttttttaca ataaacagtt ttgatttaaa atctcgtttg tatactattt    2040
tcagagactt tacttgcttc atgattagta ccaaaccact gtacaaagaa ttgtttgtta    2100
acaagaaaaa aa                                                        2112
```

<210> SEQ ID NO 63
<211> LENGTH: 3173
<212> TYPE: DNA
<213> ORGANISM: Homo sapiens

<400> SEQUENCE: 63

```
cggcgggcgg cagcagccta ggcagcagca gtagcagaag cagcagccgc cgagcagcag    60
caaggactct ggagtcagag taggactgta ggaccggagc ctgagtggaa caggagtgga   120
gctggcctgg gagagagcgg atccctccca gcaccctcag gccacccgtt gcctgcactc   180
tccctgccag acctccagag aggagagact cgggacagcc agcccaggt tcccccagct   240
ctctccatct gcctggctcc ttgggacccg ttccccagcc tcaggatggc gtcctccctg   300
cttgaggagg aagttcacta tggctccagt cccctggcca tgctgacggc agcgtgcagc   360
aaatttggtg gctctagccc tctgcgggac tcaacaactc tgggcaaagc aggcacaaag   420
aagccgtact ctgtgggcag tgacctttca gcctccaaaa ccatgggga tgcttatcca   480
gccccttta caagcactaa tgggctcctt tcacctgcag gcagtcctcc agcacccacc   540
tcaggctatg ctaatgatta ccctccctt tcccactcat tccctgggcc cacaggcacc   600
caggaccctg ggctactagt gcccaagggg cacagctctt ctgactgtct gcccagtgtc   660
tacacctctc tggacatgac acacccctat ggctcctggt acaaggcagg catccatgca   720
ggcatttcac caggcccagg caacactcct actccatggt gggatatgca ccctggaggc   780
aactggctag gtggtgggca gggccagggt gatgggctgc aagggacact gcccacaggt   840
ccagctcagc ctccactgaa cccccagctg cccacctacc catctgactt tgctcccctt   900
aatccagccc cctacccagc tccccacctc ttgcaaccag gccccagca tgtcttgccc   960
caagatgtct ataaacccaa ggcagtggga aatagtgggc agctagaagg gagtggtgga  1020
gccaaacccc cacggggtgc aagcactggg ggtagtggtg gatatggggg cagtggggca  1080
gggcgctcct cctgcgactg ccctaattgc caggagctag agcggctggg agcagcagcg  1140
gctgggctgc ggaagaagcc catccacagc tgccacatcc ctggctgcgg caaggtgtat  1200
ggcaaggctt cgcacctgaa ggcccacttg cgctggcaca caggcgagag gcccttcgtc  1260
tgcaactggc tcttctgcgg caagaggttc actcgttcgg atgagctgga gcgtcatgtg  1320
cgcactcaca cccgggagaa gaagttcacc tgcctgctct gctccaagcg ctttacccga  1380
agcgaccacc tgagcaaaca ccagcgcacc catggagaac caggcccggg tcccctccc  1440
agtggcccca aggagctggg ggagggccgc agcacggggg aagaggaggc cagtcagacg  1500
ccccgacctt ctgcctcgcc agcaacccca gagaaagccc ctggaggcag ccctgagcag  1560
agcaacttgc tggagatctg agccgggtgg aaggtctccc accccagggc tgccctgaca  1620
gtctctcttg gctctctaga ccactgcttg ccaatcactc tctttacccc atgcatgcca  1680
tccttcgggg ctctctccct ctgtctccct cctggccatt ctgggcttgg gtatctcctt  1740
gcatgcctcc tcagctcacc ttctctcttc accatgagac tggctttcca caaactctca  1800
tctcaggccc tccccttgtg cctgataacct gcactccggc ttcctagact ctggccctgc  1860
cacaccaaca cactttctat ttgggctccc aacactattt ctccatctca ctccttgaca  1920
tgtaccccttt tctgcttctc aagcttatttt cctgctgtcc ctcagcctcc aggcttcagt  1980
cttcccaact tcttacacca ttgctttcca ttctccagaa ctcttttttc cttttttacaa  2040
acacaatgat aatgataatt tattgccccc tggtggcctc ttcatcaggg gtattggggt  2100
tagtgacctg gccagagggt gccaagaggg gggcagacca gtgggatct gatcccaaag  2160
atggggtgac cccagggtca gggaggctgc ccccaggcct gtatatttaa ccccctatgta  2220
ccaggagtaa tgaatagtaa taattctatt tatgtaagtt atgatgacgg gtcaggtaga  2280
```

| | |
|---|---|
| gtgagctggg gagggaagtg gatccatttc tgctaaggaa attctagtca aatgcatctc | 2340 |
| tgtatagaca aaatgttagt ggagaagatc ttgttaatag aatgtctatc atcagaatct | 2400 |
| cagttgatag ggtttctctt gtaatgaagt ctctacaaat tgggttagct acatctctgc | 2460 |
| taaacagttg atggggtatc tcttgattag ggggatccct aatatcccca gccccagcca | 2520 |
| gaagctgtga aacctcaagt cctatggagg ggagaaggac tggaatgtac cccatctccc | 2580 |
| ttgactgcag agcaggttcc tccactgccc caccccttag acaccatgac cccatcaggt | 2640 |
| taatcccctg ttgccatggt tatggagagc ttgcagctgc catcttagat gtgctctttg | 2700 |
| gggaagccca tctaacagga ggacattggt ttgggggtgc acctcctgaa gaatgggtgg | 2760 |
| ggaaggcttt ctctaggatc agattcaaat aagtatgtat tgagtgccta ctctgtgcaa | 2820 |
| ggcactatgc tagatctggt gcctagaagc cctgagaaag aacttaaaga gctaggagga | 2880 |
| cagaggcccc caagctgatc tggtggtgca tccacgcacc cccaccctgg gactttggat | 2940 |
| gctcccatct ccacctccag tgacttttaa agccgcttcg tgcctttcct gtaacgttgg | 3000 |
| atcctccttt tctgtcccct gctgtctcaa ggccccaagt taaagggtta aagccgctgg | 3060 |
| agcttgggga gagaacattg tggaatggaa gggatcatgc cctttgtgga gtcttttttt | 3120 |
| tttaatttaa taaataaaag ttggatttga aaaaaaaaaa aaaaaaaaaa aaa | 3173 |

<210> SEQ ID NO 64
<211> LENGTH: 1616
<212> TYPE: DNA
<213> ORGANISM: Homo sapiens

<400> SEQUENCE: 64

| | |
|---|---|
| ctccctgtgt tggtggagga tgtctgcagc agcatttaaa ttctgggagg gcttggttgt | 60 |
| cagcagcagc aggaggaggc agagcacagc atcgtcggga ccagactcgt ctcaggccag | 120 |
| ttgcagcctt ctcagccaaa cgccgaccaa ggaaaactca ctaccatgag aattgcagtg | 180 |
| atttgctttt gcctcctagg catcacctgt gccataccag ttaaacaggc tgattctgga | 240 |
| agttctgagg aaaagcagct ttacaacaaa tacccagatg ctgtggccac atggctaaac | 300 |
| cctgacccat ctcagaagca gaatctccta gccccacaga cccttccaag taagtccaac | 360 |
| gaaagccatg accacatgga tgatatggat gatgaagatg atgatgacca tgtggacagc | 420 |
| caggactcca ttgactcgaa cgactctgat gatgtagatg acactgatga ttctcaccag | 480 |
| tctgatgagt ctcaccattc tgatgaatct gatgaactgg tcactgattt tcccacggac | 540 |
| ctgccagcaa ccgaagtttt cactccagtt gtccccacag tagacacata tgatggccga | 600 |
| ggtgatagtg tggtttatgg actgaggtca aaatctaaga gtttcgcag acctgacatc | 660 |
| cagtaccctg atgctacaga cgaggacatc acctcacaca tggaaagcga ggagttgaat | 720 |
| ggtgcataca aggccatccc cgttgcccag gacctgaacg cgccttctga ttgggacagc | 780 |
| cgtgggaagg acagttatga aacgagtcag ctggatgacc agagtgctga acccacagc | 840 |
| cacaagcagt ccagattata taagcggaaa gccaatgatg agagcaatga gcattccgat | 900 |
| gtgattgata gtcaggaact ttccaaagtc agccgtgaat tccacagcca tgaatttcac | 960 |
| agccatgaag atatgctggt tgtagacccc aaaagtaagg aagaagataa acacctgaaa | 1020 |
| tttcgtattt ctcatgaatt agatagtgca tcttctgagg tcaattaaaa ggagaaaaaa | 1080 |
| tacaatttct cactttgcat ttagtcaaaa gaaaaaatgc tttatagcaa aatgaaagag | 1140 |
| aacatgaaat gcttctttct cagtttattg gttgaatgtg tatctatttg agtctggaaa | 1200 |
| taactaatgt gttgataat agtttagtt tgtggcttca tggaaactcc ctgtaaacta | 1260 |

| aaagcttcag ggttatgtct atgttcattc tatagaagaa atgcaaacta tcactgtatt | 1320 |
| ttaatatttg ttattctctc atgaatagaa atttatgtag aagcaaacaa atacttttta | 1380 |
| cccacttaaa aagagaatat aacatttat gtcactataa tcttttgttt tttaagttag | 1440 |
| tgtatatttt gttgtgatta tcttttgtg gtgtgaataa atcttttatc ttgaatgtaa | 1500 |
| taagaatttg gtggtgtcaa ttgcttattt gttttcccac ggttgtccag caattaataa | 1560 |
| aacataacct ttttactgc ctaaaaaaa aaaaaaaaa aaaaaaaaaa aaaaaa | 1616 |

<210> SEQ ID NO 65
<211> LENGTH: 1574
<212> TYPE: DNA
<213> ORGANISM: Homo sapiens

<400> SEQUENCE: 65

| tcaccacggc ggcagccctt taaacccctc acccagccag cgccccatcc tgtctgtccg | 60 |
| aacccagaca caagtcttca ctccttcctg cgagccctga ggaagccttg tgagtgcatt | 120 |
| ggctggggct tggagggaag ttgggctgga gctggacagg agcagtgggt gcatttcagg | 180 |
| caggctctcc tgaggtccca ggcgccagct ccagctccct ggctagggaa acccacccctc | 240 |
| tcagtcagca tgggggccca agctccaggc agggtgggct ggatcactag cgtcctggat | 300 |
| ctctctcaga ctgggcagcc ccgggctcat tgaaatgccc cggatgactt ggctagtgca | 360 |
| gaggaattga tggaaaccac cggggtgaga gggaggctcc ccatctcagc cagccacatc | 420 |
| cacaaggtgt gtgtaagggt gcaggcgccg gccggttagg ccaaggctct actgtctgtt | 480 |
| gccctccag gagaacttcc aaggagcttt ccccagacat ggccaacaag ggtccttcct | 540 |
| atggcatgag ccgcgaagtg cagtccaaaa tcgagaagaa gtatgacgag gagctggagg | 600 |
| agcggctggt ggagtggatc atagtgcagt gtggccctga tgtgggccgc ccagaccgtg | 660 |
| ggcgcttggg cttccaggtc tggctgaaga atggcgtgat tctgagcaag ctggtgaaca | 720 |
| gcctgtaccc tgatggctcc aagccggtga aggtgcccga aacccacccc tccatggtct | 780 |
| tcaagcagat ggagcaggtg gctcagttcc tgaaggcggc tgaggactat ggggtcatca | 840 |
| agactgacat gttccagact gttgacctct ttgaaggcaa agacatggca gcagtgcaga | 900 |
| ggaccctgat ggctttgggc agcttggcag tgaccaagaa tgatgggcac taccgtggag | 960 |
| atcccaactg gtttatgaag aaagcgcagg agcataagag ggaattcaca gagagccagc | 1020 |
| tgcaggaggg aaagcatgtc attggccttc agatgggcag caacagaggg gcctcccagg | 1080 |
| ccggcatgac aggctacgga cgacctcggc agatcatcag ttagagcgga gagggctagc | 1140 |
| cctgagcccg gcctccccc agctccttgg ctgcagccat cccgcttagc ctgcctcacc | 1200 |
| cacacccgtg tggtaccttc agccctggcc aagctttgag gctctgtcac tgagcaatgg | 1260 |
| taactgcacc tgggcagctc ctccctgtgc ccccagcctc agcccaactt cttacccgaa | 1320 |
| agcatcactg ccttggcccc tccctcccgg ctgcccccat cacctctact gtctcctccc | 1380 |
| tgggctaagc aggggagaag cgggctgggg gtagcctgga tgtgggccaa gtccactgtc | 1440 |
| ctccttggcg gcaaaagccc attgaagaag aaccagccca gcctgccccc tatcttgtcc | 1500 |
| tggaatattt tgggggttgg aactcaaaaa aaaaaaaaaa aaatcaatct tttctcaaaa | 1560 |
| aaaaaaaaaa aaaa | 1574 |

<210> SEQ ID NO 66
<211> LENGTH: 3829
<212> TYPE: DNA

<213> ORGANISM: Homo sapiens

<400> SEQUENCE: 66

```
caggcagcgc tgcgtcctgc tgcgcacgtg ggaagccctg gccccggcca ccccgcgat      60
gccgcgcgct ccccgctgcc gagccgtgcg ctccctgctg cgcagccact accgcgaggt    120
gctgccgctg ccacgttcg tgcggcgcct ggggcccag gctggcggc tggtgcagcg       180
cggggacccg gcggctttcc gcgcgctggt ggcccagtgc ctggtgtgcg tgccctggga    240
cgcacggccg ccccccgccg cccctcctt ccgccaggtg tcctgcctga aggagctggt     300
ggcccgagtg ctgcagaggc tgtgcgagcg cggcgcgaag aacgtgctgg ccttcggctt    360
cgcgctgctg gacggggccc gcggggccc ccccgaggcc ttcaccacca gcgtgcgcag    420
ctacctgccc aacacggtga ccgacgcact gcggggagc ggggcgtggg ggctgctgct    480
gcgccgcgtg ggcgacgacg tgctggttca cctgctggca cgctgcgcgc tctttgtgct    540
ggtggctccc agctgcgcct accaggtgtg cgggccgccg ctgtaccagc tcggcgctgc    600
cactcaggcc cggcccccgc cacacgctag tggaccccga aggcgtctgg gatgcgaacg    660
ggcctggaac catagcgtca gggaggccgg ggtcccctg gcctgccag ccccgggtgc      720
gaggaggcgc gggggcagtg ccagccgaag tctgccgttg cccaagaggc caggcgtgg     780
cgctgcccct gagccggagc ggacgcccgt tgggcagggg tcctgggccc accggggcag    840
gacgcgtgga ccgagtgacc gtggtttctg tgtggtgtca cctgccagac cgccgaaga    900
agccacctct ttggagggtg cgctctctgg cacgcgccac tcccacccat ccgtgggccg    960
ccagcaccac gcgggccccc catccacatc gcggccacca cgtccctggg acacgccttg   1020
tcccccggtg tacgccgaga ccaagcactt cctctactcc tcaggcgaca aggagcagct   1080
gcggccctcc ttcctactca gctctctgag gcccagcctg actggcgctc ggaggctcgt   1140
ggagaccatc tttctggggtt ccaggccctg gatgccaggg actccccgca ggttgccccg   1200
cctgccccag cgctactggc aaatgcggcc cctgtttctg gagctgcttg gaaccacgc    1260
gcagtgcccc tacggggtgc tcctcaagac gcactgcccg ctgcgagctg cggtcacccc   1320
agcagccggt gtctgtgccc gggagaagcc ccagggctct gtggcggccc ccgaggagga   1380
ggacacagac ccccgtcgcc tggtgcagct gctccgccag cacagcagcc cctggcaggt   1440
gtacggcttc gtgcgggcct gcctgcgccg gctggtgccc ccaggcctct ggggctccag   1500
gcacaacgaa cgccgcttcc tcaggaacac caagaagttc atctccctgg ggaagcatgc   1560
caagctctcg ctgcaggagc tgacgtggaa gatgagcgtg cgggactgcg cttggctgcg   1620
caggagccca ggggttggct gtgttccggc cgcagagcac cgtctgcgtg aggagatcct   1680
ggccaagttc ctgcactggc tgatgagtgt gtacgtcgtc gagctgctca ggtctttctt   1740
ttatgtcacg gagaccacgt ttcaaaagaa caggctcttt ttctaccgga agagtgtctg   1800
gagcaagttg caaagcattg gaatcagaca gcacttgaag agggtgcagc tgcgggagct   1860
gtcggaagca gaggtcaggc agcatcggga agccaggccc gccctgctga cgtccagact   1920
ccgcttcatc cccaagcctg acgggctgcg gccgattgtg aacatggact acgtcgtggg   1980
agccagaacg ttccgcagag aaaagagggc cgagcgtctc acctcgaggg tgaaggcact   2040
gttcagcgtg ctcaactacg agcgggcgcg gcgccccggc ctcctgggcg cctctgtgct   2100
gggcctggac gatatccaca gggcctggcg caccttcgtg ctgcgtgtgc gggcccagga   2160
cccgccgcct gagctgtact ttgtcaaggt ggatgtgacg ggcgcgtacg acaccatccc   2220
ccaggacagg ctcacggagg tcatcgccag catcatcaaa ccccagaaca cgtactgcgt   2280
```

```
gcgtcggtat gccgtggtcc agaaggccgc ccatgggcac gtccgcaagg ccttcaagag    2340
ccacgtctct accttgacag acctccagcc gtacatgcga cagttcgtgg ctcacctgca    2400
ggagaccagc ccgctgaggg atgccgtcgt catcgagcag agctcctccc tgaatgaggc    2460
cagcagtggc ctcttcgacg tcttcctacg cttcatgtgc caccacgccg tgcgcatcag    2520
gggcaagtcc tacgtccagt gccaggggat cccgcagggc tccatcctct ccacgctgct    2580
ctgcagcctg tgctacggcg acatggagaa caagctgttt gcggggattc ggcgggacgg    2640
gctgctcctg cgtttggtgg atgatttctt gttggtgaca cctcacctca cccacgcgaa    2700
aaccttcctc agctatgccc ggacctccat cagagccagt ctcaccttca accgcggctt    2760
caaggctggg aggaacatgc gtcgcaaact cttggggtc ttgcggctga agtgtcacag    2820
cctgtttctg gatttgcagg tgaacagcct ccagacggtg tgcaccaaca tctacaagat    2880
cctcctgctg caggcgtaca ggtttcacgc atgtgtgctg cagctcccat tcatcagca    2940 agtttggaag aaccccacat tttcctgcg cgtcatctct gacacggcct ccctctgcta    3000
ctccatcctg aaagccaaga acgcagggat gtcgctgggg gccaagggcg ccgccggccc    3060
tctgccctcc gaggccgtgc agtggctgtg ccaccaagca ttcctgctca agctgactcg    3120
acaccgtgtc acctacgtgc cactcctggg gtcactcagg acagcccaga cgcagctgag    3180
tcggaagctc ccggggacga cgctgactgc cctggaggcc gcagccaacc cggcactgcc    3240
ctcagacttc aagaccatcc tggactgatg gccacccgcc cacagccagg ccgagagcag    3300
acaccagcag ccctgtcacg ccgggctcta cgtcccaggg agggaggggc ggcccacacc    3360
caggcccgca ccgctgggag tctgaggcct gagtgagtgt ttggccgagg cctgcatgtc    3420
cggctgaagg ctgagtgtcc ggctgaggcc tgagcgagtg tccagccaag gctgagtgt    3480 ccagcacacc tgccgtcttc acttccccac aggctggcgc tcggctccac cccagggcca    3540
gcttttcctc accaggagcc cggcttccac tccccacata ggaatagtcc atccccagat    3600
tcgccattgt tcaccccctcg ccctgccctc ctttgccttc acccccacc atccaggtgg    3660 agaccctgag aaggaccctg ggagctctgg gaatttggag tgaccaaagg tgtgccctgt    3720
acacaggcga ggaccctgca cctggatggg ggtccctgtg ggtcaaattg gggggaggtg    3780
ctgtgggagt aaaatactga atatatgagt ttttcagttt tgaaaaaaa              3829
```

<210> SEQ ID NO 67
<211> LENGTH: 6244
<212> TYPE: DNA
<213> ORGANISM: Homo sapiens

<400> SEQUENCE: 67

```
ggcgaggcga ggtttgctgg ggtgaggcag cggcgcggcc gggccgggcc gggccacagg      60
cggtggcggc gggaccatgg aggcggcggt cgctgctccg cgtccccggc tgctcctcct     120
cgtgctggcg gcgcggcgg cggcggcggc ggcgctgctc ccgggggcga cggcgttaca     180
gtgtttctgc cacctctgta caaaagacaa ttttacttgt gtgacagatg ggctctgctt     240
tgtctctgtc acagagacca cagacaaagt tatacacaac agcatgtgta tagctgaaat     300
tgacttaatt cctcgagata ggccgtttgt atgtgcaccc tcttcaaaaa ctgggtctgt     360
gactacaaca tattgctgca atcaggacca ttgcaataaa atagaacttc caactactgg     420
tttaccattg cttgttcaga gaacaattgc gagaactatt gtgttacaag aaagcattgg     480
caaaggtcga tttggagaag tttggagagg aaagtggcgg ggagaagaag ttgctgttaa     540
```

```
gatattctcc tctagagaag aacgttcgtg gttccgtgag gcagagattt atcaaactgt    600
aatgttacgt catgaaaaca tcctgggatt tatagcagca gacaataaag acaatggtac    660
ttggactcag ctctggttgg tgtcagatta tcatgagcat ggatcccttt ttgattactt    720
aaacagatac acagttactg tggaaggaat gataaaactt gctctgtcca cggcgagcgg    780
tcttgcccat cttcacatgg agattgttgg tacccaagga aagccagcca ttgctcatag    840
agatttgaaa tcaaagaata tcttggtaaa gaagaatgga acttgctgta ttgcagactt    900
aggactggca gtaagacatg attcagccac agataccatt gatattgctc caaaccacag    960
agtgggaaca aaaaggtaca tggcccctga agttctcgat gattccataa atatgaaaca   1020
ttttgaatcc ttcaaacgtg ctgacatcta tgcaatgggc ttagtattct gggaaattgc   1080
tcgacgatgt tccattggtg gaattcatga agattaccaa ctgccttatt atgatcttgt   1140
accttctgac ccatcagttg aagaaatgag aaaagttgtt tgtgaacaga gttaaggcc    1200 aaatatccca acagatggc agagctgtga agccttgaga gtaatggcta aaattatgag   1260
agaatgttgg tatgccaatg gagcagctag gcttacagca ttgcggatta agaaaacatt   1320
atcgcaactc agtcaacagg aaggcatcaa aatgtaattc tacagctttg cctgaactct   1380 cctttttct tcagatctgc tcctgggttt taatttggga ggtcaattgt tctacctcac    1440
tgagagggaa cagaaggata ttgcttcctt ttgcagcagt gtaataaagt caattaaaaa   1500
cttcccagga tttctttgga cccaggaaac agccatgtgg gtccttttctg tgcactatga   1560 acgcttcttt cccaggacag aaaatgtgta gtctacccttt atttttatt aacaaaactt   1620 gttttttaaa aagatgattg ctggtcttaa ctttaggtaa ctctgctgtg ctggagatca   1680
tctttaaggg caaaggagtt ggattgctga attacaatga acatgtctt attactaaag    1740 aaagtgattt actcctggtt agtacattct cagaggattc tgaaccacta gagttttcctt   1800 gattcagact ttgaatgtac tgttctatag ttttcagga tcttaaaact aacacttata    1860
aaactcttat cttgagtcta aaaatgacct catatagtag tgaggaacat aattcatgca   1920
attgtatttt gtatactatt attgttcttt cacttattca gaacattaca tgccttcaaa   1980
atgggattgt actataccag taagtgccac ttctgtgtct ttctaatgga atgagtagaa   2040
attgctgaaa gtctctatgt taaaacctat agtgtttgaa ttcaaaaagc ttatttatct   2100
gggtaaccca acttttctctg ttttgtttt tggaagggtt tttgtggtat gtcatttggt   2160
attctattct gaaaatgcct ttctcctacc aaaatgtgct taagccacta agaaatgaa    2220 gtggcattaa ttagtaaatt attagcatgg tcatgtttga atattctcac atcaagcttt   2280
tgcattttaa ttgtgttgtc taagtatact tttaaaaaat caagtggcac tctagatgct   2340
tatagtactt taatatttgt agcatacaga ctaattttc taaaagggaa agtctgtcta   2400
gctgcttgtg aaaagttatg tggtattctg taagccattt ttttctttat ctgttcaaag   2460 acttatttt taagacatga attacattta aattagaat atggttaata ttaataata    2520 ggcctttttc taggaaggcg aaggtagtta ataatttgaa tagataacag atgtgcaaga   2580
aagtcacatt tgttatgtat gtaggagtaa acgttcggtg gatcctctgt ctttgtaact   2640
gaggttagag ctagtgtggt tttgaggtct cactacactt tgaggaaggc agcttttaat   2700
tcagtgtttc cttatgtgtg cgtacattgc aactgcttac atgtaattta tgtaatgcat   2760
tcagtgcacc cttgttactt gggagaggtg gtagctaaag aacattctga gtataggttt   2820
ttctccattt acagatgtct ttggtcaaat attgaaagca aacttgtcat ggtcttctta   2880
cattaagttg aaactagctt ataataactg gttttactt ccaatgctat gaagtctctg   2940
```

```
cagggctttt acagttttcg aagtcctttt atcactgtga tcttattctg aggggagaaa   3000
aaactatcat agctctgagg caagacttcg actttatagt gctatcagtt ccccgataca   3060
gggtcagagt aacccataca gtattttggt caggaagaga aagtggccat ttacactgaa   3120
tgagttgcat tctgataatg tcttatctct tatacgtaga ataaatttga aagactattt   3180
gatcttaaaa ccaaagtaat tttagaatga gtgacatatt acataggaat ttagtgtcaa   3240
tttcatgtgt ttaaaaacat catgggaaaa atgcttagag gttactattt tgactacaaa   3300 gttgagttttt tttctgtagt taccataatt tcattgaagc aaatgaatga gtttgagagg   3360
tttgttttta tagttgtgtt gtattacttg tttaataata atctctaatt ctgtgatcag   3420
gtactttttt tgtggggggtt tttttttgt tttttttttt ttgttgttgt ttttgggcca   3480
tttctaagcc taccagatct gctttatgaa atccagggga ccaatgcatt ttatcactaa   3540 aactatttt atataatttt aagaatatac caaaagttgt ctgatttaaa gttgtaatac   3600
atgatttctc actttcatgt aaggttatcc actttgctg aagatatttt ttattgaatc   3660
aaagattgag ttacaattat acttttctta cctaagtgga taaaatgtac ttttgatgaa   3720
tcagggaatt ttttaaagt tggagtttag ttctaaattg actttacgta ttactgcagt   3780
taattccttt tttggctagg gatggtttga taaaccacaa ttggctgata ttgaaaatga   3840
aagaaactta aaaggtggga tggatcatga ttactgtcga taactgcaga taaatttgat   3900
tagagtaata atttttgtcat ttaaaaacac agttgtttat actgcccatc ctaggatgct   3960
caccttccaa gattcaacgt ggctaaaaca tcttctggta aattgtgcgt ccatattcat   4020
tttgtcagta gccaggagaa atggggatgg gggaaatacg acttagtgag gcatagacat   4080
ccctggtcca tcctttctgt ctccagctgt ttcttggaac ctgctctcct gcttgctggt   4140
ccctgacgca gagaccgttg cctccccac agccgtttga ctgaaggctg ctctggagac   4200
ctagagtaaa acggctgatg gaagttgtgg gacccacttc catttccttc agtcattaga   4260
ggtggaaggg aggggtctcc aagtttggag attgagcaga tgaggcttgg gatgcccctg   4320
ctttgacttc agccatggat gaggagtggg atggcagcaa ggtggctcct gtggcagtgg   4380
agttgtgcca gaaacagtgg ccagttgtat cgcctataag acagggtaag gtctgaagag   4440
ctgagcctgt aattctgctg taataatgat agtgctcaag aagtgccttg agttggtgta   4500
cagtgccatg gccatcaaga atcccagatt tcaggtttta ttacaaaatg taagtggtca   4560
cttggcgatt ttgtagtaca tgcatgagtt accttttttc tctatgtctg agaactgtca   4620
gattaaaaca gatggcaaa gagatcgtta gagtgcacaa caaaatcact atcccattag   4680
acacatcatc aaaagcttat ttttattctt gcactggaag aatcgtaagt caactgtttc   4740
ttgaccatgg cagtgttctg gctccaaatg gtagtgattc caaataatgg ttctgttaac   4800
actttggcag aaaatgccag ctcagatatt ttgagatact aaggattatc tttggacatg   4860
tactgcagct tcttgtctct gttttggatt actggaatac ccatgggccc tctcaagagt   4920
gctggacttc taggacatta agatgattgt cagtacatta aacttttcaa tcccattatg   4980
caatcttgtt tgtaaatgta aacttctaaa aatatggtta ataacattca acctgtttat   5040
tacaacttaa aaggaacttc agtgaatttg tttttatttt ttaacaagat ttgtgaactg   5100
aatatcatga accatgtttt gatacccctt tttcacgttg tgccaacgga atagggtgtt   5160
tgatatttct tcatatgtta aggagatgct tcaaaatgtc aattgcttta aacttaaatt   5220
acctctcaag agaccaaggt acatttacct cattgtgtat ataatgttta atatttgtca   5280
```

```
gagcattctc caggtttgca gttttatttc tataaagtat gggtattatg ttgctcagtt      5340
actcaaatgg tactgtattg tttatatttg taccccaaat aacatcgtct gtactttctg      5400
ttttctgtat tgtatttgtg caggattctt taggctttat cagtgtaatc tctgccttt      5460 aagatatgta cagaaaatgt ccatataaat ttccattgaa gtcgaatgat actgagaagc      5520
ctgtaaagag gagaaaaaaa cataagctgt gtttccccat aagtttttt aaattgtata       5580 ttgtatttgt agtaatattc caaaagaatg taaataggaa atagaagagt gatgcttatg      5640
ttaagtccta acactacagt agaagaatgg aagcagtgca aataaattac attttttccca     5700 agtgccagtg gcatatttta aaataaagtg tatacgttgg aatgagtcat gccatatgta     5760
gttgctgtag atggcaacta gaacctttga gttacaagag tctttagaag ttttctaacc     5820
ctgcctagtg caagttacaa tattatagcg tgttcgggga gtgccctcct gtctgcaggt     5880
gtgtctctgt gcctgggggc ttttctccac atgcttaggg gtgtgggtct tccattgggg    5940
catgatggac ctgtctacag gtgatctctg ttgcctttgg gtcagcacat ttgttagtct    6000 cctggggtg aaaacttggc ttacaagaga actggaaaaa tgatgagatg tggtcccaa      6060 acccttgatt gactctgggg aggggctttg tgaataggat tgctctcaca ttaaagatag    6120
ttacttcaat ttgaaggctg gatttaggga ttttttttt tccttataac aaagacatca    6180
ccaggatatg aagcttttgt tgaaagttgg aaaaaagtg aaattaaaga cattcccaga    6240
caaa                                                                 6244

<210> SEQ ID NO 68
<211> LENGTH: 931
<212> TYPE: DNA
<213> ORGANISM: Homo sapiens

<400> SEQUENCE: 68
tttcgtcggc ccgccccttg gcttctgcac tgatggtggg tggatgagta atgcatccag       60
gaagcctgga ggcctgtggt ttccgcaccc gctgccaccc ccgcccctag cgtggacatt      120
tatcctctag cgctcaggcc ctgccgccat cgccgcagat ccagcgccca gagagacacc      180
agagaaccca ccatggcccc cttttgagccc ctggcttctg gcatcctgtt gttgctgtgg     240
ctgatagccc ccagcagggc ctgcacctgt gtcccacccc acccacagac ggccttctgc     300
aattccgacc tcgtcatcag ggccaagttc gtggggacac cagaagtcaa ccagaccacc     360
ttataccagc gttatgagat caagatgacc aagatgtata aagggttcca agccttaggg     420
gatgccgctg acatccggtt cgtctacacc ccgccatgg agagtgtctg cggatacttc     480
cacaggtccc acaaccgcag cgaggagttt ctcattgctg gaaaactgca ggatggactc     540
ttgcacatca ctacctgcag tttttgtggct ccctggaaca gcctgagctt agctcagcgc     600
cggggcttca ccaagaccta cactgttggc tgtgaggaat gcacagtgtt tccctgttta    660 tccatccct gcaaactgca gagtggcact cattgcttgt ggacggacca gctcctccaa      720
ggctctgaaa agggcttcca gtcccgtcac cttgcctgcc tgcctcggga gccagggctg    780
tgcacctggc agtccctgcg gtcccagata gcctgaatcc tgcccggagt ggaagctgaa    840
gcctgcacag tgtccaccct gttcccactc ccatctttct tccggacaat gaaataaaga    900
gttaccaccc agcagaaaaa aaaaaaaaaa a                                    931

<210> SEQ ID NO 69
<211> LENGTH: 3677
<212> TYPE: DNA
<213> ORGANISM: Homo sapiens
```

<400> SEQUENCE: 69

```
tcgcggaggc ttggggcagc cgggtagctc ggaggtcgtg gcgctggggg ctagcaccag        60
cgctctgtcg ggaggcgcag cggttaggtg gaccggtcag cggactcacc ggccagggcg       120
ctcggtgctg gaatttgata ttcattgatc cgggttttat ccctcttctt ttttcttaaa       180
catttttttt taaaactgta ttgtttctcg ttttaattta ttttgcttg ccattcccca        240
cttgaatcgg gccgacggct tggggagatt gctctacttc cccaaatcac tgtggatttt       300
ggaaaccagc agaaagagga aagaggtagc aagagctcca gagagaagtc gaggaagaga       360
gagacggggt cagagagagc gcgcgggcgt gcgagcagcg aaagcgacag ggcaaagtg        420
agtgacctgc ttttgggggt gaccgccgga gcgcggcgtg agccctcccc cttgggatcc       480
cgcagctgac cagtcgcgct gacggacaga cagacagaca ccgcccccag ccccagctac       540
cacctcctcc ccggccggcg gcggacagtg gacgcggcgg cgagccgcgg gcaggggccg       600
gagcccgcgc ccggaggcgg ggtggagggg gtcgggctc gcggcgtcgc actgaaactt        660
ttcgtccaac ttctgggctg ttctcgcttc ggaggagccg tggtccgcgc ggggaagcc        720
gagccgagcg gagccgcgag aagtgctagc tcgggccggg aggagccgca gccggaggag       780
ggggaggagg aagaagagaa ggaagaggag aggggccgc agtggcgact cggcgctcgg        840
aagccgggct catggacggg tgaggcgcg gtgtgcgcag acagtgctcc agccgcgcgc        900
gctcccagg ccctggcccg ggcctcgggc cggggaggaa gagtagctcg ccgaggcgcc        960
gaggagagcg ggccgcccca cagcccgagc cggagaggga gcgcgagccg cgccggcccc      1020
ggtcgggcct ccgaaaccat gaactttctg ctgtcttggg tgcattggag ccttgccttg      1080
ctgctctacc tccaccatgc caagtggtcc caggctgcac ccatggcaga aggaggaggg      1140
cagaatcatc acgaagtggt gaagttcatg gatgtctatc agcgcagcta ctgccatcca      1200
atcgagaccc tggtggacat cttccaggag taccctgatg agatcgagta catcttcaag      1260
ccatcctgtg tgcccctgat gcgatgcggg ggctgctgca atgacgaggg cctggagtgt      1320
gtgcccactg aggagtccaa catcaccatg cagattatgc ggatcaaacc tcaccaaggc      1380
cagcacatag gagagatgag cttcctacag cacaacaaat gtgaatgcag accaaagaaa      1440
gatagagcaa gacaagaaaa aaaatcagtt cgaggaaagg gaaaggggca aaaacgaaag      1500
cgcaagaaat cccggtataa gtcctggagc gtgtacgttg gtgcccgctg ctgtctaatg      1560
ccctggagcc tccctggccc ccatccctgt gggccttgct cagagcggag aaagcatttg      1620
tttgtacaag atccgcagac gtgtaaatgt tcctgcaaaa acacagactc gcgttgcaag      1680
gcgaggcagc ttgagttaaa cgaacgtact tgcagatgtg acaagccgag gcggtgagcc      1740
gggcaggagg aaggagcctc cctcagggtt tcgggaacca gatctctcac caggaaagac      1800
tgatacagaa cgatcgatac agaaaccacg ctgccgccac cacaccatca ccatcgacag      1860
aacagtcctt aatccagaaa cctgaaatga aggaagagga gactctgcgc agagcacttt      1920
gggtccggag ggcgagactc cggcggaagc attcccgggc gggtgaccca gcacggtccc      1980
tcttggaatt ggattcgcca ttttattttt cttgctgcta aatcaccgag cccggaagat      2040
tagagagttt tatttctggg attcctgtag acacacccac ccacatacat acatttatat      2100
atatatatat tatatatata taaaaataaa tatctctatt ttatatatat aaaatatata      2160
tattcttttt ttaaattaac agtgctaatg ttattggtgt cttcactgga tgtatttgac      2220
tgctgtggac ttgagttggg aggggaatgt tcccactcag atcctgacag ggaagaggag      2280
```

```
gagatgagag actctggcat gatctttttt ttgtcccact tggtgggcc agggtcctct    2340
cccctgccca ggaatgtgca aggccagggc atggggcaa atatgaccca gttttgggaa    2400
caccgacaaa cccagccctg gcgctgagcc tctctacccc aggtcagacg gacagaaaga   2460
cagatcacag gtacagggat gaggacaccg gctctgacca ggagtttggg gagcttcagg   2520
acattgctgt gctttgggga ttccctccac atgctgcacg cgcatctcgc ccccaggggc   2580
actgcctgga agattcagga gcctggcgg ccttcgctta ctctcacctg cttctgagtt    2640
gcccaggaga ccactggcag atgtcccggc gaagagaaga gacacattgt tggaagaagc   2700
agcccatgac agctcccctt cctgggactc gccctcatcc tcttcctgct ccccttcctg   2760
gggtgcagcc taaaaggacc tatgtcctca caccattgaa accactagtt ctgtccccc    2820
aggagacctg gttgtgtgtg tgtgagtggt tgaccttcct ccatcccctg gtccttccct   2880
tcccttcccg aggcacagag agacagggca ggatccacgt gcccattgtg gaggcagaga   2940
aaagagaaag tgttttatat acggtactta tttaatatcc ctttttaatt agaaattaaa   3000
acagttaatt taattaaaga gtaggttttt ttttcagtat tcttggttaa tatttaattt   3060
caactattta tgagatgtat cttttgctct ctcttgctct cttatttgta ccggttttg    3120
tatataaaat tcatgtttcc aatctctctc tccctgatcg gtgacagtca ctagcttatc   3180
ttgaacagat atttaatttt gctaacactc agctctgccc tccccgatcc cctggctccc   3240
cagcacacat tcctttgaaa taaggtttca atatacatct acatactata tatatatttg   3300
gcaacttgta tttgtgtgta tatatatata tatatgttta tgtatatatg tgattctgat   3360
aaaatagaca ttgctattct gttttttata tgtaaaaaca aaacaagaaa aaatagagaa   3420
ttctacatac taaatctctc tccttttta attttaatat ttgttatcat ttatttattg   3480
gtgctactgt ttatccgtaa taattgtggg gaaaagatat taacatcacg tctttgtctc   3540
tagtgcagtt tttcgagata ttccgtagta catatttatt tttaaacaac gacaaagaaa   3600
tacagatata tcttaaaaaa aaaaaagcat tttgtattaa agaatttaat tctgatctca   3660
aaaaaaaaaa aaaaaaa                                                  3677

<210> SEQ ID NO 70
<211> LENGTH: 2151
<212> TYPE: DNA
<213> ORGANISM: Homo sapiens

<400> SEQUENCE: 70
gcctctccaa aggctgcaga agtttcttgc taacaaaaag tccgcacatt cgagcaaaga     60
caggctttag cgagttatta aaaacttagg ggcgctcttg tccccacag ggcccgaccg     120
cacacagcaa ggcgatggcc cagctgtaag ttggtagcac tgagaactag cagcgcgcgc    180
ggagcccgct gagacttgaa tcaatctggt ctaacggttt ccctaaacc gctaggagcc    240
ctcaatcggc gggacagcag ggcgcgtcct ctgccactct cgctccgagg tcccgcgcc    300
agagacgcag ccgcgctccc accacccaca cccaccgcgc cctcgttcgc ctcttctccg    360
ggagccagtc cgcgccaccg ccgccgccca ggccatcgcc accctccgca gccatgtcca    420
ccaggtccgt gtcctcgtcc tcctaccgca ggatgttcgg cggccggg accgcgagcc      480
ggccgagctc cagccggagc tacgtgacta cgtccacccg cacctacagc ctgggcagcg    540
cgctgcgccc cagcaccagc cgcagcctct acgcctcgtc cccgggcggc gtgtatgcca    600
cgcgctcctc tgccgtgcgc ctgcggagca gcgtgcccgg ggtgcggctc ctgcaggact    660
cggtggactt ctcgctggcc gacgccatca acaccgagtt caagaacacc cgcaccaacg    720
```

```
agaaggtgga gctgcaggag ctgaatgacc gcttcgccaa ctacatcgac aaggtgcgct    780
tcctggagca gcagaataag atcctgctgg ccgagctcga gcagctcaag gccaaggca     840 agtcgcgcct gggggacctc tacgaggagg agatgcggga gctgcgccgg caggtggacc    900
agctaaccaa cgacaaagcc cgcgtcgagg tggagcgcga caacctggcc gaggacatca    960
tgcgcctccg ggagaaattg caggaggaga tgcttcagag agaggaagcc gaaaacaccc   1020
tgcaatcttt cagacaggat gttgacaatg cgtctctggc acgtcttgac cttgaacgca   1080
aagtggaatc tttgcaagaa gagattgcct ttttgaagaa actccacgaa gaggaaatcc   1140
aggagctgca ggctcagatt caggaacagc atgtccaaat cgatgtggat gtttccaagc   1200
ctgacctcac ggctgccctg cgtgacgtac gtcagcaata tgaaagtgtg gctgccaaga   1260
acctgcagga ggcagaagaa tggtacaaat ccaagtttgc tgacctctct gaggctgcca   1320
accggaacaa tgacgccctg cgccaggcaa gcaggagtc cactgagtac cggagacagg    1380
tgcagtccct cacctgtgaa gtggatgccc ttaaaggaac caatgagtcc ctggaacgcc   1440
agatgcgtga atggaagag  aactttgccg ttgaagctgc taactaccaa gacactattg   1500
gccgcctgca ggatgagatt cagaatatga aggaggaaat ggctcgtcac cttcgtgaat   1560
accaagacct gctcaatgtt aagatggccc ttgacattga gattgccacc tacaggaagc   1620
tgctggaagg cgaggagagc aggatttctc tgcctcttcc aaactttttcc tccctgaacc   1680 tgagggaaac taatctggat tcactccctc tggttgatac ccactcaaaa aggacacttc   1740
tgattaagac ggttgaaact agagatggac aggttatcaa cgaaacttct cagcatcacg   1800
atgaccttga ataaaaattg cacacactca gtgcagcaat atattaccag caagaataaa   1860
aaagaaatcc atatcttaaa gaaacagctt tcaagtgcct ttctgcagtt tttcaggagc   1920
gcaagataga tttggaatag gaataagctc tagttcttaa caaccgacac tcctacaaga   1980
tttagaaaaa agtttacaac ataatctagt ttacagaaaa atcttgtgct agaatacttt   2040
ttaaaaggta ttttgaatac cattaaaact gcttttttt  ttccagcaag tatccaacca   2100
acttggttct gcttcaataa atctttggaa aaactcaaaa aaaaaaaaa a             2151
```

<210> SEQ ID NO 71
<211> LENGTH: 3207
<212> TYPE: DNA
<213> ORGANISM: Homo sapiens

<400> SEQUENCE: 71

```
ggcccacaga ggagcacagc tgtgtttggc tgcagggcca agagcgctgt caagaagacc     60
cacacgcccc cctccagcag ctgaattcct gcagctcagc agccgccgcc agagcaggac    120
gaaccgccaa tcgcaaggca cctctgagaa cttcaggatg cagatgtctc agccctcac    180 ctgcctagtc ctgggcctgg cccttgtctt tggtgaaggg tctgctgtgc accatccccc    240
atcctacgtg gcccacctgg cctcagactt cggggtgagg gtgtttcagc aggtggcgca    300
ggcctccaag gaccgcaacg tggttttctc accctatggg gtggcctcgg tgttggccat    360
gctccagctg acaacaggag gagaaaccca gcagcagatt caagcagcta tgggattcaa    420
gattgatgac aagggcatgg cccccgccct ccggcatctg tacaaggagc tcatgggcc     480 atggaacaag gatgagatca gcaccacaga cgcgatcttc gtccagcggg atctgaagct    540
ggtccagggc ttcatgcccc acttcttcag gctgttccgg agcacggtca agcaagtgga    600
cttttcagag gtggagagag ccagattcat catcaatgac tgggtgaaga cacacacaaa    660
```

```
aggtatgatc agcaacttgc ttgggaaagg agccgtggac cagctgacac ggctggtgct    720
ggtgaatgcc ctctacttca acggccagtg gaagactccc ttccccgact ccagcaccca    780
ccgccgcctc ttccacaaat cagacggcag cactgtctct gtgcccatga tggctcagac    840
caacaagttc aactatactg agttcaccac gcccgatggc cattactacg acatcctgga    900
actgccctac cacggggaca ccctcagcat gttcattgct gccccttatg aaaagaggt     960 gcctctctct gccctcacca acattctgag tgcccagctc atcagccact ggaaaggcaa   1020
catgaccagg ctgccccgcc tcctggttct gcccaagttc tccctggaga ctgaagtcga   1080
cctcaggaag cccctagaga acctgggaat gaccgacatg ttcagacagt ttcaggctga   1140
cttcacgagt ctttcagacc aagagcctct ccacgtcgcg caggcgctgc agaaagtgaa   1200
gatcgaggtg aacgagagtg gcacggtggc ctcctcatcc acagctgtca tagtctcagc   1260
ccgcatggcc cccgaggaga tcatcatgga cagacccttc ctctttgtgg tccggcacaa   1320
ccccacagga acagtccttt tcatgggcca agtgatggaa ccctgaccct ggggaaagac   1380
gccttcatct gggacaaaac tggagatgca tcgggaaaga agaaactccg aagaaaagaa   1440
ttttagtgtt aatgactctt tctgaaggaa gagaagacat ttgcctttg ttaaaagatg    1500 gtaaaccaga tctgtctcca agaccttggc ctctccttgg aggacctta ggtcaaactc    1560 cctagtctcc acctgagacc ctggagaga agtttgaagc acaactccct taaggtctcc    1620
aaaccagacg tgtgacgcctg cgggaccatc tgggcacct gcttccaccc gtctctctgc   1680
ccactcgggt ctgcagacct ggttcccact gaggcccttt gcaggatgga actacggggc   1740
ttacaggagc ttttgtgtgc ctggtagaaa ctatttctgt tccagtcaca ttgccatcac   1800
tcttgtactg cctgccaccg cggaggaggc tggtgacagg ccaaaggcca gtggaagaaa   1860
caccctttca tctcagagtc cactgtggca ctggccaccc ctccccagta caggggtgct   1920
gcaggtggca gagtgaatgt ccccatcat gtggcccaac tctcctggcc tggccatctc    1980
cctccccaga aacagtgtgc atgggttatt ttggagtgta ggtgacttgt ttactcattg   2040
aagcagattt ctgcttcctt ttattttat aggaatagag gaagaatgt cagatgcgtg     2100 cccagctctt cacccccaa tctcttggtg gggaggggtg tacctaaata tttatcatat    2160
ccttgccctt gagtgcttgt tagagagaaa gagaactact aaggaaaata atattattta   2220
aactcgctcc tagtgtttct ttgtggtctg tgtcaccgta tctcaggaag tccagccact   2280
tgactggcac acacccctcc ggacatccag cgtgacggag cccacactgc caccttgtgg   2340
ccgcctgaga ccctcgcgcc cccgcgcgcc ctctttttcc ccttgatgga aattgaccat   2400
acaatttcat cctccttcag gggatcaaaa ggacggagtg ggggacaga gactcagatg    2460 aggacagagt ggtttccaat gtgttcaata gatttaggag cagaaatgca aggggctgca   2520
tgacctacca ggacagaact ttccccaatt acagggtgac tcacagccgc attggtgact   2580
cacttcaatg tgtcatttcc ggctgctgtg tgtgagcagt ggacacgtga gggggggtg    2640 ggtgagagag acaggcagct cggattcaac taccttagat aatatttctg aaaacctacc   2700
agccagaggg tagggcacaa agatggatgt aatgcacttt gggaggccaa ggcgggagga   2760
ttgcttgagc ccaggagttc aagaccagcc tgggcaacat accaagaccc ccgtctctttt  2820 aaaaatatat atattttaaa tacttaaaa tatatatttc taatatcttt aaatatatat    2880
atatatttta aagaccaatt tatgggagaa ttgcacacag atgtgaaatg aatgtaatct   2940
aatagaagcc taatcagccc accatgttct ccactgaaaa atcctctttc tttgggtttt   3000
ttctttcttt ctttttttgat tttgcactgg acggtgacgt cagccatgta caggatccac   3060
```

```
aggggtggtg tcaaatgcta ttgaaattgt gttgaattgt atgcttttc acttttgata      3120 aataaacatg taaaaatgtt tcaaaaaaat aataaaataa ataaatacga agaatatgtc      3180
aggacagtca aaaaaaaaaa aaaaaaa                                          3207

<210> SEQ ID NO 72
<211> LENGTH: 19
<212> TYPE: DNA
<213> ORGANISM: Homo sapiens

<400> SEQUENCE: 72
tgccttcctc cgctgaaac                                                   19

<210> SEQ ID NO 73
<211> LENGTH: 18
<212> TYPE: DNA
<213> ORGANISM: Homo sapiens

<400> SEQUENCE: 73
accacgcacc agtgtgac                                                    18

<210> SEQ ID NO 74
<211> LENGTH: 24
<212> TYPE: DNA
<213> ORGANISM: Homo sapiens

<400> SEQUENCE: 74
tcccaacttc ttctggagcc tggg                                             24

<210> SEQ ID NO 75
<211> LENGTH: 22
<212> TYPE: DNA
<213> ORGANISM: Homo sapiens

<400> SEQUENCE: 75
gaaatgaagg agaagtttag ca                                               22

<210> SEQ ID NO 76
<211> LENGTH: 23
<212> TYPE: DNA
<213> ORGANISM: Homo sapiens

<400> SEQUENCE: 76
gctttataac aggataccat gac                                              23

<210> SEQ ID NO 77
<211> LENGTH: 29
<212> TYPE: DNA
<213> ORGANISM: Homo sapiens

<400> SEQUENCE: 77
acagatgcac catcaggaat ggaattaca                                        29

<210> SEQ ID NO 78
<211> LENGTH: 20
<212> TYPE: DNA
<213> ORGANISM: Homo sapiens

<400> SEQUENCE: 78
gaagctgacc tggaagagaa                                                  20

<210> SEQ ID NO 79
```

-continued

```
<211> LENGTH: 22
<212> TYPE: DNA
<213> ORGANISM: Homo sapiens

<400> SEQUENCE: 79
ccacagaatt tagctcggta tg                                              22

<210> SEQ ID NO 80
<211> LENGTH: 26
<212> TYPE: DNA
<213> ORGANISM: Homo sapiens

<400> SEQUENCE: 80
cctatcaagt ttgagctttc tggctg                                          26

<210> SEQ ID NO 81
<211> LENGTH: 19
<212> TYPE: DNA
<213> ORGANISM: Homo sapiens

<400> SEQUENCE: 81
gagactctca gggtcgaaa                                                  19

<210> SEQ ID NO 82
<211> LENGTH: 19
<212> TYPE: DNA
<213> ORGANISM: Homo sapiens

<400> SEQUENCE: 82
ctgtgggcgg attagggct                                                  19

<210> SEQ ID NO 83
<211> LENGTH: 24
<212> TYPE: DNA
<213> ORGANISM: Homo sapiens

<400> SEQUENCE: 83
atttctacca ctccaaacgc cggc                                            24

<210> SEQ ID NO 84
<211> LENGTH: 20
<212> TYPE: DNA
<213> ORGANISM: Homo sapiens

<400> SEQUENCE: 84
tgagggagaa caagaccgat                                                 20

<210> SEQ ID NO 85
<211> LENGTH: 19
<212> TYPE: DNA
<213> ORGANISM: Homo sapiens

<400> SEQUENCE: 85
actagtaggt gtgcagaga                                                  19

<210> SEQ ID NO 86
<211> LENGTH: 23
<212> TYPE: DNA
<213> ORGANISM: Homo sapiens

<400> SEQUENCE: 86
cactgcgccc ttaactgcat cca                                             23
```

```
<210> SEQ ID NO 87
<211> LENGTH: 21
<212> TYPE: DNA
<213> ORGANISM: Homo sapiens

<400> SEQUENCE: 87
gcgaattcag catctgcaaa g                                              21

<210> SEQ ID NO 88
<211> LENGTH: 18
<212> TYPE: DNA
<213> ORGANISM: Homo sapiens

<400> SEQUENCE: 88
ctttcttcgg gcaggctt                                                  18

<210> SEQ ID NO 89
<211> LENGTH: 25
<212> TYPE: DNA
<213> ORGANISM: Homo sapiens

<400> SEQUENCE: 89
accacaagca cctagaccat gaggt                                          25

<210> SEQ ID NO 90
<211> LENGTH: 20
<212> TYPE: DNA
<213> ORGANISM: Homo sapiens

<400> SEQUENCE: 90
gtcggccaag ttgatgaatg                                                20

<210> SEQ ID NO 91
<211> LENGTH: 21
<212> TYPE: DNA
<213> ORGANISM: Homo sapiens

<400> SEQUENCE: 91
gatgagcgtg aagtggattt g                                              21

<210> SEQ ID NO 92
<211> LENGTH: 23
<212> TYPE: DNA
<213> ORGANISM: Homo sapiens

<400> SEQUENCE: 92
ccattgacga ggaggaggag gat                                            23

<210> SEQ ID NO 93
<211> LENGTH: 21
<212> TYPE: DNA
<213> ORGANISM: Homo sapiens

<400> SEQUENCE: 93
tgtggtcaag actggatgat g                                              21

<210> SEQ ID NO 94
<211> LENGTH: 20
<212> TYPE: DNA
<213> ORGANISM: Homo sapiens

<400> SEQUENCE: 94
cagaagtggc ttcgaaatga                                                20
```

```
<210> SEQ ID NO 95
<211> LENGTH: 24
<212> TYPE: DNA
<213> ORGANISM: Homo sapiens

<400> SEQUENCE: 95
tctctaggaa gcctcacttg gccg                                          24

<210> SEQ ID NO 96
<211> LENGTH: 21
<212> TYPE: DNA
<213> ORGANISM: Homo sapiens

<400> SEQUENCE: 96
aatggaacag cccttctacc a                                             21

<210> SEQ ID NO 97
<211> LENGTH: 21
<212> TYPE: DNA
<213> ORGANISM: Homo sapiens

<400> SEQUENCE: 97
gctcggtttc aggagtttgt a                                             21

<210> SEQ ID NO 98
<211> LENGTH: 23
<212> TYPE: DNA
<213> ORGANISM: Homo sapiens

<400> SEQUENCE: 98
tcatacacag ctacgggata cgg                                           23

<210> SEQ ID NO 99
<211> LENGTH: 21
<212> TYPE: DNA
<213> ORGANISM: Homo sapiens

<400> SEQUENCE: 99
gttgcttcaa ggacacatta g                                             21

<210> SEQ ID NO 100
<211> LENGTH: 20
<212> TYPE: DNA
<213> ORGANISM: Homo sapiens

<400> SEQUENCE: 100
gcagatgagc cctcagattt                                               20

<210> SEQ ID NO 101
<211> LENGTH: 24
<212> TYPE: DNA
<213> ORGANISM: Homo sapiens

<400> SEQUENCE: 101
tgccctcact gcaacagagc attt                                          24

<210> SEQ ID NO 102
<211> LENGTH: 19
<212> TYPE: DNA
<213> ORGANISM: Homo sapiens

<400> SEQUENCE: 102
gaaggaggag ggcagaatc                                                19
```

<210> SEQ ID NO 103
<211> LENGTH: 20
<212> TYPE: DNA
<213> ORGANISM: Homo sapiens

<400> SEQUENCE: 103
gtctcgattg gatggcagta                                           20

<210> SEQ ID NO 104
<211> LENGTH: 26
<212> TYPE: DNA
<213> ORGANISM: Homo sapiens

<400> SEQUENCE: 104
agttcatgga tgtctatcag cgcagc                                    26

<210> SEQ ID NO 105
<211> LENGTH: 20
<212> TYPE: DNA
<213> ORGANISM: Homo sapiens

<400> SEQUENCE: 105
ccacaaatca gacggcagca                                           20

<210> SEQ ID NO 106
<211> LENGTH: 20
<212> TYPE: DNA
<213> ORGANISM: Homo sapiens

<400> SEQUENCE: 106
gtcgtagtaa tggccatcgg                                           20

<210> SEQ ID NO 107
<211> LENGTH: 25
<212> TYPE: DNA
<213> ORGANISM: Homo sapiens

<400> SEQUENCE: 107
cccatgatgg ctcagaccaa caagt                                     25

<210> SEQ ID NO 108
<211> LENGTH: 18
<212> TYPE: DNA
<213> ORGANISM: Homo sapiens

<400> SEQUENCE: 108
ccaaccgcga gaagatga                                             18

<210> SEQ ID NO 109
<211> LENGTH: 20
<212> TYPE: DNA
<213> ORGANISM: Homo sapiens

<400> SEQUENCE: 109
ccagaggcgt acagggatag                                           20

<210> SEQ ID NO 110
<211> LENGTH: 23
<212> TYPE: DNA
<213> ORGANISM: Homo sapiens

<400> SEQUENCE: 110

```
ccatgtacgt tgctatccag gct                                           23

<210> SEQ ID NO 111
<211> LENGTH: 19
<212> TYPE: DNA
<213> ORGANISM: Homo sapiens

<400> SEQUENCE: 111
agtcctgagt ccggatgaa                                                19

<210> SEQ ID NO 112
<211> LENGTH: 18
<212> TYPE: DNA
<213> ORGANISM: Homo sapiens

<400> SEQUENCE: 112
cctccctcag tcgtctct                                                 18

<210> SEQ ID NO 113
<211> LENGTH: 24
<212> TYPE: DNA
<213> ORGANISM: Homo sapiens

<400> SEQUENCE: 113
tgacggaggg tggcatcaaa tacc                                          24

<210> SEQ ID NO 114
<211> LENGTH: 22
<212> TYPE: DNA
<213> ORGANISM: Homo sapiens

<400> SEQUENCE: 114
gccagcttgt cttcaatgaa at                                            22

<210> SEQ ID NO 115
<211> LENGTH: 21
<212> TYPE: DNA
<213> ORGANISM: Homo sapiens

<400> SEQUENCE: 115
caaagccagc ttctgttcaa g                                             21

<210> SEQ ID NO 116
<211> LENGTH: 24
<212> TYPE: DNA
<213> ORGANISM: Homo sapiens

<400> SEQUENCE: 116
atccaccatg agttggtagg cagc                                          24

<210> SEQ ID NO 117
<211> LENGTH: 23
<212> TYPE: DNA
<213> ORGANISM: Homo sapiens

<400> SEQUENCE: 117
gccaagaaga aagtgaacat cat                                           23

<210> SEQ ID NO 118
<211> LENGTH: 20
<212> TYPE: DNA
<213> ORGANISM: Homo sapiens

<400> SEQUENCE: 118
```
atagggattc cgggagtcat                          20

<210> SEQ ID NO 119
<211> LENGTH: 24
<212> TYPE: DNA
<213> ORGANISM: Homo sapiens

<400> SEQUENCE: 119
tcagaacaac agcctgccac ctta                     24

<210> SEQ ID NO 120
<211> LENGTH: 22
<212> TYPE: DNA
<213> ORGANISM: Homo sapiens

<400> SEQUENCE: 120
tgactccttc aacaccttct tc                       22

<210> SEQ ID NO 121
<211> LENGTH: 18
<212> TYPE: DNA
<213> ORGANISM: Homo sapiens

<400> SEQUENCE: 121
tgccagtgcg aacttcat                            18

<210> SEQ ID NO 122
<211> LENGTH: 24
<212> TYPE: DNA
<213> ORGANISM: Homo sapiens

<400> SEQUENCE: 122
ccgggctgtg tttgtagact tgga                     24

<210> SEQ ID NO 123
<211> LENGTH: 17
<212> TYPE: DNA
<213> ORGANISM: Homo sapiens

<400> SEQUENCE: 123
agccacatca tccctgt                             17

<210> SEQ ID NO 124
<211> LENGTH: 22
<212> TYPE: DNA
<213> ORGANISM: Homo sapiens

<400> SEQUENCE: 124
cgtagatgtt atgtctgctc at                       22

<210> SEQ ID NO 125
<211> LENGTH: 22
<212> TYPE: DNA
<213> ORGANISM: Homo sapiens

<400> SEQUENCE: 125
tttagcagca tctgcaaccc gc                       22

<210> SEQ ID NO 126
<211> LENGTH: 24
<212> TYPE: DNA
<213> ORGANISM: Homo sapiens

```
<400> SEQUENCE: 126
gaggatttgg aaagggtgtt tatt                                      24

<210> SEQ ID NO 127
<211> LENGTH: 21
<212> TYPE: DNA
<213> ORGANISM: Homo sapiens

<400> SEQUENCE: 127
acagagggct acaatgtgat g                                         21

<210> SEQ ID NO 128
<211> LENGTH: 26
<212> TYPE: DNA
<213> ORGANISM: Homo sapiens

<400> SEQUENCE: 128
acgtcttgct cgagatgtga tgaagg                                    26

<210> SEQ ID NO 129
<211> LENGTH: 18
<212> TYPE: DNA
<213> ORGANISM: Homo sapiens

<400> SEQUENCE: 129
taaaccctgc gtggcaat                                             18

<210> SEQ ID NO 130
<211> LENGTH: 27
<212> TYPE: DNA
<213> ORGANISM: Homo sapiens

<400> SEQUENCE: 130
acatttcgga taatcatcca atagttg                                   27

<210> SEQ ID NO 131
<211> LENGTH: 24
<212> TYPE: DNA
<213> ORGANISM: Homo sapiens

<400> SEQUENCE: 131
aagtagttgg acttccaggt cgcc                                      24

<210> SEQ ID NO 132
<211> LENGTH: 17
<212> TYPE: DNA
<213> ORGANISM: Homo sapiens

<400> SEQUENCE: 132
ccgtggcctt agctgtg                                              17

<210> SEQ ID NO 133
<211> LENGTH: 21
<212> TYPE: DNA
<213> ORGANISM: Homo sapiens

<400> SEQUENCE: 133
ctgctggatg acgtgagtaa a                                         21

<210> SEQ ID NO 134
<211> LENGTH: 24
<212> TYPE: DNA
<213> ORGANISM: Homo sapiens
```

```
<400> SEQUENCE: 134
tctctctttc tggcctggag gcta                                          24

<210> SEQ ID NO 135
<211> LENGTH: 25
<212> TYPE: DNA
<213> ORGANISM: Homo sapiens

<400> SEQUENCE: 135
aaatgttaac aaatgtggca attat                                         25

<210> SEQ ID NO 136
<211> LENGTH: 20
<212> TYPE: DNA
<213> ORGANISM: Homo sapiens

<400> SEQUENCE: 136
aacaatgcct ccactccaaa                                               20

<210> SEQ ID NO 137
<211> LENGTH: 20
<212> TYPE: DNA
<213> ORGANISM: Homo sapiens

<400> SEQUENCE: 137
tccacacaac accaggactt                                               20

<210> SEQ ID NO 138
<211> LENGTH: 22
<212> TYPE: DNA
<213> ORGANISM: Homo sapiens

<400> SEQUENCE: 138
tgaaaactac ccctaaaagc ca                                            22

<210> SEQ ID NO 139
<211> LENGTH: 21
<212> TYPE: DNA
<213> ORGANISM: Homo sapiens

<400> SEQUENCE: 139
tatccaagac ccaggcatac t                                             21

<210> SEQ ID NO 140
<211> LENGTH: 21
<212> TYPE: DNA
<213> ORGANISM: Homo sapiens

<400> SEQUENCE: 140
tagattcggg caagtccacc a                                             21

<210> SEQ ID NO 141
<211> LENGTH: 20
<212> TYPE: DNA
<213> ORGANISM: Homo sapiens

<400> SEQUENCE: 141
aagatgaggc agaggtccaa                                               20

<210> SEQ ID NO 142
<211> LENGTH: 20
<212> TYPE: DNA
```

```
<213> ORGANISM: Homo sapiens

<400> SEQUENCE: 142
tccagaatgt cacaggtcca                                               20

<210> SEQ ID NO 143
<211> LENGTH: 20
<212> TYPE: DNA
<213> ORGANISM: Homo sapiens

<400> SEQUENCE: 143
tgctggtaca agttgtggga                                               20
```